United States Patent
Pevarello et al.

(10) Patent No.: US 11,623,919 B2
(45) Date of Patent: Apr. 11, 2023

(54) HETEROCYCLIC P2X7 ANTAGONISTS

(71) Applicant: AXXAM S.P.A., Bresso (IT)

(72) Inventors: Paolo Pevarello, Bresso (IT); Mariangela Sodano, Bresso (IT); Elda Severi, Bresso (IT); Rocco Vitalone, Bresso (IT); Russell Thomas, Bresso (IT); Valentina Cusano, Bresso (IT)

(73) Assignee: BREYE THERAPEUTICS APS, Hørsholm (DK)

(*) Notice: Subject to any disclaimer, the term of this patent is extended or adjusted under 35 U.S.C. 154(b) by 412 days.

(21) Appl. No.: 16/607,737

(22) PCT Filed: May 2, 2018

(86) PCT No.: PCT/EP2018/061180
§ 371 (c)(1),
(2) Date: Oct. 24, 2019

(87) PCT Pub. No.: WO2018/202694
PCT Pub. Date: Nov. 8, 2018

(65) Prior Publication Data
US 2020/0055831 A1 Feb. 20, 2020

(30) Foreign Application Priority Data
May 3, 2017 (EP) ..................................... 17169277

(51) Int. Cl.
| C07D 271/07 | (2006.01) |
| C07D 417/06 | (2006.01) |
| C07D 413/10 | (2006.01) |
| C07D 413/06 | (2006.01) |
| C07D 285/08 | (2006.01) |
| C07D 495/04 | (2006.01) |

(52) U.S. Cl.
CPC ......... *C07D 271/07* (2013.01); *C07D 285/08* (2013.01); *C07D 413/06* (2013.01); *C07D 413/10* (2013.01); *C07D 417/06* (2013.01); *C07D 495/04* (2013.01)

(58) Field of Classification Search
CPC .. C07D 271/07; C07D 285/08; C07D 413/06; C07D 413/10; C07D 417/06; C07D 495/04
USPC ...................................................... 514/230.5
See application file for complete search history.

(56) References Cited

U.S. PATENT DOCUMENTS 5,066,662 A 11/1991 Hobbs et al.

FOREIGN PATENT DOCUMENTS

| GB | 1 508 210 | 4/1978 |
| JP | 61-106575 | 5/1986 |
| PL | 213249 B1 | 2/2013 |
| RU | 2347778 C2 | 2/2009 |
| SU | 598564 A3 | 3/1978 |
| WO | WO 01/72703 | 10/2001 |
| WO | WO 01/79156 | 10/2001 |
| WO | WO 02/22559 | 3/2002 |
| WO | WO 02/22562 | 3/2002 |
| WO | WO 2004/099146 | 11/2004 |
| WO | 2004/106305 A1 | 12/2004 |
| WO | WO 2009/108551 | 9/2009 |
| WO | WO 2009/132000 | 10/2009 |
| WO | WO 2015/099107 | 7/2015 |
| WO | WO 2015/119018 | 8/2015 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
International Search Report, PCT/EP2018/061180, dated Jul. 9, 2018.
Takacs, K. et al. : IIBeitrage zur Chemie von 1.2.4-0xadiazolen mit C-5-Heteroatom-Bindung, I. Herstellung N-monosubstituierter Amidoxime I, Chemi Sche Berichte, vol. 103, No. 8, 1970, pp. 2330-2335, XP055420479, ISSN: 0009-2940, DOI: 10. 1002/cber. 19701030803 p. 2331, reaction scheme; compound 4 p. 2332; compounds 4a, 4g, 4i.

(Continued)

*Primary Examiner* — Kristin A Vajda
(74) *Attorney, Agent, or Firm* — Nixon & Vanderhye

(57) ABSTRACT

Disclosed are compounds of formula (I) or a pharmaceutically acceptable salt thereof, pharmaceutical compositions containing them, and to a process for the preparation of the compounds:

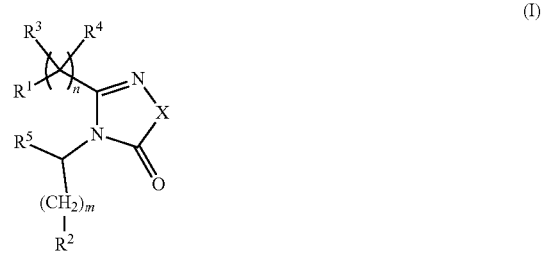

(I)

$R^1$ is independently selected from hydrogen atom, amine group, monocyclic or bicyclic aliphatic, aromatic, heteroaliphatic or heteroaromatic ring. $R^2$ is independently selected from monocyclic or bicylic aliphatic, heteroaliphatic, aromatic or heteroaromatic ring, $C_1$-$C_6$ alkyl, alkenyl or alkynyl chain. n is 1 or 2; preferably n is 1. m is 0, 1 or 2; preferably m is 0. $R^3$ and $R^4$ can be, independently, —H, —F, $C_1$-$C_4$ alkyl, —OH, —O$C_1$-$C_4$ alkyl; preferably they are both —H. X is O or S. $R^5$ is —H or —$CH_3$ optionally substituted by one or more fluorine atoms; preferably $R^5$ is hydrogen. The compounds can be used in the treatment of conditions or diseases mediated by P2X7 receptor.

8 Claims, 1 Drawing Sheet

(56) References Cited

OTHER PUBLICATIONS

Database CAPLUS [Online] Chemical Abstracts Service, Columbus, Ohio, US; 2013, Pitucha, Monika et al: "Antitumor applications of semicarbazide derivatives and I,2,4-triazolino-5-one derivatives with 1-methylpyrrole domain", XP002782431, retrieved from STN Database accession No. 2013:1196002, abstract.

Gerfaud, T. et al.: "Unexpected C-C Bond Cleavage: Synthesis of 1,2,4-Oxadiazol-5-ones from Amidoximes with Pentafluorophenyl or Trifluoromethyl Anion Acting as Leaving Group", Organic Letters, vol. 13, No. 23, 2011, pp. 6172-6175, XP55420520, ISSN: 1523-7060, DOI: 10.1021/ol202554m entry 9; p. 6174; table 2; compound 4i.

Moormann, A.E. et al.: "3-Methyl-4H-[I,2,4]-oxadiazol-5-one: a versatile synthon for protecting monosubstituted acetamidines", Tetrahedron, vol. 60, No. 48, 2004, pp. 10907-10914, XP004608831, ISSN: 0040-4020, DOI: 10.1016/J.TET.2004.09.030.

Harada, K. et al.: "Reactions of Aliphatic Nitro Compounds and Glycocyamidines", Nippon Kagaku Kaishi: Journal of the Chemical Society of Japan, No. 1, 1995, pp. 47-56, XP055487381, ISSN: 0369-4577, DOI: 10.1246/nikkashi.1995.47 p. 49; figure 2; compound 4e.

Takacs, K. et al.: "Beitrage zur Chemie von I,2,4-Oxadiazolen mit C-5-Heteroatom-Bindung, II. Synthese von 5,6-Dihydro-4H-1,2,4-oxadiazinen durch Ringerweiterung von Delta2-1,2,4-Oxadiazolin-5-onen", Chemische Berichte, vol. 108, No. 6, 1975, pp. 1911-1923, XP55420485, ISSN: 0009-2940, DOI: 10. 1002/cber. 19751080614 reaction schemes; p. 1912-p. 1913; compounds 3c, 3d, 9b.

Sumengen, D. et al.: liThe preparation and rearrangements of 3,4-disubstituted I,2,4-oxadiazoline-5-thiones, Journal of the Chemical Society, Perkin Transactions 1, No. 4, 1983, pp. 687-691, XP55420354, ISSN: 0300-922X, DOI: 10.1039/P19830000687 Scheme, derivatives b-d, f-h, j-l; p. 687; compounds (2), (4).

Un, R. et al.: "Reactions of N-alkylamide oximes with ethyl chloroformate. Preparation of 3,4-dialkyl-delta2-1,2,4-oxadiazolin-5-ones", Chimica Acta Turcica, vol. 4, No. 2, 1976, pp. 131-156, XP009506346, p. 134; compounds 31-42.

Areschka, A. et al.: "Benzofuranes. LXI. Potential antihypertensive 3 benzofuranylacetamidoximes", European Journal of Medicinal Chemistry, vol. 12, No. 1, 1977, pp. 87-91, XP009501218, ISSN: 0223-5234 p. 88; table I; compounds 29-56 p. 89; table II; compounds 67, 69, 70.

Park, J.-H. et al.: "P2X7 receptor antagonists: a patent review (2010-2015)", Expert Opinion on Therapeutic Patents, Oct. 31, 2016 (Oct. 31, 2016), pp. 1-11, XP055327737, ISSN: 1354-3776, DOI: 10.1080/13543776.2017.1246538 the whole document.

Romagnoli, R. et al.: "The P2X7 receptor as a therapeutic target", Expert Opinion on Therapeutic Targets, vol. 12, No. 1, 2008, pp. 647-661, XP009105531, ISSN: 1744-7631, DOI:10.1517/14728222. 12.5.647 the whole document.

Romagnoli, R. et al.: II Recent progress in the discovery of antagonists acting at P2X7 receptor, Expert Opinion on Therapeutic Patents, vol. 15, No. 3, 2005, pp. 271-287, XP002534885, ISSN: 1354-3776, DOI: 10.1517/13543776.15.3.271 the whole document.

Written Opinion, PCT/EP2018/061180, dated Jul. 9, 2018.

Diaz-Hernandez et al., "In vivo P2X7 inhibition reduces amyloid plaques in Alzheimer's disease through GSK3β and secretases," Neurobiology of Aging 33 (2012) 1816-1828.

Office Action issued in Russian Patent Application No. 2019134453 dated Aug. 26, 2021.

* cited by examiner

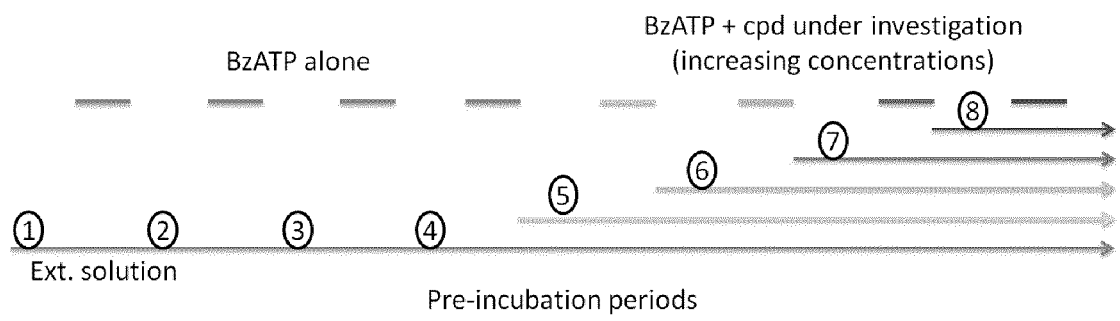

HETEROCYCLIC P2X7 ANTAGONISTS

The present invention relates to novel heterocyclic compounds of formula (I) having P2X7 receptor (P2X7) antagonistic properties, pharmaceutical compositions comprising these compounds, chemical processes for preparing these compounds and their use in the treatment or prophylaxis of diseases associated with P2X7 receptor activity in animals, in particular humans.

P2X7 belongs to the family of P2X ionotropic receptors. P2X7 is activated by extracellular nucleotides, notably adenosine triphosphate (ATP). P2X7 is distinguished from other P2X family members by the specific localization (CNS and immunocompetent cells in particular), by the high concentrations of ATP (in the mM range) required to activate it and by its ability to form a large pore upon prolonged or repeated stimulation. P2X7 is a ligand-gated ion channel and is present on a variety of cell types, largely those known to be involved in the inflammatory and/or immune process, specifically, macrophages, mast cells and lymphocytes (T and B). Activation of the P2X7 receptor by extracellular nucleotides, e.g., ATP, leads to the release of interleukin-1β (1L-1β) and giant cell formation (macrophages/microglial cells), degranulation (mast cells) and L-selectin shedding (lymphocytes). P2X7 receptors are also located on antigen-presenting cells (APC), keratinocytes, salivary acinar cells (parotid cells), hepatocytes, erythrocytes, erythroleukaemic cells, monocytes, fibroblasts, bone marrow cells, neurones, and renal mesangial cells. The P2X7 receptor is also known to be a pain sensor in the nervous system. Experiments using P2X7 deficient mice demonstrate the role of P2X7 in the development of pain as these mice were protected from the development of both adjuvant-induced inflammatory pain and partial nerve ligation induced neuropathic pain. There is also growing evidence that P2X7 or its downstream effectors, such as IL-1β, are involved in the pathophysiology of several neurological disorders, such as, Alzheimer's Disease (J. I. Diaz-Hernandez et al., Neurobiol. Aging 2012, 1816-1828: In vivo P2X7 inhibition reduces Aβ plaques in AD through GSK3β). P2X7 is thought to have an important function in neurotransmission within the CNS through its activation on postsynaptic and/or presynaptic neurons and glia. Data has emerged using in situ hybridization that P2X7 receptor mRNA is widely distributed throughout the rat brain. Specifically, areas of high P2X7 mRNA expression were found in the anterior olfactory nucleus, cerebral cortex, piriform cortex (Pir), lateral septal nucleus (LS), hippocampal pyramidal cell layers of CA1, CA3, CA4, pontine nuclei, external cuneate nucleus, and medial vestibular nucleus. P2X7 hybridization signals were also observed in the motor neurons of the trigeminal motor nucleus, facial nucleus, hypoglossal nucleus, and the anterior horn of the spinal cord.

Hence there is a therapeutic rationale for the use of P2X7 antagonists in the treatment of a variety of disease states. These states include but are not limited to diseases associated with the CNS such as Alzheimer's Disease, Parkinson's Disease, Huntington's Disease, Amyotrophic Lateral Sclerosis, spinal cord injury, cerebral ischemia, head trauma, meningitis, sleep disorders, mood and anxiety disorders, HIV-induced neuroinflammation, and chronic neuropathic and inflammatory pain. Furthermore, peripheral inflammatory disorders and autoimmune diseases including but not limited to rheumatoid arthritis, ostheoarthritis, psoriasis, allergic dermatitis, asthma, chronic obstructive pulmonary disease, airways hyper-responsiveness, septic shock, bronchitis, glomerulonephritis, irritable bowel syndrome, fatty liver disease, liver fibrosis, skin injury, lung emphysema, muscular dystrophy, fibrosis, atherosclerosis, burn injury, Crohn's Disease, ulcerative colitis, age-related macular degeneration, growth and metastasis of malignant cells, Sjögren's syndrome, myoblastic leukaemia, diabetes, osteoporosis, ischemic heart disease are all examples where the involvement of P2X7 receptors has been implicated. In view of the clinical importance of P2X7, the identification of compounds that modulate P2X7 receptor function represents an attractive avenue into the development of new therapeutic agents.

P2X7 inhibitors are described in various patent applications:

WO2004099146 discloses benzamide inhibitors of the P2X7 receptor and their use in the treatment of inflammatory diseases.

WO2009108551 discloses heteroarylamide analogs and their use in P2X7 receptor mediated conditions.

WO2009132000 discloses quinoline and isoquinoline substituted P2X7 receptor antagonists and their use in P2X7 receptor mediated conditions.

WO2015119018 discloses thiazole and oxazole derivatives as P2X7 receptor antagonists and their use in P2X7 receptor mediated conditions.

WO2015/099107 A1 discloses pyrimidinone substituted P2X7 receptor antagonist and their use in P2X7 receptor mediated conditions.

However there is still an unmet need for compounds which are able to efficiently antagonize P2X7 and that can be delivered in the different target organs which are sites of a P2X7 mediated pathology, including the brain. Such compounds are provided herein.

Various embodiments of the invention are presented hereafter.

The present invention relates to oxadiazolones compounds of the following formula (I) or a pharmaceutically acceptable salt thereof:

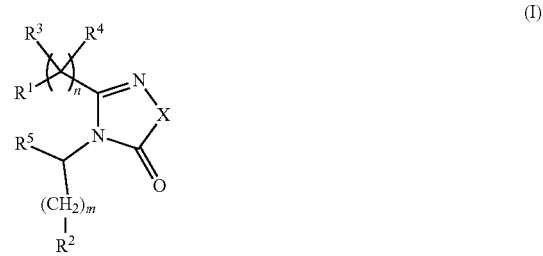

including any stereochemically isomeric form thereof, wherein:

$R^1$ is independently selected from hydrogen, amine, monocyclic or bicyclic aliphatic, aromatic, heteroaliphatic or heteroaromatic ring, optionally substituted by one or more substituents chosen from $C_1$-$C_4$ alkyl optionally substituted by one or more halogen atom(s), halogen, $C_1$-$C_4$ alkoxy or phenyl group, optionally substituted by $C_1$-$C_4$ alkyl;

$R^2$ is independently selected from monocyclic or bicyclic aliphatic, heteroaliphatic, aromatic or heteroaromatic ring, $C_1$-$C_6$ alkyl, alkenyl or alkynyl chain, optionally substituted by one or more substituents chosen from $C_1$-$C_4$ alkyl optionally substituted by one or more halogen atom(s), halogen, $C_1$-$C_4$ alkoxy, cyano, $C_1$-$C_4$ alkylthio, SO—$C_1$-$C_4$ alkyl, $SO_2$—$C_1$-$C_4$ alkyl, $N(C_1$-$C_4$ alkyl$)_2$;

n is 1 or 2; preferably n is 1;

m is 0, 1 or 2; preferably m is 0;

$R^3$ and $R^4$ can be, independently, —H, —F, $C_1$-$C_4$ alkyl, —OH, —O$C_1$-$C_4$ alkyl; preferably they are both —H;

X is O or S;

$R^5$ is —H or —$CH_3$ optionally substituted by one or more fluorine atoms; preferably $R^5$ is hydrogen.

As used in the foregoing definitions:

The terms "halo", "halogen" and "halide", which may be used interchangeably, refer to a substituent fluoro, chloro, bromo, or iodo.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration.

Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, trifluoromethanesulfonic, ethanesulfonic, benzenesulfonic, p-toluenesulfonic, cyclamic, salicylic, p-aminosalicylic, pamoic and the like.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

Preferably, $R^1$ is independently selected from hydrogen atom, mono or substituted ammines, or aliphatic, aromatic, heteroaliphatic or heteroaromatic ring selected from cyclopentyl, cyclohexyl, piperidine, morpholine, pyrrolidine, piperazine, phenyl, pyridine, oxazole, pyrazole or thiazole, wherein each of said moieties may be optionally substituted by one or more substituents selected from $C_1$-$C_4$ alkyl, optionally substituted by one or more halogen atom(s), halogen, $C_1$-$C_4$ alkoxy or phenyl group optionally substituted by $C_1$-$C_4$ alkyl, or the above reported aliphatic, aromatic, heteroaliphatic or heteroaromatic rings may be condensed with another aromatic, heteroaromatic or heteroaliphatic ring.

Preferably, $R^2$ is independently selected from phenyl, pyridine, pyrimidine, pyrazole, imidazole, naphthalene, quinoline, thiazole, furan, oxazole, oxadiazole, $C_3$-$C_7$ cycloalkyl, pyran, tetrahydropyran, dioxane, $C_1$-$C_4$ alkyloxy, aliphatic, aromatic or heteroaromatic bicyclic rings, $C_1$-$C_4$ alkyl chain or $C_3$-$C_5$ alkynyl chain, wherein each of said moieties may be optionally substituted with one or more $C_1$-$C_4$ alkyl optionally substituted by one or more halogen atom(s), halogen or $C_1$-$C_4$ alkoxy.

Preferably, $R^3$ and $R^4$ are, independently, H, F, —$CH_3$, —OH, —O$CH_2CH_3$, more preferably they are both H.

X is preferably O.

A preferred embodiment of the invention relates to compounds of Formula (I) as defined above wherein:

$R^1$ is independently selected from hydrogen atom or from the group consisting of cyclopentyl, cyclohexyl, piperidine, morpholine, pyrrolidine, piperazine, ammines, phenyl, pyridine, oxazole, pyrazole or thiazole wherein each of said group is optionally substituted with methyl, methoxy, halogen, trifluoromethyl or phenyl group optionally substituted by methyl; and each of the above reported aliphatic, aromatic or heteroaliphatic or heteroaromatic ring may be condensed with another aromatic or heteroaromatic ring;

$R^2$ is independently selected from phenyl, pyridine, pyrimidine, pyrazole, imidazole, naphthalene, quinoline, thiazole, furan, oxazole, oxadiazole, $C_3$-$C_7$ cycloalkyl, pyran, tetrahydropyran, dioxane, aliphatic bicyclic rings, $C_1$-$C_3$alkyloxy, $C_1$-$C_4$ alkyl chain or $C_3$-$C_5$ alkynyl chain; wherein each one of the above aliphatic, aromatic and heteroaliphatic ring is optionally substituted with methyl, methoxy, halogen and/or trifluoromethyl group).

n is 1 or 2; preferably n is 1;

m is 0, 1 or 2; preferably m is 0;

$R^3$ and $R^4$ are, independently, —H, F, $CH_3$, —OH or —O$CH_2CH_3$; preferably they are both hydrogen;

X is O or S; preferably O;

$R^5$ is H or —$CH_3$; preferably $R^5$ is H;

Another preferred embodiment of the invention relates to compounds of Formula (I) as defined above wherein:

$R^1$ is independently selected from hydrogen atom, 3,3-difluorocyclopenthyl, cyclohexyl, 4,4-difluorocyclohexyl, piperidinyl, 3,3-difluoropiperidinyl, 4,4-difluoropiperidinyl, 4,4-difluoro-2-methylpiperidinyl, 3-(4-methylphenyl)piperidinyl, 4H,5H,6H,7H-thieno[3,2-c]pyridine-5-yl, 1,2,3,4-tetrahydroisoquinolin-2-yl, 3,4-dihydro-2H-1,4-benzoxazin-4-yl, pyrrolidinyl, 4-phenylpiperazinyl, phenyl, 2-fluorophenyl, 3-fluorophenyl, 4-fluorophenyl, 2-chlorophenyl, 2-trifluoromethylphenyl, 3-methoxyphenyl, 4-methoxyphenyl, 2,3-dichlorophenyl, 2,4-dichlorophenyl, 2-chloro-3-trifluoromethylphenyl, 2,4-difluorophenyl, 2-chloro-4-fluorophenyl, 2-chloro-6-fluorophenyl, 2-, 3- or 4-pyridine, 2-methylpyridin-3-yl, dimethyl-1,2-oxazol-4-yl, trimethyl-1H-pyrazol-4-yl and 4-methyl-1,3-thiazol-5-yl;

$R^2$ is independently selected from 2-phenylmethyl, 1-phenylethyl, 2-phenylethyl, phenyl, 2-, 3-, 4-fluorophenyl, 2-, 4-chlorophenyl, 2-methoxyphenyl, 3-methoxyphenyl, 4-methoxyphenyl, 2-, 4-trifluoromethylphenyl, 2-, 4-methylphenyl, 2,3-dichlorophenyl, 2,4-dichlorophenyl, 2,4-difluorophenyl, 2-chloro-4-fluorophenyl, 2-chloro-6-fluorophenyl, 2-chloro-3-trifluoromethylphenyl, 2,4-dimethoxyphenyl, 3,5-dimethoxyphenyl, 2-bromo-5-fluorophenyl, 4-fluoro-2-methylphenyl, 2-pyridinyl, 3-pyridinyl, 4-pyridine, 2-methylpyridin-3-yl, 6-trifluoromethylpyridin-3-yl, 2-methyl-6-(trifluoromethyl)pyridin-3-yl, naphthalen-1-yl, quinolin-5-yl, 1,3-thiazol-2-y, 1,3-thiazol-5-yl, 4-methyl-1,3-thiazol-5-yl, 5-methyl-1,2-oxazol-3-yl, 1,2-oxazol-3-yl 1,2-oxazol-5-yl, 1,3-oxazol-2-yl, 1,3-oxazol-5-yl, dimethyl-1,2-oxazol-4-yl, 3-(trifluoromethyl)-1H-pyrazol-1-yl, 1,3-dimethyl-1H-pyrazol-5-yl, 1-methyl-1H-imidazol-2-yl, furan-3-yl, 5-(trifluoromethyl)furan-2-yl, 5-methyl-1,3,4-oxadiazol-2-yl, 5-methyl-1,2,4-oxadiazol-3-yl, 3-methyl-1,2,4-oxadiazol-5-yl, pyrimidin-2-yl, pyrimidin-5-yl, 5-fluoropyrimidin-2-yl, cyclopropyl, cyclobutyl, cyclopentyl, cyclopent-3-en-1-yl, cyclohexyl, 1-fluorocyclohexyl, 2-methylcyclohexyl, 2,2-dimethylcyclohexyl, 4,4-dimethylcyclohexyl, 2,2-difluorocyclohexyl, 4,4-diflurocyclohexyl, 4-(trifluoromethyl)cyclohexyl, 4-fluorocyclohexyl, 3,3-diflurocyclopentyl, 6,6-difluorobicyclo[3.1.0]hexan-3-yl, bicyclo[2.2.1]heptan-1-yl, bicyclo[2.2.1]heptan-2-yl, 1,4-dioxaspiro[4.5]decan-8-yl, oxan-2-yl, oxan-3-yl, oxan-4-yl, 1,4-dioxane-2-yl, methoxy, ethoxy, propoxy, hydrogen, methyl, ethyl, propyl, 2-methylpropyl, but-1-ynyl, prop-1-ynyl, piperidin-1-yl, 4,4-difluoropiperidin-1-yl;

n is 1 or 2; preferably n is 1;

m is 0, 1 or 2; preferably m is 0;

$R^3$ and $R^4$ are, independently, —H, —CH$_3$, —OH and —OCH$_2$CH$_3$; preferably $R^3$ and $R^4$ are both hydrogen;

X is O or S; preferably X is O;

$R^5$ is —H or —CH$_3$; preferably $R^5$ is —H;

Most preferably, a compound of formula (I) according to this invention is selected from the group consisting of:

| Ex. | IUPAC Name |
|---|---|
| 1 | 4-[(2-chloro-6-fluorophenyl)methyl]-3-[(4-fluorophenyl)methyl]-4,5-dihydro-1,2,4-oxadiazol-5-one |
| 2 | 4-[(2,4-dimethoxyphenyl)methyl]-3-[(4-fluorophenyl)methyl]-4,5-dihydro-1,2,4-oxadiazol-5-one |
| 3 | 3-[(4-fluorophenyl)methyl]-4-[(4-methoxyphenyl)methyl]-4,5-dihydro-1,2,4-oxadiazol-5-one |
| 4 | 4-[(3,5-dimethoxyphenyl)methyl]-3-[(4-fluorophenyl)methyl]-4,5-dihydro-1,2,4-oxadiazol-5-one |
| 5 | 4-[(2-bromo-5-fluorophenyl)methyl]-3-[(4-fluorophenyl)methyl]-4,5-dihydro-1,2,4-oxadiazol-5-one |
| 6 | 3-benzyl-4-[(2-chloro-6-fluorophenyl)methyl]-4,5-dihydro-1,2,4-oxadiazol-5-one |
| 7 | 4-[(2-chloro-6-fluorophenyl)methyl]-3-[(3-methoxyphenyl)methyl]-4,5-dihydro-1,2,4-oxadiazol-5-one |
| 8 | 3-[(4-fluorophenyl)methyl]-4-[(4-methyl-1,3-thiazol-5-yl)methyl]-4,5-dihydro-1,2,4-oxadiazol-5-one |
| 9 | 4-[(2,4-dichlorophenyl)methyl]-3-[(4-fluorophenyl)methyl]-4,5-dihydro-1,2,4-oxadiazol-5-one |
| 10 | 3-[(4-fluorophenyl)methyl]-4-(1-phenylethyl)-4,5-dihydro-1,2,4-oxadiazol-5-one |
| 11 | 4-[1-(4-fluorophenyl)ethyl]-3-[(4-fluorophenyl)methyl]-4,5-dihydro-1,2,4-oxadiazol-5-one |
| 12 | 4-(cyclohexylmethyl)-3-[(4-fluorophenyl)methyl]-4,5-dihydro-1,2,4-oxadiazol-5-one |
| 13 | 4-[(2-chloro-6-fluorophenyl)methyl]-3-[(2,3-dichlorophenyl)methyl]-4,5-dihydro-1,2,4-oxadiazol-5-one |
| 14 | 3-[(2-chloro-4-fluorophenyl)methyl]-4-[(2-chloro-6-fluorophenyl)methyl]-4,5-dihydro-1,2,4-oxadiazol-5-one |
| 15 | 4-[(2-chloro-6-fluorophenyl)methyl]-3-[(2,4-difluorophenyl)methyl]-4,5-dihydro-1,2,4-oxadiazol-5-one |
| 16 | 3-{[2-chloro-3-(trifluoromethyl)phenyl]methyl}-4-[(2-chloro-6-fluorophenyl)methyl]-4,5-dihydro-1,2,4-oxadiazol-5-one |
| 17 | 4-[(2-chloro-6-fluorophenyl)methyl]-3-[(2,4-dichlorophenyl)methyl]-4,5-dihydro-1,2,4-oxadiazol-5-one |
| 18 | bis[(2-chloro-6-fluorophenyl)methyl]-4,5-dihydro-1,2,4-oxadiazol-5-one |
| 19 | 4-[(2-chloro-6-fluorophenyl)methyl]-3-[(2-fluorophenyl)methyl]-4,5-dihydro-1,2,4-oxadiazol-5-one |
| 20 | 4-[(2-chloro-6-fluorophenyl)methyl]-3-[(2-chlorophenyl)methyl]-4,5-dihydro-1,2,4-oxadiazol-5-one |
| 21 | 4-benzyl-3-[(2-chloro-6-fluorophenyl)methyl]-4,5-dihydro-1,2,4-oxadiazol-5-one |
| 22 | 3-[(2-chloro-6-fluorophenyl)methyl]-4-[(2-chlorophenyl)methyl]-4,5-dihydro-1,2,4-oxadiazol-5-one |
| 23 | 3-[(2-chloro-6-fluorophenyl)methyl]-4-{[2-(trifluoromethyl)phenyl]methyl}-4,5-dihydro-1,2,4-oxadiazol-5-one |
| 24 | 3-[(2-chloro-6-fluorophenyl)methyl]-4-[(2-methylpyridin-3-yl)methyl]-4,5-dihydro-1,2,4-oxadiazol-5-one |
| 25 | 3-[(2-chloro-6-fluorophenyl)methyl]-4-[(4-fluoro-2-methylphenyl)methyl]-4,5-dihydro-1,2,4-oxadiazol-5-one |
| 26 | 3-[(2-chloro-6-fluorophenyl)methyl]-4-[(3-fluorophenyl)methyl]-4,5-dihydro-1,2,4-oxadiazol-5-one |
| 27 | 3-[(2-chloro-6-fluorophenyl)methyl]-4-[(2-methylphenyl)methyl]-4,5-dihydro-1,2,4-oxadiazol-5-one |
| 28 | 3-[(2-chloro-6-fluorophenyl)methyl]-4-[(2-methoxyphenyl)methyl]-4,5-dihydro-1,2,4-oxadiazol-5-one |
| 29 | 3-[(2-chloro-6-fluorophenyl)methyl]-4-(naphthalen-1-ylmethyl)-4,5-dihydro-1,2,4-oxadiazol-5-one |
| 30 | 3-[(2-chloro-6-fluorophenyl)methyl]-4-(quinolin-5-ylmethyl)-4,5-dihydro-1,2,4-oxadiazol-5-one |
| 31 | 3-[(2-chloro-6-fluorophenyl)methyl]-4-[(4-methyl-1,3-thiazol-5-yl)methyl]-4,5-dihydro-1,2,4-oxadiazol-5-one |

| Ex. | IUPAC Name |
|---|---|
| 32 | 3-[(2-chloro-6-fluorophenyl)methyl]-4-(1,3-oxazol-2-ylmethyl)-4,5-dihydro-1,2,4-oxadiazol-5-one |
| 33 | 3-[(2-chloro-6-fluorophenyl)methyl]-4-(1,3-thiazol-5-ylmethyl)-4,5-dihydro-1,2,4-oxadiazol-5-one |
| 34 | 3-[(2-chloro-6-fluorophenyl)methyl]-4-(1,3-thiazol-2-ylmethyl)-4,5-dihydro-1,2,4-oxadiazol-5-one |
| 35 | 3-[(2-chloro-6-fluorophenyl)methyl]-4-{[3-(trifluoromethyl)-1H-pyrazol-1-yl]methyl}-4,5-dihydro-1,2,4-oxadiazol-5-one |
| 36 | 3-[(2-chloro-6-fluorophenyl)methyl]-4-[(dimethyl-1,2-oxazol-4-yl)methyl]-4,5-dihydro-1,2,4-oxadiazol-5-one |
| 37 | 3-[(2-chloro-6-fluorophenyl)methyl]-4-{[6-(trifluoromethyl)pyridin-3-yl]methyl}-4,5-dihydro-1,2,4-oxadiazol-5-one |
| 38 | 3-[(2-chloro-6-fluorophenyl)methyl]-4-(pyrimidin-5-ylmethyl)-4,5-dihydro-1,2,4-oxadiazol-5-one |
| 39 | 3-[(2-chloro-6-fluorophenyl)methyl]-4-(pyrimidin-2-ylmethyl)-4,5-dihydro-1,2,4-oxadiazol-5-one |
| 40 | 3-[(2-chloro-6-fluorophenyl)methyl]-4-(1,3-oxazol-5-ylmethyl)-4,5-dihydro-1,2,4-oxadiazol-5-one |
| 41 | 3-[(2-chloro-6-fluorophenyl)methyl]-4-[(5-methyl-1,3,4-oxadiazol-2-yl)methyl]-4,5-dihydro-1,2,4-oxadiazol-5-one |
| 42 | 3-[(2-chloro-6-fluorophenyl)methyl]-4-(pyridin-3-ylmethyl)-4,5-dihydro-1,2,4-oxadiazol-5-one |
| 43 | 3-[(2-chloro-6-fluorophenyl)methyl]-4-(pyridin-4-ylmethyl)-4,5-dihydro-1,2,4-oxadiazol-5-one |
| 44 | 3-[(2-chloro-6-fluorophenyl)methyl]-4-(furan-3-ylmethyl)-4,5-dihydro-1,2,4-oxadiazol-5-one |
| 45 | 3-[(2-chloro-6-fluorophenyl)methyl]-4-[(5-fluoropyrimidin-2-yl)methyl]-4,5-dihydro-1,2,4-oxadiazol-5-one |
| 46 | 3-[(2-chloro-6-fluorophenyl)methyl]-4-[(1,3-dimethyl-1H-pyrazol-5-yl)methyl]-4,5-dihydro-1,2,4-oxadiazol-5-one |
| 47 | 3-[(2-chloro-6-fluorophenyl)methyl]-4-[(1-methyl-1H-imidazol-2-yl)methyl]-4,5-dihydro-1,2,4-oxadiazol-5-one |
| 48 | 3-[(2-chloro-6-fluorophenyl)methyl]-4-[1-(4-fluorophenyl)ethyl]-4,5-dihydro-1,2,4-oxadiazol-5-one |
| 49 | 3-[(2-chloro-6-fluorophenyl)methyl]-4-(1-phenylethyl)-4,5-dihydro-1,2,4-oxadiazol-5-one |
| 50 | 4-[(2,3-dichlorophenyl)methyl]-3-[(4-fluorophenyl)methyl]-4,5-dihydro-1,2,4-oxadiazol-5-one |
| 51 | 4-[(2-chloro-4-fluorophenyl)methyl]-3-[(4-fluorophenyl)methyl]-4,5-dihydro-1,2,4-oxadiazol-5-one |
| 52 | 4-{[2-chloro-3-(trifluoromethyl)phenyl]methyl}-3-[(4-fluorophenyl)methyl]-4,5-dihydro-1,2,4-oxadiazol-5-one |
| 53 | 4-[(2,4-difluorophenyl)methyl]-3-[(4-fluorophenyl)methyl]-4,5-dihydro-1,2,4-oxadiazol-5-one |
| 54 | bis[(4-fluorophenyl)methyl]-4,5-dihydro-1,2,4-oxadiazol-5-one |
| 55 | 3-[(2-chloro-6-fluorophenyl)methyl]-4-[(4-fluorophenyl)methyl]-4,5-dihydro-1,2,4-oxadiazol-5-one |
| 56 | 3-[(2-chloro-6-fluorophenyl)methyl]-4-[(2-fluorophenyl)methyl]-4,5-dihydro-1,2,4-oxadiazol-5-one |
| 57 | 3-[(2-chloro-6-fluorophenyl)methyl]-4-[(3-methoxyphenyl)methyl]-4,5-dihydro-1,2,4-oxadiazol-5-one |
| 58 | 4-{[2-chloro-3-(trifluoromethyl)phenyl]methyl}-3-[(2-chloro-6-fluorophenyl)methyl]-4,5-dihydro-1,2,4-oxadiazol-5-one |
| 59 | 3-[(2-chloro-6-fluorophenyl)methyl]-4-[(2,3-dichlorophenyl)methyl]-4,5-dihydro-1,2,4-oxadiazol-5-one |
| 60 | 4-[(2-chloro-4-fluorophenyl)methyl]-3-[(2-chloro-6-fluorophenyl)methyl]-4,5-dihydro-1,2,4-oxadiazol-5-one |
| 61 | 3-[(2-chloro-6-fluorophenyl)methyl]-4-[(2,4-difluorophenyl)methyl]-4,5-dihydro-1,2,4-oxadiazol-5-one |
| 62 | 3-[(2-chloro-6-fluorophenyl)methyl]-4-(pyridin-2-ylmethyl)-4,5-dihydro-1,2,4-oxadiazol-5-one |
| 63 | 3-[(2-chloro-6-fluorophenyl)methyl]-4-{[4-(trifluoromethyl)phenyl]methyl}-4,5-dihydro-1,2,4-oxadiazol-5-one |
| 64 | 3-[(2-chloro-6-fluorophenyl)methyl]-4-{[2-methyl-6-(trifluoromethyl)pyridin-3-yl]methyl}-4,5-dihydro-1,2,4-oxadiazol-5-one |
| 65 | 3-[(2-chloro-6-fluorophenyl)methyl]-4-[(4-chlorophenyl)methyl]-4,5-dihydro-1,2,4-oxadiazol-5-one |
| 66 | 3-[(2-chloro-6-fluorophenyl)methyl]-4-{[5-(trifluoromethyl)furan-2-yl]methyl}-4,5-dihydro-1,2,4-oxadiazol-5-one |
| 67 | 3-[(2-chloro-6-fluorophenyl)methyl]-4-[(4-methylphenyl)methyl]-4,5-dihydro-1,2,4-oxadiazol-5-one |
| 68 | 3-[(2-chloro-6-fluorophenyl)methyl]-4-[(4-methoxyphenyl)methyl]-4,5-dihydro-1,2,4-oxadiazol-5-one |
| 69 | 3-[(2-chloro-6-fluorophenyl)methyl]-4-(cyclobutylmethyl)-4,5-dihydro-1,2,4-oxadiazol-5-one |
| 70 | 3-[(2-chloro-6-fluorophenyl)methyl]-4-{1,4-dioxaspiro[4.5]decan-8-ylmethyl}-4,5-dihydro-1,2,4-oxadiazol-5-one |

-continued

| Ex. | IUPAC Name |
|---|---|
| 71 | 3-[(2,3-dichlorophenyl)methyl]-4-[(4-fluorophenyl)methyl]-4,5-dihydro-1,2,4-oxadiazol-5-one |
| 72 | 3-{[2-chloro-3-(trifluoromethyl)phenyl]methyl}-4-[(4-fluorophenyl)methyl]-4,5-dihydro-1,2,4-oxadiazol-5-one |
| 73 | 3-[(2-chloro-4-fluorophenyl)methyl]-4-[(4-fluorophenyl)methyl]-4,5-dihydro-1,2,4-oxadiazol-5-one |
| 74 | 3-[(2,4-dichlorophenyl)methyl]-4-[(4-fluorophenyl)methyl]-4,5-dihydro-1,2,4-oxadiazol-5-one |
| 75 | 3-[(2-fluorophenyl)methyl]-4-[(4-fluorophenyl)methyl]-4,5-dihydro-1,2,4-oxadiazol-5-one |
| 76 | 3-[(2-chlorophenyl)methyl]-4-[(4-fluorophenyl)methyl]-4,5-dihydro-1,2,4-oxadiazol-5-one |
| 77 | 3-[2-(2-chloro-6-fluorophenyl)propan-2-yl]-4-[(4-fluorophenyl)methyl]-4,5-dihydro-1,2,4-oxadiazol-5-one |
| 78 | 3-[1-(2-chloro-6-fluorophenyl)ethyl]-4-[(4-fluorophenyl)methyl]-4,5-dihydro-1,2,4-oxadiazol-5-one |
| 79 | 4-[(4-fluorophenyl)methyl]-3-(pyridin-4-ylmethyl)-4,5-dihydro-1,2,4-oxadiazol-5-one |
| 80 | 3-[(2,4-difluorophenyl)methyl]-4-[(4-fluorophenyl)methyl]-4,5-dihydro-1,2,4-oxadiazol-5-one |
| 81 | 4-[(2-chloro-6-fluorophenyl)methyl]-3-[(3-fluorophenyl)methyl]-4,5-dihydro-1,2,4-oxadiazol-5-one |
| 82 | 3-[(2-chloro-6-fluorophenyl)methyl]-4-(cyclohexylmethyl)-4,5-dihydro-1,2,4-oxadiazol-5-one |
| 83 | 3-[(2-chloro-6-fluorophenyl)methyl]-4-(cyclopropylmethyl)-4,5-dihydro-1,2,4-oxadiazol-5-one |
| 84 | 3-[(2-chloro-6-fluorophenyl)methyl]-4-[(4,4-difluorocyclohexyl)methyl]-4,5-dihydro-1,2,4-oxadiazol-5-one |
| 85 | 3-[(2-chloro-6-fluorophenyl)methyl]-4-(cyclopentylmethyl)-4,5-dihydro-1,2,4-oxadiazol-5-one |
| 86 | 3-[(2-chloro-6-fluorophenyl)methyl]-4-[(4,4-dimethylcyclohexyl)methyl]-4,5-dihydro-1,2,4-oxadiazol-5-one |
| 87 | 3-[(2-chloro-6-fluorophenyl)methyl]-4-[(2-methylcyclohexyl)methyl]-4,5-dihydro-1,2,4-oxadiazol-5-one |
| 88 | 4-{bicyclo[2.2.1]heptan-2-ylmethyl}-3-[(2-chloro-6-fluorophenyl)methyl]-4,5-dihydro-1,2,4-oxadiazol-5-one |
| 89 | 3-[(2-chloro-6-fluorophenyl)methyl]-4-(oxan-3-ylmethyl)-4,5-dihydro-1,2,4-oxadiazol-5-one |
| 90 | 3-[(2-chloro-6-fluorophenyl)methyl]-4-(pent-2-yn-1-yl)-4,5-dihydro-1,2,4-oxadiazol-5-one |
| 91 | 4-{bicyclo [2.2.1]heptan-1-ylmethyl}-3-[(2-chloro-6-fluorophenyl)methyl]-4,5-dihydro-1,2,4-oxadiazol-5-one |
| 92 | 3-[(2-chloro-6-fluorophenyl)methyl]-4-(cycloheptylmethyl)-4,5-dihydro-1,2,4-oxadiazol-5-one |
| 93 | 3-[(2-chloro-6-fluorophenyl)methyl]-4-(oxan-4-ylmethyl)-4,5-dihydro-1,2,4-oxadiazol-5-one |
| 94 | 3-[(2-chloro-6-fluorophenyl)methyl]-4-(oxan-2-ylmethyl)-4,5-dihydro-1,2,4-oxadiazol-5-one |
| 95 | 4-(but-2-yn-1-yl)-3-[(2-chloro-6-fluorophenyl)methyl]-4,5-dihydro-1,2,4-oxadiazol-5-one |
| 96 | 3-[(2-chloro-6-fluorophenyl)methyl]-4-[(1-fluorocyclohexyl)methyl]-4,5-dihydro-1,2,4-oxadiazol-5-one |
| 97 | 3-[(2-chloro-6-fluorophenyl)methyl]-4-[(2,2-difluorocyclohexyl)methyl]-4,5-dihydro-1,2,4-oxadiazol-5-one |
| 98 | 3-[(2-chloro-6-fluorophenyl)methyl]-4-(1,4-dioxan-2-ylmethyl)-4,5-dihydro-1,2,4-oxadiazol-5-one |
| 99 | 3-[(2-chloro-6-fluorophenyl)methyl]-4-[(2,2-dimethylcyclohexyl)methyl]-4,5-dihydro-1,2,4-oxadiazol-5-one |
| 100 | 3-[(2-chloro-6-fluorophenyl)methyl]-4-(methoxymethyl)-4,5-dihydro-1,2,4-oxadiazol-5-one |
| 101 | 3-[(2-chloro-6-fluorophenyl)methyl]-4-(ethoxymethyl)-4,5-dihydro-1,2,4-oxadiazol-5-one |
| 102 | 3-[(2-chloro-6-fluorophenyl)methyl]-4-(propoxymethyl)-4,5-dihydro-1,2,4-oxadiazol-5-one |
| 104 | 4-[(4-fluorophenyl)methyl]-3-(pyridin-2-ylmethyl)-4,5-dihydro-1,2,4-oxadiazol-5-one |
| 105 | 4-[(4-fluorophenyl)methyl]-3-{[2-(trifluoromethyl)phenyl]methyl}-4,5-dihydro-1,2,4-oxadiazol-5-one |
| 107 | 3-[(3-fluorophenyl)methyl]-4-[(4-fluorophenyl)methyl]-4,5-dihydro-1,2,4-oxadiazol-5-one |
| 108 | 3-benzyl-4-[(4-fluorophenyl)methyl]-4,5-dihydro-1,2,4-oxadiazol-5-one |
| 109 | 4-[(4-fluorophenyl)methyl]-3-[(3-methoxyphenyl)methyl]-4,5-dihydro-1,2,4-oxadiazol-5-one |
| 110 | 4-(cyclohexylmethyl)-3-(pyridin-2-ylmethyl)-4,5-dihydro-1,2,4-oxadiazol-5-one |
| 111 | 4-(cyclohexylmethyl)-3-(pyridin-4-ylmethyl)-4,5-dihydro-1,2,4-oxadiazol-5-one |

-continued

| Ex. | IUPAC Name |
|---|---|
| 112 | 4-(cyclohexylmethyl)-3-[(4-methoxyphenyl)methyl]-4,5-dihydro-1,2,4-oxadiazol-5-one |
| 113 | 3-{[2-chloro-3-(trifluoromethyl)phenyl]methyl}-4-(cyclohexylmethyl)-4,5-dihydro-1,2,4-oxadiazol-5-one |
| 114 | 3-[(2-chloro-4-fluorophenyl)methyl]-4-(cyclohexylmethyl)-4,5-dihydro-1,2,4-oxadiazol-5-one |
| 115 | 4-(cyclohexylmethyl)-3-[(2,3-dichlorophenyl)methyl]-4,5-dihydro-1,2,4-oxadiazol-5-one |
| 116 | 4-(cyclohexylmethyl)-3-{[2-(trifluoromethyl)phenyl]methyl}-4,5-dihydro-1,2,4-oxadiazol-5-one |
| 117 | 3-[(2-chlorophenyl)methyl]-4-(cyclohexylmethyl)-4,5-dihydro-1,2,4-oxadiazol-5-one |
| 118 | 4-(cyclohexylmethyl)-3-[(2,4-dichlorophenyl)methyl]-4,5-dihydro-1,2,4-oxadiazol-5-one |
| 119 | 4-(cyclohexylmethyl)-3-[(2,4-difluorophenyl)methyl]-4,5-dihydro-1,2,4-oxadiazol-5-one |
| 120 | 4-(cyclohexylmethyl)-3-[(2-fluorophenyl)methyl]-4,5-dihydro-1,2,4-oxadiazol-5-one |
| 121 | 3-[2-(2-chloro-6-fluorophenyl)propan-2-yl]-4-(cyclohexylmethyl)-4,5-dihydro-1,2,4-oxadiazol-5-one |
| 122 | 3-[1-(2-chloro-6-fluorophenyl)ethyl]-4-(cyclohexylmethyl)-4,5-dihydro-1,2,4-oxadiazol-5-one |
| 123 | 4-(cyclohexylmethyl)-3-(pyridin-3-ylmethyl)-4,5-dihydro-1,2,4-oxadiazol-5-one |
| 125 | 4-(cyclohexylmethyl)-3-[(3-fluorophenyl)methyl]-4,5-dihydro-1,2,4-oxadiazol-5-one |
| 126 | 3-benzyl-4-(cyclohexylmethyl)-4,5-dihydro-1,2,4-oxadiazol-5-one |
| 127 | 4-(cyclohexylmethyl)-3-[(3-methoxyphenyl)methyl]-4,5-dihydro-1,2,4-oxadiazol-5-one |
| 128 | 3-[(2-chloro-6-fluorophenyl)methyl]-4-[(3,3-difluorocyclopentyl)methyl]-4,5-dihydro-1,2,4-oxadiazol-5-one |
| 129 | bis(cyclohexylmethyl)-4,5-dihydro-1,2,4-oxadiazol-5-one |
| 130 | 4-[(2-chloro-6-fluorophenyl)methyl]-3-(cyclohexylmethyl)-4,5-dihydro-1,2,4-oxadiazol-5-one |
| 131 | 3-(cyclohexylmethyl)-4-[(4-fluorophenyl)methyl]-4,5-dihydro-1,2,4-oxadiazol-5-one |
| 132 | 4-[(2-chloro-6-fluorophenyl)methyl]-3-[(4,4-difluorocyclohexyl)methyl]-4,5-dihydro-1,2,4-oxadiazol-5-one |
| 133 | 4-(cyclohexylmethyl)-3-[(4,4-difluorocyclohexyl)methyl]-4,5-dihydro-1,2,4-oxadiazol-5-one |
| 134 | 4-(cyclohexylmethyl)-3-[(4,4-difluorocyclohexyl)methyl]-4,5-dihydro-1,2,4-oxadiazol-5-one |
| 135 | 3-{[2-chloro-3-(trifluoromethyl)phenyl](hydroxy)methyl}-4-[(2-chloro-6-fluorophenyl)methyl]-4,5-dihydro-1,2,4-oxadiazol-5-one |
| 136 | 4-benzyl-3-{[2-chloro-3-(trifluoromethyl)phenyl](hydroxy)methyl}-4,5-dihydro-1,2,4-oxadiazol-5-one |
| 137 | 4-[(2-chloro-6-fluorophenyl)methyl]-3-[(2,4-difluorophenyl)(hydroxy)methyl]-4,5-dihydro-1,2,4-oxadiazol-5-one |
| 138 | 4-[(2-chloro-6-fluorophenyl)methyl]-3-[(2,3-dichlorophenyl)(hydroxy)methyl]-4,5-dihydro-1,2,4-oxadiazol-5-one |
| 139 | 3-[(2-chloro-6-fluorophenyl)methyl]-4-[(4-fluorophenyl)methyl]-4,5-dihydro-1,2,4-thiadiazol-5-one |
| 140 | 3-[(2-chloro-6-fluorophenyl)methyl]-4-(cyclohexylmethyl)-4,5-dihydro-1,2,4-thiadiazol-5-one |
| 141 | 3-[(2-chloro-6-fluorophenyl)methyl]-4-[(4,4-difluorocyclohexyl)methyl]-4,5-dihydro-1,2,4-thiadiazol-5-one |
| 142 | 3-(2-chloro-6-fluorobenzyl)-4-(2-cyclohexylethyl)-1,2,4-oxadiazol-5(4H)-one |
| 143 | 3-(2-chloro-6-fluorobenzyl)-4-[2-(piperidin-1-yl)ethyl]-1,2,4-oxadiazol-5(4H)-one |
| 144 | 4-(2-chloro-6-fluorobenzyl)-3-[2-(2-chloro-6-fluorophenyl)ethyl]-1,2,4-oxadiazol-5(4H)-one |
| 145 | 3-[2-(2-chloro-6-fluorophenyl)ethyl]-4-(4-fluorobenzyl)-1,2,4-oxadiazol-5(4H)-one |
| 146 | 3-[2-(2-chloro-6-fluorophenyl)ethyl]-4-(cyclohexylmethyl)-1,2,4-oxadiazol-5(4H)-one |
| 147 | 3-[2-(2-chloro-6-fluorophenyl)ethyl]-4-[(4,4-difluorocyclohexyl)methyl]-1,2,4-oxadiazol-5(4H)-one |
| 148 | 3-(2-chloro-6-fluorobenzyl)-4-[(3,3-difluorocyclopentyl)methyl]-1,2,4-oxadiazol-5(4H)-one |
| 149 | 3-(2-chloro-6-fluorobenzyl)-4-[(3,3-difluorocyclopentyl)methyl]-1,2,4-oxadiazol-5(4H)-one |
| 150 | 4-[(4,4-difluorocyclohexyl)methyl]-3-[(2-fluorophenyl)methyl]-4,5-dihydro-1,2,4-oxadiazol-5-one |
| 151 | 4-[(4,4-difluorocyclohexyl)methyl]-3-[(3-fluorophenyl)methyl]-4,5-dihydro-1,2,4-oxadiazol-5-one |

| Ex. | IUPAC Name |
|---|---|
| 152 | 4-[(4,4-difluorocyclohexyl)methyl]-3-[(4-fluorophenyl)methyl]-4,5-dihydro-1,2,4-oxadiazol-5-one |
| 153 | 4-[(4,4-difluorocyclohexyl)methyl]-3-[(2,4-difluorophenyl)methyl]-4,5-dihydro-1,2,4-oxadiazol-5-one |
| 154 | 4-[(4,4-difluorocyclohexyl)methyl]-3-[(4-methoxyphenyl)methyl]-4,5-dihydro-1,2,4-oxadiazol-5-one |
| 155 | 3-{[2-chloro-3-(trifluoromethyl)phenyl]methyl}-4-[(4,4-difluorocyclohexyl)methyl]-4,5-dihydro-1,2,4-oxadiazol-5-one |
| 156 | 3-[(2,3-dichlorophenyl)methyl]-4-[(4,4-difluorocyclohexyl)methyl]-4,5-dihydro-1,2,4-oxadiazol-5-one |
| 157 | 4-[(4,4-difluorocyclohexyl)methyl]-3-{[2-(trifluoromethyl)phenyl]methyl}-4,5-dihydro-1,2,4-oxadiazol-5-one |
| 158 | 3-[(2-chlorophenyl)methyl]-4-[(4,4-difluorocyclohexyl)methyl]-4,5-dihydro-1,2,4-oxadiazol-5-one |
| 159 | 3-[(2,4-dichlorophenyl)methyl]-4-[(4,4-difluorocyclohexyl)methyl]-4,5-dihydro-1,2,4-oxadiazol-5-one |
| 160 | 4-[(4,4-difluorocyclohexyl)methyl]-3-[(3-methoxyphenyl)methyl]-4,5-dihydro-1,2,4-oxadiazol-5-one |
| 161 | 3-benzyl-4-[(4,4-difluorocyclohexyl)methyl]-4,5-dihydro-1,2,4-oxadiazol-5-one |
| 162 | 3-[(2-chloro-4-fluorophenyl)methyl]-4-[(4,4-difluorocyclohexyl)methyl]-4,5-dihydro-1,2,4-oxadiazol-5-one |
| 163 | 3-(cyclohexylmethyl)-4-[1-(4-fluorophenyl)ethyl]-4,5-dihydro-1,2,4-oxadiazol-5-one |
| 164 | 3-[(4,4-difluorocyclohexyl)methyl]-4-[1-(4-fluorophenyl)ethyl]-4,5-dihydro-1,2,4-oxadiazol-5-one |
| 165 | 3-[(4,4-difluorocyclohexyl)methyl]-4-[(2-fluorophenyl)methyl]-4,5-dihydro-1,2,4-oxadiazol-5-one |
| 166 | 3-[(4,4-difluorocyclohexyl)methyl]-4-{[4-(trifluoromethyl)phenyl]methyl}-4,5-dihydro-1,2,4-oxadiazol-5-one |
| 167 | 4-{[2-chloro-3-(trifluoromethyl)phenyl]methyl}-3-[(4,4-dfluorocyclohexyl)methyl]-4,5-dihydro-1,2,4-oxadiazol-5-one |
| 168 | 3-[(4,4-difluorocyclohexyl)methyl]-4-{[5-(trifluoromethyl)furan-2-yl]methyl}-4,5-dihydro-1,2,4-oxadiazol-5-one |
| 169 | 3-[(4,4-difluorocyclohexyl)methyl]-4-[(5-methyl-1,2-oxazol-3-yl)methyl]-4,5-dihydro-1,2,4-oxadiazol-5-one |
| 170 | 4-[(2-chlorophenyl)methyl]-3-[(4,4-difluorocyclohexyl)methyl]-4,5-dihydro-1,2,4-oxadiazol-5-one |
| 171 | 3-[(4,4-difluorocyclohexyl)methyl]-4-[(4-fluoro-2-methylphenyl)methyl]-4,5-dihydro-1,2,4-oxadiazol-5-one |
| 172 | 3-[(4,4-difluorocyclohexyl)methyl]-4-(2-phenylethyl)-4,5-dihydro-1,2,4-oxadiazol-5-one |
| 173 | 3-[(2-chloro-6-fluorophenyl)methyl]-4-({6,6-difluorobicyclo[3.1.0]-hexan-3-yl}methyl)-4,5-dihydro-1,2,4-oxadiazol-5-one |
| 174 | 3-[(2-chloro-6-fluorophenyl)methyl]-4-methyl-4,5-dihydro-1,2,4-oxadiazol-5-one |
| 175 | 3-[(2-chloro-6-fluorophenyl)methyl]-4-ethyl-4,5-dihydro-1,2,4-oxadiazol-5-one |
| 176 | 3-[(2-chloro-6-fluorophenyl)methyl]-4-propyl-4,5-dihydro-1,2,4-oxadiazol-5-one |
| 177 | 4-butyl-3-[(2-chloro-6-fluorophenyl)methyl]-4,5-dihydro-1,2,4-oxadiazol-5-one |
| 178 | 3-[(2-chloro-6-fluorophenyl)methyl]-4-(2-methylpropyl)-4,5-dihydro-1,2,4-oxadiazol-5-one |
| 179 | 3-[(2-chloro-6-fluorophenyl)methyl]-4-(3-cyclohexylpropyl)-4,5-dihydro-1,2,4-oxadiazol-5-one |
| 180 | 3-[(2-chloro-6-fluorophenyl)methyl]-4-[3-(piperidin-1-yl)propyl]-4,5-dihydro-1,2,4-oxadiazol-5-one |
| 181 | 3-[(2-chloro-6-fluorophenyl)methyl]-4-[2-(4,4-difluoropiperidin-1-yl)ethyl]-4,5-dihydro-1,2,4-oxadiazol-5-one |
| 182 | 3-[(2-chloro-6-fluorophenyl)methyl]-4-[3-(4,4-difluoropiperidin-1-yl)propyl]-4,5-dihydro-1,2,4-oxadiazol-5-one |
| 183 | 3-[(2-chloro-6-fluorophenyl)methyl]-4-(cyclopent-3-en-1-ylmethyl)-4,5-dihydro-1,2,4-oxadiazol-5-one |
| 184 | 3-[(2-chloro-6-fluorophenyl)methyl]-4-{[4-(trifluoromethyl)cyclohexyl]methyl}-1,2,4-oxadiazol-5(4H)-one |
| 185 | 3-[(2-chloro-6-fluorophenyl)methyl]-4-[(4-fluorocyclohexyl)methyl]-4,5-dihydro-1,2,4-oxadiazol-5-one |
| 186 | 3-(diethoxymethyl)-4-[(4-fluorophenyl)methyl]-4,5-dihydro-1,2,4-oxadiazol-5-one |
| 187 | 4-[(2-chloro-6-fluorophenyl)methyl]-3-(diethoxymethyl)-4,5-dihydro-1,2,4-oxadiazol-5-one |
| 188 | 3-[(4,4-difluorocyclohexyl)methyl]-4-(1-phenylethyl)-4,5-dihydro-1,2,4-oxadiazol-5-one |
| 189 | 3-[(4,4-difluorocyclohexyl)methyl]-4-{[6-(trifluoromethyl)pyridin-3-yl]methyl}-4,5-dihydro-1,2,4-oxadiazol-5-one |

| Ex. | IUPAC Name |
|---|---|
| 190 | 3-[(4,4-difluorocyclohexyl)methyl]-4-[(5-fluoropyrimidin-2-yl)methyl]-4,5-dihydro-1,2,4-oxadiazol-5-one |
| 191 | 3-[(4,4-difluorocyclohexyl)methyl]-4-(1,3-thiazol-2-ylmethyl)-4,5-dihydro-1,2,4-oxadiazol-5-one |
| 192 | 3-[(4,4-difluorocyclohexyl)methyl]-4-{[2-methyl-6-(trifluoromethyl)-pyridin-3-yl]methyl}-4,5-dihydro-1,2,4-oxadiazol-5-one |
| 193 | 3-[(4,4-difluorocyclohexyl)methyl]-4-[(1,3-thiazol-5-yl)methyl]-1,2,4-oxadiazol-5(4H)-one |
| 194 | 3-[(4,4-difluorocyclohexyl)methyl]-4-[(1,3-oxazol-2-yl)methyl]-1,2,4-oxadiazol-5(4H)-one |
| 195 | 3-[(4,4-difluorocyclohexyl)methyl]-4-[(1,3-dimethyl-1H-pyrazol-5-yl)methyl]-1,2,4-oxadiazol-5(4H)-one |
| 196 | 3-[(4,4-difluorocyclohexyl)methyl]-4-[(5-methyl-1,2,4-oxadiazol-3-yl)methyl]-1,2,4-oxadiazol-5(4H)-one |
| 197 | 3-[(4,4-difluorocyclohexyl)methyl]-4-[(3-methyl-1,2,4-oxadiazol-5-yl)methyl]-1,2,4-oxadiazol-5(4H)-one |
| 198 | 3-[(4,4-difluorocyclohexyl)methyl]-4-{[3-(trifluoromethyl)-1H-pyrazol-1-yl]methyl}-1,2,4-oxadiazol-5(4H)-one |
| 199 | 3-[(4,4-difluorocyclohexyl)methyl]-4-[(1,2-oxazol-5-yl)methyl]-1,2,4-oxadiazol-5(4H)-one |
| 200 | 3-[(4,4-difluorocyclohexyl)methyl]-4-[(4-methyl-1,3-thiazol-5-yl)methyl]-1,2,4-oxadiazol-5(4H)-one |
| 201 | 3-[(4,4-difluorocyclohexyl)methyl]-4-[(1-methyl-1H-imidazol-2-yl)methyl]-4,5-dihydro-1,2,4-oxadiazol-5-one |
| 202 | 3-[(4,4-difluorocyclohexyl)methyl]-4-[(4-fluorophenyl)methyl]-4,5-dihydro-1,2,4-thiadiazol-5-one |
| 203 | 4-[(2-chloro-6-fluorophenyl)methyl]-3-[(4,4-difluorocyclohexyl)methyl]-4,5-dihydro-1,2,4-thiadiazol-5-one |
| 204 | 3-[(3,3-difluorocyclopentyl)methyl]-4-[(4-fluorophenyl)methyl]-4,5-dihydro-1,2,4-oxadiazol-5-one |
| 205 | 4-[(2-chloro-6-fluorophenyl)methyl]-3-[(3,3-difluorocyclopentyl)methyl]-4,5-dihydro-1,2,4-oxadiazol-5-one |
| 206 | 4-(cyclohexylmethyl)-3-[(3,3-difluorocyclopentyl)methyl]-4,5-dihydro-1,2,4-oxadiazol-5-one |
| 207 | 4-[(4,4-difluorocyclohexyl)methyl]-3-[(3,3-difluorocyclopentyl)methyl]-4,5-dihydro-1,2,4-oxadiazol-5-one |
| 208 | 3-[(dimethyl-1,2-oxazol-4-yl)methyl]-4-[(4-fluorophenyl)methyl]-4,5-dihydro-1,2,4-oxadiazol-5-one |
| 209 | 4-[(2-chloro-6-fluorophenyl)methyl]-3-[(dimethyl-1,2-oxazol-4-yl)methyl]-4,5-dihydro-1,2,4-oxadiazol-5-one |
| 210 | 4-(cyclohexylmethyl)-3-[(dimethyl-1,2-oxazol-4-yl)methyl]-4,5-dihydro-1,2,4-oxadiazol-5-one |
| 211 | 4-[(4,4-difluorocyclohexyl)methyl]-3-[(dimethyl-1,2-oxazol-4-yl)methyl]-4,5-dihydro-1,2,4-oxadiazol-5-one |
| 212 | 4-[(4-fluorophenyl)methyl]-3-[(trimethyl-1H-pyrazol-4-yl)methyl]-4,5-dihydro-1,2,4-oxadiazol-5-one |
| 213 | 4-[(2-chloro-6-fluorophenyl)methyl]-3-[(trimethyl-1H-pyrazol-4-yl)methyl]-4,5-dihydro-1,2,4-oxadiazol-5-one |
| 214 | 4-(cyclohexylmethyl)-3-[(trimethyl-1H-pyrazol-4-yl)methyl]-4,5-dihydro-1,2,4-oxadiazol-5-one |
| 215 | 4-[(4,4-difluorocyclohexyl)methyl]-3-[(trimethyl-1H-pyrazol-4-yl)methyl]-4,5-dihydro-1,2,4-oxadiazol-5-one |
| 216 | 4-[(4-fluorophenyl)methyl]-3-[(2-methylpyridin-3-yl)methyl]-4,5-dihydro-1,2,4-oxadiazol-5-one |
| 217 | 4-[(2-chloro-6-fluorophenyl)methyl]-3-[(2-methylpyridin-3-yl)methyl]-4,5-dihydro-1,2,4-oxadiazol-5-one |
| 218 | 4-(cyclohexylmethyl)-3-[(2-methylpyridin-3-yl)methyl]-4,5-dihydro-1,2,4-oxadiazol-5-one |
| 219 | 4-[(4,4-difluorocyclohexyl)methyl]-3-[(2-methylpyridin-3-yl)methyl]-4,5-dihydro-1,2,4-oxadiazol-5-one |
| 220 | 4-[(2-chloro-6-fluorophenyl)methyl]-3-[(4,4-difluoropiperidin-1-yl)methyl]-4,5-dihydro-1,2,4-oxadiazol-5-one |
| 221 | 3-[(4,4-difluoropiperidin-1-yl)methyl]-4-[(4-fluorophenyl)methyl]-4,5-dihydro-1,2,4-oxadiazol-5-one |
| 222 | 4-(cyclohexylmethyl)-3-[(4,4-difluoropiperidin-1-yl)methyl]-4,5-dihydro-1,2,4-oxadiazol-5-one |
| 223 | 4-[(4,4-difluorocyclohexyl)methyl]-3-[(4,4-difluoropiperidin-1-yl)methyl]-4,5-dihydro-1,2,4-oxadiazol-5-one |
| 224 | 4-[(2-chloro-6-fluorophenyl)methyl]-3-[(3,3-difluoropiperidin-1-yl)methyl]-4,5-dihydro-1,2,4-oxadiazol-5-one |
| 225 | 3-[(3,3-difluoropiperidin-1-yl)methyl]-4-[(4-fluorophenyl)methyl]-4,5-dihydro-1,2,4-oxadiazol-5-one |
| 226 | 4-[(2-chloro-6-fluorophenyl)methyl]-3-[(4,4-difluoro-2-methylpiperidin-1-yl)methyl]-4,5-dihydro-1,2,4-oxadiazol-5-one |
| 227 | 3-[(4,4-difluoro-2-methylpiperidin-1-yl)methyl]-4-[(4-fluorophenyl)methyl]-4,5-dihydro-1,2,4-oxadiazol-5-one |

| Ex. | IUPAC Name |
|---|---|
| 228 | 3-(3,4-dihydro-2H-1,4-benzoxazin-4-ylmethyl)-4-[(4-fluorophenyl)methyl]-4,5-dihydro-1,2,4-oxadiazol-5-one |
| 229 | 4-[(2-chloro-6-fluorophenyl)methyl]-3-(3,4-dihydro-2H-1,4-benzoxazin-4-ylmethyl)-4,5-dihydro-1,2,4-oxadiazol-5-one |
| 230 | 4-(cyclohexylmethyl)-3-(3,4-dihydro-2H-1,4-benzoxazin-4-ylmethyl)-4,5-dihydro-1,2,4-oxadiazol-5-one |
| 231 | 4-[(4,4-difluorocyclohexyl)methyl]-3-(3,4-dihydro-2H-1,4-benzoxazin-4-ylmethyl)-4,5-dihydro-1,2,4-oxadiazol-5-one |
| 232 | 4-[(4-fluorophenyl)methyl]-3-{4H,5H,6H,7H-thieno[3,2-c]pyridin-5-ylmethyl}-4,5-dihydro-1,2,4-oxadiazol-5-one |
| 233 | 4-[(2-chloro-6-fluorophenyl)methyl]-3-{4H,5H,6H,7H-thieno[3,2-c]pyridin-5-ylmethyl}-4,5-dihydro-1,2,4-oxadiazol-5-one |
| 234 | 4-(cyclohexylmethyl)-3-{4H,5H,6H,7H-thieno[3,2-c]pyridin-5-ylmethyl}-4,5-dihydro-1,2,4-oxadiazol-5-one |
| 235 | 4-[(4,4-difluorocyclohexyl)methyl]-3-{4H,5H,6H,7H-thieno[3,2-c]pyridin-5-ylmethyl}-4,5-dihydro-1,2,4-oxadiazol-5-one |
| 236 | 4-[(4-fluorophenyl)methyl]-3-[(4-phenylpiperazin-1-yl)methyl]-4,5-dihydro-1,2,4-oxadiazol-5-one |
| 237 | 4-[(2-chloro-6-fluorophenyl)methyl]-3-[(4-phenylpiperazin-1-yl)methyl]-4,5-dihydro-1,2,4-oxadiazol-5-one |
| 238 | 4-(cyclohexylmethyl)-3-[(4-phenylpiperazin-1-yl)methyl]-4,5-dihydro-1,2,4-oxadiazol-5-one |
| 239 | 4-[(4,4-difluorocyclohexyl)methyl]-3-[(4-phenylpiperazin-1-yl)methyl]-4,5-dihydro-1,2,4-oxadiazol-5-one |
| 240 | 4-[(4-fluorophenyl)methyl]-3-(piperidin-1-ylmethyl)-4,5-dihydro-1,2,4-oxadiazol-5-one |
| 241 | 4-[(2-chloro-6-fluorophenyl)methyl]-3-[(piperidin-1-yl)methyl]-1,2,4-oxadiazol-5(4H)-one |
| 242 | 4-[(2-chloro-6-fluorophenyl)methyl]-3-{[3-(4-methylphenyl)-piperidin-1-yl]methyl}-4,5-dihydro-1,2,4-oxadiazol-5-one |
| 243 | 4-[(4-fluorophenyl)methyl]-3-{[3-(4-methylphenyl)piperidin-1-yl]methyl}-4,5-dihydro-1,2,4-oxadiazol-5-one |
| 244 | 4-[(2-chloro-6-fluorophenyl)methyl]-3-(1,2,3,4-tetrahydroisoquinolin-2-ylmethyl)-4,5-dihydro-1,2,4-oxadiazol-5-one |
| 245 | 4-[(4,4-difluorocyclohexyl)methyl]-3-(1,2,3,4-tetrahydroisoquinolin-2-ylmethyl)-4,5-dihydro-1,2,4-oxadiazol-5-one |
| 246 | 4-[(2-chloro-6-fluorophenyl)methyl]-3-(pyrrolidin-1-ylmethyl)-4,5-dihydro-1,2,4-oxadiazol-5-one |
| 247 | 4-(4-fluorobenzyl)-3-[(4-methyl-1,3-thiazol-5-yl)methyl]-1,2,4-oxadiazol-5(4H)-one |
| 248 | 4-(2-chloro-6-fluorobenzyl)-3-[(4-methyl-1,3-thiazol-5-yl)methyl]-1,2,4-oxadiazol-5(4H)-one |
| 249 | 4-(cyclohexylmethyl)-3-[(4-methyl-1,3-thiazol-5-yl)methyl]-1,2,4-oxadiazol-5(4H)-one |
| 250 | 4-[(4,4-difluorocyclohexyl)methyl]-3-[(4-methyl-1,3-thiazol-5-yl)methyl]-1,2,4-oxadiazol-5(4H)-one |
| 251 | 4-[(3,3-difluorocyclopentyl)methyl]-3-[(4-methyl-1,3-thiazol-5-yl)methyl]-1,2,4-oxadiazol-5(4H)-one |

Compounds of formula (I) can generally be prepared by reacting a compound of formula (II):

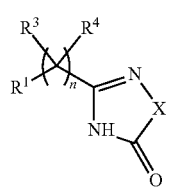

(II)

wherein the meanings of n, X and $R^1$, $R^3$, and $R^4$ are as defined above, with a compound of formula (III):

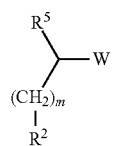

(III)

wherein the meanings of $R^2$, $R^5$ and m are as defined above; and W is a suitable leaving group; and optionally converting the obtained compound of formula (I) into an addition salt thereof, and/or preparing stereochemically isomeric forms thereof.

The reaction of a compound of formula (II) with a compound of formula (III), may be carried out in a at least one reaction-inert solvent and optionally in the presence of at least one suitable coupling reagent and/or a suitable base thereof.

W in the compound of Formula (III) is an appropriate leaving group such as, for example, halo, e.g. chloro, bromo, or in some instances W may also be an alcohol and the like reactive leaving groups. The reaction of a compound of formula (II) with a compound of formula (III), may be performed in a reaction-inert solvent such as, for example, acetonitrile, dimethyl acetamide, THF or DMF, and optionally in the presence of a suitable base such as, for example, sodium carbonate, potassium carbonate or sodium methoxide. Stirring may enhance the rate of the reaction. The reaction may conveniently be carried out at a temperature ranging between room temperature and the reflux temperature of the reaction mixture.

Compounds of formula (III) are known in the art.

Compounds of formula (II) can be prepared according to the following scheme:

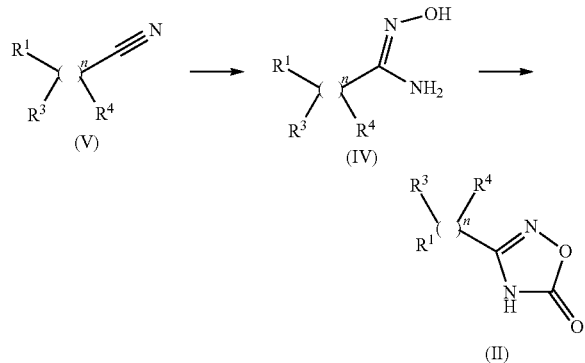

(II)

Compounds of formula (II), wherein n, $R^1$, $R^3$, and $R^4$ are as defined in formula (I), can be obtained by cyclization of the respective N'-hydroxyethanimidamide derivatives (IV).

The reaction is performed in a suitable solvent, such as 1,4-dioxane, in the presence of CDI, as a cyclization agent, and DBU, as base, preferably at a temperature of 105° C.

Compounds of formula (IV), wherein n, $R^1$, $R^3$, and $R^4$ are as defined in formula (I), can be prepared from opportune nitrile derivative (V) by reaction with hydroxylamine hydrochloride, in presence of $K_2CO_3$, as the base; using EtOH such as solvent, preferably at temperatures between rt and reflux.

The nitrile derivative (V), the starting materials and some of the intermediates are known compounds and are commercially available or may be prepared according to conventional reaction procedures generally known in the art.

Compounds of formula (IIa) can be also prepared according to the following scheme:

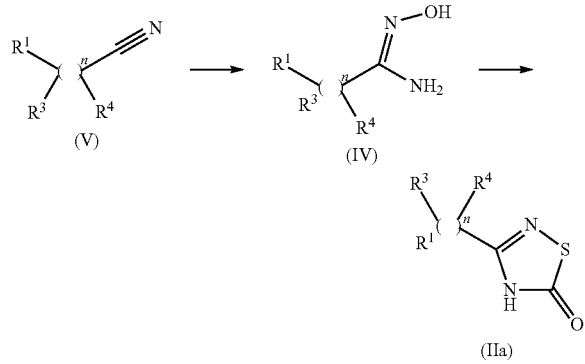

(IIa)

Compounds of formula (IIa), wherein n, $R^1$, $R^3$, and $R^4$ are as defined in formula (I), can be obtained by cyclization of the respective N'-hydroxyethanimidamide (IV).

The reaction is performed in a suitable solvent, such as THF, using 1,1'-Thiocarbonyldiimidazole, in the presence of Boron trifluoride diethyl etherate, as Lewis Acid, preferably at room temperature.

Compounds of formula (IV), wherein n, $R^1$, $R^3$, and $R^4$ are as defined in formula (I), can be prepared from opportune nitrile derivative (V) by reaction with hydroxylamine hydrochloride, in presence of $K_2CO_3$, as the base; using EtOH such as solvent, preferably at temperatures between rt and reflux.

The nitrile derivative (V), the starting materials and some of the intermediates are known compounds and are commercially available or may be prepared according to conventional reaction procedures generally known in the art.

The said process further optionally comprising asymmetric reaction using chiral auxiliaries based synthesis (using carbohydrate, chiral amine or cyclic ketimine) and/or catalytic asymmetric Strecker synthesis (using guanidine, chiral Schiff base or BINOL-based catalyst).

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (1) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable salts and stereoisomeric forms thereof possess P2X7 receptor antagonizing properties as demonstrated in the Pharmacological Examples. Other examples of art-known group transformation reactions to convert compounds of formula (I) into other compounds of formula (I) are hydrolysis of carboxylic esters to the corresponding carboxylic acid or alcohol; hydrolysis of amides to the corresponding carboxylic acids or amines; alcohols may be converted into esters and ethers; primary amines may be converted into secondary or tertiary amines; double bonds may be hydrogenated to the corresponding single bond. The starting materials and some of the intermediates are known compounds and are commercially available or may be prepared according to conventional reaction procedures generally known in the art. The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials. In the preparation of the compounds of formula I and the starting materials and/or intermediates described herein it may be useful to protect certain groups which are sensitive to the reaction conditions. The evaluation of the usefulness of the optional protection, as well as the selection of the suitable protecting agent, according to the reaction carried out in the preparation of the compounds of the invention and the functional group to be protected, are within the common knowledge of the skilled person. The removal of the optional protective groups is carried out according to conventional techniques. For a general reference to the use of protective groups in organic chemistry, see Theodora W. Greene and Peter G. M. Wuts "Protective groups in organic synthesis", John Wiley & Sons, Inc., II Ed., 1991.

The preparation of the salts of the compounds of formula I is carried out according to known methods. Therefore the present compounds of formula (I) are useful as a medicine especially in the treatment of a condition or disease mediated by the P2X7 receptor, in particular P2X7 receptor antagonistic activity. Subsequently the present compounds may be used for the manufacture of a medicine for treatment of a condition or a disease mediated by P2X7 receptor activity, in particular P2X7 receptor antagonistic activity.

The present invention also provides the use of a compound of formula (I) or a pharmaceutically acceptable salt thereof for the manufacture of a medicament for the treatment of conditions or diseases selected from P2X7 receptor mediated conditions or diseases. In an embodiment, the present invention provides a compound of formula (I) for use as a medicine or for use in the treatment of conditions or diseases selected from P2X7 receptor mediated conditions or diseases. Further, the present invention also provides a method of treatment of a condition mediated by P2X7 receptor activity, in a mammalian subject, which method comprises administering to a mammal in need of such treatment a therapeutically effective amount of a compound of formula (I) or a pharmaceutically acceptable salt thereof. In view of the above described mechanisms of action, the compounds of the invention are useful for the treatment of neurodegenerative disorders of various origins such as Alzheimer's Disease and other dementia conditions such as Lewys body, fronto-temporal dementia and taupathies; amyotrophic lateral sclerosis, Multiple Sclerosis, Parkinson's Disease and other parkinsonian syndromes; HIV-induced neuroinflammation; essential tremors; other spino cerebellar degenerations and Charcot-Marie-Toot neuropathy. The compounds of the invention are also useful for the treatment of neurological conditions such as epilepsy including simple partial seizure, complex partial seizure, secondary generalized seizure, further including absence seizure, myoclonic seizure, clonic seizure, tonic seizure, tonic clonic seizure and atonic seizure.

The compounds of the invention are also useful for the treatment of cognitive disorders and of psychiatric disorders. Psychiatric disorders include, and are not limited to major depression, dysthymia, mania, bipolar disorder (such as bipolar disorder type I, bipolar disorder type II), cyclothymic disorder, rapid cycling, ultradian cycling, mania, hypomania, schizophrenia, schizophreniform disorders, schizoaffective disorders, personality disorders, attention disorders with or without hyperactive behaviour, delusional disorders, brief psychotic disorders, shared psychotic disorders, psychotic disorder due to a general medical condition, substance-induced psychotic disorders or a psychotic disorder not otherwise specified, anxiety disorders such as generalised anxiety disorder, panic disorders, post-traumatic stress disorder, impulse control disorders, phobic disorders, dissociative states and moreover in smoke, drug addiction and alcoholism. In particular bipolar disorders, psychosis, anxiety and addiction.

The compounds of the present invention are useful in the prevention or treatment of neuropathic pain. Neuropathic pain syndromes include, and are not limited to: diabetic neuropathy; sciatica; non-specific lower back pain; multiple sclerosis pain; fibromyalgia; HIV-related neuropathy; neuralgia, such as post-herpetic neuralgia and trigeminal neuralgia, Morton's neuralgia, causalgia; and pain resulting from physical trauma, amputation, phantom limb, cancer, toxins or chronic inflammatory conditions; central pain such as the one observed in thalamic syndromes, mixed central and peripheral forms of pain such as complex regional pain syndromes (CRPS) also called reflex sympathetic dystrophies.

The compounds of the invention are also useful for the treatment of chronic pain. Chronic pain includes, and is not limited to, chronic pain caused by inflammation or an inflammatory-related condition, ostheoarthritis, rheumatoid arthritis, acute injury or trauma, upper back pain or lower back pain (resulting from systematic, regional or primary spine disease such as radiculopathy), bone pain (due to osteoarthritis, osteoporosis, bone metastasis or unknown reasons), pelvic pain, spinal cord injury-associated pain, cardiac chest pain, non-cardiac chest pain, central post-stroke pain, myofascial pain, sickle cell pain, cancer pain, Fabry's disease, AIDS pain, geriatric pain or pain caused by headache, temporomandibular joint syndrome, gout, fibrosis or thoracic outlet syndromes, in particular rheumatoid arthritis and osteoarthritis.

The compounds of the invention are also useful in the treatment of acute pain caused by acute injury, illness, sport-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea, endometriosis or surgery (such as open heart or bypass surgery), post-operative pain, kidney stone pain, gallbladder pain, gallstone pain, obstetric pain or dental pain.

The compounds of the invention are also useful in the treatment of headaches such as migraine, tension type headache, transformed migraine or evolutive headache, cluster headache, as well as secondary headache disorders, such as the ones derived from infections, metabolic disorders or other systemic illnesses and other acute headaches, paroxysmal hemicrania and the like, resulting from a worsening of the above mentioned primary and secondary headaches.

Compounds of the invention are also useful in the treatment of diseases such as vertigo, tinnitus, muscle spasm, and other disorders including and not limited to cardiovascular diseases (such as cardiac arrhythmia, cardiac infarction or angina pectoris, hypertension, cardiac ischemia, cerebral ischemia) endocrine disorders (such as acromegaly or diabetes insipidus) diseases in which the pathophysiology of the disorder involves excessive or hypersecretory or otherwise inappropriate cellular secretion of an endogenous substance (such as catecholamine, a hormone or a growth factor).

The compounds of the invention are also useful in the selective treatment of liver disease, such as inflammatory liver diseases, for example chronic viral hepatitis B, chronic viral hepatitis C, alcoholic liver injury, primary biliary cirrhosis, autoimmune hepatitis, liver fibrosis, non-alcoholic steatohepatitis and liver transplant rejection.

The compounds of the invention inhibit inflammatory processes affecting all body systems. Therefore are useful in the treatment of inflammatory processes of the muscular-skeletal system of which the following is a list of examples but it is not comprehensive of all target disorders: arthritic conditions such as ankylosing spondylitis, cervical arthritis, fibromyalgia, gout, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrinological systems: periarthritis nodosa, thyroiditis, aplastic anaemia, scleroderma, myasthenia gravis, multiple sclerosis and other demyelinating disorders, encephalomyelitis, sarcoidosis, nephritic syndrome, Bechet's syndrome, polymyositis, gingivitis.

Compounds of the invention are also useful in the treatment of gastrointestinal (GI) tract disorders such as inflammatory bowel disorders including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varialoforme, ulcerative colitis, peptic ulceration, pyrosis, and other damage to the GI tract, for example, by *Helicobacter pylori*, gastroesophageal reflux disease, gastroparesis, such as diabetic gastroparesis; and other functional bowel disorders, such as non-ulcerative dyspepsia (NUD); emesis, diarrhoea, and visceral inflammation.

Compounds of the invention are also useful in the treatment of disorders of the genito-urinary tract such as overactive bladder, prostatitis (chronic bacterial and chronic non-bacterial prostatitis), prostadynia, interstitial cystitis, urinary incontinence and benign prostatic hyperplasia, annexities, pelvic inflammation, bartholinities and vaginitis. In particular, overactive bladder and urinary incontinence.

The compounds of the invention are also useful in the treatment of ophthalmic diseases such as retinitis, retinopathies, uveitis and acute injury to the eye tissue, age-related macular degeneration or glaucoma, conjunctivitis.

The compounds of the invention are also useful in the treatment of eating disorders such as anorexia nervosa including the subtypes restricting type and binge-eating/purging type; bulimia nervosa including the subtypes purging type and non-purging type; obesity; compulsive eating disorders; binge eating disorder; and eating disorder not otherwise specified.

The compounds of the invention are also useful in the treatment of allergic dermatitis, hyper-responsiveness of the airway, chronic obstructive pulmonary disease (COPD), bronchitis, septic shock, Sjögren's syndrome, glomerulonephritis, atherosclerosis, growth and metastases of malignant cells, myoblastic leukaemia, diabetes, meningitis, osteoporosis, burn injury, ischaemic heart disease, stroke, peripheral vascular disease, varicose veins, glaucoma.

The term "treating" and "treatment", as used herein, refers to curative, palliative and prophylactic treatment, including reversing, alleviating, inhibiting the progress of, or preventing the disease, disorder or condition to which such term applies, or one or more symptoms of such disease, disorder or condition.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the CASe of oral liquid preparations such as suspensions, syrups, elixirs and solutions; or solid pharmaceutical carriers such as starches, sugars, kaolin, lubricants, binders, disintegrating agents and the like in the CASe of powders, pills, capsules and tablets. Because of their easy administration, tablets and capsules represent the most advantageous oral dosage unit form, in which CASe solid pharmaceutical carriers are obviously employed. For parenteral injection compositions, the pharmaceutical carrier will mainly comprise sterile water, although other ingredients may be included in order to improve solubility of the active ingredient.

Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (1), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage.

"Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium lauryl sulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the CASe of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume). The pharmaceutically acceptable flavours which can mask the bitter tasting ingredients in the low-dosage formulations comprise preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of diseases linked to the mediation of the ligand-gated ion channels will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

As used herein, a "therapeutically effective amount" of a compound, is the quantity of a compound which, when administered to an individual or animal, results in a sufficiently high level of that compound in the individual or animal to cause a discernible P2X7 receptor antagonistic response.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

Nomenclature and Structures

In general, the nomenclature used in this Application is based on ChemSketch™ (ACDLabs) and generated according to the IUPAC systematic nomenclature. Chemical structures shown herein were prepared using ISIS® version 2.2. Any open valency appearing on a carbon, oxygen, sulfur, or nitrogen atom in the structures herein indicates the presence of a hydrogen atom unless indicated otherwise. Where a nitrogen-containing heteroaryl ring is shown with an open valency on a nitrogen atom and variables such as $R^1$, $R^2$, $R^3$ etc. are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structure herein are intended to encompass all naturally occurring isotopes of such atoms. Thus, for example, the hydrogen atoms represented herein are meant to include deuterium and tritium, and the carbon atoms are meant to include $^{13}C$ and $^{14}C$ isotopes.

Abbreviations

Abbreviations which may be used in the description of the Schemes and the Examples that follows are:

CC: Column Chromatography; DCM: Dichloromethane; DEAD: Diethylazodicarboxylate; DMF: Dimethylformamide; EP: petroleum ether; EtOAc: Ethyl acetate; EtOH: Ethanol; hrs: hours; MeCN: Acetonitrile; min: Minute(s); N: Normal; NMR: Nuclear Magnetic Resonance; $PPh_3$: Triphenylphospine; $PPh_3O$: Triphenylphospine oxide; r.t.: Room Temperature; THF: Tetrahydrofuran; LC-MS: Liquid Chromatography-Mass Spectrometry; $K_2CO_3$: potassium carbonate; $Na_2SO_4$: sodium sulphate; HPLC: High-performance liquid chromatography; o.n.: overnight; $CH_3ONa$: sodium methoxide; NaCl: sodium chloride; CDI: 1,1'-Carbonyldiimidazole; DBU: 1,5-diazabiciclo(5.4.0)undec-5-ene; HCl: Hydrochloric acid; Y: yield

EXPERIMENTAL PART

The following examples illustrate the present invention. Unless explicitly stated otherwise, all particulars (especially percentages and amounts) relate to the weight.

A Synthesis of the Intermediates

Most substituted nitrile derivatives used, as starting materials, were purchased from chemical providers:

| Structure of nitrile derivatives | CAS number |
|---|---|
| | 459-22-3 |
| | 501-00-8 |
| | 326-62-5 |
| | 19924-43-7 |
| | 104-47-2 |
| | 2856-63-5 |
| | 75279-55-9 |
| | 149489-22-5 |
| | 1260829-70-6 |
| | 3218-45-9 |
| | 656-35-9 |
| | 22902-81-4 |
| | 6306-60-1 |
| | 75279-56-0 |
| | 140-29-4 |
| | 2739-97-1 |
| | 6443-85-2 |
| | 13121-99-8 |

| Structure of nitrile derivatives | CAS number |
|---|---|
| (2-(trifluoromethyl)phenyl)acetonitrile | 3038-47-9 |
| cyclohexylacetonitrile | 4435-14-7 |
| 2-(4,4-difluorocyclohexyl)acetonitrile | 959600-88-5 |
| 3-(2-chloro-6-fluorophenyl)propanenitrile | 1057676-61-5 |
| 2-(2-methylpyridin-3-yl)acetonitrile | 101166-73-8 |
| 2-(4,4-difluoropiperidin-1-yl)acetonitrile | 824413-96-9 |
| 2-(3,3-difluoropiperidin-1-yl)acetonitrile | 1893257-09-7 |
| 2-(piperidin-1-yl)acetonitrile | 3010-03-5 |
| 2-(3,4-dihydroisoquinolin-2(1H)-yl)acetonitrile | 91349-97-2 |
| 2-(6,7-dihydrothieno[3,2-c]pyridin-5(4H)-yl)acetonitrile | 1016871-73-0 |
| 2-(2H-benzo[b][1,4]oxazin-4(3H)-yl)acetonitrile | 308851-73-2 |

| Structure of nitrile derivatives | CAS number |
|---|---|
| 2-(4-phenylpiperazin-1-yl)acetonitrile | 65884-01-7 |
| 2-(3,3-difluoropyrrolidin-1-yl)acetonitrile | 1701764-04-6 |
| 2-(pyrrolidin-1-yl)acetonitrile | 29134-29-0 |
| 2-(4-methylthiazol-5-yl)acetonitrile | 50382-33-7 |
| 2-(3,5-dimethylisoxazol-4-yl)acetonitrile | 35166-42-8 |
| 2-(1,3,5-trimethyl-1H-pyrazol-4-yl)acetonitrile | 113619-01-5 |
| 3,3-diethoxypropanenitrile | 6136-93-2 |

Some nitrile derivatives used, as starting materials, were synthesised according to this general procedure:

$K_2CO_3$ (1.5 eq) was added to a solution of opportune amine (1.0 eq) and Bromoacetonitrile (1.1 eq) in ACN (10 mL) and the mixture was stirred on at rt. Then, precipitated salts were filtered off and the filtrate was evaporated under reduced pressure. The residue was purified by flash chromatography (DCM/AcOEt 1:1 v/v) giving pure nitrile derivatives. (y=61-97%).

Using this procedure, intermediates 0a (y=64%), 0b (y=70%) were prepared starting from the corresponding, commercially available starting materials.

| Intermediate | Structure |
|---|---|
| 0a | 2-(4,4-difluoro-2-methylpiperidin-1-yl)acetonitrile |

| Intermediate | Structure |
|---|---|
| 0b | 3-(p-tolyl)piperidin-1-yl acetonitrile |

Preparation of N'-hydroxyethanimidamide Derivatives (IV) (Typical Procedure)

Hydroxylamine hydrochloride (2.5 eq) and $K_2CO_3$ (2.5 eq) were dissolved in EtOH (20-40 mL) and the mixture was stirred for 30 min at r.t.; then a suitable nitrile derivative (1.0 eq) (V) was added and the reaction mixture was heated at reflux for 12 hrs. The precipitated solid was filtered off and the filtrate was condensed under reduced pressure. The residue was purified by CC (DCM/EtOAc 1:1 v/v) giving the pure N'-hydroxyethanimidamide. (y=35-97%)

Using this procedure, intermediates 1a (y=64%), 1b (y=70%), 1c (y=72%), 1d (y=80%), 1e (y=55%), 1f (y=82%), 1g (y=79%), 1h (y=72%), 1i (y=46%), 1j (y=68%), 1k (y=69%), 1l (y=82%), 1m (y=96%), 1n (y=71%), 1o (y=79%), 1p (y=94%), 1q (y=95%), 1r (y=72%), 1s (y=97%), 1u (y=71%), 1v (y=47%), 1w (y=76%), 1x (y=92%), 1y (y=56%), 1z (y=91%), 1aa (y=76%), 1bb (y=90%), 1cc (y=79%), 1dd (y=72%), 1ee (y=87%), 1ff (y=85%), 1gg (y=61%), 1hh (y=69%), 1ii (y=66%), 1jj (y=88%), 1kk (y=95%), 1ll (y=90%), 1mm (y=84%), were prepared starting from the corresponding, commercially available nitrile derivative.

| Intermediate | Structure |
|---|---|
| 1a | 4-F-phenyl N'-hydroxyethanimidamide |
| 1b | 3-F-phenyl N'-hydroxyethanimidamide |
| 1c | 2-F-phenyl N'-hydroxyethanimidamide |
| 1d | 3-MeO-phenyl N'-hydroxyethanimidamide |
| 1e | 4-MeO-phenyl N'-hydroxyethanimidamide |
| 1f | 2-Cl-phenyl N'-hydroxyethanimidamide |
| 1g | 2-Cl-6-F-phenyl N'-hydroxyethanimidamide |
| 1h | 2-Cl-6-F-phenyl α,α-dimethyl N'-hydroxyethanimidamide |
| 1i | 2-Cl-6-F-phenyl α-methyl N'-hydroxyethanimidamide |
| 1j | 2,3-diCl-phenyl N'-hydroxyethanimidamide |
| 1k | 2,4-diF-phenyl N'-hydroxyethanimidamide |
| 1l | 2-Cl-3-CF3-phenyl N'-hydroxyethanimidamide |
| 1m | 2,4-diCl-phenyl N'-hydroxyethanimidamide |
| 1n | 2-Cl-4-F-phenyl N'-hydroxyethanimidamide |
| 1o | phenyl N'-hydroxyethanimidamide |

-continued

| Intermediate | Structure |
|---|---|
| 1p | (pyridin-2-yl)acetamide oxime |
| 1q | (pyridin-3-yl)acetamide oxime |
| 1r | (pyridin-4-yl)acetamide oxime |
| 1s | 2-(2-(trifluoromethyl)phenyl)acetamide oxime |
| 1u | 2-cyclohexylacetamide oxime |
| 1v | 2-(4,4-difluorocyclohexyl)acetamide oxime |
| 1w | 3-(2-chloro-6-fluorophenyl)propanamide oxime |
| 1x | 2-(2-methylpyridin-3-yl)acetamide oxime |
| 1y | 2-(4,4-difluoropiperidin-1-yl)acetamide oxime |
| 1z | 2-(3,3-difluoropiperidin-1-yl)acetamide oxime |
| 1aa | 2-(piperidin-1-yl)acetamide oxime |

-continued

| Intermediate | Structure |
|---|---|
| 1bb | 2-(3,4-dihydroisoquinolin-2(1H)-yl)acetamide oxime |
| 1cc | 2-(4,4-difluoro-2-methylpiperidin-1-yl)acetamide oxime |
| 1dd | 2-(6,7-dihydrothieno[3,2-c]pyridin-5(4H)-yl)acetamide oxime |
| 1ee | 2-(3-(p-tolyl)piperidin-1-yl)acetamide oxime |
| 1ff | 2-(pyrrolidin-1-yl)acetamide oxime |
| 1gg | 2-(3,3-difluorocyclopentyl)acetamide oxime |
| 1hh | 2-(2H-benzo[b][1,4]oxazin-4(3H)-yl)acetamide oxime |
| 1ii | 2-(4-phenylpiperazin-1-yl)acetamide oxime |
| 1jj | 2-(4-methylthiazol-5-yl)acetamide oxime |
| 1kk | 2,2-diethoxyacetamide oxime |

-continued

| Intermediate | Structure |
|---|---|
| 1ll | 3-methyl-5-methyl-isoxazole with -CH2-C(=N-OH)-NH2 group |
| 1mm | 1,3,5-trimethyl-pyrazole with -CH2-C(=N-OH)-NH2 group |

Preparation of 1,2,4-oxadiazol-5(4H)-one (II)
(Typical Procedure)

To a solution of a suitable intermediate IV (1.0 eq) in 1,4-dioxane (10-30 mL) CDI (1.5 eq) and DBU (1.1 eq) were added at r.t., and the mixture was stirred for 3 hrs at 105° C. After cooling, the mixture was diluted with water, washed with EtOAc, adjusted to pH 2 with 3N HCl and extracted with EtOAc. The EtOAc extracts were washed with brine, dried over $Na_2SO_4$ and concentrated in vacuo. The crude residue was purified by CC (Hexane/EtOAc 1:1 v/V) yielding the pure 1,2,4-oxadiazol-5(4H)-one. (y=20-98%)

Using this procedure:
intermediate 2a (y=87%) was prepared starting from 1a;
intermediate 2b (y=86%) was prepared starting from 1b;
intermediate 2c (y=85%) was prepared starting from 1c;
intermediate 2d (y=61%) was prepared starting from 1d;
intermediate 2e (y=88%) was prepared starting from 1e;
intermediate 2f (y=59%) was prepared starting from 1f;
intermediate 2g (y=85%) was prepared starting from 1g;
intermediate 2h (y=61%) was prepared starting from 1h;
intermediate 2i (y=41%) was prepared starting from 1i;
intermediate 2j (y=90%) was prepared starting from 1j;
intermediate 2k (y=76%) was prepared starting from 1k;
intermediate 2l (y=77%) was prepared starting from 1l;
intermediate 2m (y=76%) was prepared starting from 1m;
intermediate 2n (y=76%) was prepared starting from 1n;
intermediate 2o (y=61%) was prepared starting from 1o;
intermediate 2p (y=48%) was prepared starting from 1p;
intermediate 2q (y=20%) was prepared starting from 1q;
intermediate 2r (y=46%) was prepared starting from 1r;
intermediate 2s (y=98%) was prepared starting from 1s;
intermediate 2u (y=72%) was prepared starting from 1u;
intermediate 2v (y=72%) was prepared starting from 1v;
intermediate 2w (y=75%) was prepared starting from 1w;
intermediate 2x (y=60%) was prepared starting from 1x;
intermediate 2y (y=40%) was prepared starting from 1y;
intermediate 2z (y=82%) was prepared starting from 1z;
intermediate 2aa (y=86%) was prepared starting from 1aa;
intermediate 2bb (y=89%) was prepared starting from 1bb;
intermediate 2cc (y=67%) was prepared starting from 1cc;
intermediate 2dd (y=44%) was prepared starting from 1dd;
intermediate 2ee (y=52%) was prepared starting from 1ee;
intermediate 2ff (y=84%) was prepared starting from 1ff;
intermediate 2gg (y=61%) was prepared starting from 1gg;
intermediate 2hh (y=56%) was prepared starting from 1hh;
intermediate 2ii (y=83%) was prepared starting from 1ii;
intermediate 2jj (y=40%) was prepared starting from 1jj;
intermediate 2kk (y=57%) was prepared starting from 1kk;
intermediate 2ll (y=57%) was prepared starting from 1ll;
intermediate 2 mm (y=50%) was prepared starting from 1 mm;

| Intermediate | Structure |
|---|---|
| 2a | 4-fluorobenzyl-1,2,4-oxadiazol-5(4H)-one |
| 2b | 3-fluorobenzyl-1,2,4-oxadiazol-5(4H)-one |
| 2c | 2-fluorobenzyl-1,2,4-oxadiazol-5(4H)-one |
| 2d | 3-methoxybenzyl-1,2,4-oxadiazol-5(4H)-one |
| 2e | 4-methoxybenzyl-1,2,4-oxadiazol-5(4H)-one |
| 2f | 2-chlorobenzyl-1,2,4-oxadiazol-5(4H)-one |
| 2g | 2-chloro-6-fluorobenzyl-1,2,4-oxadiazol-5(4H)-one |

-continued

| Intermediate | Structure |
|---|---|
| 2h | 2-(2-chloro-6-fluorophenyl)propan-2-yl-1,2,4-oxadiazol-5(4H)-one |
| 2i | 1-(2-chloro-6-fluorophenyl)ethyl-1,2,4-oxadiazol-5(4H)-one |
| 2j | (2,3-dichlorobenzyl)-1,2,4-oxadiazol-5(4H)-one |
| 2k | (2,4-difluorobenzyl)-1,2,4-oxadiazol-5(4H)-one |
| 2l | (2-chloro-3-(trifluoromethyl)benzyl)-1,2,4-oxadiazol-5(4H)-one |
| 2m | (2,4-dichlorobenzyl)-1,2,4-oxadiazol-5(4H)-one |
| 2n | (2-chloro-4-fluorobenzyl)-1,2,4-oxadiazol-5(4H)-one |
| 2o | benzyl-1,2,4-oxadiazol-5(4H)-one |

-continued

| Intermediate | Structure |
|---|---|
| 2p | (pyridin-2-ylmethyl)-1,2,4-oxadiazol-5(4H)-one |
| 2q | (pyridin-3-ylmethyl)-1,2,4-oxadiazol-5(4H)-one |
| 2r | (pyridin-4-ylmethyl)-1,2,4-oxadiazol-5(4H)-one |
| 2s | (2-(trifluoromethyl)benzyl)-1,2,4-oxadiazol-5(4H)-one |
| 2u | (cyclohexylmethyl)-1,2,4-oxadiazol-5(4H)-one |
| 2v | ((4,4-difluorocyclohexyl)methyl)-1,2,4-oxadiazol-5(4H)-one |
| 2w | 2-(2-chloro-6-fluorophenyl)ethyl-1,2,4-oxadiazol-5(4H)-one |
| 2x | ((2-methylpyridin-3-yl)methyl)-1,2,4-oxadiazol-5(4H)-one |
| 2y | ((4,4-difluoropiperidin-1-yl)methyl)-1,2,4-oxadiazol-5(4H)-one |

| Intermediate | Structure |
|---|---|
| 2z | 3,3-difluoropiperidine-CH2-(1,3,4-oxadiazol-2(3H)-one) |
| 2aa | piperidine-CH2-(1,3,4-oxadiazol-2(3H)-one) |
| 2bb | 1,2,3,4-tetrahydroisoquinoline-CH2-(1,3,4-oxadiazol-2(3H)-one) |
| 2cc | 2-methyl-4,4-difluoropiperidine-CH2-(1,3,4-oxadiazol-2(3H)-one) |
| 2dd | 4,5,6,7-tetrahydrothieno[3,2-c]pyridine-CH2-(1,3,4-oxadiazol-2(3H)-one) |
| 2ee | 3-(p-tolyl)piperidine-CH2-(1,3,4-oxadiazol-2(3H)-one) |
| 2ff | pyrrolidine-CH2-(1,3,4-oxadiazol-2(3H)-one) |
| 2gg | 3,3-difluorocyclopentyl-CH2-(1,3,4-oxadiazol-2(3H)-one) |
| 2hh | 3,4-dihydro-2H-benzo[b][1,4]oxazine-CH2-(1,3,4-oxadiazol-2(3H)-one) |
| 2ii | 4-phenylpiperazine-CH2-(1,3,4-oxadiazol-2(3H)-one) |
| 2jj | 4-methylthiazol-5-yl-CH2-(1,3,4-oxadiazol-2(3H)-one) |
| 2kk | (diethoxymethyl)-(1,3,4-oxadiazol-2(3H)-one) |
| 2ll | 3,5-dimethylisoxazol-4-yl-CH2-(1,3,4-oxadiazol-2(3H)-one) |
| 2mm | 1,3,5-trimethyl-1H-pyrazol-4-yl-CH2-(1,3,4-oxadiazol-2(3H)-one) |

Preparation of 1,2,4-thiadiazol-5(4H)-one (IIa)
(Typical Procedure)

A mixture of a suitable intermediate VI (1.0 eq) and TCDI (1.5 eq) in THF (20 mL) was stirred at rt for 30 minutes. The mixture was diluted with water and extracted with EtOAc; the extract was washed with water and dried over $Na_2SO_4$, filtered and the solvent evaporated in vacuo. The obtained residue was dissolved in THF (20 mL), and Boron trifluoride diethyl etherate (3.0 eq) was added to the solution, and the resulting mixture was stirred at rt for a further 1 hrs. The mixture was diluted with water and extracted with EtOAc; the extract was washed with water and dried over $Na_2SO_4$, filtered and the solvent evaporated in vacuum. The product was used without purification in the next step. In this way pure 1,2,4-thiadiazol-5(4H)-one was obtained. (y=66-82%)

Using this procedure:

intermediate 3a (y=66%) was prepared starting from intermediate 1g;

intermediate 3b (y=82%) was prepared starting from intermediate 1v;

| Intermediate | Structure |
|---|---|
| 3a | (2-chloro-6-fluorobenzyl)-1,2,4-thiadiazol-5(4H)-one structure |
| 3b | (4,4-difluorocyclohexylmethyl)-1,2,4-thiadiazol-5(4H)-one structure |

General Procedures for the Synthesis of Final Compounds

Method A

Preparation of Examples 1-7

To a solution of intermediate 2 (1.0 eq), a suitable, commercially available alcohol (1.0 eq), and $PPh_3$ (4.0 eq) in THF (5-10 mL) at 0° C. a DEAD solution 40 wt % in toluene (4.0 eq) was added dropwise; the reaction mixture was stirred at r.t. for 24 hrs under inert atmosphere. The solvent was concentrated under reduced pressure; the residue dissolved in a minimal amount of diethyl ether, and cooled at −20° C. to form a white precipitate ($PPh_3O$ and reduced DEAD) which was filtered off. The filtrate was concentrated under reduced pressure. The crude product was purified by HPLC, giving the pure desired compound. (y=9%-66%)

According to this procedure the following compounds were prepared using the suitable intermediates and alcohols:

| Example | Yield | Int. | Alcohol |
|---|---|---|---|
| Ex. 1 | 60% | Int. 2a | 2-Chloro-6-fluorobenzyl alcohol (CAS: 56456-50-9). |
| Ex. 2 | 34% | Int. 2a | 2,4-Dimethoxybenzyl alcohol (CAS: 7314-44-5). |
| Ex. 3 | 9% | Int. 2a | 4-Methoxybenzyl alcohol (CAS: 105-13-5). |
| Ex. 4 | 66% | Int. 2a | 3,5-Dimethoxybenzyl alcohol (CAS: 705-76-0). |
| Ex. 5 | 39% | Int. 2a | 2-Bromo-5-fluorobenzyl alcohol (CAS: 202865-66-5). |
| Ex. 6 | 26% | Int. 2o | 2-Chloro-6-fluorobenzyl alcohol (CAS: 56456-50-9). |
| Ex. 7 | 16% | Int. 2d | 2-Chloro-6-fluorobenzyl alcohol (CAS: 56456-50-9). |

Method B

Preparation of Examples 8-49

To a cold (0° C.) solution of intermediate 2 (1.0 eq) in MeCN/DMF (5:1 v/v 5-10 mL/1-3 mL) $K_2CO_3$ (2.5 eq) was added, followed by the suitable commercially available halide (1.2 eq). The reaction was allowed to warm to r.t., and was stirred at same temperature o.n. The reaction was quenched by addition of water and extracted with EtOAc. The organic layers were combined, washed with brine, dried over $Na_2SO_4$ and concentrated under reduced pressure. The crude product was purified by HPLC giving pure desired compound. (y=14%-83%)

According to this procedure the following compounds were prepared using the suitable intermediates and reactants:

| Ex. | Yield | Int. | Reactant |
|---|---|---|---|
| 8 | 68% | 2a | 5-(chloromethyl)-4-methyl-1,3-thiazole (CAS: 10014-52-5). |
| 9 | 50% | 2a | 2,4-Dichlorobenzyl chloride (CAS: 94-99-5). |
| 10 | 40% | 2a | (1-chloroethyl)benzene (CAS: 672-65-1). |
| 11 | 59% | 2a | 1-(1-bromoethyl)-4-fluorobenzene (CAS: 65130-46-3). |
| 12 | 66% | 2a | (Bromomethyl)cyclohexane (CAS: 2550-36-9). |
| 13 | 49% | 2j | 2-chloro-6-fluorobenzyl chloride (CAS: 55117-15-2). |
| 14 | 56% | 2n | 2-chloro-6-fluorobenzyl chloride (CAS: 55117-15-2). |
| 15 | 56% | 2k | 2-chloro-6-fluorobenzyl chloride (CAS: 55117-15-2). |
| 16 | 48% | 2l | 2-chloro-6-fluorobenzyl chloride (CAS: 55117-15-2). |
| 17 | 64% | 2m | 2-chloro-6-fluorobenzyl chloride (CAS: 55117-15-2). |
| 18 | 70% | 2g | 2-chloro-6-fluorobenzyl chloride (CAS: 55117-15-2). |
| 19 | 61% | 2c | 2-chloro-6-fluorobenzyl chloride (CAS: 55117-15-2). |
| 20 | 61% | 2f | 2-chloro-6-fluorobenzyl chloride (CAS: 55117-15-2). |
| 21 | 46% | 2g | benzyl chloride (CAS: 100-44-7). |
| 22 | 67% | 2g | 2-chlorobenzyl chloride (CAS: 611-19-8). |
| 23 | 37% | 2g | 2-(trifluoromethyl)benzyl chloride (CAS: 21742-00-7). |
| 24 | 56% | 2g | 3-(chloromethyl)-2-methylpyridine (CAS: 120277-68-1). |
| 25 | 83% | 2g | (1-chloromethyl)-4-fluoro-2-methylbenzene (CAS: 80141-92-0). |
| 26 | 73% | 2g | 3-fluorobenzyl chloride (CAS: 456-42-8). |
| 27 | 57% | 2g | 2-methylbenzyl chloride (CAS: 552-45-4). |
| 28 | 66% | 2g | 1-(chloromethyl)-2-methoxybenzene (CAS: 7035-02-1). |
| 29 | 33% | 2g | 1-(chloromethyl)-naphthalene (CAS: 86-52-2). |

-continued

| Ex. | Yield | Int. | Reactant |
|---|---|---|---|
| 30 | 80% | 2g | 5-(chloromethyl)quinoline (CAS: 110333-07-8). |
| 31 | 33% | 2g | 5-(chloromethyl)-4-methyl-1,3-thiazole (CAS: 10014-52-5). |
| 32 | 66% | 2g | 2-Chloromethyl-oxazole (CAS: 185246-17-7). |
| 33 | 14% | 2g | 5-(Chloromethyl)thiazole hydrochloride (CAS: 131052-44-3). |
| 34 | 50% | 2g | 2-(Chloromethyl)thiazole (CAS: 3364-78-1). |
| 35 | 30% | 2g | 1-(chloromethyl)-3-(trifluoromethyl)-1H-pyrazole (CAS: 860807-20-1). |
| 36 | 78% | 2g | 4-(Chloromethyl)-3,5-dimethylisoxazole (CAS: 19788-37-5). |
| 37 | 35% | 2g | 5-Chloromethyl-2-(trifluoromethyl)pyridine (CAS: 386715-33-9). |
| 38 | 21% | 2g | 5-(Chloromethyl)pyrimidine hydrochloride (CAS: 1337879-54-5). |
| 39 | 64% | 2g | 2-(Chloromethyl)pyrimidine hydrochloride (CAS: 936643-80-0). |
| 40 | 33% | 2g | 5-(Chloromethyl)oxazole (CAS: 172649-57-9). |
| 41 | 27% | 2g | 2-(Chloromethyl)-5-methyl-1,3,4-oxadiazole (CAS: 3914-42-9). |
| 42 | 28% | 2g | 3-Picolylchloride hydrochloride (CAS: 6959-48-4). |
| 43 | 15% | 2g | 4-(Chloromethyl)pyridine hydrochloride (CAS: 1822-51-1). |
| 44 | 20% | 2g | 3-(chloromethyl)-furan (CAS: 14497-29-1). |
| 45 | 50% | 2g | 2-(chloromethyl)-5-fluoropyrimidine (CAS: 1196151-61-7). |
| 46 | 54% | 2g | 5-(Chloromethyl)-1,3-dimethyl-1H-pyrazole (CAS: 852227-86-2). |
| 47 | 77% | 2g | 2-(Chloromethyl)-1-methyl-1H-imidazole (CAS: 19225-92-4). |
| 48 | 51% | 2g | 1-(1-bromoethyl)-4-fluorobenzene (CAS: 65130-46-3). |
| 49 | 40% | 2g | (1-chloroethyl)benzene (CAS: 672-65-1). |

Method C

Preparation of Examples 50-80

To a Cold (0° C.) Solution of Intermediate 2 (1.0 Eq) in MeCN/DMF (5:1 v/v 5-10 mL/1-3 mL) $K_2CO_3$ was added (1.1 eq), followed by the commercially available halide (0.8 eq). The reaction was allowed to warmed to rt, and then stirred at same temperature for 3 hrs. The reaction was quenched by addition of water and extracted with EtOAc. The organic layers were combined, washed with brine, dried over $Na_2SO_4$ and concentrated under reduced pressure. The crude product was purified by HPLC giving pure desired compound. (y=12%-97%)

According to this procedure the following compounds were prepared using the suitable intermediates and reactants:

| Ex. | Yield | Int. | Reactant |
|---|---|---|---|
| 50 | 62% | 2a | 1-(bromomethyl)-2,3-diclorobenzene (CAS: 57915-78-3). |
| 51 | 55% | 2a | 2-chloro-4-fluorobenzyl bromide (CAS: 45767-66-6). |
| 52 | 46% | 2a | 2-chloro-3-(trifluoromethyl)benzyl bromide (CAS: 261763-22-8). |
| 53 | 65% | 2a | 2,4-difluorobenzyl bromide (CAS: 23915-07-3). |
| 54 | 58% | 2a | 4-Fluorobenzyl bromide (CAS: 459-46-1). |
| 55 | 71% | 2g | 4-Fluorobenzyl bromide (CAS: 459-46-1). |
| 56 | 94% | 2g | 2-Fluorobenzyl bromide (CAS: 446-48-0). |
| 57 | 90% | 2g | 3-Methoxybenzyl bromide (CAS: 874-98-6). |
| 58 | 75% | 2g | 2-chloro-3-(trifluoromethyl)benzyl bromide (CAS: 261763-22-8). |
| 59 | 57% | 2g | 1-(bromomethyl)-2,3-diclorobenzene (CAS: 57915-78-3). |
| 60 | 70% | 2g | 2-chloro-4-fluorobenzyl bromide (CAS: 45767-66-6). |
| 61 | 62% | 2g | 2,4-difluorobenzyl bromide (CAS: 23915-07-3). |
| 62 | 51% | 2g | 2-(Bromomethyl)pyridine hydrobromide (CAS: 31106-82-8). |
| 63 | 88% | 2g | 4-(Trifluoromethyl)benzyl bromide (CAS: 402-49-3). |
| 64 | 72% | 2g | 3-Bromomethyl-2-methyl-6-trifluoromethyl-pyridine (CAS: 917396-30-6). |
| 65 | 81% | 2g | 4-Chlorobenzyl bromide (CAS: 622-95-7). |
| 66 | 90% | | 2-(Bromomethyl)-5-(trifluoromethyl)furan (CAS: 17515-77-4). |
| 67 | 73% | 2g | 1-(Bromomethyl)-4-methylbenzene (CAS: 104-81-4). |
| 68 | 97% | 2g | 1-(Bromomethyl)-4-methoxybenzene (CAS: 2746-25-0). |
| 69 | 12% | 2g | bromomethyl)-cyclobutane (CAS: 17247-58-4); reaction conditions: 96 hrs at rt. |
| 70 | 25% | 2g | 8-(bromomethyl)-1,4-dioxaspiro[4.5]decane (CAS: 74286-87-6); reaction conditions: 5 days at 60° C. |
| 71 | 51% | 2j | 4-Fluorobenzyl bromide (CAS: 459-46-1). |
| 72 | 61% | 2l | 4-Fluorobenzyl bromide (CAS: 459-46-1). |
| 73 | 50% | 2n | 4-Fluorobenzyl bromide (CAS: 459-46-1). |
| 74 | 57% | 2m | 4-Fluorobenzyl bromide (CAS: 459-46-1). |
| 75 | 78% | 2c | 4-Fluorobenzyl bromide (CAS: 459-46-1). |
| 76 | 93% | 2f | 4-Fluorobenzyl bromide (CAS: 459-46-1). |
| 77 | 74% | 2h | 4-Fluorobenzyl bromide (CAS: 459-46-1). |
| 78 | 50% | 2i | 4-Fluorobenzyl bromide (CAS: 459-46-1). |
| 79 | 30% | 2r | 4-Fluorobenzyl bromide (CAS: 459-46-1). |
| 80 | 71% | 2k | 4-Fluorobenzyl bromide (CAS: 459-46-1). |

Method D

Preparation of Examples 81-134, Examples 139-147 and Examples 150-251

To a cooled (0° C.) solution of intermediates 2 or 3 (1.0 eq) in DMF (5-12 mL) CH$_3$ONa (1.5 or 3.0 eq) was added, and the mixture was stirred at same temperature for 10 min. Then, a suitable, commercially available halide (2.5 or 5.0 eq), was added, and the reaction mixture was allowed to warmed to rt, stirred at a suitable temperature for a variable time (see specific examples). The reaction was quenched by adding water and extracted with EtOAc. The organic layers were combined, washed with aqueous saturated NaCl, dried over Na$_2$SO$_4$ and concentrated under reduced pressure. The crude product was purified by HPLC yielding the pure desired compound. (y=3%-96%)

Using this procedure compounds:

Example 81 (yield 89%) was prepared starting from intermediate 2b and 2-chloro-6-fluorobenzyl chloride (CAS: 55117-15-2); reaction conditions: o.n. at rt.

Example 82 (yield 64%) was prepared starting from intermediate 2g and (Bromomethyl)cyclohexane (CAS: 2550-36-9); reaction conditions: o.n. at 70° C.

Example 83 (yield 74%) was prepared starting from intermediate 2g and (Bromomethyl)-cyclopropane (CAS: 7051-34-5); reaction conditions: o.n. at rt.

Example 84 (yield 67%) was prepared starting from intermediate 2g and 4-(Bromomethyl)-1,1-difluorocyclohexane (CAS: 858121-94-5); reaction conditions: o.n. at 70° C.

Example 85 (yield 58%) was prepared starting from intermediate 2g and (Bromomethyl)-cyclopentane (CAS: 3814-30-0); reaction conditions: o.n. at 80° C.

Example 86 (yield 50%) was prepared starting from intermediate 2g and 4-(Bromomethyl)-1,1-dimethylcyclohexane (CAS: 1432681-20-3); reaction conditions: 24 hrs at 60° C.

Example 87 (yield 28%) was prepared starting from intermediate 2g and 1-(Bromomethyl)-1-methylcyclohexane (CAS: 408307-48-2); reaction conditions: 2 weeks at 60° C.

Example 88 (yield 18%) was prepared starting from intermediate 2g and 2-(Bromomethyl)-bicyclo[2.2.1]heptane (CAS: 55932-58-6); reaction conditions: 2 weeks at rt, then 7 days at 60° C.

Example 89 (yield 36%) was prepared starting from intermediate 2g and 3-(Bromomethyl)tetrahydro-2H-pyran (CAS: 116131-44-3); reaction conditions: 5 days at rt.

Example 90 (yield 68%) was prepared starting from intermediate 2g and 1-Bromo-2-pentyne (CAS: 16400-32-1); reaction conditions: 2 hrs at rt.

Example 91 (yield 34%) was prepared starting from intermediate 2g and 1-(Bromomethyl)-bicyclo[2.2.1]heptane (CAS: 61192-17-4); reaction conditions: 5 days at 70° C.

Example 92 (yield 23%) was prepared starting from intermediate 2g and (Bromomethyl)-cycloheptane (CAS: 3814-32-2); reaction conditions: 9 days at rt.

Example 93 (yield 35%) was prepared starting from intermediate 2g and 4-(Bromomethyl)tetrahydro-2H-pyran (CAS: 125552-89-8); reaction conditions: 5 days at rt.

Example 94 (yield 24%) was prepared starting from intermediate 2g and 2-(Bromomethyl)tetrahydro-2H-pyran (CAS: 34723-82-5); reaction conditions: 5 days at rt.

Example 95 (yield 84%) was prepared starting from intermediate 2g and 1-Bromo-2-butyne (CAS: 3355-28-0); reaction conditions: 3 hrs at rt.

Example 96 (yield 3%) was prepared starting from intermediate 2g and 1-(bromomethyl)-1-fluoro-cyclohexane (CAS: 17171-00-5); reaction conditions: 7 days at 70° C.

Example 97 (yield 19%) was prepared starting from intermediate 2g and 2-(bromomethyl)-1,1-difluoro-cyclohexane (CAS: 1817326-97-4); reaction conditions: 5 days at 70° C.

Example 98 (yield 14%) was prepared starting from intermediate 2g and 2-(chloromethyl)-1,4-Dioxane (CAS: 21048-16-8); reaction conditions: 1 month at 60° C.

Example 99 (yield 25%) was prepared starting from intermediate 2g and 2-(bromomethyl)-1,1-dimethyl-cyclohexane (CAS: 1501249-61-1); reaction conditions: 7 days at 60° C.

Example 100 (yield 37%) was prepared starting from intermediate 2g and bromomethoxy-methane (CAS: 13057-17-5); reaction conditions: 5 days at rt.

Example 101 (yield 70%) was prepared starting from intermediate 2g and bromomethoxy-ethane (CAS: 53588-92-4); reaction conditions: o.n. at rt.

Example 102 (yield 37%) was prepared starting from intermediate 2g and 1-(bromomethoxy)-propane (CAS: 59375-50-7); reaction conditions: 4 days at rt.

Example 104 (yield 65%) was prepared starting from intermediate 2p and 4-Fluorobenzyl bromide (CAS: 459-46-1); reaction conditions: 2 hrs at rt.

Example 105 (yield 90%) was prepared starting from intermediate 2s and 4-Fluorobenzyl bromide, CAS: 459-46-1; reaction conditions: 2 hrs at rt.

Example 107 (yield 77%) was prepared starting from intermediate 2b and 4-Fluorobenzyl bromide (CAS: 459-46-1); reaction conditions: 3 hrs at rt.

Example 108 (yield 79%) was prepared starting from intermediate 2o and 4-Fluorobenzyl bromide (CAS: 459-46-1); reaction conditions: 2 hrs at rt.

Example 109 (yield 93%) was prepared starting from intermediate 2d and 4-Fluorobenzyl bromide (CAS: 459-46-1); reaction conditions: 2 hrs at rt.

Example 110 (yield 28%) was prepared starting from intermediate 2p and (Bromomethyl)cyclohexane (CAS: 2550-36-9); reaction conditions: 24 hrs at rt, then 24 hrs at 60° C.

Example 111 (yield 29%) was prepared starting from intermediate 2r and (Bromomethyl)cyclohexane (CAS: 2550-36-9); reaction conditions: o.n. at rt, then 3 hrs at 80° C.

Example 112 (yield 88%) was prepared starting from intermediate 2e and (Bromomethyl)cyclohexane (CAS: 2550-36-9); reaction conditions: o.n. at 60° C.

Example 113 (yield 59%) was prepared starting from intermediate 2l and (Bromomethyl)cyclohexane (CAS: 2550-36-9); reaction conditions: o.n. at 70° C.

Example 114 (yield 84%) was prepared starting from intermediate 2n and (Bromomethyl)cyclohexane (CAS: 2550-36-9); reaction conditions: o.n. at 70° C.

Example 115 (yield 31%) was prepared starting from intermediate 2j and (Bromomethyl)cyclohexane (CAS: 2550-36-9); reaction conditions: 48 hrs at 60° C.

Example 116 (yield 50%) was prepared starting from intermediate 2s and (Bromomethyl)cyclohexane (CAS: 2550-36-9); reaction conditions: o.n. at 60° C.

Example 117 (yield 61%) was prepared starting from intermediate 2f and (Bromomethyl)cyclohexane (CAS: 2550-36-9); reaction conditions: o.n. at 60° C.

Example 118 (yield 29%) was prepared starting from intermediate 2m and (Bromomethyl)cyclohexane (CAS: 2550-36-9); reaction conditions: o.n. at 60° C.

Example 119 (yield 80%) was prepared starting from intermediate 2k and (Bromomethyl)cyclohexane (CAS: 2550-36-9); reaction conditions: o.n. at 70° C.

Example 120 (yield 89%) was prepared starting from intermediate 2c and (Bromomethyl)cyclohexane (CAS: 2550-36-9); reaction conditions: o.n. at 70° C.

Example 121 (yield 53%) was prepared starting from intermediate 2h and (Bromomethyl)cyclohexane (CAS: 2550-36-9); reaction conditions: o.n. at 70° C.

Example 122 (yield 50%) was prepared starting from intermediate 2i and (Bromomethyl)cyclohexane (CAS: 2550-36-9); reaction conditions: o.n. at 70° C.

Example 123 (yield 21%) was prepared starting from intermediate 2q and (Bromomethyl)cyclohexane (CAS: 2550-36-9); reaction conditions: o.n. at 60° C.

Example 125 (yield 78%) was prepared starting from intermediate 2b and (Bromomethyl)cyclohexane (CAS: 2550-36-9); reaction conditions: o.n. at 70° C.

Example 126 (yield 75%) was prepared starting from intermediate 2o and (Bromomethyl)cyclohexane (CAS: 2550-36-9); reaction conditions: o.n. at 60° C.

Example 127 (yield 90%) was prepared starting from intermediate 2d and (Bromomethyl)cyclohexane (CAS: 2550-36-9); reaction conditions: o.n. at 60° C.

Example 128 (yield 70%) was prepared starting from intermediate 2g and 3-(bromomethyl)-1,1-difluorocyclopentane (CAS: 1695914-13-6); reaction conditions: 24 hrs at 60° C.

Example 129 (yield 96%) was prepared starting from intermediate 2u and (Bromomethyl)cyclohexane (CAS: 2550-36-9); reaction conditions: o.n. at 70° C.

Example 130 (yield 93%) was prepared starting from intermediate 2u and 2-chloro-6-fluorobenzylchloride (CAS: 55117-15-2); reaction conditions: o.n. at rt.

Example 131 (yield 85%) was prepared starting from intermediate 2u and 4-Fluorobenzyl bromide (CAS: 459-46-1); reaction conditions: 3 hrs at rt.

Example 132 (yield 91%) was prepared starting from intermediate 2v and 2-chloro-6-fluorobenzylchloride (CAS: 55117-15-2); reaction conditions: o.n. at rt.

Example 133 (yield 64%) was prepared starting from intermediate 2v and (Bromomethyl)cyclohexane (CAS: 2550-36-9); reaction conditions: o.n. at 70° C.

Example 134 (yield 50%) was prepared starting from intermediate 2v and 4-Fluorobenzyl bromide (CAS: 459-46-1); reaction conditions: 3 hrs at rt.

Example 139 (yield 48%) was prepared starting from intermediate 3a and 4-Fluorobenzyl bromide (CAS: 459-46-1); reaction conditions: o.n. at rt.

Example 140 (yield 24%) was prepared starting from intermediate 3a and (Bromomethyl)cyclohexane (CAS: 2550-36-9); reaction conditions: o.n. at 60° C.

Example 141 (yield 44%) was prepared starting from intermediate 3a and 4-(Bromomethyl)-1,1-difluorocyclohexane (CAS: 858121-94-5); reaction conditions: o.n. at 60° C.

Example 142 (yield 59%) was prepared starting from intermediate 2g and 1-Bromo-2-cyclohexylethane (CAS: 1647-26-3); reaction conditions: o.n. at 60° C.

Example 143 (yield 45%) was prepared starting from intermediate 2g and 1-(2-Bromoethyl)piperidine (CAS: 56477-57-7); reaction conditions: o.n. at 60° C.

Example 144 (yield 76%) was prepared starting from intermediate 2w and 2-chloro-6-fluorobenzylchloride (CAS: 55117-15-2); reaction conditions: 2 hrs at 60° C.

Example 145 (yield 60%) was prepared starting from intermediate 2w and 4-Fluorobenzyl bromide (CAS: 459-46-1); reaction conditions: 2 hrs at rt.

Example 146 (yield 69%) was prepared starting from intermediate 2w and (Bromomethyl)cyclohexane (CAS: 2550-36-9); reaction conditions: 48 hrs at 50° C.

Example 147 (yield 19%) was prepared starting from intermediate 2w and 4-(Bromomethyl)-1,1-difluorocyclohexane (CAS: 858121-94-5); reaction conditions: 48 hrs at 50° C.

Example 150 (yield 69%) was prepared starting from intermediate 2c and 4-(Bromomethyl)-1,1-difluorocyclohexane (CAS: 858121-94-5); reaction conditions: 48 hrs at 50° C.

Example 151 (yield 47%) was prepared starting from intermediate 2b and 4-(Bromomethyl)-1,1-difluorocyclohexane (CAS: 858121-94-5); reaction conditions: 48 hrs at 50° C.

Example 152 (yield 44%) was prepared starting from intermediate 2a and 4-(Bromomethyl)-1,1-difluorocyclohexane (CAS: 858121-94-5); reaction conditions: 48 hrs at 50° C.

Example 153 (yield 56%) was prepared starting from intermediate 2k and 4-(Bromomethyl)-1,1-difluorocyclohexane (CAS: 858121-94-5); reaction conditions: 48 hrs at 50° C.

Example 154 (yield 33%) was prepared starting from intermediate 2e and 4-(Bromomethyl)-1,1-difluorocyclohexane (CAS: 858121-94-5); reaction conditions: 48 hrs at 50° C.

Example 155 (yield 39%) was prepared starting from intermediate 2l and 4-(Bromomethyl)-1,1-difluorocyclohexane (CAS: 858121-94-5); reaction conditions: 48 hrs at 50° C.

Example 156 (yield 57%) was prepared starting from intermediate 2j and 4-(Bromomethyl)-1,1-difluorocyclohexane (CAS: 858121-94-5); reaction conditions: 48 hrs at 50° C.

Example 157 (yield 48%) was prepared starting from intermediate 2s and 4-(Bromomethyl)-1,1-difluorocyclohexane (CAS: 858121-94-5); reaction conditions: 48 hrs at 50° C.

Example 158 (yield 40%) was prepared starting from intermediate 2f and 4-(Bromomethyl)-1,1-difluorocyclohexane (CAS: 858121-94-5); reaction conditions: 48 hrs at 50° C.

Example 159 (yield 42%) was prepared starting from intermediate 2m and 4-(Bromomethyl)-1,1-difluorocyclohexane (CAS: 858121-94-5); reaction conditions: 48 hrs at 50° C.

Example 160 (yield 62%) was prepared starting from intermediate 2d and 4-(Bromomethyl)-1,1-difluorocyclohexane (CAS: 858121-94-5); reaction conditions: 48 hrs at 50° C.

Example 161 (yield 63%) was prepared starting from intermediate 2o and 4-(Bromomethyl)-1,1-difluorocyclohexane (CAS: 858121-94-5); reaction conditions: 48 hrs at 50° C.

Example 162 (yield 48%) was prepared starting from intermediate 2n and 4-(Bromomethyl)-1,1-difluorocyclohexane (CAS: 858121-94-5); reaction conditions: 48 hrs at 50° C.

Example 163 (yield 47%) was prepared starting from intermediate 2u and 1-(1-Bromoethyl)-4-fluorobenzene (CAS: 65130-46-3); reaction conditions: 24 hrs at rt.

Example 164 (yield 48%) was prepared starting from intermediate 2v and 1-(1-Bromoethyl)-4-fluorobenzene (CAS: 65130-46-3); reaction conditions: 24 hrs at rt.

Example 165 (yield 72%) was prepared starting from intermediate 2v and 2-Fluorobenzyl bromide (CAS: 446-48-0); reaction conditions: o.n. at 60° C.

Example 166 (yield 84%) was prepared starting from intermediate 2v and 4-(Trifluoromethyl)benzyl bromide (CAS: 402-49-3); reaction conditions: o.n. at 60° C.

Example 167 (yield 71%) was prepared starting from intermediate 2v and 2-chloro-3-(trifluoromethyl)benzyl bromide (CAS: 261763-22-8); reaction conditions: o.n. at 60° C.

Example 168 (yield 75%) was prepared starting from intermediate 2v and 2-(Bromomethyl)-5-(trifluoromethyl)furan (CAS: 17515-77-4); reaction conditions: 2 hrs at rt.

Example 169 (yield 74%) was prepared starting from intermediate 2v and 3-Bromomethyl-5-methyl-isoxazole (CAS: 130628-75-0); reaction conditions: 2 hrs at rt.

Example 170 (yield 86%) was prepared starting from intermediate 2v and 2-chlorobenzyl chloride (CAS: 611-19-8); reaction conditions: o.n. at 60° C.

Example 171 (yield 65%) was prepared starting from intermediate 2v and (1-chloromethyl)-4-fluoro-2-methylbenzene (CAS: 80141-92-0); reaction conditions: o.n. at 60° C.

Example 172 (yield 53%) was prepared starting from intermediate 2v and (2-Bromoethyl)benzene (CAS: 103-63-9); reaction conditions: o.n. at 60° C.

Example 173 (yield 55%) was prepared starting from intermediate 2g and 3-(bromomethyl)-6,6-difluorobicyclo[3.1.0]hexane (CAS: 1393569-74-8); reaction conditions: o.n. at 60° C.

Example 174 (yield 95%) was prepared starting from intermediate 2g and Iodomethane (CAS: 74-88-4); reaction conditions: 2 hrs at rt.

Example 175 (yield 58%) was prepared starting from intermediate 2g and Bromoethane (CAS: 74-96-4); reaction conditions: 2 hrs at rt.

Example 176 (yield 71%) was prepared starting from intermediate 2g and 1-bromopropane (CAS: 106-94-5); reaction conditions: o.n. at 60° C.

Example 177 (yield 86%) was prepared starting from intermediate 2g and 1-bromobutane (CAS: 109-65-9); reaction conditions: o.n. at 60° C.

Example 178 (yield 38%) was prepared starting from intermediate 2g and 1-Bromo-2-methylpropane (CAS: 78-77-3); reaction conditions: 3 days at 60° C.

Example 179 (yield 84%) was prepared starting from intermediate 2g and 3-cyclohexylpropyl bromide (CAS: 34094-21-8); reaction conditions: o.n. at 60° C.

Example 180 (yield 75%) was prepared starting from intermediate 2g and 1-(3-bromopropyl)piperidine hydrobromide (CAS: 58689-34-2); reaction conditions: 2 days at 60° C.

Example 181 (yield 18%) was prepared starting from intermediate 2g and 1-(2-bromoethyl)-4,4-difluoropiperidine hydrobromide (CAS: 1996969-81-3); reaction conditions: 2 days at 60° C.

Example 182 (yield 26%) was prepared starting from intermediate 2g and 1-(3-bromopropyl)-4,4-difluoropiperidine hydrobromide (CAS: 1782084-16-5); reaction conditions: 2 days at 60° C.

Example 183 (yield 57%) was prepared starting from intermediate 2g and 4-(bromomethyl)-1-cyclopentene (CAS: 80864-33-1); reaction conditions: 2 hrs at rt and o.n. at 60° C.

Example 184 (yield 47%) was prepared starting from intermediate 2g and 1-(bromomethyl)-4-(trifluoromethyl)cyclohexane (CAS: 858121-96-7); reaction conditions: o.n. at 60° C.

Example 185 (yield 56%) was prepared starting from intermediate 2g and 1-(bromomethyl)-4-fluorocyclohexane (CAS: 1784609-74-0); reaction conditions: o.n. at 60° C.

Example 186 (yield 23%) was prepared starting from intermediate 2kk and 4-Fluorobenzyl bromide (CAS: 459-46-1); reaction conditions: 3 hrs at rt.

Example 187 (yield 23%) was prepared starting from intermediate 2kk and 2-chloro-6-fluorobenzylchloride (CAS: 55117-15-2); reaction conditions: 3 hrs at rt.

Example 188 (yield 18%) was prepared starting from intermediate 2v and 1-chloroethylbenzene (CAS: 672-65-1); reaction conditions: one week at 60° C.

Example 189 (yield 76%) was prepared starting from intermediate 2v and 5-Chloromethyl-2-(trifluoromethyl)pyridine (CAS: 386715-33-9); reaction conditions: 3 days at 60° C.

Example 190 (yield 83%) was prepared starting from intermediate 2v and 2-(chloromethyl)-5-fluoropyrimidine (CAS: 1196151-61-7); reaction conditions: 3 days at 60° C.

Example 191 (yield 47%) was prepared starting from intermediate 2v and 2-(Chloromethyl)thiazole (CAS: 3364-78-1); reaction conditions: 3 days at 60° C.

Example 192 (yield 84%) was prepared starting from intermediate 2v and 3-Bromomethyl-2-methyl-6-trifluoromethyl-pyridine (CAS: 917396-30-6); reaction conditions: 4 hrs at rt.

Example 193 (yield 41%) was prepared starting from intermediate 2v and 5-(Chloromethyl)thiazole hydrochloride (CAS: 131052-44-3); reaction conditions: o.n. at 60° C.

Example 194 (yield 46%) was prepared starting from intermediate 2v and 2-Chloromethyl-oxazole (CAS: 185246-17-7); reaction conditions: o.n. at 60° C.

Example 195 (yield 39%) was prepared starting from intermediate 2v and 5-(Chloromethyl)-1,3-dimethyl-1H-pyrazole (CAS: 852227-86-2); reaction conditions: o.n. at 60° C.

Example 196 (yield 45%) was prepared starting from intermediate 2v and 3-(chloromethyl)-5-methyl-1,2,4-oxadiazole (CAS: 1192-80-9); reaction conditions: o.n. at 60° C.

Example 197 (yield 29%) was prepared starting from intermediate 2v and 5-(Chloromethyl)-3-methyl-1,2,4-oxadiazole (CAS: 1192-81-0); reaction conditions: o.n. at 60° C.

Example 198 (yield 37%) was prepared starting from intermediate 2v and 1-(chloromethyl)-3-(trifluoromethyl)-1H-pyrazole (CAS: 860807-20-1); reaction conditions: o.n. at 60° C.

Example 199 (yield 35%) was prepared starting from intermediate 2v and 5-(Chloromethyl)oxazole (CAS: 172649-57-9); reaction conditions: o.n. at 60° C.

Example 200 (yield 54%) was prepared starting from intermediate 2v and Thiazole, 5-(chloromethyl)-4-methyl-, hydrochloride (CAS 1301739-54-7); reaction conditions: o.n. at 60° C.

Example 201 (yield 35%) was prepared starting from intermediate 2v and 2-(Chloromethyl)-1-methyl-1H-imidazole hydrochloride (CAS 19225-92-4); reaction conditions: o.n. at rt.

Example 202 (yield 39%) was prepared starting from intermediate 3b and 4-Fluorobenzyl bromide (CAS 459-46-1); reaction conditions: 3 hrs at rt.

Example 203 (yield 21%) was prepared starting from intermediate 3b and 2-chloro-6-fluorobenzylchloride (CAS: 55117-15-2); reaction conditions: o.n. at rt.

Example 204 (yield 70%) was prepared starting from intermediate 2gg and 4-Fluorobenzyl bromide (CAS: 459-46-1); reaction conditions: 2 hrs at rt.

Example 205 (yield 67%) was prepared starting from intermediate 2gg and 2-chloro-6-fluorobenzylchloride (CAS: 55117-15-2); reaction conditions: o.n. at 60° C.

Example 206 (yield 62%) was prepared starting from intermediate 2gg and (Bromomethyl)cyclohexane (CAS: 2550-36-9); reaction conditions: 24 hrs at 60° C.

Example 207 (yield 70%) was prepared starting from intermediate 2gg and 4-(Bromomethyl)-1,1-difluorocyclohexane (CAS: 858121-94-5); reaction conditions: 24 hrs at 60° C.

Example 208 (yield 72%) was prepared starting from intermediate 2ll and 4-Fluorobenzyl bromide (CAS: 459-46-1); reaction conditions: 2 hrs at rt.

Example 209 (yield 86%) was prepared starting from intermediate 2ll and 2-chloro-6-fluorobenzylchloride (CAS: 55117-15-2); reaction conditions: o.n. at 60° C.

Example 210 (yield 28%) was prepared starting from intermediate 2ll and (Bromomethyl)cyclohexane (CAS: 2550-36-9); reaction conditions: 2 hrs at rt.

Example 211 (yield 31%) was prepared starting from intermediate 2ll and 4-(Bromomethyl)-1,1-difluorocyclohexane (CAS: 858121-94-5); reaction conditions: 2 hrs at rt.

Example 212 (yield 41%) was prepared starting from intermediate 2 mm and 4-Fluorobenzyl bromide (CAS: 459-46-1); reaction conditions: 24 hrs at rt.

Example 213 (yield 32%) was prepared starting from intermediate 2 mm and 2-chloro-6-fluorobenzylchloride (CAS: 55117-15-2); reaction conditions: o.n. at 60° C.

Example 214 (yield 39%) was prepared starting from intermediate 2 mm and (Bromomethyl)cyclohexane (CAS: 2550-36-9); reaction conditions: o.n. at 60° C.

Example 215 (yield 46%) was prepared starting from intermediate 2 mm and 4-(Bromomethyl)-1,1-difluorocyclohexane (CAS: 858121-94-5); reaction conditions: o.n. at 60° C.

Example 216 (yield 29%) was prepared starting from intermediate 2x and 4-Fluorobenzyl bromide (CAS: 459-46-1); reaction conditions: 2 hrs at rt.

Example 217 (yield 49%) was prepared starting from intermediate 2x and 2-chloro-6-fluorobenzylchloride (CAS: 55117-15-2); reaction conditions: o.n. at 60° C.

Example 218 (yield 37%) was prepared starting from intermediate 2x and (Bromomethyl)cyclohexane (CAS: 2550-36-9); reaction conditions: 24 hrs. at 60° C.

Example 219 (yield 36%) was prepared starting from intermediate 2x and 4-(Bromomethyl)-1,1-difluorocyclohexane (CAS: 858121-94-5); reaction conditions: 34 hrs at 60° C.

Example 220 (yield 20%) was prepared starting from intermediate 2y and 2-chloro-6-fluorobenzylchloride (CAS: 55117-15-2); reaction conditions: o.n. at rt.

Example 221 (yield 22%) was prepared starting from intermediate 2y and 4-Fluorobenzyl bromide (CAS: 459-46-1); reaction conditions: 2 hrs at rt.

Example 222 (yield 26%) was prepared starting from intermediate 2y and (Bromomethyl)cyclohexane (CAS: 2550-36-9); reaction conditions: 24 hrs. at 60° C.

Example 223 (yield 20%) was prepared starting from intermediate 2y and 4-(Bromomethyl)-1,1-difluorocyclohexane (CAS: 858121-94-5); reaction conditions: 34 hrs at 60° C.

Example 224 (yield 58%) was prepared starting from intermediate 2z and 2-chloro-6-fluorobenzylchloride (CAS: 55117-15-2); reaction conditions: 3 hrs at rt.

Example 225 (yield 83%) was prepared starting from intermediate 2z and 4-Fluorobenzyl bromide (CAS: 459-46-1); reaction conditions: 3 hrs at rt.

Example 226 (yield 53%) was prepared starting from intermediate 2cc and 2-chloro-6-fluorobenzylchloride (CAS: 55117-15-2); reaction conditions: 3 hrs at rt.

Example 227 (yield 68%) was prepared starting from intermediate 2cc and 4-Fluorobenzyl bromide (CAS: 459-46-1); reaction conditions: 3 hrs at rt.

Example 228 (yield 37%) was prepared starting from intermediate 2hh and 4-Fluorobenzyl bromide (CAS: 459-46-1); reaction conditions: 3 hrs at rt.

Example 229 (yield 48%) was prepared starting from intermediate 2hh and 2-chloro-6-fluorobenzylchloride (CAS: 55117-15-2); reaction conditions: o.n. at rt.

Example 230 (yield 30%) was prepared starting from intermediate 2hh and (Bromomethyl)cyclohexane (CAS: 2550-36-9); reaction conditions: o.n. at 70° C.

Example 231 (yield 36%) was prepared starting from intermediate 2hh and 4-(Bromomethyl)-1,1-difluorocyclohexane (CAS: 858121-94-5); reaction conditions: o.n. at 70° C.

Example 232 (yield 34%) was prepared starting from intermediate 2dd and 4-Fluorobenzyl bromide (CAS: 459-46-1); reaction conditions: 3 hrs at rt.

Example 233 (yield 28%) was prepared starting from intermediate 2dd and 2-chloro-6-fluorobenzylchloride (CAS: 55117-15-2); reaction conditions: 3 hrs at rt.

Example 234 (yield 23%) was prepared starting from intermediate 2dd and (Bromomethyl)cyclohexane (CAS: 2550-36-9); reaction conditions: o.n. at 70° C.

Example 235 (yield 23%) was prepared starting from intermediate 2dd and 4-(Bromomethyl)-1,1-difluorocyclohexane (CAS: 858121-94-5); reaction conditions: o.n. at 70° C.

Example 236 (yield 54%) was prepared starting from intermediate 2ii and 4-Fluorobenzyl bromide (CAS: 459-46-1); reaction conditions: 3 hrs at rt.

Example 237 (yield 55%) was prepared starting from intermediate 2ii and 2-chloro-6-fluorobenzylchloride (CAS: 55117-15-2); reaction conditions: 3 hrs at rt.

Example 238 (yield 41%) was prepared starting from intermediate 2ii and (Bromomethyl)cyclohexane (CAS: 2550-36-9); reaction conditions: o.n. at 70° C.

Example 239 (yield 44%) was prepared starting from intermediate 2ii and 4-(Bromomethyl)-1,1-difluorocyclohexane (CAS: 858121-94-5); reaction conditions: o.n. at 70° C.

Example 240 (yield 19%) was prepared starting from intermediate 2aa and 4-Fluorobenzyl bromide (CAS: 459-46-1); reaction conditions: 3 hrs at rt.

Example 241 (yield 66%) was prepared starting from intermediate 2aa and 2-chloro-6-fluorobenzylchloride (CAS: 55117-15-2); reaction conditions: 3 hrs at rt.

Example 242 (yield 65%) was prepared starting from intermediate Zee and 2-chloro-6-fluorobenzylchloride (CAS: 55117-15-2); reaction conditions: 3 hrs at rt.

Example 243 (yield 36%) was prepared starting from intermediate Zee and 4-Fluorobenzyl bromide (CAS: 459-46-1); reaction conditions: 3 hrs at rt.

Example 244 (yield 32%) was prepared starting from intermediate 2bb and 2-chloro-6-fluorobenzylchloride (CAS: 55117-15-2); reaction conditions: 3 hrs at rt.

Example 245 (yield 19%) was prepared starting from intermediate 2bb and 4-(bromomethyl)-1,1-difluorocyclohexane (CAS: 858121-94-5); reaction conditions: 2 days at 50° C.

Example 246 (yield 11%) was prepared starting from intermediate 2ff and 2-chloro-6-fluorobenzylchloride (CAS: 55117-15-2); reaction conditions: 3 hrs at rt.

Example 247 (yield 20%) was prepared starting from intermediate 2jj and 4-Fluorobenzyl bromide (CAS: 459-46-1); reaction conditions: o.n. at rt Example 248 (yield 20%) was prepared starting from intermediate 2jj and 2-chloro-6-fluorobenzylchloride (CAS: 55117-15-2); reaction conditions: o.n. at rt Example 249 (yield 25%) was prepared starting from intermediate 2jj and (Bromomethyl)cyclohexane; CAS: 2550-36-9; reaction conditions: o.n. at 70° C.

Example 250 (yield 30%) was prepared starting from intermediate 2jj and 4-(Bromomethyl)-1,1-difluorocyclohexane (CAS: 858121-94-5), reaction conditions: o.n. at 70° C.

Example 251 (yield 35%) was prepared starting from intermediate 2jj and 3-(bromomethyl)-1,1-difluorocyclopentane; CAS: 1695914-13-6; reaction conditions: o.n. at 70° C.

Method E

Preparation of Examples 135-138

To a mixture of intermediate 2 (1.0 eq), $Cs_2CO_3$ (1.0 eq) and NaI (0.05 eq) in DMSO (5-12 mL) a suitable, commercially available halide (0.75 or 1.0 eq) was added dropwise, and the reaction mixture was stirred at r.t. for 3 hrs. The reaction mixture was quenched by addition of $NH_4Cl$ and extracted with EtOAc. The organic layers were combined and concentrated under reduced pressure. The crude product was purified by HPLC giving the pure desired compound. (y=19%-39%)

Using this procedure compounds:

Example 135 (yield 33%) was prepared starting from intermediate 2l and 2-chloro-6-fluorobenzyl chloride (CAS: 55117-15-2).

Example 136 (yield 27%) was prepared starting from intermediate 2l and benzyl chloride (CAS: 100-44-7).

Example 137 (yield 39%) was prepared starting from intermediate 2k and 2-chloro-6-fluorobenzyl chloride (CAS: 55117-15-2).

Example 138 (yield 19%) was prepared starting from intermediate 2j and 2-chloro-6-fluorobenzyl chloride (CAS: 55117-15-2).

Preparation of Examples 148-149

Example 148 and example 149 compounds, were obtained by enantiomeric separation of the racemate of Example 128; for separation procedures, see analytical methods.

Table 1 lists final compounds that were prepared according to the experimental procedure described for Example 1.

TABLE 1

| Example | Structure | IUPAC Name |
|---|---|---|
| 1 | 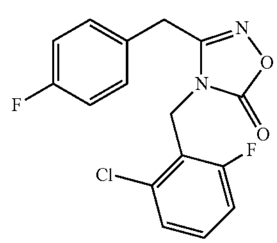 [SMILES: O=c1onc(Cc2ccc(F)cc2)n1Cc1c(F)cccc1Cl] | 4-[(2-chloro-6-fluorophenyl)methyl]-3-[(4-fluorophenyl)methyl]-4,5-dihydro-1,2,4-oxadiazol-5-one |
| 2 | 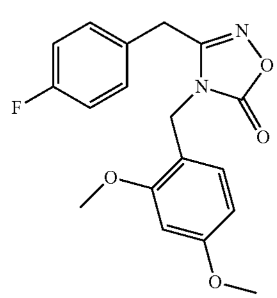 [SMILES: COc1ccc(Cn2c(Cc3ccc(F)cc3)noc2=O)c(OC)c1] | 4-[(2,4-dimethoxyphenyl)methyl]-3-[(4-fluorophenyl)methyl]-4,5-dihydro-1,2,4-oxadiazol-5-one |

TABLE 1-continued

| Example | Structure | IUPAC Name |
|---|---|---|
| 3 | 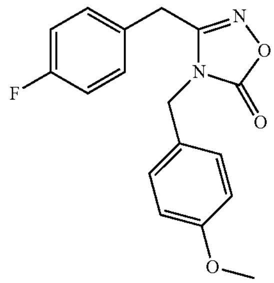 [SMILES: COc1ccc(Cn2c(Cc3ccc(F)cc3)noc2=O)cc1] | 3-[(4-fluorophenyl)methyl]-4-[(4-methoxyphenyl)methyl]-4,5-dihydro-1,2,4-oxadiazol-5-one |
| 4 | 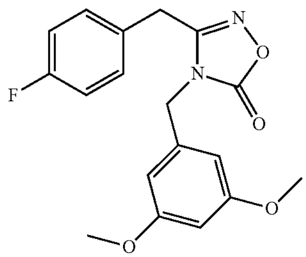 [SMILES: COc1cc(Cn2c(Cc3ccc(F)cc3)noc2=O)cc(OC)c1] | 4-[(3,5-dimethoxyphenyl)methyl]-3-[(4-fluorophenyl)methyl]-4,5-dihydro-1,2,4-oxadiazol-5-one |
| 5 | 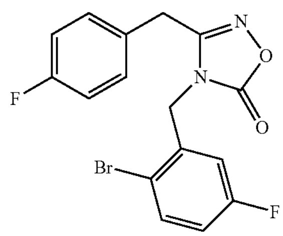 [SMILES: O=c1onc(Cc2ccc(F)cc2)n1Cc1cc(F)ccc1Br] | 4-[(2-bromo-5-fluorophenyl)methyl]-3-[(4-fluorophenyl)methyl]-4,5-dihydro-1,2,4-oxadiazol-5-one |
| 6 | 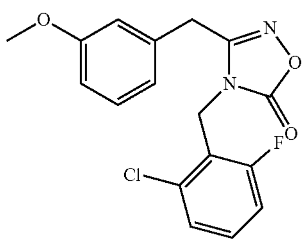 [SMILES: COc1cccc(Cc2noc(=O)n2Cc2c(F)cccc2Cl)c1] | 3-benzyl-4-[(2-chloro-6-fluorophenyl)methyl]-4,5-dihydro-1,2,4-oxadiazol-5-one |
| 7 | 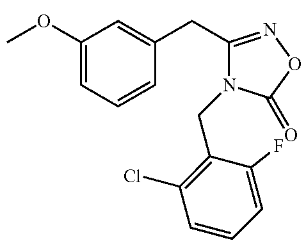 [SMILES: COc1cccc(Cc2noc(=O)n2Cc2c(F)cccc2Cl)c1] | 4-[(2-chloro-6-fluorophenyl)methyl]-3-[(3-methoxyphenyl)methyl]-4,5-dihydro-1,2,4-oxadiazol-5-one |
| 8 | 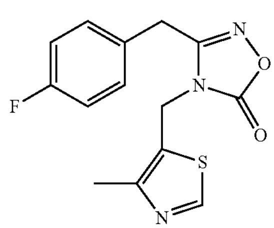 [SMILES: Cc1ncsc1Cn1c(Cc2ccc(F)cc2)noc1=O] | 3-[(4-fluorophenyl)methyl]-4-[(4-methyl-1,3-thiazol-5-yl)methyl]-4,5-dihydro-1,2,4-oxadiazol-5-one |

TABLE 1-continued

| Example | Structure | IUPAC Name |
|---|---|---|
| 9 | 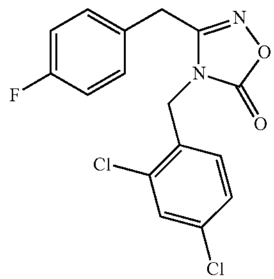 | 4-[(2,4-dichlorophenyl)methyl]-3-[(4-fluorophenyl)methyl]-4,5-dihydro-1,2,4-oxadiazol-5-one |
| 10 | 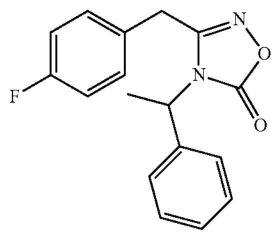 [SMILES: CC(c1ccccc1)n1c(Cc2ccc(F)cc2)noc1=O] | 3-[(4-fluorophenyl)methyl]-4-(1-phenylethyl)-4,5-dihydro-1,2,4-oxadiazol-5-one |
| 11 | 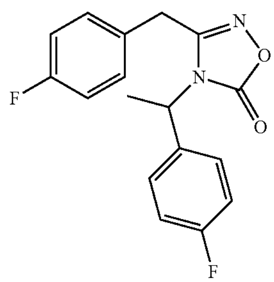 [SMILES: CC(c1ccc(F)cc1)n1c(Cc2ccc(F)cc2)noc1=O] | 4-[1-(4-fluorophenyl)ethyl]-3-[(4-fluorophenyl)methyl]-4,5-dihydro-1,2,4-oxadiazol-5-one |
| 12 | 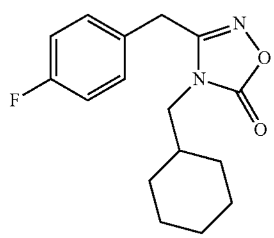 [SMILES: O=c1onc(Cc2ccc(F)cc2)n1CC1CCCCC1] | 4-(cyclohexylmethyl)-3-[(4-fluorophenyl)methyl]-4,5-dihydro-1,2,4-oxadiazol-5-one |
| 13 | 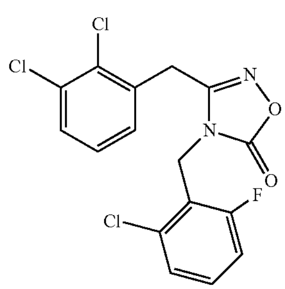 [SMILES: O=c1onc(Cc2cccc(Cl)c2Cl)n1Cc1c(F)cccc1Cl] | 4-[(2-chloro-6-fluorophenyl)methyl]-3-[(2,3-dichlorophenyl)methyl]-4,5-dihydro-1,2,4-oxadiazol-5-one |
| 14 | 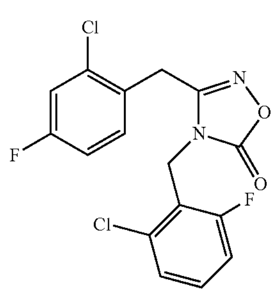 | 3-[(2-chloro-4-fluorophenyl)methyl]-4-[(2-chloro-6-fluorophenyl)methyl]-4,5-dihydro-1,2,4-oxadiazol-5-one |

TABLE 1-continued

| Example | Structure | IUPAC Name |
|---------|-----------|------------|
| 15 | 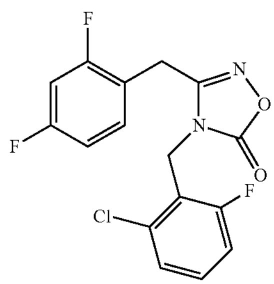 [SMILES: O=c1onc(Cc2ccc(F)cc2F)n1Cc1c(F)cccc1Cl] | 4-[(2-chloro-6-fluorophenyl)methyl]-3-[(2,4-difluorophenyl)methyl]-4,5-dihydro-1,2,4-oxadiazol-5-one |
| 16 | 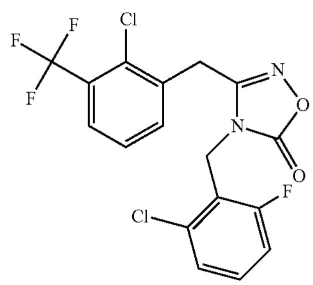 [SMILES: O=c1onc(Cc2cccc(C(F)(F)F)c2Cl)n1Cc1c(F)cccc1Cl] | 3-{[2-chloro-3-(trifluoromethyl)phenyl]methyl}-4-[(2-chloro-6-fluorophenyl)methyl]-4,5-dihydro-1,2,4-oxadiazol-5-one |
| 17 | 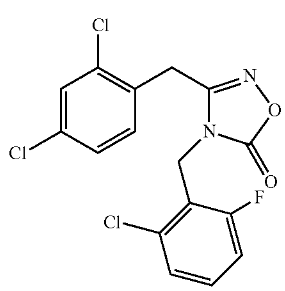 [SMILES: O=c1onc(Cc2ccc(Cl)cc2Cl)n1Cc1c(F)cccc1Cl] | 4-[(2-chloro-6-fluorophenyl)methyl]-3-[(2,4-dichlorophenyl)methyl]-4,5-dihydro-1,2,4-oxadiazol-5-one |
| 18 | 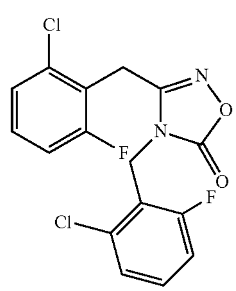 [SMILES: O=c1onc(Cc2c(F)cccc2Cl)n1Cc1c(F)cccc1Cl] | bis[(2-chloro-6-fluorophenyl)methyl]-4,5-dihydro-1,2,4-oxadiazol-5-one |
| 19 | 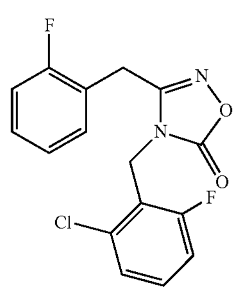 [SMILES: O=c1onc(Cc2ccccc2F)n1Cc1c(F)cccc1Cl] | 4-[(2-chloro-6-fluorophenyl)methyl]-3-[(2-fluorophenyl)methyl]-4,5-dihydro-1,2,4-oxadiazol-5-one |

TABLE 1-continued

| Example | Structure | IUPAC Name |
|---|---|---|
| 20 | 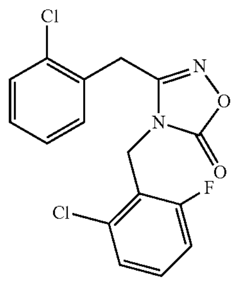 [SMILES: O=c1onc(Cc2ccccc2Cl)n1Cc1c(F)cccc1Cl] | 4-[(2-chloro-6-fluorophenyl)methyl]-3-[(2-chlorophenyl)methyl]-4,5-dihydro-1,2,4-oxadiazol-5-one |
| 21 | 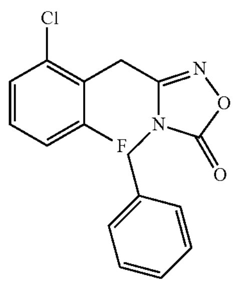 [SMILES: O=c1onc(Cc2c(F)cccc2Cl)n1Cc1ccccc1] | 4-benzyl-3-[(2-chloro-6-fluorophenyl)methyl]-4,5-dihydro-1,2,4-oxadiazol-5-one |
| 22 | 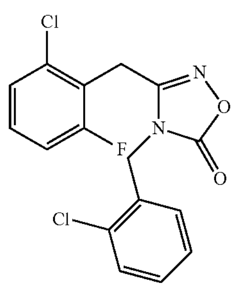 [SMILES: O=c1onc(Cc2c(F)cccc2Cl)n1Cc1ccccc1Cl] | 3-[(2-chloro-6-fluorophenyl)methyl]-4-[(2-chlorophenyl)methyl]-4,5-dihydro-1,2,4-oxadiazol-5-one |
| 23 | 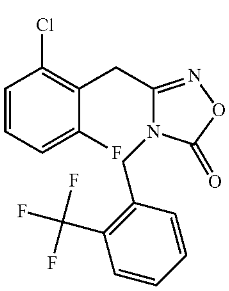 [SMILES: O=c1onc(Cc2c(F)cccc2Cl)n1Cc1ccccc1C(F)(F)F] | 3-[(2-chloro-6-fluorophenyl)methyl]-4-{[2-(trifluoromethyl)phenyl]methyl}-4,5-dihydro-1,2,4-oxadiazol-5-one |
| 24 | 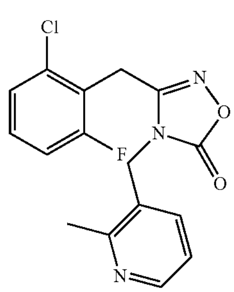 [SMILES: Cc1ncccc1Cn1c(Cc2c(F)cccc2Cl)noc1=O] | 3-[(2-chloro-6-fluorophenyl)methyl]-4-[(2-methylpyridin-3-yl)methyl]-4,5-dihydro-1,2,4-oxadiazol-5-one |

TABLE 1-continued

| Example | Structure | IUPAC Name |
|---|---|---|
| 25 | 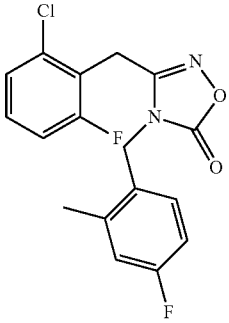 [SMILES: Cc1cc(F)ccc1Cn1c(Cc2c(F)cccc2Cl)noc1=O] | 3-[(2-chloro-6-fluorophenyl)methyl]-4-[(4-fluoro-2-methylphenyl)methyl]-4,5-dihydro-1,2,4-oxadiazol-5-one |
| 26 | 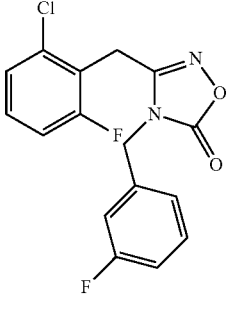 [SMILES: O=c1onc(Cc2c(F)cccc2Cl)n1Cc1cccc(F)c1] | 3-[(2-chloro-6-fluorophenyl)methyl]-4-[(3-fluorophenyl)methyl]-4,5-dihydro-1,2,4-oxadiazol-5-one |
| 27 | 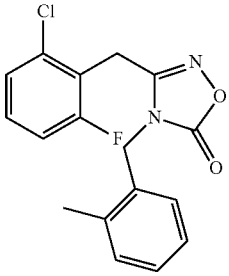 [SMILES: Cc1ccccc1Cn1c(Cc2c(F)cccc2Cl)noc1=O] | 3-[(2-chloro-6-fluorophenyl)methyl]-4-[(2-methylphenyl)methyl]-4,5-dihydro-1,2,4-oxadiazol-5-one |
| 28 | 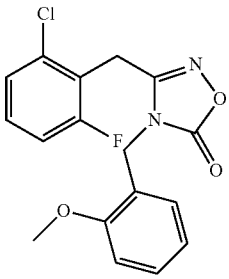 [SMILES: COc1ccccc1Cn1c(Cc2c(F)cccc2Cl)noc1=O] | 3-[(2-chloro-6-fluorophenyl)methyl]-4-[(2-methoxyphenyl)methyl]-4,5-dihydro-1,2,4-oxadiazol-5-one |
| 29 | 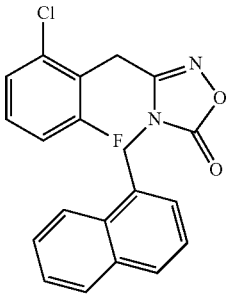 [SMILES: O=c1onc(Cc2c(F)cccc2Cl)n1Cc1cccc2ccccc12] | 3-[(2-chloro-6-fluorophenyl)methyl]-4-(naphthalen-1-ylmethyl)-4,5-dihydro-1,2,4-oxadiazol-5-one |

TABLE 1-continued

| Example | Structure | IUPAC Name |
|---|---|---|
| 30 | 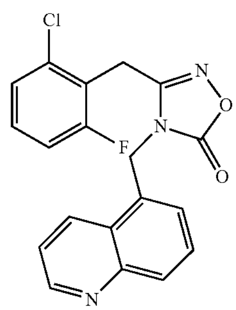 [SMILES: O=c1onc(Cc2c(F)cccc2Cl)n1Cc1cccc2ncccc12] | 3-[(2-chloro-6-fluorophenyl)methyl]-4-(quinolin-5-ylmethyl)-4,5-dihydro-1,2,4-oxadiazol-5-one |
| 31 | 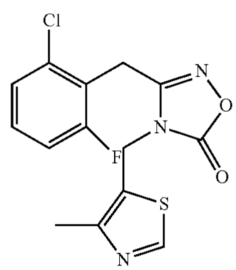 [SMILES: Cc1ncsc1Cn1c(Cc2c(F)cccc2Cl)noc1=O] | 3-[(2-chloro-6-fluorophenyl)methyl]-4-[(4-methyl-1,3-thiazol-5-yl)methyl]-4,5-dihydro-1,2,4-oxadiazol-5-one |
| 32 | 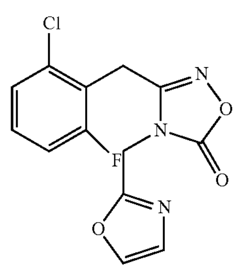 [SMILES: O=c1onc(Cc2c(F)cccc2Cl)n1Cc1ncco1] | 3-[(2-chloro-6-fluorophenyl)methyl]-4-(1,3-oxazol-2-ylmethyl)-4,5-dihydro-1,2,4-oxadiazol-5-one |
| 33 | 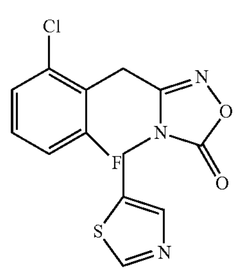 [SMILES: O=c1onc(Cc2c(F)cccc2Cl)n1Cc1cncs1] | 3-[(2-chloro-6-fluorophenyl)methyl]-4-(1,3-thiazol-5-ylmethyl)-4,5-dihydro-1,2,4-oxadiazol-5-one |
| 34 | 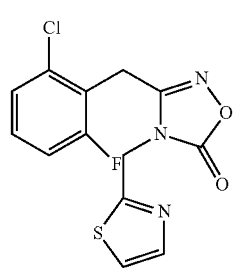 | 3-[(2-chloro-6-fluorophenyl)methyl]-4-(1,3-thiazol-2-ylmethyl)-4,5-dihydro-1,2,4-oxadiazol-5-one |

TABLE 1-continued

| Example | Structure | IUPAC Name |
|---|---|---|
| 35 | 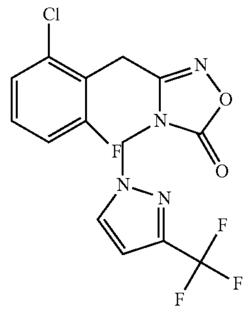 [SMILES: O=c1onc(Cc2c(F)cccc2Cl)n1Cn1ccc(C(F)(F)F)n1] | 3-[(2-chloro-6-fluorophenyl)methyl]-4-{[3-(trifluoromethyl)-1H-pyrazol-1-yl]methyl}-4,5-dihydro-1,2,4-oxadiazol-5-one |
| 36 | 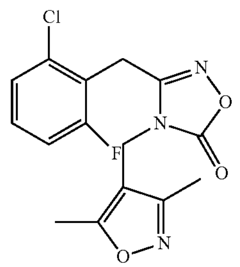 [SMILES: Cc1noc(C)c1Cn1c(Cc2c(F)cccc2Cl)noc1=O] | 3-[(2-chloro-6-fluorophenyl)methyl]-4-[(dimethyl-1,2-oxazol-4-yl)methyl]-4,5-dihydro-1,2,4-oxadiazol-5-one |
| 37 | 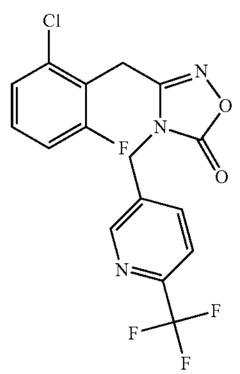 [SMILES: O=c1onc(Cc2c(F)cccc2Cl)n1Cc1ccc(C(F)(F)F)nc1] | 3-[(2-chloro-6-fluorophenyl)methyl]-4-{[6-(trifluoromethyl)pyridin-3-yl]methyl}-4,5-dihydro-1,2,4-oxadiazol-5-one |
| 38 | 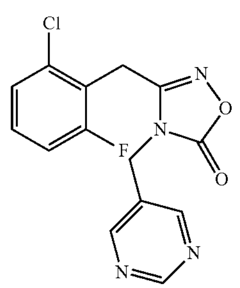 [SMILES: O=c1onc(Cc2c(F)cccc2Cl)n1Cc1cncnc1] | 3-[(2-chloro-6-fluorophenyl)methyl]-4-(pyrimidin-5-ylmethyl)-4,5-dihydro-1,2,4-oxadiazol-5-one |
| 39 | 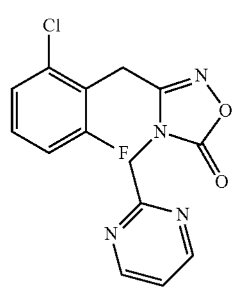 [SMILES: O=c1onc(Cc2c(F)cccc2Cl)n1Cc1ncccn1] | 3-[(2-chloro-6-fluorophenyl)methyl]-4-(pyrimidin-2-ylmethyl)-4,5-dihydro-1,2,4-oxadiazol-5-one |

TABLE 1-continued

| Example | Structure | IUPAC Name |
|---|---|---|
| 40 | 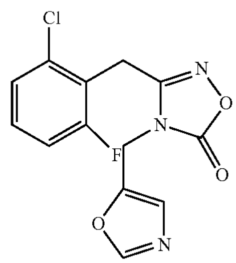 [SMILES: O=c1onc(Cc2c(F)cccc2Cl)n1Cc1cnco1] | 3-[(2-chloro-6-fluorophenyl)methyl]-4-(1,3-oxazol-5-ylmethyl)-4,5-dihydro-1,2,4-oxadiazol-5-one |
| 41 | 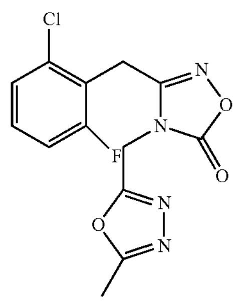 [SMILES: Cc1nnc(Cn2c(Cc3c(F)cccc3Cl)noc2=O)o1] | 3-[(2-chloro-6-fluorophenyl)methyl]-4-[(5-methyl-1,3,4-oxadiazol-2-yl)methyl]-4,5-dihydro-1,2,4-oxadiazol-5-one |
| 42 | 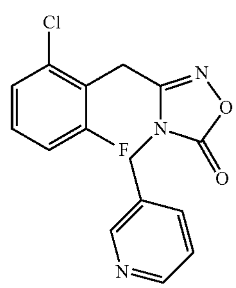 [SMILES: O=c1onc(Cc2c(F)cccc2Cl)n1Cc1cccnc1] | 3-[(2-chloro-6-fluorophenyl)methyl]-4-(pyridin-3-ylmethyl)-4,5-dihydro-1,2,4-oxadiazol-5-one |
| 43 | 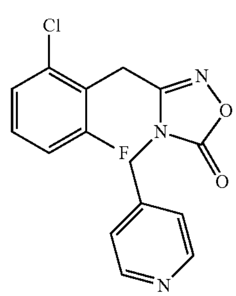 [SMILES: O=c1onc(Cc2c(F)cccc2Cl)n1Cc1ccncc1] | 3-[(2-chloro-6-fluorophenyl)methyl]-4-(pyridin-4-ylmethyl)-4,5-dihydro-1,2,4-oxadiazol-5-one |
| 44 | 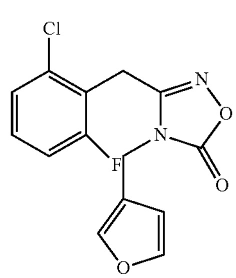 [SMILES: O=c1onc(Cc2c(F)cccc2Cl)n1Cc1ccoc1] | 3-[(2-chloro-6-fluorophenyl)methyl]-4-(furan-3-ylmethyl)-4,5-dihydro-1,2,4-oxadiazol-5-one |

TABLE 1-continued

| Example | Structure | IUPAC Name |
|---|---|---|
| 45 | 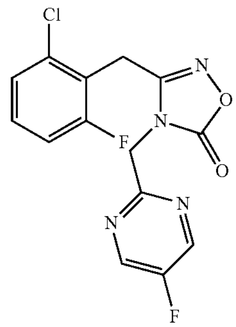 [SMILES: O=c1onc(Cc2c(F)cccc2Cl)n1Cc1ncc(F)cn1] | 3-[(2-chloro-6-fluorophenyl)methyl]-4-[(5-fluoropyrimidin-2-yl)methyl]-4,5-dihydro-1,2,4-oxadiazol-5-one |
| 46 | 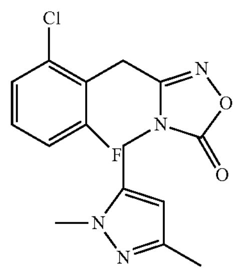 [SMILES: Cc1cc(Cn2c(Cc3c(F)cccc3Cl)noc2=O)n(C)n1] | 3-[(2-chloro-6-fluorophenyl)methyl]-4-[(1,3-dimethyl-1H-pyrazol-5-yl)methyl]-4,5-dihydro-1,2,4-oxadiazol-5-one |
| 47 | 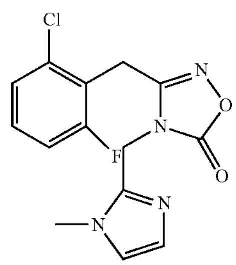 [SMILES: Cn1ccnc1Cn1c(Cc2c(F)cccc2Cl)noc1=O] | 3-[(2-chloro-6-fluorophenyl)methyl]-4-[(1-methyl-1H-imidazol-2-yl)methyl]-4,5-dihydro-1,2,4-oxadiazol-5-one |
| 48 | 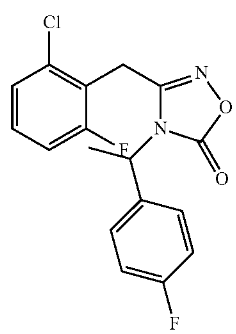 [SMILES: CC(c1ccc(F)cc1)n1c(Cc2c(F)cccc2Cl)noc1=O] | 3-[(2-chloro-6-fluorophenyl)methyl]-4-[1-(4-fluorophenyl)ethyl]-4,5-dihydro-1,2,4-oxadiazol-5-one |
| 49 | 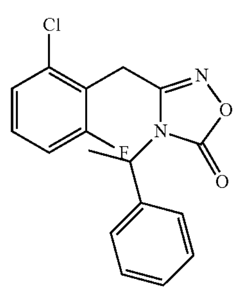 [SMILES: CC(c1ccccc1)n1c(Cc2c(F)cccc2Cl)noc1=O] | 3-[(2-chloro-6-fluorophenyl)methyl]-4-(1-phenylethyl)-4,5-dihydro-1,2,4-oxadiazol-5-one |

TABLE 1-continued

| Example | Structure | IUPAC Name |
|---|---|---|
| 50 | 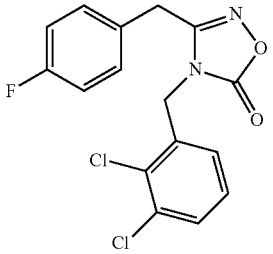 [SMILES: O=c1onc(Cc2ccc(F)cc2)n1Cc1cccc(Cl)c1Cl] | 4-[(2,3-dichlorophenyl)methyl]-3-[(4-fluorophenyl)methyl]-4,5-dihydro-1,2,4-oxadiazol-5-one |
| 51 | 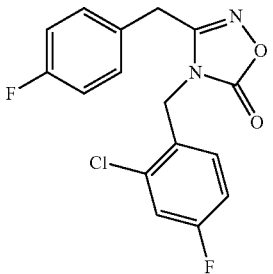 [SMILES: O=c1onc(Cc2ccc(F)cc2)n1Cc1ccc(F)cc1Cl] | 4-[(2-chloro-4-fluorophenyl)methyl]-3-[(4-fluorophenyl)methyl]-4,5-dihydro-1,2,4-oxadiazol-5-one |
| 52 | 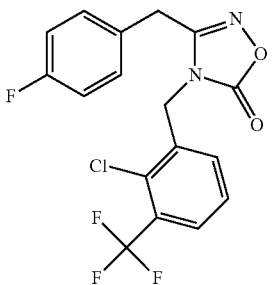 [SMILES: O=c1onc(Cc2ccc(F)cc2)n1Cc1cccc(C(F)(F)F)c1Cl] | 4-{[2-chloro-3-(trifluoromethyl)phenyl]methyl}-3-[(4-fluorophenyl)methyl]-4,5-dihydro-1,2,4-oxadiazol-5-one |
| 53 | 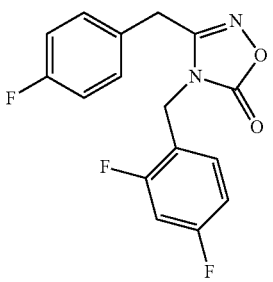 | 4-[(2,4-difluorophenyl)methyl]-3-[(4-fluorophenyl)methyl]-4,5-dihydro-1,2,4-oxadiazol-5-one |
| 54 | 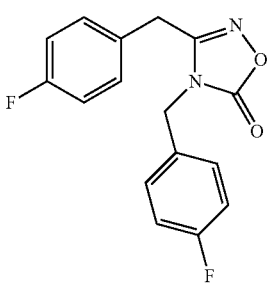 [SMILES: O=c1onc(Cc2ccc(F)cc2)n1Cc1ccc(F)cc1] | bis[(4-fluorophenyl)methyl]-4,5-dihydro-1,2,4-oxadiazol-5-one |

TABLE 1-continued

| Example | Structure | IUPAC Name |
|---|---|---|
| 55 | 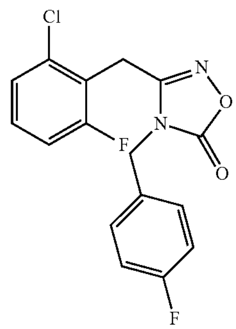 [SMILES: O=c1onc(Cc2c(F)cccc2Cl)n1Cc1ccc(F)cc1] | 3-[(2-chloro-6-fluorophenyl)methyl]-4-[(4-fluorophenyl)methyl]-4,5-dihydro-1,2,4-oxadiazol-5-one |
| 56 | 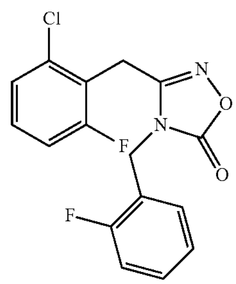 | 3-[(2-chloro-6-fluorophenyl)methyl]-4-[(2-fluorophenyl)methyl]-4,5-dihydro-1,2,4-oxadiazol-5-one |
| 57 | 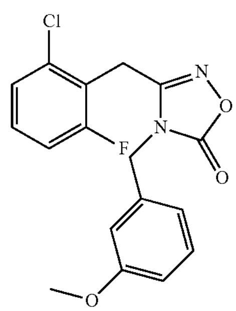 [SMILES: COc1cccc(Cn2c(Cc3c(F)cccc3Cl)noc2=O)c1] | 3-[(2-chloro-6-fluorophenyl)methyl]-4-[(3-methoxyphenyl)methyl]-4,5-dihydro-1,2,4-oxadiazol-5-one |
| 58 | 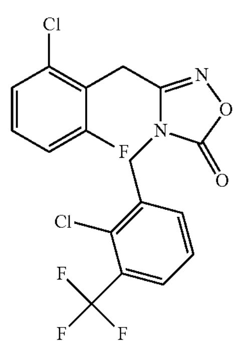 [SMILES: O=c1onc(Cc2c(F)cccc2Cl)n1Cc1cccc(C(F)(F)F)c1Cl] | 4-{[2-chloro-3-(trifluoromethyl)phenyl]methyl}-3-[(2-chloro-6-fluorophenyl)methyl]-4,5-dihydro-1,2,4-oxadiazol-5-one |
| 59 | 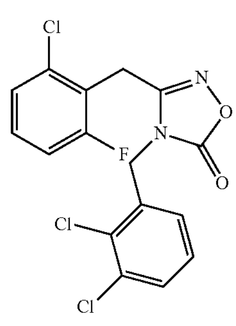 [SMILES: O=c1onc(Cc2c(F)cccc2Cl)n1Cc1cccc(Cl)c1Cl] | 3-[(2-chloro-6-fluorophenyl)methyl]-4-[(2,3-dichlorophenyl)methyl]-4,5-dihydro-1,2,4-oxadiazol-5-one |

TABLE 1-continued
| Example | Structure | IUPAC Name |
|---|---|---|
| 60 | 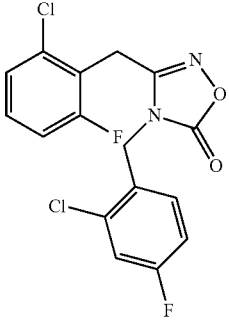 | 4-[(2-chloro-4-fluorophenyl)methyl]-3-[(2-chloro-6-fluorophenyl)methyl]-4,5-dihydro-1,2,4-oxadiazol-5-one |
| 61 | 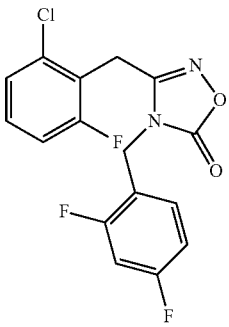 [SMILES: O=c1onc(Cc2c(F)cccc2Cl)n1Cc1ccc(F)cc1F] | 3-[(2-chloro-6-fluorophenyl)methyl]-4-[(2,4-difluorophenyl)methyl]-4,5-dihydro-1,2,4-oxadiazol-5-one |
| 62 | 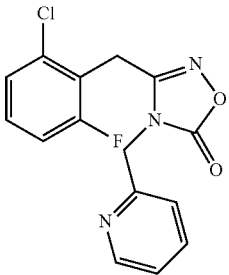 [SMILES: O=c1onc(Cc2c(F)cccc2Cl)n1Cc1ccccn1] | 3-[(2-chloro-6-fluorophenyl)methyl]-4-(pyridin-2-ylmethyl)-4,5-dihydro-1,2,4-oxadiazol-5-one |
| 63 | 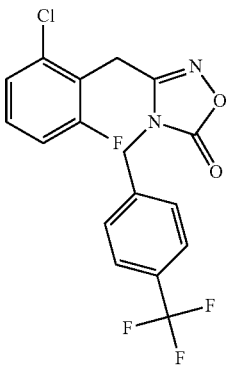 [SMILES: O=c1onc(Cc2c(F)cccc2Cl)n1Cc1ccc(C(F)(F)F)cc1] | 3-[(2-chloro-6-fluorophenyl)methyl]-4-{[4-(trifluoromethyl)phenyl]methyl}-4,5-dihydro-1,2,4-oxadiazol-5-one |

TABLE 1-continued

| Example | Structure | IUPAC Name |
|---|---|---|
| 64 | 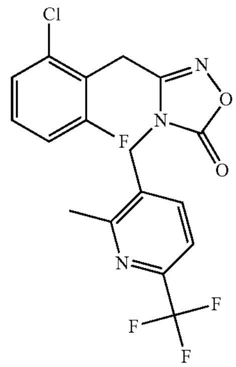 [SMILES: Cc1nc(C(F)(F)F)ccc1Cn1c(Cc2c(F)cccc2Cl)noc1=O] | 3-[(2-chloro-6-fluorophenyl)methyl]-4-{[2-methyl-6-(trifluoromethyl)pyridin-3-yl]methyl}-4,5-dihydro-1,2,4-oxadiazol-5-one |
| 65 | 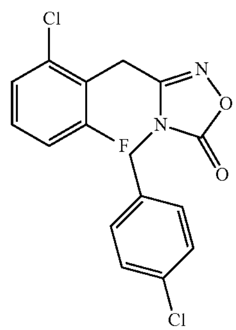 [SMILES: O=c1onc(Cc2c(F)cccc2Cl)n1Cc1ccc(Cl)cc1] | 3-[(2-chloro-6-fluorophenyl)methyl]-4-[(4-chlorophenyl)methyl]-4,5-dihydro-1,2,4-oxadiazol-5-one |
| 66 | 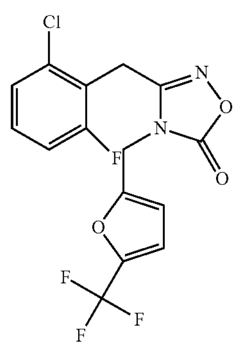 [SMILES: O=c1onc(Cc2c(F)cccc2Cl)n1Cc1ccc(C(F)(F)F)o1] | 3-[(2-chloro-6-fluorophenyl)methyl]-4-{[5-(trifluoromethyl)furan-2-yl]methyl}-4,5-dihydro-1,2,4-oxadiazol-5-one |
| 67 | 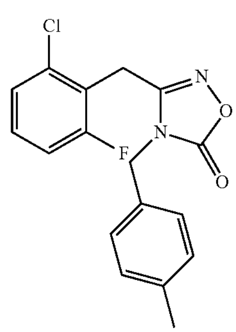 [SMILES: Cc1ccc(Cn2c(Cc3c(F)cccc3Cl)noc2=O)cc1] | 3-[(2-chloro-6-fluorophenyl)methyl]-4-[(4-methylphenyl)methyl]-4,5-dihydro-1,2,4-oxadiazol-5-one |

TABLE 1-continued

| Example | Structure | IUPAC Name |
|---|---|---|
| 68 | 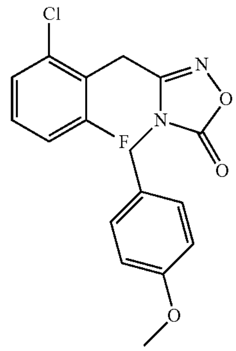 [SMILES: COc1ccc(Cn2c(Cc3c(F)cccc3Cl)noc2=O)cc1] | 3-[(2-chloro-6-fluorophenyl)methyl]-4-[(4-methoxyphenyl)methyl]-4,5-dihydro-1,2,4-oxadiazol-5-one |
| 69 | 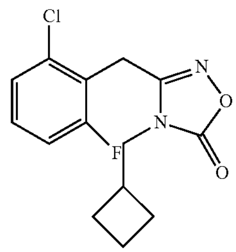 [SMILES: O=c1onc(Cc2c(F)cccc2Cl)n1CC1CCC1] | 3-[(2-chloro-6-fluorophenyl)methyl]-4-(cyclobutylmethyl)-4,5-dihydro-1,2,4-oxadiazol-5-one |
| 70 | 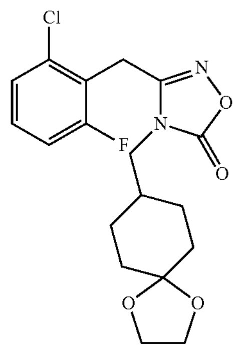 [SMILES: O=c1onc(Cc2c(F)cccc2Cl)n1CC1CCC2(CC1)OCCO2] | 3-[(2-chloro-6-fluorophenyl)methyl]-4-{1,4-dioxaspiro[4.5]decan-8-ylmethyl}-4,5-dihydro-1,2,4-oxadiazol-5-one |
| 71 | 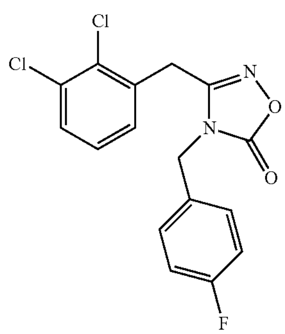 [SMILES: O=c1onc(Cc2cccc(Cl)c2Cl)n1Cc1ccc(F)cc1] | 3-[(2,3-dichlorophenyl)methyl]-4-[(4-fluorophenyl)methyl]-4,5-dihydro-1,2,4-oxadiazol-5-one |
| 72 | 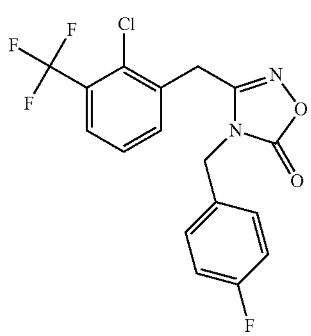 [SMILES: O=c1onc(Cc2cccc(C(F)(F)F)c2Cl)n1Cc1ccc(F)cc1] | 3-{[2-chloro-3-(trifluoromethyl)phenyl]methyl}-4-[(4-fluorophenyl)methyl]-4,5-dihydro-1,2,4-oxadiazol-5-one |

TABLE 1-continued

| Example | Structure | IUPAC Name |
|---|---|---|
| 73 | 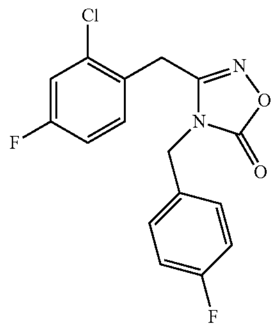 | 3-[(2-chloro-4-fluorophenyl)methyl]-4-[(4-fluorophenyl)methyl]-4,5-dihydro-1,2,4-oxadiazol-5-one |
| 74 | 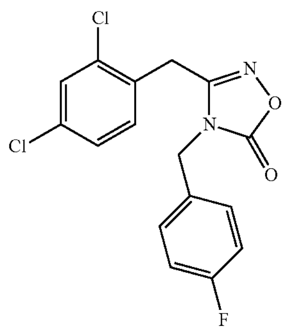 [SMILES: O=c1onc(Cc2ccc(Cl)cc2Cl)n1Cc1ccc(F)cc1] | 3-[(2,4-dichlorophenyl)methyl]-4-[(4-fluorophenyl)methyl]-4,5-dihydro-1,2,4-oxadiazol-5-one |
| 75 | 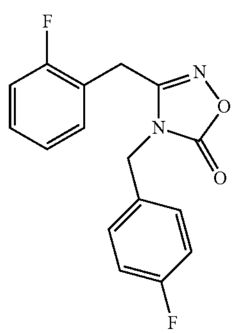 [SMILES: O=c1onc(Cc2ccccc2F)n1Cc1ccc(F)cc1] | 3-[(2-fluorophenyl)methyl]-4-[(4-fluorophenyl)methyl]-4,5-dihydro-1,2,4-oxadiazol-5-one |
| 76 | 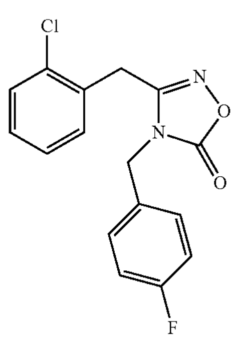 [SMILES: O=c1onc(Cc2ccccc2Cl)n1Cc1ccc(F)cc1] | 3-[(2-chlorophenyl)methyl]-4-[(4-fluorophenyl)methyl]-4,5-dihydro-1,2,4-oxadiazol-5-one |

TABLE 1-continued

| Example | Structure | IUPAC Name |
|---|---|---|
| 77 | 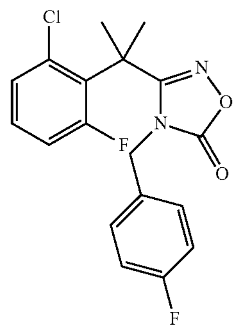 [SMILES: CC(C)(c1c(F)cccc1Cl)c1noc(=O)n1Cc1ccc(F)cc1] | 3-[2-(2-chloro-6-fluorophenyl)propan-2-yl]-4-[(4-fluorophenyl)methyl]-4,5-dihydro-1,2,4-oxadiazol-5-one |
| 78 | 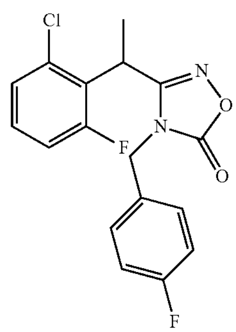 [SMILES: CC(c1c(F)cccc1Cl)c1noc(=O)n1Cc1ccc(F)cc1] | 3-[1-(2-chloro-6-fluorophenyl)ethyl]-4-[(4-fluorophenyl)methyl]-4,5-dihydro-1,2,4-oxadiazol-5-one |
| 79 | 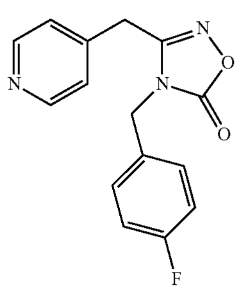 [SMILES: O=c1onc(Cc2ccncc2)n1Cc1ccc(F)cc1] | 4-[(4-fluorophenyl)methyl]-3-(pyridin-4-ylmethyl)-4,5-dihydro-1,2,4-oxadiazol-5-one |
| 80 | 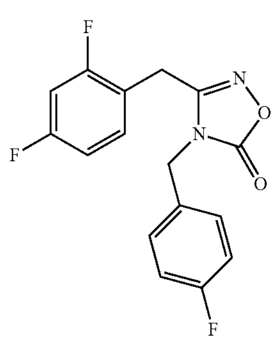 [SMILES: O=c1onc(Cc2ccc(F)cc2F)n1Cc1ccc(F)cc1] | 3-[(2,4-difluorophenyl)methyl]-4-[(4-fluorophenyl)methyl]-4,5-dihydro-1,2,4-oxadiazol-5-one |
| 81 | 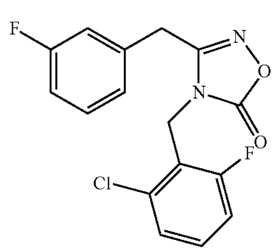 [SMILES: O=c1onc(Cc2cccc(F)c2)n1Cc1c(F)cccc1Cl] | 4-[(2-chloro-6-fluorophenyl)methyl]-3-[(3-fluorophenyl)methyl]-4,5-dihydro-1,2,4-oxadiazol-5-one |

TABLE 1-continued

| Example | Structure | IUPAC Name |
|---|---|---|
| 82 | 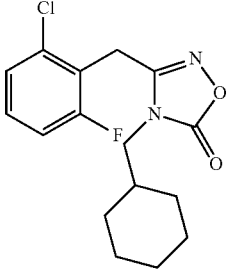 | 3-[(2-chloro-6-fluorophenyl)methyl]-4-(cyclohexylmethyl)-4,5-dihydro-1,2,4-oxadiazol-5-one |
| 83 | 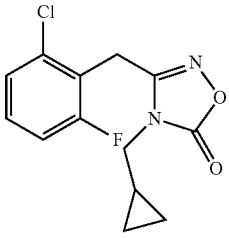 [SMILES: O=c1onc(Cc2c(F)cccc2Cl)n1CC1CC1] | 3-[(2-chloro-6-fluorophenyl)methyl]-4-(cyclopropylmethyl)-4,5-dihydro-1,2,4-oxadiazol-5-one |
| 84 | 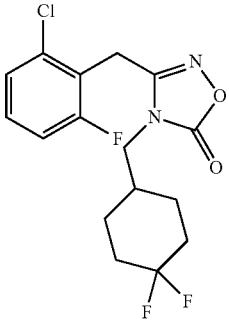 [SMILES: O=c1onc(Cc2c(F)cccc2Cl)n1CC1CCC(F)(F)CC1] | 3-[(2-chloro-6-fluorophenyl)methyl]-4-[(4,4-difluorocyclohexyl)methyl]-4,5-dihydro-1,2,4-oxadiazol-5-one |
| 85 | 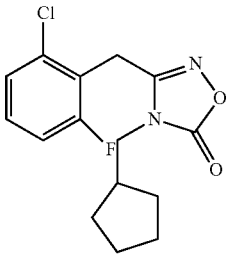 [SMILES: O=c1onc(Cc2c(F)cccc2Cl)n1CC1CCCC1] | 3-[(2-chloro-6-fluorophenyl)methyl]-4-(cyclopentylmethyl)-4,5-dihydro-1,2,4-oxadiazol-5-one |
| 86 | 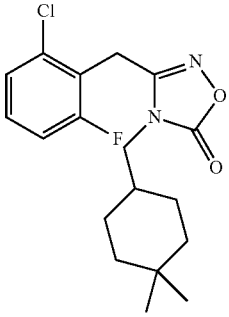 [SMILES: CC1(C)CCC(Cn2c(Cc3c(F)cccc3Cl)noc2=O)CC1] | 3-[(2-chloro-6-fluorophenyl)methyl]-4-[(4,4-dimethylcyclohexyl)methyl]-4,5-dihydro-1,2,4-oxadiazol-5-one |

TABLE 1-continued

| Example | Structure | IUPAC Name |
|---|---|---|
| 87 | 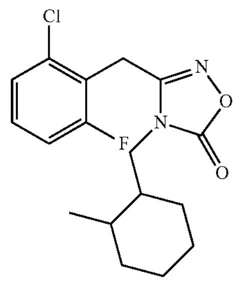 [SMILES: CC1CCCCC1Cn1c(Cc2c(F)cccc2Cl)noc1=O] | 3-[(2-chloro-6-fluorophenyl)methyl]-4-[(2-methylcyclohexyl)methyl]-4,5-dihydro-1,2,4-oxadiazol-5-one |
| 88 | 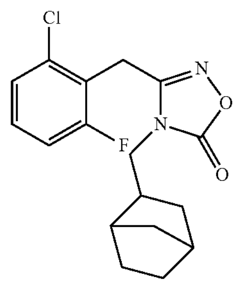 [SMILES: O=c1onc(Cc2c(F)cccc2Cl)n1CC1CC2CCC1C2] | 4-{bicyclo[2.2.1]heptan-2-ylmethyl}-3-[(2-chloro-6-fluorophenyl)methyl]-4,5-dihydro-1,2,4-oxadiazol-5-one |
| 89 | 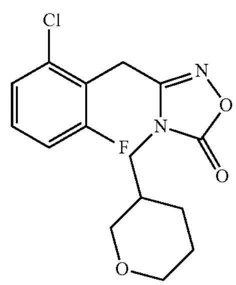 [SMILES: O=c1onc(Cc2c(F)cccc2Cl)n1CC1CCCOC1] | 3-[(2-chloro-6-fluorophenyl)methyl]-4-(oxan-3-ylmethyl)-4,5-dihydro-1,2,4-oxadiazol-5-one |
| 90 | 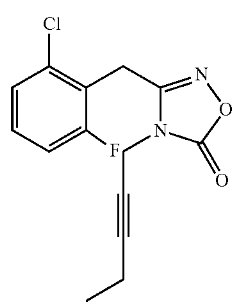 [SMILES: CCC#CCn1c(Cc2c(F)cccc2Cl)noc1=O] | 3-[(2-chloro-6-fluorophenyl)methyl]-4-(pent-2-yn-1-yl)-4,5-dihydro-1,2,4-oxadiazol-5-one |
| 91 | 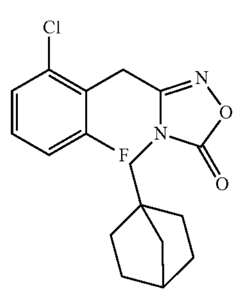 [SMILES: O=c1onc(Cc2c(F)cccc2Cl)n1CC12CCC(CC1)C2] | 4-{bicyclo[2.2.1]heptan-1-ylmethyl}-3-[(2-chloro-6-fluorophenyl)methyl]-4,5-dihydro-1,2,4-oxadiazol-5-one |

TABLE 1-continued

| Example | Structure | IUPAC Name |
|---|---|---|
| 92 | 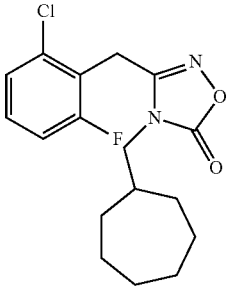 [SMILES: O=c1onc(Cc2c(F)cccc2Cl)n1CC1CCCCCC1] | 3-[(2-chloro-6-fluorophenyl)methyl]-4-(cycloheptylmethyl)-4,5-dihydro-1,2,4-oxadiazol-5-one |
| 93 | 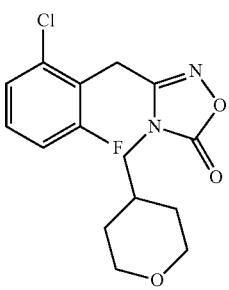 [SMILES: O=c1onc(Cc2c(F)cccc2Cl)n1CC1CCOCC1] | 3-[(2-chloro-6-fluorophenyl)methyl]-4-(oxan-4-ylmethyl)-4,5-dihydro-1,2,4-oxadiazol-5-one |
| 94 | 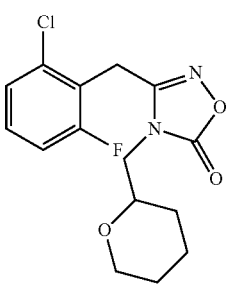 [SMILES: O=c1onc(Cc2c(F)cccc2Cl)n1CC1CCCCO1] | 3-[(2-chloro-6-fluorophenyl)methyl]-4-(oxan-2-ylmethyl)-4,5-dihydro-1,2,4-oxadiazol-5-one |
| 95 | 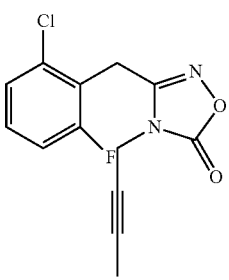 [SMILES: CC#CCn1c(Cc2c(F)cccc2Cl)noc1=O] | 4-(but-2-yn-1-yl)-3-[(2-chloro-6-fluorophenyl)methyl]-4,5-dihydro-1,2,4-oxadiazol-5-one |
| 96 | 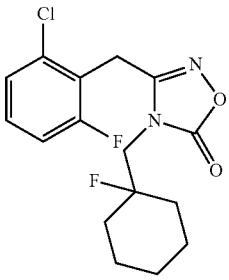 [SMILES: O=c1onc(Cc2c(F)cccc2Cl)n1CC1(F)CCCCC1] | 3-[(2-chloro-6-fluorophenyl)methyl]-4-[(1-fluorocyclohexyl)methyl]-4,5-dihydro-1,2,4-oxadiazol-5-one |

TABLE 1-continued

| Example | Structure | IUPAC Name |
|---|---|---|
| 97 | 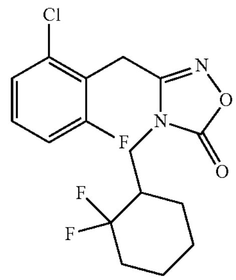 [SMILES: O=c1onc(Cc2c(F)cccc2Cl)n1CC1CCCCC1(F)F] | 3-[(2-chloro-6-fluorophenyl)methyl]-4-[(2,2-difluorocyclohexyl)methyl]-4,5-dihydro-1,2,4-oxadiazol-5-one |
| 98 | 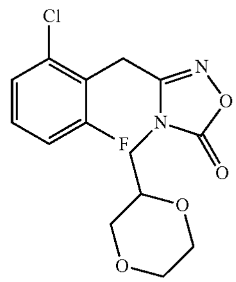 | 3-[(2-chloro-6-fluorophenyl)methyl]-4-(1,4-dioxan-2-ylmethyl)-4,5-dihydro-1,2,4-oxadiazol-5-one |
| 99 | 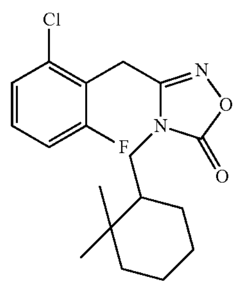 [SMILES: CC1(C)CCCCC1Cn1c(Cc2c(F)cccc2Cl)noc1=O] | 3-[(2-chloro-6-fluorophenyl)methyl]-4-[(2,2-dimethylcyclohexyl)methyl]-4,5-dihydro-1,2,4-oxadiazol-5-one |
| 100 | 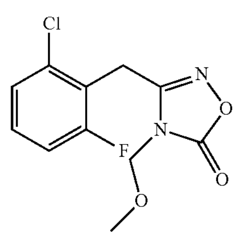 [SMILES: COCn1c(Cc2c(F)cccc2Cl)noc1=O] | 3-[(2-chloro-6-fluorophenyl)methyl]-4-(methoxymethyl)-4,5-dihydro-1,2,4-oxadiazol-5-one |
| 101 | 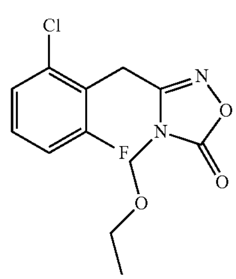 [SMILES: CCOCn1c(Cc2c(F)cccc2Cl)noc1=O] | 3-[(2-chloro-6-fluorophenyl)methyl]-4-(ethoxymethyl)-4,5-dihydro-1,2,4-oxadiazol-5-one |

TABLE 1-continued

| Example | Structure | IUPAC Name |
|---|---|---|
| 102 | 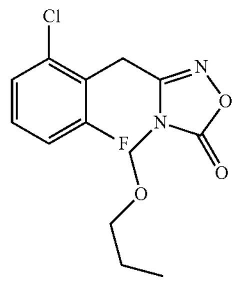 [SMILES: CCCOCn1c(Cc2c(F)cccc2Cl)noc1=O] | 3-[(2-chloro-6-fluorophenyl)methyl]-4-(propoxymethyl)-4,5-dihydro-1,2,4-oxadiazol-5-one |
| 104 | 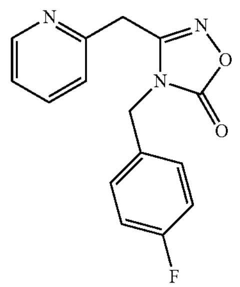 [SMILES: O=c1onc(Cc2ccccn2)n1Cc1ccc(F)cc1] | 4-[(4-fluorophenyl)methyl]-3-(pyridin-2-ylmethyl)-4,5-dihydro-1,2,4-oxadiazol-5-one |
| 105 | 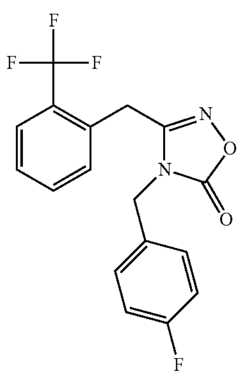 [SMILES: O=c1onc(Cc2ccccc2C(F)(F)F)n1Cc1ccc(F)cc1] | 4-[(4-fluorophenyl)methyl]-3-{[2-(trifluoromethyl)phenyl]methyl}-4,5-dihydro-1,2,4-oxadiazol-5-one |
| 107 | 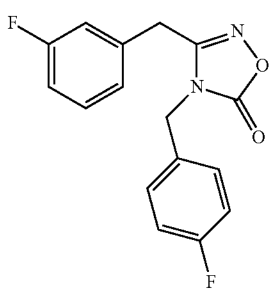 [SMILES: O=c1onc(Cc2cccc(F)c2)n1Cc1ccc(F)cc1] | 3-[(3-fluorophenyl)methyl]-4-[(4-fluorophenyl)methyl]-4,5-dihydro-1,2,4-oxadiazol-5-one |
| 108 | 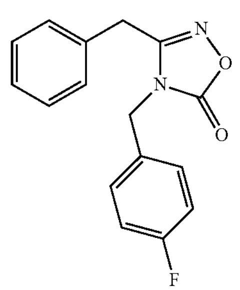 [SMILES: O=c1onc(Cc2ccccc2)n1Cc1ccc(F)cc1] | 3-benzyl-4-[(4-fluorophenyl)methyl]-4,5-dihydro-1,2,4-oxadiazol-5-one |

TABLE 1-continued

| Example | Structure | IUPAC Name |
|---------|-----------|------------|
| 109 | 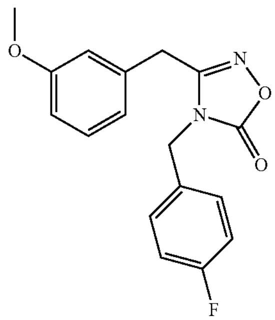 [SMILES: COc1cccc(Cc2noc(=O)n2Cc2ccc(F)cc2)c1] | 4-[(4-fluorophenyl)methyl]-3-[(3-methoxyphenyl)methyl]-4,5-dihydro-1,2,4-oxadiazol-5-one |
| 110 | 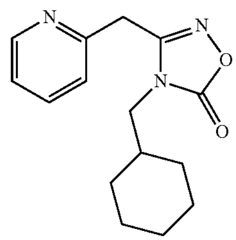 [SMILES: O=c1onc(Cc2ccccn2)n1CC1CCCCC1] | 4-(cyclohexylmethyl)-3-(pyridin-2-ylmethyl)-4,5-dihydro-1,2,4-oxadiazol-5-one |
| 111 | 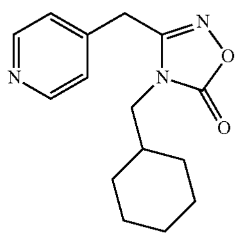 [SMILES: O=c1onc(Cc2ccncc2)n1CC1CCCCC1] | 4-(cyclohexylmethyl)-3-(pyridin-4-ylmethyl)-4,5-dihydro-1,2,4-oxadiazol-5-one |
| 112 | 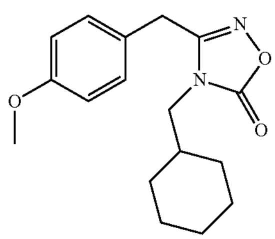 | 4-(cyclohexylmethyl)-3-[(4-methoxyphenyl)methyl]-4,5-dihydro-1,2,4-oxadiazol-5-one |
| 113 | 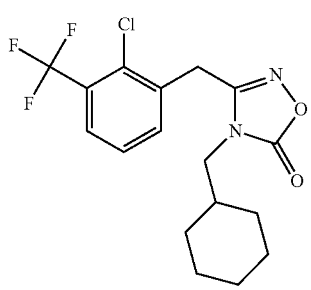 [SMILES: O=c1onc(Cc2cccc(C(F)(F)F)c2Cl)n1CC1CCCCC1] | 3-{[2-chloro-3-(trifluoromethyl)phenyl]methyl}-4-(cyclohexylmethyl)-4,5-dihydro-1,2,4-oxadiazol-5-one |
| 114 | 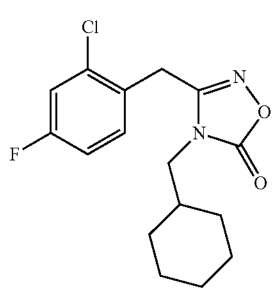 | 3-[(2-chloro-4-fluorophenyl)methyl]-4-(cyclohexylmethyl)-4,5-dihydro-1,2,4-oxadiazol-5-one |

TABLE 1-continued

| Example | Structure | IUPAC Name |
|---|---|---|
| 115 | 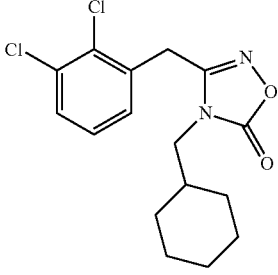 [SMILES: O=c1onc(Cc2cccc(Cl)c2Cl)n1CC1CCCCC1] | 4-(cyclohexylmethyl)-3-[(2,3-dichlorophenyl)methyl]-4,5-dihydro-1,2,4-oxadiazol-5-one |
| 116 | 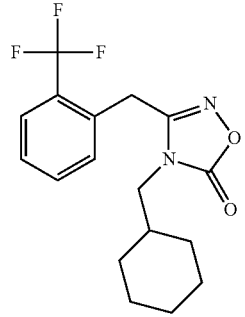 | 4-(cyclohexylmethyl)-3-{[2-(trifluoromethyl)phenyl]methyl}-4,5-dihydro-1,2,4-oxadiazol-5-one |
| 117 | 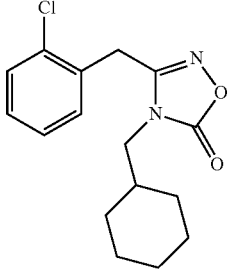 | 3-[(2-chlorophenyl)methyl]-4-(cyclohexylmethyl)-4,5-dihydro-1,2,4-oxadiazol-5-one |
| 118 | 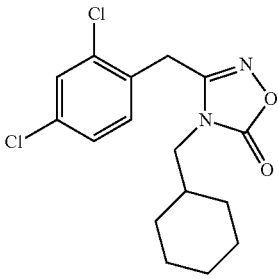 [SMILES: O=c1onc(Cc2ccc(Cl)cc2Cl)n1CC1CCCCC1] | 4-(cyclohexylmethyl)-3-[(2,4-dichlorophenyl)methyl]-4,5-dihydro-1,2,4-oxadiazol-5-one |
| 119 | 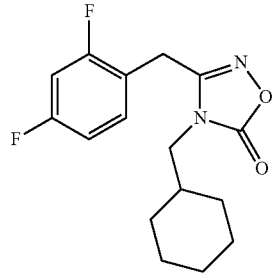 [SMILES: O=c1onc(Cc2ccc(F)cc2F)n1CC1CCCCC1] | 4-(cyclohexylmethyl)-3-[(2,4-difluorophenyl)methyl]-4,5-dihydro-1,2,4-oxadiazol-5-one |

TABLE 1-continued

| Example | Structure | IUPAC Name |
|---|---|---|
| 120 | 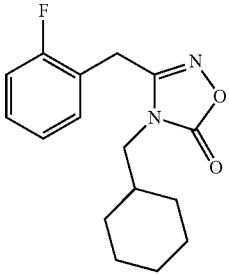 [SMILES: O=c1onc(Cc2ccccc2F)n1CC1CCCCC1] | 4-(cyclohexylmethyl)-3-[(2-fluorophenyl)methyl]-4,5-dihydro-1,2,4-oxadiazol-5-one |
| 121 | 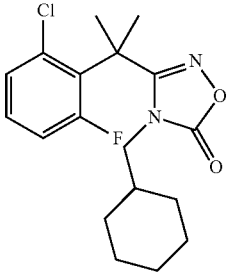 [SMILES: CC(C)(c1c(F)cccc1Cl)c1noc(=O)n1CC1CCCCC1] | 3-[2-(2-chloro-6-fluorophenyl)propan-2-yl]-4-(cyclohexylmethyl)-4,5-dihydro-1,2,4-oxadiazol-5-one |
| 122 | 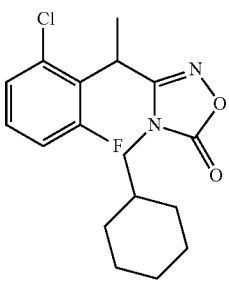 [SMILES: CC(c1c(F)cccc1Cl)c1noc(=O)n1CC1CCCCC1] | 3-[1-(2-chloro-6-fluorophenyl)ethyl]-4-(cyclohexylmethyl)-4,5-dihydro-1,2,4-oxadiazol-5-one |
| 123 | 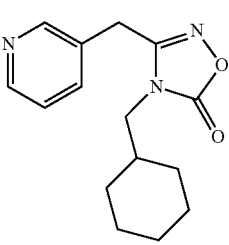 [SMILES: O=c1onc(Cc2cccnc2)n1CC1CCCCC1] | 4-(cyclohexylmethyl)-3-(pyridin-3-ylmethyl)-4,5-dihydro-1,2,4-oxadiazol-5-one |
| 125 | 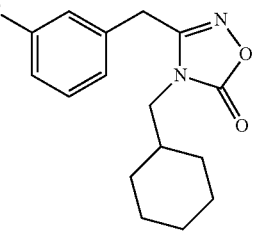 | 4-(cyclohexylmethyl)-3-[(3-fluorophenyl)methyl]-4,5-dihydro-1,2,4-oxadiazol-5-one |
| 126 | 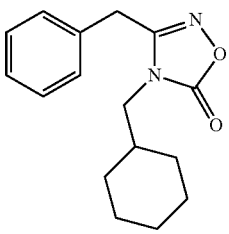 [SMILES: O=c1onc(Cc2ccccc2)n1CC1CCCCC1] | 3-benzyl-4-(cyclohexylmethyl)-4,5-dihydro-1,2,4-oxadiazol-5-one |

TABLE 1-continued

| Example | Structure | IUPAC Name |
|---|---|---|
| 127 | 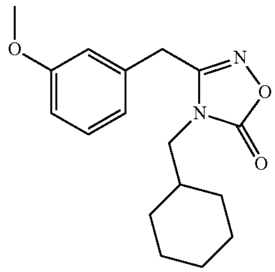 [SMILES: COc1cccc(Cc2noc(=O)n2CC2CCCCC2)c1] | 4-(cyclohexylmethyl)-3-[(3-methoxyphenyl)methyl]-4,5-dihydro-1,2,4-oxadiazol-5-one |
| 128 | 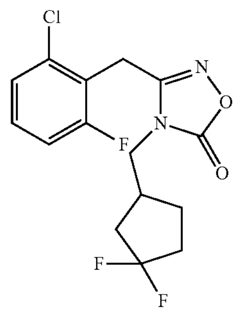 [SMILES: O=c1onc(Cc2c(F)cccc2Cl)n1CC1CCC(F)(F)C1] | 3-[(2-chloro-6-fluorophenyl)methyl]-4-[(3,3-difluorocyclopentyl)methyl]-4,5-dihydro-1,2,4-oxadiazol-5-one |
| 129 | 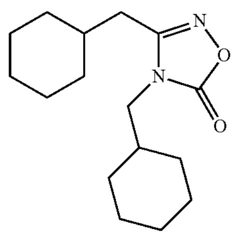 [SMILES: O=c1onc(CC2CCCCC2)n1CC1CCCCC1] | bis(cyclohexylmethyl)-4,5-dihydro-1,2,4-oxadiazol-5-one |
| 130 | 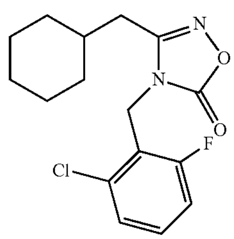 [SMILES: O=c1onc(CC2CCCCC2)n1Cc1c(F)cccc1Cl] | 4-[(2-chloro-6-fluorophenyl)methyl]-3-(cyclohexylmethyl)-4,5-dihydro-1,2,4-oxadiazol-5-one |
| 131 | 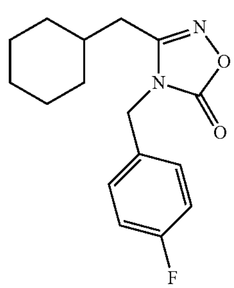 | 3-(cyclohexylmethyl)-4-[(4-fluorophenyl)methyl]-4,5-dihydro-1,2,4-oxadiazol-5-one |
| 132 | 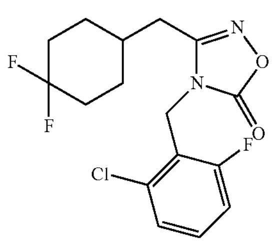 [SMILES: O=c1onc(CC2CCC(F)(F)CC2)n1Cc1c(F)cccc1Cl] | 4-[(2-chloro-6-fluorophenyl)methyl]-3-[(4,4-difluorocyclohexyl)methyl]-4,5-dihydro-1,2,4-oxadiazol-5-one |

TABLE 1-continued

| Example | Structure | IUPAC Name |
|---|---|---|
| 133 | 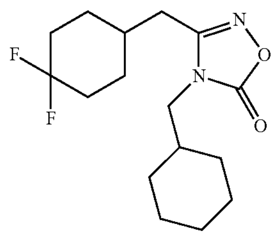 [SMILES: O=c1onc(CC2CCC(F)(F)CC2)n1CC1CCCCC1] | 4-(cyclohexylmethyl)-3-[(4,4-difluorocyclohexyl)methyl]-4,5-dihydro-1,2,4-oxadiazol-5-one |
| 134 | 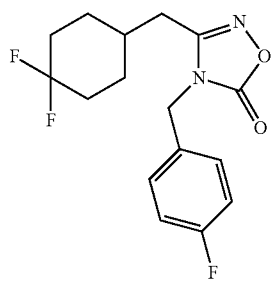 [SMILES: O=c1onc(CC2CCC(F)(F)CC2)n1Cc1ccc(F)cc1] | 4-(cyclohexylmethyl)-3-[(4,4-difluorocyclohexyl)methyl]-4,5-dihydro-1,2,4-oxadiazol-5-one |
| 135 | 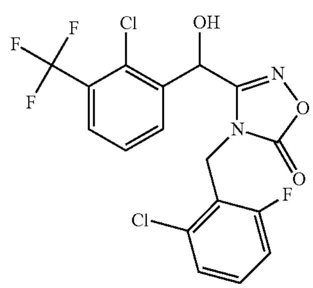 [SMILES: O=c1onc(C(O)c2cccc(C(F)(F)F)c2Cl)n1Cc1c(F)cccc1Cl] | 3-{[2-chloro-3-(trifluoromethyl)phenyl](hydroxy)methyl}-4-[(2-chloro-6-fluorophenyl)methyl]-4,5-dihydro-1,2,4-oxadiazol-5-one |
| 136 | 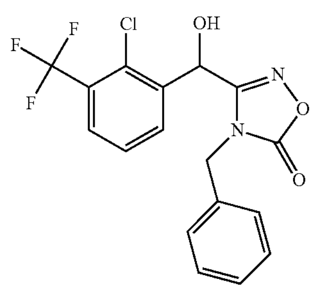 [SMILES: O=c1onc(C(O)c2cccc(C(F)(F)F)c2Cl)n1Cc1ccccc1] | 4-benzyl-3-{[2-chloro-3-(trifluoromethyl)phenyl](hydroxy)methyl}-4,5-dihydro-1,2,4-oxadiazol-5-one |
| 137 | 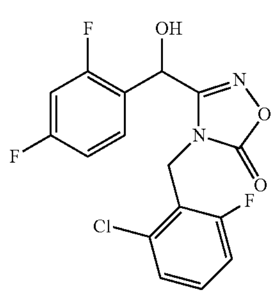 [SMILES: O=c1onc(C(O)c2ccc(F)cc2F)n1Cc1c(F)cccc1Cl] | 4-[(2-chloro-6-fluorophenyl)methyl]-3-[(2,4-difluorophenyl)(hydroxy)methyl]-4,5-dihydro-1,2,4-oxadiazol-5-one |

TABLE 1-continued

| Example | Structure | IUPAC Name |
|---|---|---|
| 138 | 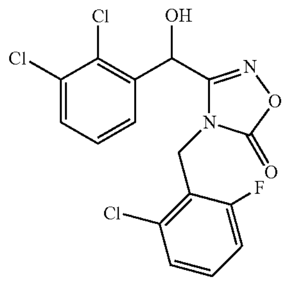 [SMILES: O=c1onc(C(O)c2cccc(Cl)c2Cl)n1Cc1c(F)cccc1Cl] | 4-[(2-chloro-6-fluorophenyl)methyl]-3-[(2,3-dichlorophenyl)(hydroxy)methyl]-4,5-dihydro-1,2,4-oxadiazol-5-one |
| 139 | 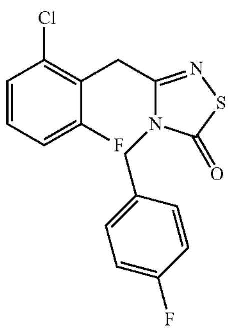 [SMILES: O=c1snc(Cc2c(F)cccc2Cl)n1Cc1ccc(F)cc1] | 3-[(2-chloro-6-fluorophenyl)methyl]-4-[(4-fluorophenyl)methyl]-4,5-dihydro-1,2,4-thiadiazol-5-one |
| 140 | 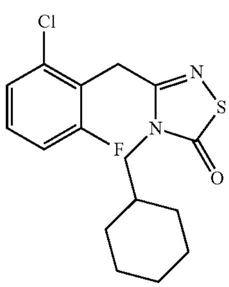 [SMILES: O=c1snc(Cc2c(F)cccc2Cl)n1CC1CCCCC1] | 3-[(2-chloro-6-fluorophenyl)methyl]-4-(cyclohexylmethyl)-4,5-dihydro-1,2,4-thiadiazol-5-one |
| 141 | 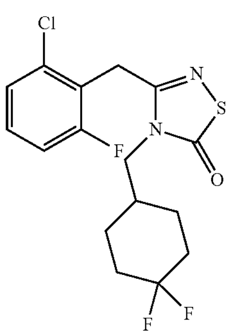 [SMILES: O=c1snc(Cc2c(F)cccc2Cl)n1CC1CCC(F)(F)CC1] | 3-[(2-chloro-6-fluorophenyl)methyl]-4-[(4,4-difluorocyclohexyl)methyl]-4,5-dihydro-1,2,4-thiadiazol-5-one |
| 142 | 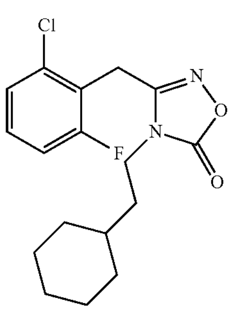 [SMILES: O=c1onc(Cc2c(F)cccc2Cl)n1CCC1CCCCC1] | 3-(2-chloro-6-fluorobenzyl)-4-(2-cyclohexylethyl)-1,2,4-oxadiazol-5(4H)-one |

TABLE 1-continued

| Example | Structure | IUPAC Name |
| --- | --- | --- |
| 143 | 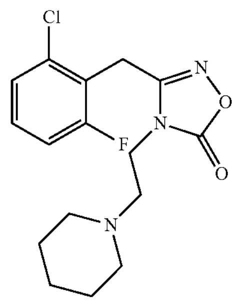 [SMILES: O=c1onc(Cc2c(F)cccc2Cl)n1CCN1CCCCC1] | 3-(2-chloro-6-fluorobenzyl)-4-[2-(piperidin-1-yl)ethyl]-1,2,4-oxadiazol-5(4H)-one |
| 144 | 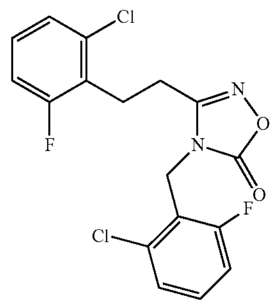 [SMILES: O=c1onc(CCc2c(F)cccc2Cl)n1Cc1c(F)cccc1Cl] | 4-(2-chloro-6-fluorobenzyl)-3-[2-(2-chloro-6-fluorophenyl)ethyl]-1,2,4-oxadiazol-5(4H)-one |
| 145 | 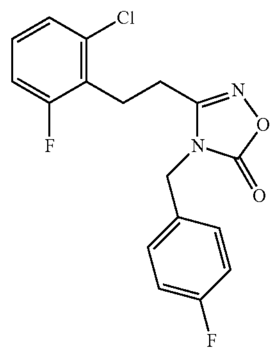 [SMILES: O=c1onc(CCc2c(F)cccc2Cl)n1Cc1ccc(F)cc1] | 3-[2-(2-chloro-6-fluorophenyl)ethyl]-4-(4-fluorobenzyl)-1,2,4-oxadiazol-5(4H)-one |
| 146 | 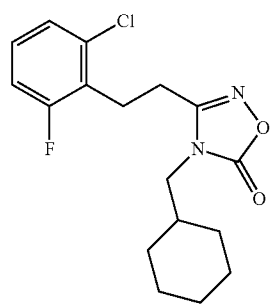 [SMILES: O=c1onc(CCc2c(F)cccc2Cl)n1CC1CCCCC1] | 3-[2-(2-chloro-6-fluorophenyl)ethyl]-4-(cyclohexylmethyl)-1,2,4-oxadiazol-5(4H)-one |
| 147 | 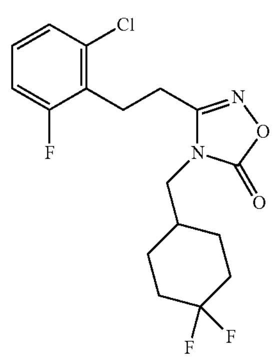 [SMILES: O=c1onc(CCc2c(F)cccc2Cl)n1CC1CCC(F)(F)CC1] | 3-[2-(2-chloro-6-fluorophenyl)ethyl]-4-[(4,4-difluorocyclohexyl)methyl]-1,2,4-oxadiazol-5(4H)-one |

TABLE 1-continued

| Example | Structure | IUPAC Name |
| --- | --- | --- |
| 148 | 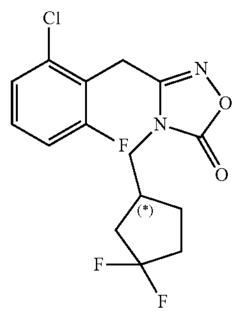 [SMILES: O=c1onc(Cc2c(F)cccc2Cl)n1CC1CCC(F)(F)C1] | 3-(2-chloro-6-fluorobenzyl)-4-[(3,3-difluorocyclopentyl)methyl]-1,2,4-oxadiazol-5(4H)-one |
| 149 | 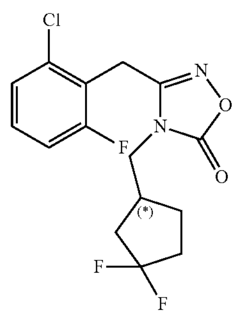 [SMILES: O=c1onc(Cc2c(F)cccc2Cl)n1CC1CCC(F)(F)C1] | 3-(2-chloro-6-fluorobenzyl)-4-[(3,3-difluorocyclopentyl)methyl]-1,2,4-oxadiazol-5(4H)-one |
| 150 | 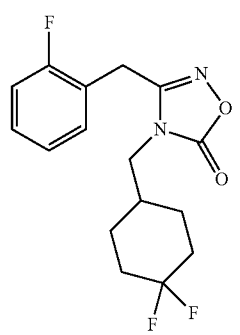 [SMILES: O=c1onc(Cc2ccccc2F)n1CC1CCC(F)(F)CC1] | 4-[(4,4-difluorocyclohexyl)methyl]-3-[(2-fluorophenyl)methyl]-4,5-dihydro-1,2,4-oxadiazol-5-one |
| 151 | 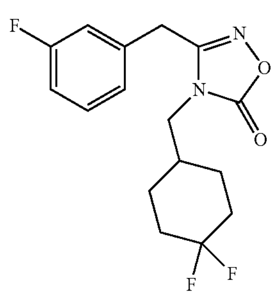 [SMILES: O=c1onc(Cc2cccc(F)c2)n1CC1CCC(F)(F)CC1] | 4-[(4,4-difluorocyclohexyl)methyl]-3-[(3-fluorophenyl)methyl]-4,5-dihydro-1,2,4-oxadiazol-5-one |
| 152 | 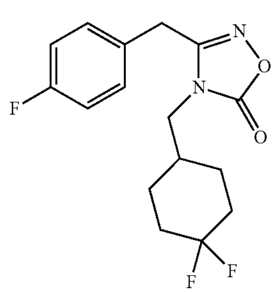 [SMILES: O=c1onc(Cc2ccc(F)cc2)n1CC1CCC(F)(F)CC1] | 4-[(4,4-difluorocyclohexyl)methyl]-3-[(4-fluorophenyl)methyl]-4,5-dihydro-1,2,4-oxadiazol-5-one |

TABLE 1-continued

| Example | Structure | IUPAC Name |
|---|---|---|
| 153 | 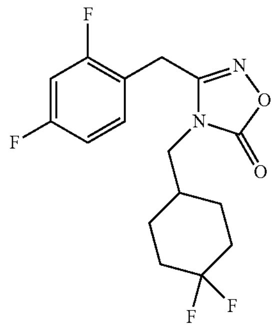 [SMILES: O=c1onc(Cc2ccc(F)cc2F)n1CC1CCC(F)(F)CC1] | 4-[(4,4-difluorocyclohexyl)methyl]-3-[(2,4-difluorophenyl)methyl]-4,5-dihydro-1,2,4-oxadiazol-5-one |
| 154 | 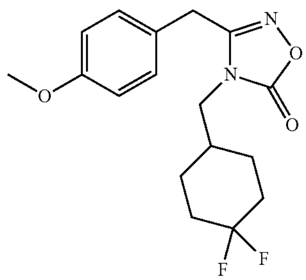 [SMILES: COc1ccc(Cc2noc(=O)n2CC2CCC(F)(F)CC2)cc1] | 4-[(4,4-difluorocyclohexyl)methyl]-3-[(4-methoxyphenyl)methyl]-4,5-dihydro-1,2,4-oxadiazol-5-one |
| 155 | 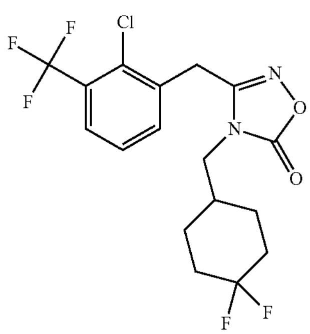 [SMILES: O=c1onc(Cc2cccc(C(F)(F)F)c2Cl)n1CC1CCC(F)(F)CC1] | 3-{[2-chloro-3-(trifluoromethyl)phenyl]methyl}-4-[(4,4-difluorocyclohexyl)methyl]-4,5-dihydro-1,2,4-oxadiazol-5-one |
| 156 | 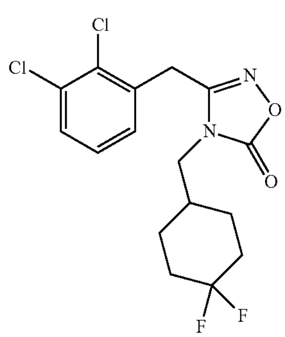 [SMILES: O=c1onc(Cc2cccc(Cl)c2Cl)n1CC1CCC(F)(F)CC1] | 3-[(2,3-dichlorophenyl)methyl]-4-[(4,4-difluorocyclohexyl)methyl]-4,5-dihydro-1,2,4-oxadiazol-5-one |

TABLE 1-continued

| Example | Structure | IUPAC Name |
|---|---|---|
| 157 | 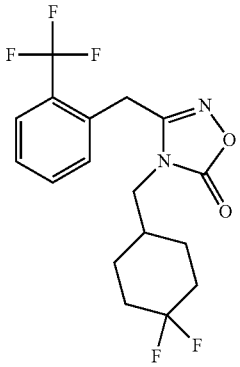 [SMILES: O=c1onc(Cc2ccccc2C(F)(F)F)n1CC1CCC(F)(F)CC1] | 4-[(4,4-difluorocyclohexyl)methyl]-3-{[2-(trifluoromethyl)phenyl]methyl}-4,5-dihydro-1,2,4-oxadiazol-5-one |
| 158 | 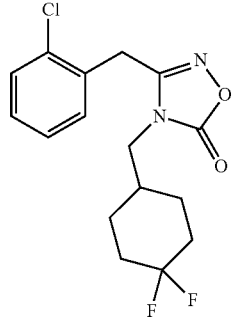 [SMILES: O=c1onc(Cc2ccccc2Cl)n1CC1CCC(F)(F)CC1] | 3-[(2-chlorophenyl)methyl]-4-[(4,4-difluorocyclohexyl)methyl]-4,5-dihydro-1,2,4-oxadiazol-5-one |
| 159 | 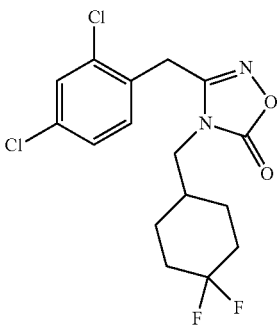 [SMILES: O=c1onc(Cc2ccc(Cl)cc2Cl)n1CC1CCC(F)(F)CC1] | 3-[(2,4-dichlorophenyl)methyl]-4-[(4,4-difluorocyclohexyl)methyl]-4,5-dihydro-1,2,4-oxadiazol-5-one |
| 160 | 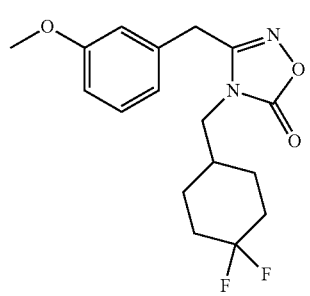 [SMILES: COc1cccc(Cc2noc(=O)n2CC2CCC(F)(F)CC2)c1] | 4-[(4,4-difluorocyclohexyl)methyl]-3-[(3-methoxyphenyl)methyl]-4,5-dihydro-1,2,4-oxadiazol-5-one |
| 161 | 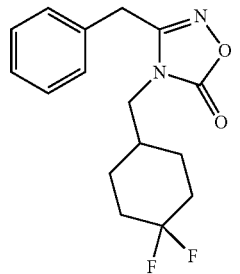 [SMILES: O=c1onc(Cc2ccccc2)n1CC1CCC(F)(F)CC1] | 3-benzyl-4-[(4,4-difluorocyclohexyl)methyl]-4,5-dihydro-1,2,4-oxadiazol-5-one |

TABLE 1-continued

| Example | Structure | IUPAC Name |
|---|---|---|
| 162 | 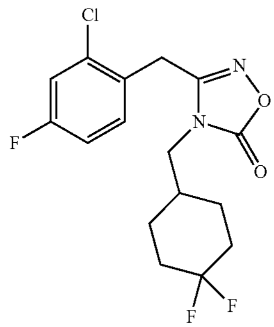 [SMILES: O=c1onc(Cc2ccc(F)cc2Cl)n1CC1CCC(F)(F)CC1] | 3-[(2-chloro-4-fluorophenyl)methyl]-4-[(4,4-difluorocyclohexyl)methyl]-4,5-dihydro-1,2,4-oxadiazol-5-one |
| 163 | 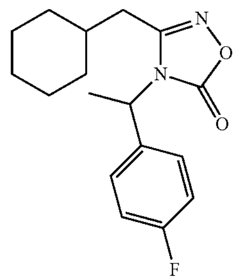 [SMILES: CC(c1ccc(F)cc1)n1c(CC2CCCCC2)noc1=O] | 3-(cyclohexylmethyl)-4-[1-(4-fluorophenyl)ethyl]-4,5-dihydro-1,2,4-oxadiazol-5-one |
| 164 | 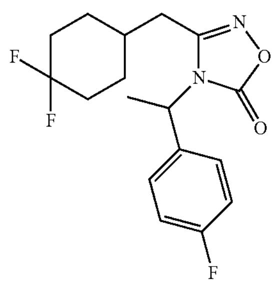 [SMILES: CC(c1ccc(F)cc1)n1c(CC2CCC(F)(F)CC2)noc1=O] | 3-[(4,4-difluorocyclohexyl)methyl]-4-[1-(4-fluorophenyl)ethyl]-4,5-dihydro-1,2,4-oxadiazol-5-one |
| 165 | 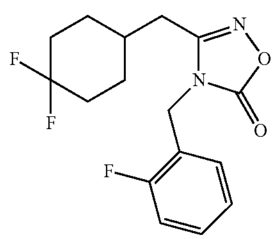 | 3-[(4,4-difluorocyclohexyl)methyl]-4-[(2-fluorophenyl)methyl]-4,5-dihydro-1,2,4-oxadiazol-5-one |
| 166 | 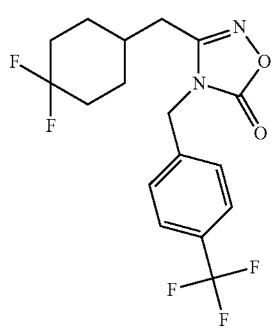 [SMILES: O=c1onc(CC2CCC(F)(F)CC2)n1Cc1ccc(C(F)(F)F)cc1] | 3-[(4,4-difluorocyclohexyl)methyl]-4-{[4-(trifluoromethyl)phenyl]methyl}-4,5-dihydro-1,2,4-oxadiazol-5-one |

TABLE 1-continued

| Example | Structure | IUPAC Name |
|---|---|---|
| 167 | 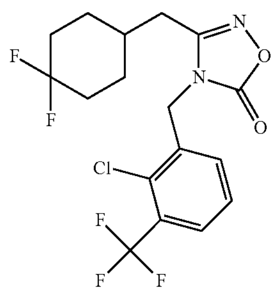 [SMILES: O=c1onc(CC2CCC(F)(F)CC2)n1Cc1cccc(C(F)(F)F)c1Cl] | 4-{[2-chloro-3-(trifluoromethyl)phenyl]methyl}-3-[(4,4-difluorocyclohexyl)methyl]-4,5-dihydro-1,2,4-oxadiazol-5-one |
| 168 | 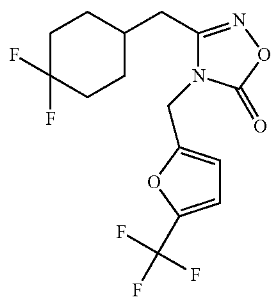 [SMILES: O=c1onc(CC2CCC(F)(F)CC2)n1Cc1ccc(C(F)(F)F)o1] | 3-[(4,4-difluorocyclohexyl)methyl]-4-{[5-(trifluoromethyl)furan-2-yl]methyl}-4,5-dihydro-1,2,4-oxadiazol-5-one |
| 169 | 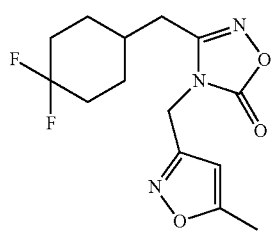 [SMILES: Cc1cc(Cn2c(CC3CCC(F)(F)CC3)noc2=O)no1] | 3-[(4,4-difluorocyclohexyl)methyl]-4-[(5-methyl-1,2-oxazol-3-yl)methyl]-4,5-dihydro-1,2,4-oxadiazol-5-one |
| 170 | 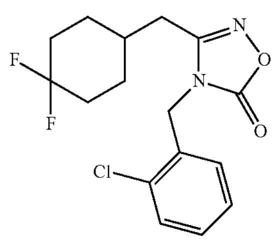 [SMILES: O=c1onc(CC2CCC(F)(F)CC2)n1Cc1ccccc1Cl] | 4-[(2-chlorophenyl)methyl]-3-[(4,4-difluorocyclohexyl)methyl]-4,5-dihydro-1,2,4-oxadiazol-5-one |
| 171 | 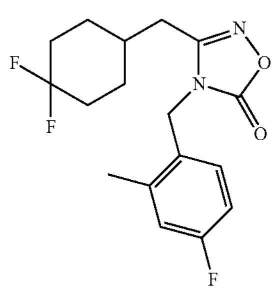 [SMILES: Cc1cc(F)ccc1Cn1c(CC2CCC(F)(F)CC2)noc1=O] | 3-[(4,4-difluorocyclohexyl)methyl]-4-[(4-fluoro-2-methylphenyl)methyl]-4,5-dihydro-1,2,4-oxadiazol-5-one |
| 172 | 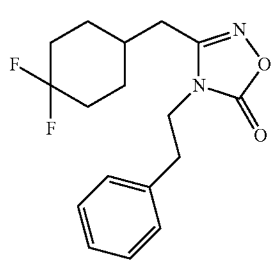 [SMILES: O=c1onc(CC2CCC(F)(F)CC2)n1CCc1ccccc1] | 3-[(4,4-difluorocyclohexyl)methyl]-4-(2-phenylethyl)-4,5-dihydro-1,2,4-oxadiazol-5-one |

TABLE 1-continued

| Example | Structure | IUPAC Name |
|---|---|---|
| 173 | 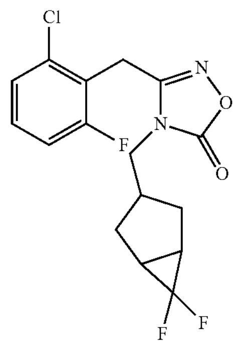 [SMILES: O=c1onc(Cc2c(F)cccc2Cl)n1CC1CC2C(C1)C2(F)F] | 3-[(2-chloro-6-fluorophenyl)methyl]-4-({6,6-difluorobicyclo[3.1.0]hexan-3-yl}methyl)-4,5-dihydro-1,2,4-oxadiazol-5-one |
| 174 | 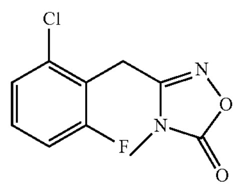 [SMILES: Cn1c(Cc2c(F)cccc2Cl)noc1=O] | 3-[(2-chloro-6-fluorophenyl)methyl]-4-methyl-4,5-dihydro-1,2,4-oxadiazol-5-one |
| 175 | 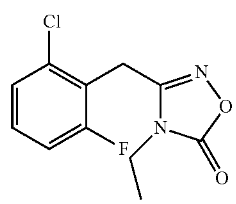 [SMILES: CCn1c(Cc2c(F)cccc2Cl)noc1=O] | 3-[(2-chloro-6-fluorophenyl)methyl]-4-ethyl-4,5-dihydro-1,2,4-oxadiazol-5-one |
| 176 | 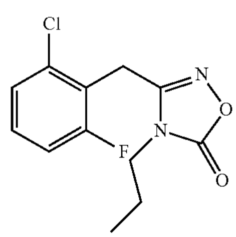 [SMILES: CCCn1c(Cc2c(F)cccc2Cl)noc1=O] | 3-[(2-chloro-6-fluorophenyl)methyl]-4-propyl-4,5-dihydro-1,2,4-oxadiazol-5-one |
| 177 | 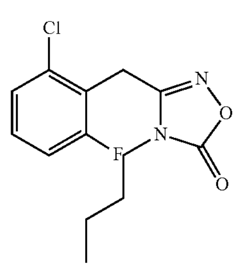 [SMILES: CCCCn1c(Cc2c(F)cccc2Cl)noc1=O] | 4-butyl-3-[(2-chloro-6-fluorophenyl)methyl]-4,5-dihydro-1,2,4-oxadiazol-5-one |
| 178 | 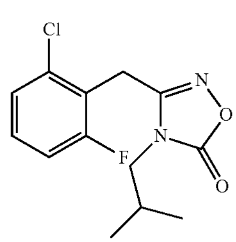 [SMILES: CC(C)Cn1c(Cc2c(F)cccc2Cl)noc1=O] | 3-[(2-chloro-6-fluorophenyl)methyl]-4-(2-methylpropyl)-4,5-dihydro-1,2,4-oxadiazol-5-one |

| Example | Structure | IUPAC Name |
|---|---|---|
| 179 | 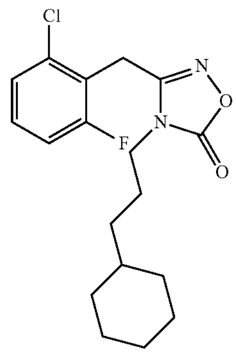 | 3-[(2-chloro-6-fluorophenyl)methyl]-4-(3-cyclohexylpropyl)-4,5-dihydro-1,2,4-oxadiazol-5-one |
| 180 | 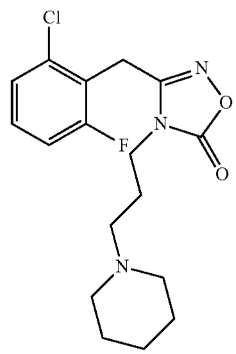 [SMILES: O=c1onc(Cc2c(F)cccc2Cl)n1CCCC1CCCCC1] | 3-[(2-chloro-6-fluorophenyl)methyl]-4-[3-(piperidin-1-yl)propyl]-4,5-dihydro-1,2,4-oxadiazol-5-one |
| 181 | 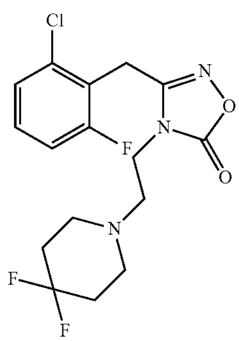 [SMILES: O=c1onc(Cc2c(F)cccc2Cl)n1CCN1CCC(F)(F)CC1] | 3-[(2-chloro-6-fluorophenyl)methyl]-4-[2-(4,4-difluoropiperidin-1-yl)ethyl]-4,5-dihydro-1,2,4-oxadiazol-5-one |
| 182 | 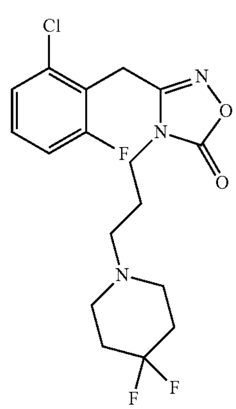 [SMILES: O=c1onc(Cc2c(F)cccc2Cl)n1CCCN1CCC(F)(F)CC1] | 3-[(2-chloro-6-fluorophenyl)methyl]-4-[3-(4,4-difluoropiperidin-1-yl)propyl]-4,5-dihydro-1,2,4-oxadiazol-5-one |

TABLE 1-continued
| Example | Structure | IUPAC Name |
|---|---|---|
| 183 | 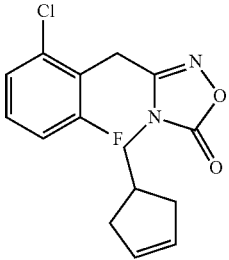 [SMILES: O=c1onc(Cc2c(F)cccc2Cl)n1CC1CC=CC1] | 3-[(2-chloro-6-fluorophenyl)methyl]-4-(cyclopent-3-en-1-ylmethyl)-4,5-dihydro-1,2,4-oxadiazol-5-one |
| 184 | 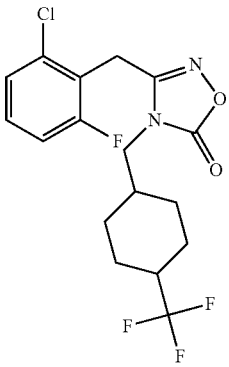 [SMILES: O=c1onc(Cc2c(F)cccc2Cl)n1CC1CCC(C(F)(F)F)CC1] | 3-[(2-chloro-6-fluorophenyl)methyl]-4-{[4-(trifluoromethyl)cyclohexyl]methyl}-1,2,4-oxadiazol-5(4H)-one |
| 185 | 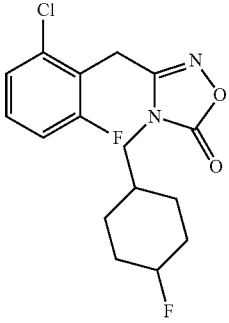 [SMILES: O=c1onc(Cc2c(F)cccc2Cl)n1CC1CCC(F)CC1] | 3-[(2-chloro-6-fluorophenyl)methyl]-4-[(4-fluorocyclohexyl)methyl]-4,5-dihydro-1,2,4-oxadiazol-5-one |
| 186 | 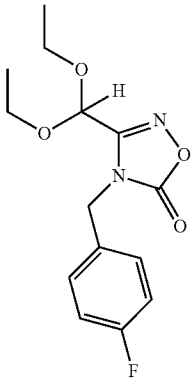 [SMILES: CCOC(OCC)c1noc(=O)n1Cc1ccc(F)cc1] | 3-(diethoxymethyl)-4-[(4-fluorophenyl)methyl]-4,5-dihydro-1,2,4-oxadiazol-5-one |

TABLE 1-continued

| Example | Structure | IUPAC Name |
|---|---|---|
| 187 | 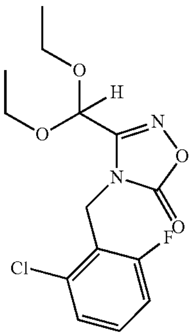 [SMILES: CCOC(OCC)c1noc(=O)n1Cc1c(F)cccc1Cl] | 4-[(2-chloro-6-fluorophenyl)methyl]-3-(diethoxymethyl)-4,5-dihydro-1,2,4-oxadiazol-5-one |
| 188 | 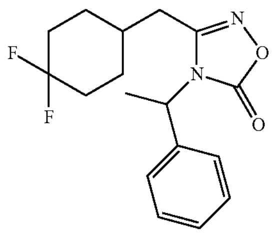 [SMILES: CC(c1ccccc1)n1c(CC2CCC(F)(F)CC2)noc1=O] | 3-[(4,4-difluorocyclohexyl)methyl]-4-(1-phenylethyl)-4,5-dihydro-1,2,4-oxadiazol-5-one |
| 189 | 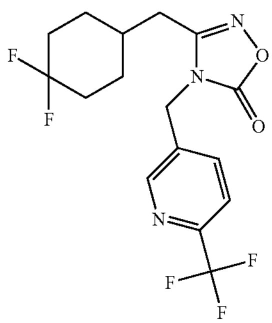 [SMILES: O=c1onc(CC2CCC(F)(F)CC2)n1Cc1ccc(C(F)(F)F)nc1] | 3-[(4,4-difluorocyclohexyl)methyl]-4-{[6-(trifluoromethyl)pyridin-3-yl]methyl}-4,5-dihydro-1,2,4-oxadiazol-5-one |
| 190 | 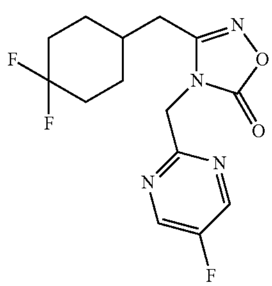 [SMILES: O=c1onc(CC2CCC(F)(F)CC2)n1Cc1ncc(F)cn1] | 3-[(4,4-difluorocyclohexyl)methyl]-4-[(5-fluoropyrimidin-2-yl)methyl]-4,5-dihydro-1,2,4-oxadiazol-5-one |
| 191 | 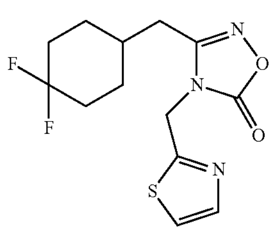 [SMILES: O=c1onc(CC2CCC(F)(F)CC2)n1Cc1nccs1] | 3-[(4,4-difluorocyclohexyl)methyl]-4-(1,3-thiazol-2-ylmethyl)-4,5-dihydro-1,2,4-oxadiazol-5-one |

TABLE 1-continued

| Example | Structure | IUPAC Name |
|---|---|---|
| 192 | 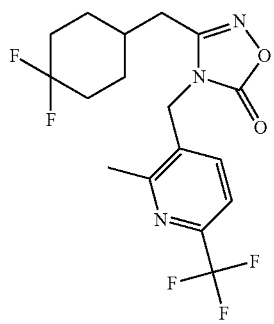 [SMILES: Cc1nc(C(F)(F)F)ccc1Cn1c(CC2CCC(F)(F)CC2)noc1=O] | 3-[(4,4-difluorocyclohexyl)methyl]-4-{[2-methyl-6-(trifluoromethyl)pyridin-3-yl]methyl}-4,5-dihydro-1,2,4-oxadiazol-5-one |
| 193 | 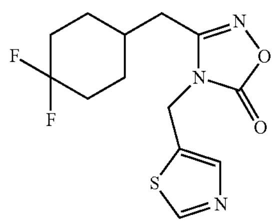 [SMILES: O=c1onc(CC2CCC(F)(F)CC2)n1Cc1cncs1] | 3-[(4,4-difluorocyclohexyl)methyl]-4-[(1,3-thiazol-5-yl)methyl]-1,2,4-oxadiazol-5(4H)-one |
| 194 | 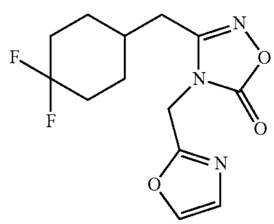 [SMILES: O=c1onc(CC2CCC(F)(F)CC2)n1Cc1ncco1] | 3-[(4,4-difluorocyclohexyl)methyl]-4-[(1,3-oxazol-2-yl)methyl]-1,2,4-oxadiazol-5(4H)-one |
| 195 | 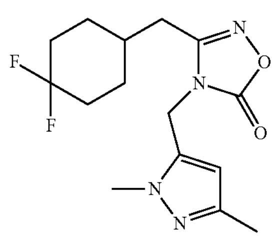 [SMILES: Cc1cc(Cn2c(CC3CCC(F)(F)CC3)noc2=O)n(C)n1] | 3-[(4,4-difluorocyclohexyl)methyl]-4-[(1,3-dimethyl-1H-pyrazol-5-yl)methyl]-1,2,4-oxadiazol-5(4H)-one |
| 196 | 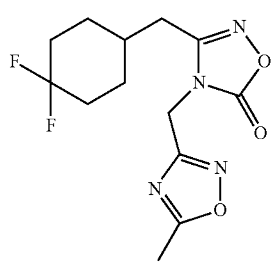 [SMILES: Cc1nc(Cn2c(CC3CCC(F)(F)CC3)noc2=O)no1] | 3-[(4,4-difluorocyclohexyl)methyl]-4-[(5-methyl-1,2,4-oxadiazol-3-yl)methyl]-1,2,4-oxadiazol-5(4H)-one |
| 197 | 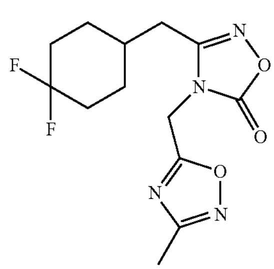 [SMILES: Cc1noc(Cn2c(CC3CCC(F)(F)CC3)noc2=O)n1] | 3-[(4,4-difluorocyclohexyl)methyl]-4-[(3-methyl-1,2,4-oxadiazol-5-yl)methyl]-1,2,4-oxadiazol-5(4H)-one |

TABLE 1-continued

| Example | Structure | IUPAC Name |
|---|---|---|
| 198 | 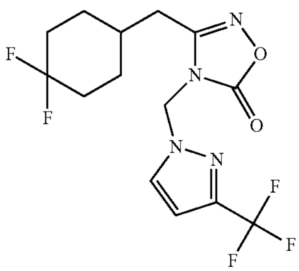 [SMILES: O=c1onc(CC2CCC(F)(F)CC2)n1Cn1ccc(C(F)(F)F)n1] | 3-[(4,4-difluorocyclohexyl)methyl]-4-{[3-(trifluoromethyl)-1H-pyrazol-1-yl]methyl}-1,2,4-oxadiazol-5(4H)-one |
| 199 | 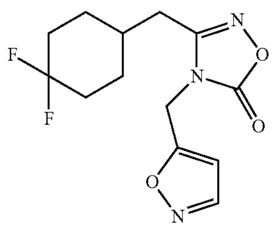 [SMILES: O=c1onc(CC2CCC(F)(F)CC2)n1Cc1ccno1] | 3-[(4,4-difluorocyclohexyl)methyl]-4-[(1,2-oxazol-5-yl)methyl]-1,2,4-oxadiazol-5(4H)-one |
| 200 | 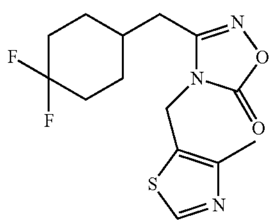 [SMILES: Cc1ncsc1Cn1c(CC2CCC(F)(F)CC2)noc1=O] | 3-[(4,4-difluorocyclohexyl)methyl]-4-[(4-methyl-1,3-thiazol-5-yl)methyl]-1,2,4-oxadiazol-5(4H)-one |
| 201 | 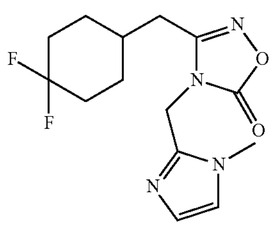 [SMILES: Cn1ccnc1Cn1c(CC2CCC(F)(F)CC2)noc1=O] | 3-[(4,4-difluorocyclohexyl)methyl]-4-[(1-methyl-1H-imidazol-2-yl)methyl]-4,5-dihydro-1,2,4-oxadiazol-5-one |
| 202 | 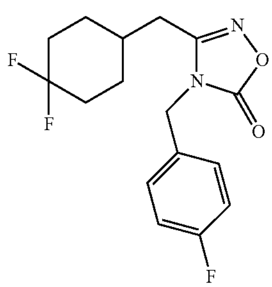 [SMILES: O=c1onc(CC2CCC(F)(F)CC2)n1Cc1ccc(F)cc1] | 3-[(4,4-difluorocyclohexyl)methyl]-4-[(4-fluorophenyl)methyl]-4,5-dihydro-1,2,4-thiadiazol-5-one |
| 203 | 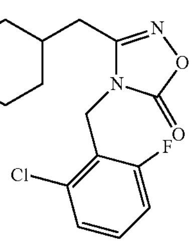 | 4-[(2-chloro-6-fluorophenyl)methyl]-3-[(4,4-difluorocyclohexyl)methyl]-4,5-dihydro-1,2,4-thiadiazol-5-one |

TABLE 1-continued

| Example | Structure | IUPAC Name |
|---|---|---|
| 204 | 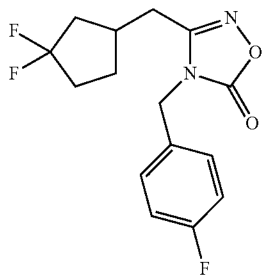 [SMILES: O=c1onc(CC2CCC(F)(F)C2)n1Cc1ccc(F)cc1] | 3-[(3,3-difluorocyclopentyl)methyl]-4-[(4-fluorophenyl)methyl]-4,5-dihydro-1,2,4-oxadiazol-5-one |
| 205 | 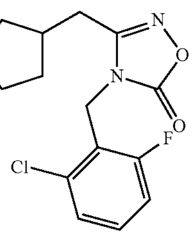 | 4-[(2-chloro-6-fluorophenyl)methyl]-3-[(3,3-difluorocyclopentyl)methyl]-4,5-dihydro-1,2,4-oxadiazol-5-one |
| 206 | 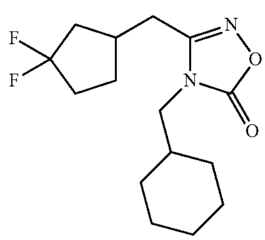 [SMILES: O=c1onc(CC2CCC(F)(F)C2)n1CC1CCCCC1] | 4-(cyclohexylmethyl)-3-[(3,3-difluorocyclopentyl)methyl]-4,5-dihydro-1,2,4-oxadiazol-5-one |
| 207 | 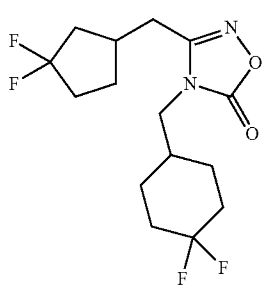 [SMILES: O=c1onc(CC2CCC(F)(F)C2)n1CC1CCC(F)(F)CC1] | 4-[(4,4-difluorocyclohexyl)methyl]-3-[(3,3-difluorocyclopentyl)methyl]-4,5-dihydro-1,2,4-oxadiazol-5-one |
| 208 | 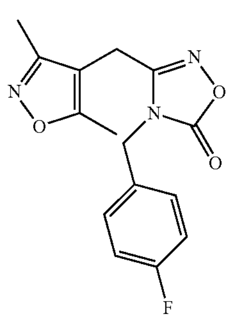 [SMILES: Cc1noc(C)c1Cc1noc(=O)n1Cc1ccc(F)cc1] | 3-[(dimethyl-1,2-oxazol-4-yl)methyl]-4-[(4-fluorophenyl)methyl]-4,5-dihydro-1,2,4-oxadiazol-5-one |

TABLE 1-continued

| Example | Structure | IUPAC Name |
|---|---|---|
| 209 | 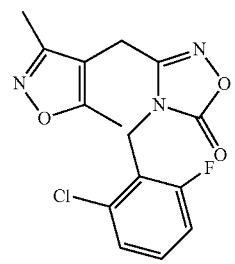 [SMILES: Cc1noc(C)c1Cc1noc(=O)n1Cc1c(F)cccc1Cl] | 4-[(2-chloro-6-fluorophenyl)methyl]-3-[(dimethyl-1,2-oxazol-4-yl)methyl]-4,5-dihydro-1,2,4-oxadiazol-5-one |
| 210 | 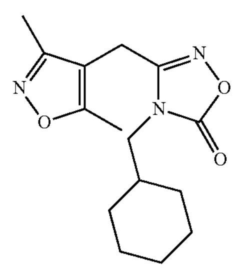 [SMILES: Cc1noc(C)c1Cc1noc(=O)n1CC1CCCCC1] | 4-(cyclohexylmethyl)-3-[(dimethyl-1,2-oxazol-4-yl)methyl]-4,5-dihydro-1,2,4-oxadiazol-5-one |
| 211 | 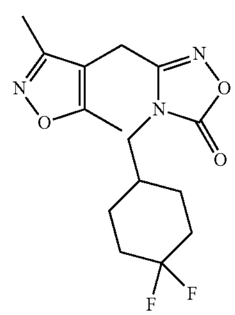 [SMILES: Cc1noc(C)c1Cc1noc(=O)n1CC1CCC(F)(F)CC1] | 4-[(4,4-difluorocyclohexyl)methyl]-3-[(dimethyl-1,2-oxazol-4-yl)methyl]-4,5-dihydro-1,2,4-oxadiazol-5-one |
| 212 | 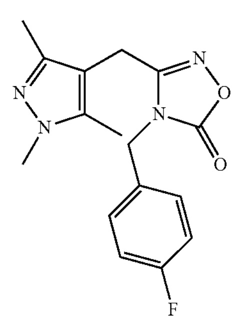 [SMILES: Cc1nn(C)c(C)c1Cc1noc(=O)n1Cc1ccc(F)cc1] | 4-[(4-fluorophenyl)methyl]-3-[(trimethyl-1H-pyrazol-4-yl)methyl]-4,5-dihydro-1,2,4-oxadiazol-5-one |
| 213 | 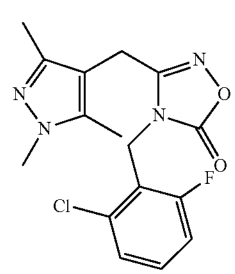 [SMILES: Cc1nn(C)c(C)c1Cc1noc(=O)n1Cc1c(F)cccc1Cl] | 4-[(2-chloro-6-fluorophenyl)methyl]-3-[(trimethyl-1H-pyrazol-4-yl)methyl]-4,5-dihydro-1,2,4-oxadiazol-5-one |

TABLE 1-continued

| Example | Structure | IUPAC Name |
| --- | --- | --- |
| 214 | 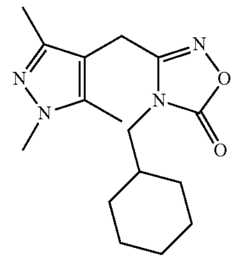 [SMILES: Cc1nn(C)c(C)c1Cc1noc(=O)n1CC1CCCCC1] | 4-(cyclohexylmethyl)-3-[(trimethyl-1H-pyrazol-4-yl)methyl]-4,5-dihydro-1,2,4-oxadiazol-5-one |
| 215 | 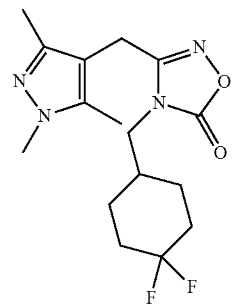 [SMILES: Cc1nn(C)c(C)c1Cc1noc(=O)n1CC1CCC(F)(F)CC1] | 4-[(4,4-difluorocyclohexyl)methyl]-3-[(trimethyl-1H-pyrazol-4-yl)methyl]-4,5-dihydro-1,2,4-oxadiazol-5-one |
| 216 | 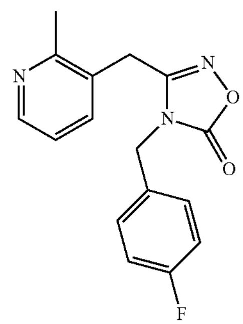 [SMILES: Cc1ncccc1Cc1noc(=O)n1Cc1ccc(F)cc1] | 4-[(4-fluorophenyl)methyl]-3-[(2-methylpyridin-3-yl)methyl]-4,5-dihydro-1,2,4-oxadiazol-5-one |
| 217 | 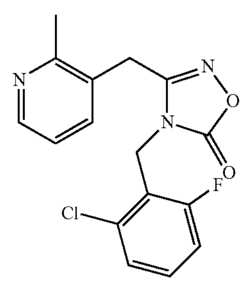 [SMILES: Cc1ncccc1Cc1noc(=O)n1Cc1c(F)cccc1Cl] | 4-[(2-chloro-6-fluorophenyl)methyl]-3-[(2-methylpyridin-3-yl)methyl]-4,5-dihydro-1,2,4-oxadiazol-5-one |
| 218 | 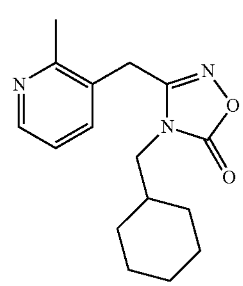 [SMILES: Cc1ncccc1Cc1noc(=O)n1CC1CCCCC1] | 4-(cyclohexylmethyl)-3-[(2-methylpyridin-3-yl)methyl]-4,5-dihydro-1,2,4-oxadiazol-5-one |

TABLE 1-continued

| Example | Structure | IUPAC Name |
|---|---|---|
| 219 | 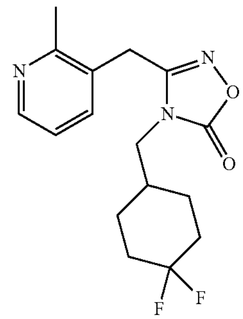 [SMILES: Cc1ncccc1Cc1noc(=O)n1CC1CCC(F)(F)CC1] | 4-[(4,4-difluorocyclohexyl)methyl]-3-[(2-methylpyridin-3-yl)methyl]-4,5-dihydro-1,2,4-oxadiazol-5-one |
| 220 | 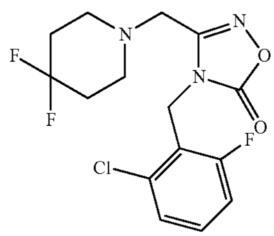 | 4-[(2-chloro-6-fluorophenyl)methyl]-3-[(4,4-difluoropiperidin-1-yl)methyl]-4,5-dihydro-1,2,4-oxadiazol-5-one |
| 221 | 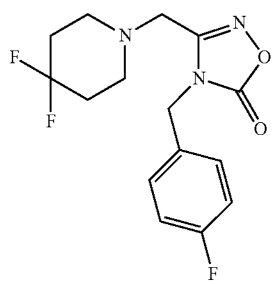 [SMILES: O=c1onc(CN2CCC(F)(F)CC2)n1Cc1ccc(F)cc1] | 3-[(4,4-difluoropiperidin-1-yl)methyl]-4-[(4-fluorophenyl)methyl]-4,5-dihydro-1,2,4-oxadiazol-5-one |
| 222 | 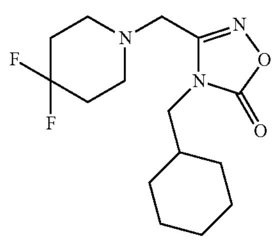 [SMILES: O=c1onc(CN2CCC(F)(F)CC2)n1CC1CCCCC1] | 4-(cyclohexylmethyl)-3-[(4,4-difluoropiperidin-1-yl)methyl]-4,5-dihydro-1,2,4-oxadiazol-5-one |
| 223 | 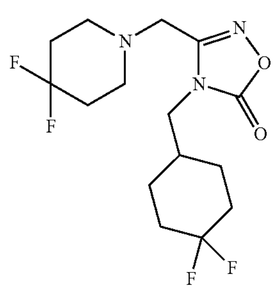 [SMILES: O=c1onc(CN2CCC(F)(F)CC2)n1CC1CCC(F)(F)CC1] | 4-[(4,4-difluorocyclohexyl)methyl]-3-[(4,4-difluoropiperidin-1-yl)methyl]-4,5-dihydro-1,2,4-oxadiazol-5-one |

TABLE 1-continued

| Example | Structure | IUPAC Name |
|---|---|---|
| 224 | 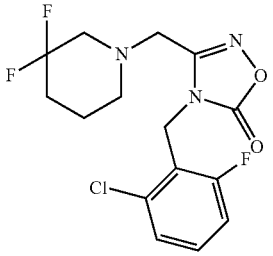 [SMILES: O=c1onc(CN2CCCC(F)(F)C2)n1Cc1c(F)cccc1Cl] | 4-[(2-chloro-6-fluorophenyl)methyl]-3-[(3,3-difluoropiperidin-1-yl)methyl]-4,5-dihydro-1,2,4-oxadiazol-5-one |
| 225 | 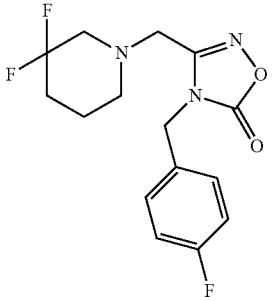 [SMILES: O=c1onc(CN2CCCC(F)(F)C2)n1Cc1ccc(F)cc1] | 3-[(3,3-difluoropiperidin-1-yl)methyl]-4-[(4-fluorophenyl)methyl]-4,5-dihydro-1,2,4-oxadiazol-5-one |
| 226 | 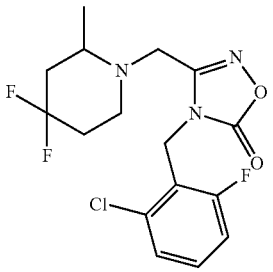 [SMILES: CC1CC(F)(F)CCN1Cc1noc(=O)n1Cc1c(F)cccc1Cl] | 4-[(2-chloro-6-fluorophenyl)methyl]-3-[(4,4-difluoro-2-methylpiperidin-1-yl)methyl]-4,5-dihydro-1,2,4-oxadiazol-5-one |
| 227 | 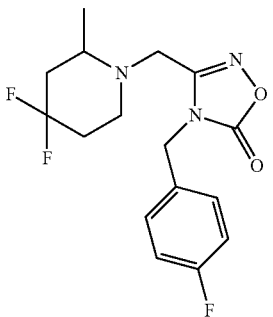 [SMILES: CC1CC(F)(F)CCN1Cc1noc(=O)n1Cc1ccc(F)cc1] | 3-[(4,4-difluoro-2-methylpiperidin-1-yl)methyl]-4-[(4-fluorophenyl)methyl]-4,5-dihydro-1,2,4-oxadiazol-5-one |
| 228 | 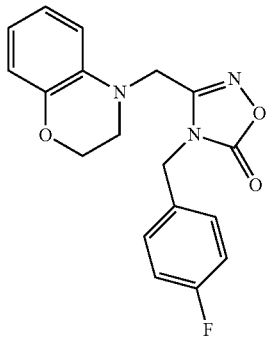 [SMILES: O=c1onc(CN2CCOc3ccccc32)n1Cc1ccc(F)cc1] | 3-(3,4-dihydro-2H-1,4-benzoxazin-4-ylmethyl)-4-[(4-fluorophenyl)methyl]-4,5-dihydro-1,2,4-oxadiazol-5-one |

TABLE 1-continued

| Example | Structure | IUPAC Name |
|---|---|---|
| 229 | 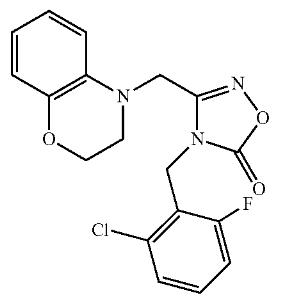 [SMILES: O=c1onc(CN2CCOc3ccccc32)n1Cc1c(F)cccc1Cl] | 4-[(2-chloro-6-fluorophenyl)methyl]-3-(3,4-dihydro-2H-1,4-benzoxazin-4-ylmethyl)-4,5-dihydro-1,2,4-oxadiazol-5-one |
| 230 | 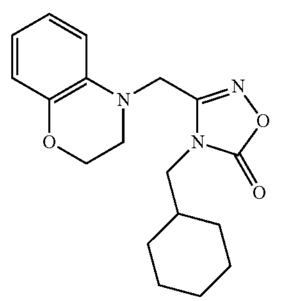 [SMILES: O=c1onc(CN2CCOc3ccccc32)n1CC1CCCCC1] | 4-(cyclohexylmethyl)-3-(3,4-dihydro-2H-1,4-benzoxazin-4-ylmethyl)-4,5-dihydro-1,2,4-oxadiazol-5-one |
| 231 | 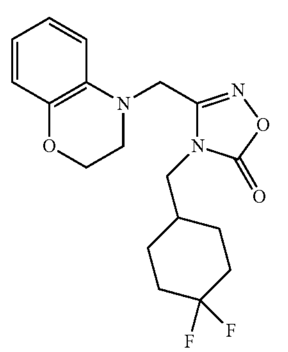 [SMILES: O=c1onc(CN2CCOc3ccccc32)n1CC1CCC(F)(F)CC1] | 4-[(4,4-difluorocyclohexyl)methyl]-3-(3,4-dihydro-2H-1,4-benzoxazin-4-ylmethyl)-4,5-dihydro-1,2,4-oxadiazol-5-one |
| 232 | 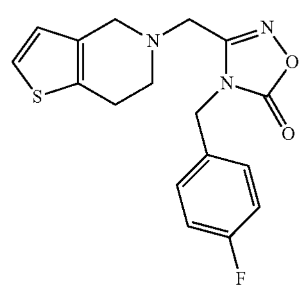 [SMILES: O=c1onc(CN2CCc3sccc3C2)n1Cc1ccc(F)cc1] | 4-[(4-fluorophenyl)methyl]-3-{4H,5H,6H,7H-thieno[3,2-c]pyridin-5-ylmethyl}-4,5-dihydro-1,2,4-oxadiazol-5-one |
| 233 | 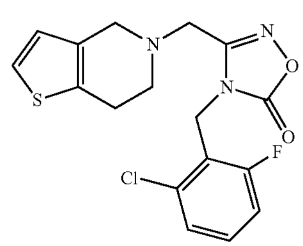 [SMILES: O=c1onc(CN2CCc3sccc3C2)n1Cc1c(F)cccc1Cl] | 4-[(2-chloro-6-fluorophenyl)methyl]-3-{4H,5H,6H,7H-thieno[3,2-c]pyridin-5-ylmethyl}-4,5-dihydro-1,2,4-oxadiazol-5-one |

TABLE 1-continued

| Example | Structure | IUPAC Name |
|---|---|---|
| 234 | 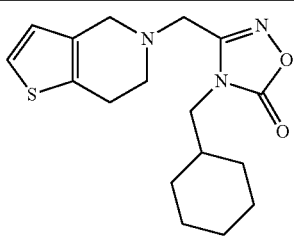 | 4-(cyclohexylmethyl)-3-{4H,5H,6H,7H-thieno[3,2-c]pyridin-5-ylmethyl}-4,5-dihydro-1,2,4-oxadiazol-5-one |
| 235 | 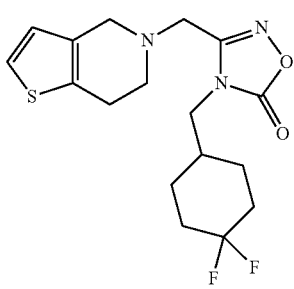 [SMILES: O=c1onc(CN2CCc3sccc3C2)n1CC1CCC(F)(F)CC1] | 4-[(4,4-difluorocyclohexyl)methyl]-3-{4H,5H,6H,7H-thieno[3,2-c]pyridin-5-ylmethyl}-4,5-dihydro-1,2,4-oxadiazol-5-one |
| 236 | 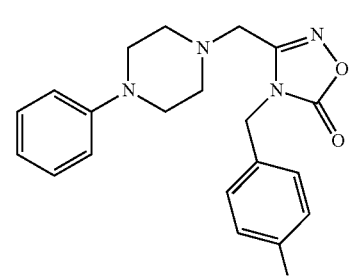 | 4-[(4-fluorophenyl)methyl]-3-[(4-phenylpiperazin-1-yl)methyl]-4,5-dihydro-1,2,4-oxadiazol-5-one |
| 237 | 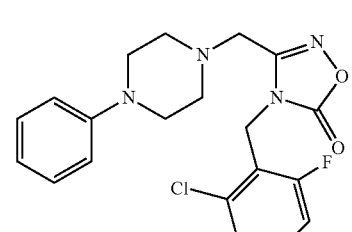 | 4-[(2-chloro-6-fluorophenyl)methyl]-3-[(4-phenylpiperazin-1-yl)methyl]-4,5-dihydro-1,2,4-oxadiazol-5-one |
| 238 | 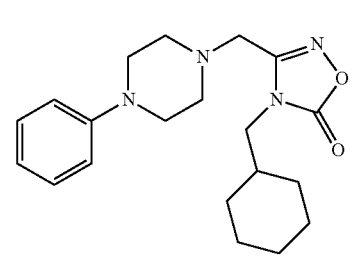 [SMILES: O=c1onc(CN2CCN(c3ccccc3)CC2)n1CC1CCCCC1] | 4-(cyclohexylmethyl)-3-[(4-phenylpiperazin-1-yl)methyl]-4,5-dihydro-1,2,4-oxadiazol-5-one |
| 239 | 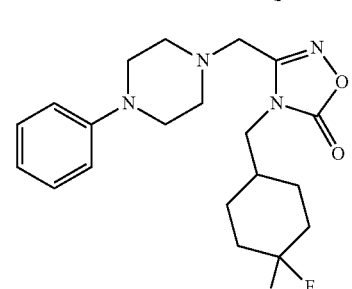 | 4-[(4,4-difluorocyclohexyl)methyl]-3-[(4-phenylpiperazin-1-yl)methyl]-4,5-dihydro-1,2,4-oxadiazol-5-one |

TABLE 1-continued

| Example | Structure | IUPAC Name |
|---|---|---|
| 240 | 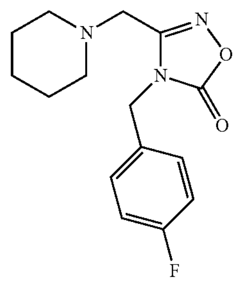 [SMILES: O=c1onc(CN2CCCCC2)n1Cc1ccc(F)cc1] | 4-[(4-fluorophenyl)methyl]-3-(piperidin-1-ylmethyl)-4,5-dihydro-1,2,4-oxadiazol-5-one |
| 241 | 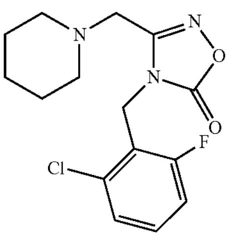 [SMILES: O=c1onc(CN2CCCCC2)n1Cc1c(F)cccc1Cl] | 4-[(2-chloro-6-fluorophenyl)methyl]-3-[(piperidin-1-yl)methyl]-1,2,4-oxadiazol-5(4H)-one |
| 242 | 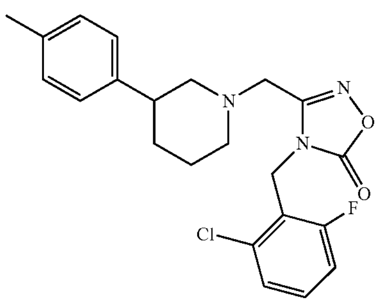 [SMILES: Cc1ccc(C2CCCN(Cc3noc(=O)n3Cc3c(F)cccc3Cl)C2)cc1] | 4-[(2-chloro-6-fluorophenyl)methyl]-3-{[3-(4-methylphenyl)piperidin-1-yl]methyl}-4,5-dihydro-1,2,4-oxadiazol-5-one |
| 243 | 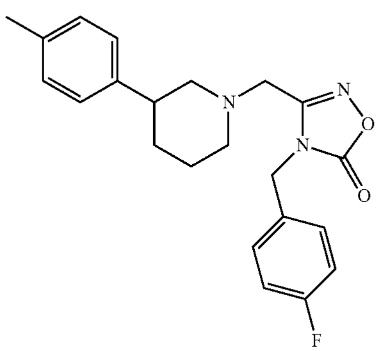 [SMILES: Cc1ccc(C2CCCN(Cc3noc(=O)n3Cc3ccc(F)cc3)C2)cc1] | 4-[(4-fluorophenyl)methyl]-3-{[3-(4-methylphenyl)piperidin-1-yl]methyl}-4,5-dihydro-1,2,4-oxadiazol-5-one |
| 244 | 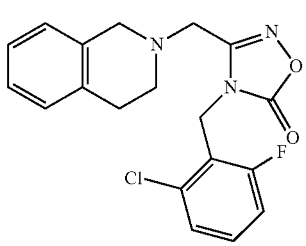 [SMILES: O=c1onc(CN2CCc3ccccc3C2)n1Cc1c(F)cccc1Cl] | 4-[(2-chloro-6-fluorophenyl)methyl]-3-(1,2,3,4-tetrahydroisoquinolin-2-ylmethyl)-4,5-dihydro-1,2,4-oxadiazol-5-one |

TABLE 1-continued

| Example | Structure | IUPAC Name |
|---|---|---|
| 245 | 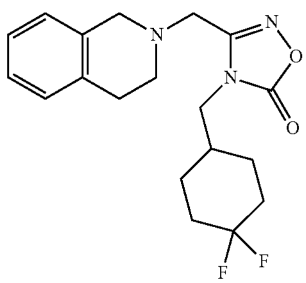 [SMILES: O=c1onc(CN2CCc3ccccc3C2)n1CC1CCC(F)(F)CC1] | 4-[(4,4-difluorocyclohexyl)methyl]-3-(1,2,3,4-tetrahydroisoquinolin-2-ylmethyl)-4,5-dihydro-1,2,4-oxadiazol-5-one |
| 246 | 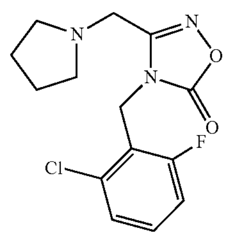 [SMILES: O=c1onc(CN2CCCC2)n1Cc1c(F)cccc1Cl] | 4-[(2-chloro-6-fluorophenyl)methyl]-3-(pyrrolidin-1-ylmethyl)-4,5-dihydro-1,2,4-oxadiazol-5-one |
| 247 | 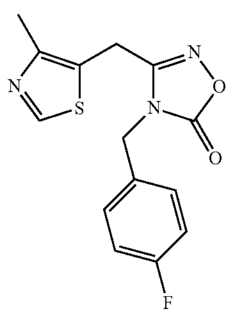 [SMILES: Cc1ncsc1Cc1noc(=O)n1Cc1ccc(F)cc1] | 4-(4-fluorobenzyl)-3-[(4-methyl-1,3-thiazol-5-yl)methyl]-1,2,4-oxadiazol-5(4H)-one |
| 248 | 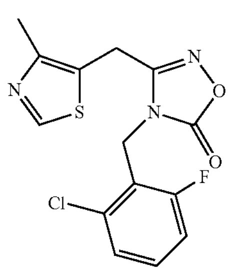 [SMILES: Cc1ncsc1Cc1noc(=O)n1Cc1c(F)cccc1Cl] | 4-(2-chloro-6-fluorobenzyl)-3-[(4-methyl-1,3-thiazol-5-yl)methyl]-1,2,4-oxadiazol-5(4H)-one |
| 249 | 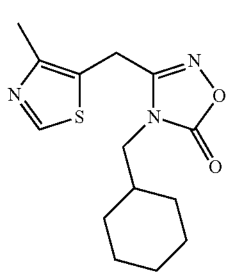 [SMILES: Cc1ncsc1Cc1noc(=O)n1CC1CCCCC1] | 4-(cyclohexylmethyl)-3-[(4-methyl-1,3-thiazol-5-yl)methyl]-1,2,4-oxadiazol-5(4H)-one |

TABLE 1-continued

| Example | Structure | IUPAC Name |
|---------|-----------|------------|
| 250 | 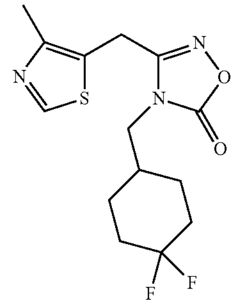 [SMILES: Cc1ncsc1Cc1noc(=O)n1CC1CCC(F)(F)CC1] | 4-[(4,4-difluorocyclohexyl)methyl]-3-[(4-methyl-1,3-thiazol-5-yl)methyl]-1,2,4-oxadiazol-5(4H)-one |
| 251 | 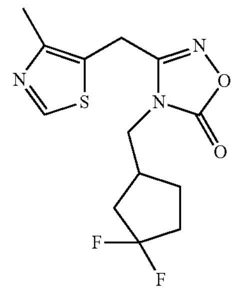 [SMILES: Cc1ncsc1Cc1noc(=O)n1CC1CCC(F)(F)C1] | 4-[(3,3-difluorocyclopentyl)methyl]-3-[(4-methyl-1,3-thiazol-5-yl)methyl]-1,2,4-oxadiazol-5(4H)-one |

Purification System

HPLC Preparative

HPLC system WATERS Quaternary Gradient Mobile 2535 equipped with WATERS UV/Visible Detector 2489 set to a dual-wavelength UV detection. Two mobile phases were used, mobile phase A: water (MilliQ) 0.05% TFA; mobile phase B: acetonitrile (Chromasolv Sigma-Aldrich) 0.05% TFA, and the run gradient conditions were set specifically for each compound. The purifications were achieved on a LUNA C18 Phenomenex Column 5 μm 19×150. An injection volume between 100 and 500 μl was used and the flow was 15 ml/min.

Racemate Separation

The two enantiomers 148 and 149 were obtained by resolution of the racemic mixture 128 using a WATERS Quaternary Gradient Mobile 2535 equipped with WATERS UV/Visible Detector 2489 set to a dual-wavelength UV detection at 220 and 260 nm. The chiral resolution was achieved on the Kromasil 5-Amycoat column (250 mm×4.6 mm, particle size 5 μm) using N-Hexane (Chromasolv Sigma-Aldrich)—Ethanol (Chromasolv Sigma-Aldrich) 90-10 (v/v) as isocratic mobile phase; The sample was eluted from the column at a flow rate of 1.0 ml/min at room temperature (Pressure: ≈600 psi). The mixture was dissolved in Ethanol at concentration of 1% (w/v) and the injection volume was 15 μL.

LCMS

LCMS General Procedure

The HPLC measurement was performed using a Dionex 3000 module comprising a quaternary pump with degasser, an autosampler, a column oven (set at 29° C.), a diode-array detector DAD and a column as specified in the respective methods below. Flow from the column was split to a MS spectrometer. The MS detector (LCQ Fleet Thermo Scientific) was configured with an electrospray ionization source. Mass spectra were acquired by scanning from 50 to 800 in 0.48 second. The capillary needle voltage was 5 kV in positive and negative ionization mode and the source temperature was maintained at 275° C. Nitrogen was used as the nebulizer gas, the flow was 8 l/min. Data acquisition was performed with Thermo Xcalibur Qual Browser.

LCMS—Procedure

In addition to the general procedure, reversed-phase HPLC was carried out on a Kinetex XB-$C_{18}$ column Phenomenex (1.7 μm, 50×2.1 mm) with a flow rate of 0.300 ml/min. Two mobile phases were used, mobile phase A: ammonium formate buffer solution at pH 3.5; mobile phase B: acetonitrile (Chromasolv Sigma-Aldrich), and they were employed to run a gradient conditions from 15% B to 98% in 4.5 minutes, hold these condition for 1.35 minutes and then 15% B in 0.1 minutes and hold these conditions for 3 minutes in order to reequilibrate the column. An injection volume of 1 μl was used.

TABLE 2

Retention time ($R_t$) in minutes, [M + H]+, [M − H]− and [M − H + HCOOH]− peaks observed in LCMS procedure.

| Example | $R_t$ | [M + H]+ | [M − H]− | [M − H + HCOOH]− | Example | $R_t$ | [M + H]+ | [M − H]− | [M − H + HCOOH]− |
|---------|-------|----------|----------|-------------------|---------|-------|----------|----------|-------------------|
| 1 | 4.80 | 337.8 | — | — | 2 | 4.94 | — | 343.6 | — |
| 3 | 4.80 | — | 313.7 | — | 4 | 5.27 | 345.2 | — | 389.0 |
| 5 | 5.49 | — | — | 426.2 | 6 | 5.39 | 319.1 | — | — |
| 7 | 5.34 | 349.64 | — | — | 8 | 4.52 | 306.3 | — | 350.3 |
| 9 | 5.68 | — | — | 397.92 | 10 | 5.38 | 299.1 | — | — |
| 11 | 5.38 | — | — | 361.1 | 12 | 5.63 | 291.2 | — | — |

TABLE 2-continued

Retention time (R$_t$) in minutes, [M + H]+, [M − H]⁻ and [M − H + HCOOH]⁻ peaks observed in LCMS procedure.

| Example | R$_t$ | [M + H]⁺ | [M − H]⁻ | [M − H + HCOOH]⁻ | Example | R$_t$ | [M + H]⁺ | [M − H]⁻ | [M − H + HCOOH]⁻ |
|---|---|---|---|---|---|---|---|---|---|
| 13 | 5.81 | 388.2 | — | — | 14 | 5.59 | 372.4 | — | — |
| 15 | 5.45 | 355.6 | — | — | 16 | 5.84 | — | 420.2 | — |
| 17 | 5.88 | 388.3 | 386.6 | — | 18 | 5.50 | 371.9 | — | — |
| 19 | 5.36 | 337.1 | — | — | 20 | 5.52 | 354.2 | — | — |
| 21 | 5.43 | 319.4 | — | — | 22 | 5.61 | 353.8 | — | — |
| 23 | 5.72 | 387.8 | — | — | 24 | 4.24 | 334.5 | — | — |
| 25 | 5.57 | 351.1 | — | — | 26 | 5.41 | 337.3 | — | — |
| 27 | 5.59 | 333.3 | — | — | 28 | 5.48 | 349.9 | — | — |
| 29 | 5.75 | 369.1 | — | — | 30 | 4.84 | 370.7 | — | — |
| 31 | 4.72 | 340.5 | — | — | 32 | 4.55 | 310.3 | — | — |
| 33 | 4.59 | 326.1 | — | — | 34 | 4.82 | 326.5 | — | — |
| 35 | 5.44 | — | — | 421.1 | 36 | 4.87 | 338.2 | — | — |
| 37 | 5.26 | — | — | 432.4 | 38 | 4.09 | 321.2 | — | — |
| 39 | 4.42 | 321.5 | — | — | 40 | 4.45 | 310.3 | — | — |
| 41 | 4.40 | 325.8 | — | — | 42 | 4.34 | 320.4 | — | — |
| 43 | 4.13 | 320.4 | — | — | 44 | 5.08 | 309.1 | — | — |
| 45 | 4.77 | 339.8 | — | — | 46 | 4.66 | 337.3 | — | — |
| 47 | 2.67 | 323.4 | — | — | 48 | 5.52 | 351.1 | — | — |
| 49 | 5.50 | 339.9 | — | — | 50 | 5.64 | — | — | 398.5 |
| 51 | 5.48 | — | — | 381.8 | 52 | 5.67 | — | — | 431.6 |
| 53 | 5.32 | 321.6 | — | 366.2 | 54 | 5.26 | 303.0 | — | 347.0 |
| 55 | 5.48 | 337.5 | — | — | 56 | 5.43 | 337.1 | — | — |
| 57 | 5.41 | 349.6 | — | — | 58 | 5.82 | 422.3 | — | — |
| 59 | 5.79 | 388.3 | — | — | 60 | 5.68 | 372.1 | — | — |
| 61 | 5.49 | 355.3 | — | — | 62 | 4.80 | 320.4 | — | — |
| 63 | 5.68 | 387.0 | — | — | 64 | 5.35 | 402.1 | — | 445.9 |
| 65 | 5.60 | — | — | 398.2 | 66 | 5.47 | 377.1 | — | — |
| 67 | 5.56 | 333.3 | — | — | 68 | 5.32 | 349.1 | — | — |
| 69 | 5.41 | 296.9 | — | — | 70 | 5.10 | 383.0 | — | — |
| 71 | 5.66 | — | 352.3 | 398.1 | 72 | 5.71 | — | 385.7 | 431.2 |
| 73 | 5.50 | 337.2 | — | — | 74 | 5.73 | — | 352.0 | 398.1 |
| 75 | 5.24 | 303.0 | — | — | 76 | 5.41 | 319.1 | — | — |
| 77 | 5.73 | 365.8 | — | — | 78 | 5.56 | 351.1 | — | — |
| 79 | 4.04 | 286.1 | — | — | 80 | 5.34 | 321.2 | — | 365.1 |
| 81 | 5.35 | 337.1 | — | — | 82 | 5.80 | 325.7 | — | — |
| 83 | 5.13 | 283.0 | — | — | 84 | 5.42 | — | — | 405.1 |
| 85 | 5.62 | 311.0 | — | — | 86 | 5.84 | 353.7 | 351.2 | — |
| 87 | 6.09 | 339.8 | — | — | 88 | 5.92 | 337.2 | — | — |
| 89 | 4.95 | 327.2 | — | — | 90 | 5.35 | 295.3 | — | — |
| 91 | 5.94 | 337.7 | — | — | 92 | 6.10 | 339.0 | — | — |
| 93 | 4.73 | 344.8 [M + H$_3$O]⁺ | — | — | 94 | 5.50 | 327.0 | — | — |
| 95 | 5.08 | 281.0 | — | — | 96 | 5.72 | 343.2 | — | — |
| 97 | 5.54 | 361.1 | — | — | 98 | 4.74 | 329.1 | — | — |
| 99 | 6.25 | 353.4 | — | — | 100 | 4.78 | 273.3 | — | — |
| 101 | 5.05 | 287.4 | — | — | 102 | 5.37 | 301.1 | — | — |
| 104 | 4.45 | 286.1 | — | — | 105 | 5.46 | 353.01 | — | 397.4 |
| 107 | 5.23 | — | — | 347.0 | 108 | 5.20 | 285.0 | — | — |
| 109 | 5.21 | 315.0 | — | — | 110 | 4.87 | 274.1 | — | — |
| 111 | 4.51 | 274.1 | — | — | 112 | 5.59 | 303.6 | — | — |
| 113 | 6.06 | 375.1 | — | — | 114 | 5.94 | — | — | 368.6 |
| 115 | 6.15 | — | 340.9 | — | 116 | 5.94 | 341.4 | — | — |
| 117 | 5.84 | 307.3 | — | — | 118 | 6.24 | — | 340.5 | — |
| 119 | 5.65 | 309.2 | — | — | 120 | 5.63 | 291.2 | — | — |
| 121 | 6.25 | 353.9 | — | — | 122 | 6.08 | 339.2 | — | — |
| 123 | 4.54 | 274.3 | — | — | | | | | |
| 125 | 5.63 | 291.0 | — | — | 126 | 5.63 | 273.2 | — | — |
| 127 | 5.56 | 303.2 | — | — | 128 | 5.34 | 347.2 | — | — |
| 129 | 6.22 | 279.6 | — | — | 130 | 5.95 | 325.8 | — | — |
| 131 | 5.75 | 291.4 | — | — | 132 | 5.38 | 360.9 | — | — |
| 133 | 5.28 | — | — | 358.1 | 134 | 5.44 | — | — | 370.9 |
| 135 | 5.47 | — | 873.4 [Dimer] | — | 136 | 5.40 | — | 767.6 [Dimer] | — |
| 137 | 5.14 | — | 740.7 [Dimer] | — | 138 | 5.44 | — | 806.2 [Dimer] | — |
| 139 | 5.65 | 353.0 | — | — | 140 | 6.26 | 341.3 | — | — |
| 141 | 5.76 | 377.1 | — | — | 142 | 6.21 | 339.3 | — | — |
| 143 | 3.50 | 340.2 | — | — | 144 | 5.79 | 386.5 | — | — |
| 145 | 5.72 | 351.1 | — | — | 146 | 6.17 | 339.1 | — | — |
| 147 | 5.75 | 375.1 | — | — | 148 | 5.34 | 347.2 | — | — |
| 149 | 5.34 | 347.2 | — | — | 150 | 5.38 | — | — | — |
| 151 | 5.40 | — | — | 370.9 | 152 | 5.40 | — | — | 371.0 |
| 153 | 5.45 | — | — | — | 154 | 5.36 | — | — | — |
| 155 | 5.68 | — | 409.4 | — | 156 | 5.65 | — | 376.9 | — |
| 157 | 5.55 | — | 375.9 | — | 158 | 5.46 | — | — | 386.8 |
| 159 | 5.73 | — | 376.2 | — | 160 | 5.29 | 339.1 | — | 383.1 |

TABLE 2-continued

Retention time (R_t) in minutes, [M + H]+, [M − H]− and [M − H + HCOOH]− peaks observed in LCMS procedure.

| Example | R_t | [M + H]+ | [M − H]− | [M − H + HCOOH]− | Example | R_t | [M + H]+ | [M − H]− | [M − H + HCOOH]− |
|---|---|---|---|---|---|---|---|---|---|
| 161 | 5.28 | 309.2 | — | 353.2 | 162 | 5.49 | — | — | 405.4 |
| 163 | 5.80 | 305.7 | — | 349.9 | 164 | 5.46 | — | — | 385.2 |
| 165 | 5.34 | — | — | 361.0 | 166 | 5.62 | — | — | 421.3 |
| 167 | 5.74 | — | — | 455.6 | 168 | 5.42 | — | — | 411.1 |
| 169 | 4.98 | — | 312.0 | — | 170 | 5.51 | — | — | — |
| 171 | 5.50 | — | — | 385.2 | 172 | 5.42 | — | — | 366.9 |
| 173 | 5.46 | 359.1 | — | — | 174 | 4.44 | 243.0 | — | — |
| 175 | 4.75 | 257.0 | — | — | 176 | 5.05 | 271.0 | — | — |
| 177 | 5.31 | 285.0 | — | — | 178 | 5.28 | 285.0 | — | — |
| 179 | 6.36 | 353.2 | — | 397.4 | 180 | 2.46 | 354.43 | | |
| 181 | 5.20 | 376.5 | — | — | 182 | 4.01 | 390.5 | — | — |
| 183 | 5.44 | 309.0 | — | — | 184 | 5.73 | — | 391.0 | — |
| 185 | 5.34 | 343.1 | — | — | 186 | 5.35 | 296.7 | — | — |
| 187 | 5.50 | 331.2 | — | — | 188 | 5.46 | — | — | 367.1 |
| 189 | 5.26 | 378.1 | — | 422.1 | 190 | 4.85 | 329.2 | 327.3 | — |
| 191 | 4.87 | 316.2 | — | — | 192 | 5.37 | 392.3 | — | 436.1 |
| 193 | 4.55 | — | — | 360.0 | 194 | 4.62 | 300.1 | — | 344.3 |
| 195 | 4.67 | 327.2 | — | 371.0 | 196 | 4.74 | 315.1 | — | 359.5 |
| 197 | 4.76 | — | — | 359.3 | 198 | 5.39 | — | — | 411.0 |
| 199 | 4.71 | — | — | 344.2 | 200 | 4.73 | 330.2 | — | 374.0 |
| 201 | 4.01 | 313.1 | — | — | 202 | 5.60 | — | — | 387.2 |
| 203 | 5.72 | 377.0 | — | 421.6 | 204 | 5.27 | — | — | 357.8 |
| 205 | 5.35 | 347.0 | — | — | 206 | 5.15 | 301.1 | — | — |
| 207 | — | — | — | 381.2 | 208 | 4.75 | — | — | 348.2 |
| 209 | 4.88 | 338.1 | — | 372.1 | 210 | 5.13 | 292.2 | — | 336.6 |
| 211 | 4.91 | — | — | 372.4 | 212 | 4.50 | 317.2 | — | — |
| 213 | 4.57 | 351.5 | — | — | 214 | 4.81 | 305.4 | — | — |
| 215 | 4.57 | 341.4 | — | — | 216 | 4.02 | 300.3 | — | 343.8 |
| 217 | 4.08 | 334.5 | — | — | 218 | 4.54 | 288.4 | — | — |
| 219 | 4.18 | 324.4 | — | 368.2 | 220 | 5.39 | 362.2 | — | — |
| 221 | 5.29 | 328.1 | — | 372.2 | 222 | — | 316.2 | — | — |
| 223 | — | — | — | 396.2 | 224 | 5.31 | 362.3 | — | — |
| 225 | 5.25 | 328.1 | — | — | 226 | 5.51 | 376.3 | — | — |
| 227 | 5.37 | 342.1 | — | 386.1 | 228 | 5.28 | 342.0 | — | 386.1 |
| 229 | 5.34 | 376.0 | — | — | 230 | 5.61 | 330.1 | — | — |
| 231 | 5.32 | 366.1 | — | 410.3 | 232 | 5.59 | 346.1 | — | — |
| 233 | 5.72 | 380.3 | — | — | 234 | 5.98 | 334.2 | — | — |
| 235 | 5.57 | 370.2 | — | 414.3 | 236 | 5.60 | 369.2 | — | 403.1 |
| 237 | 5.76 | 403.4 | — | — | 238 | 6.06 | 357.4 | — | — |
| 239 | 5.63 | 393.2 | — | 437.0 | 240 | 5.26 | 292.1 | — | — |
| 241 | 5.47 | 326.3 | — | — | 242 | 6.51 | 416.5 | — | — |
| 243 | 6.32 | 382.3 | — | — | 244 | 5.81 | 374.3 | — | — |
| 245 | 5.63 | 330.1 | — | — | 246 | 3.07 | 312.2 | — | — |
| 247 | 4.50 | 306.1 | — | 349.7 | 248 | 4.60 | 340.1 | — | — |
| 249 | 4.88 | 294.2 | — | — | 250 | 4.63 | — | — | 373.8 |
| 251 | 5.00 | — | — | 359.6 | | | | | |

NMR Characterization $^1$H NMR spectra were recorded on a Varian Mercury NMR 400 MHz spectrometer using CDCl$_3$, DMSO-d6 or CD$_3$OD as solvents Chemical shifts (δ) are reported in parts per million (ppm) relative to residual signal of non-fully deuterated solvents pick for $^1$H NMR assigned as 7.26 ppm for CHCl$_3$, 3.31 ppm for CHD$_2$OD and 2.50 ppm for DMSO-d$_5$.

| Example | $^1$H-NMR 400 |
|---|---|
| 1 | $^1$H NMR (CD$_3$OD) δ ppm 3.96 (s, 2 H) 4.97 (s, 2 H) 6.95 (t, J = 8.71 Hz, 2 H) 7.01 (t, J = 9.29 Hz, 1 H) 7.14 (dd, J = 8.31, 5.38 Hz, 2 H) 7.19 (d, J = 8.22 Hz, 1 H) 7.25-7.33 (m, 1 H) |
| 2 | $^1$H NMR (CDCl$_3$) δ ppm 3.77 (s, 3 H) 3.79 (s, 3 H) 4.02 (s, 2 H) 4.95 (s, 2 H) 6.41-6.48 (m, 2 H) 7.01 (t, J = 8.48 Hz, 2 H) 7.12 (d, J = 7.97 Hz, 1 H) 7.22-7.30 (m, 2 H) |
| 3 | $^1$H NMR (CDCl$_3$) δ ppm 3.79 (s, 3 H) 3.95 (s, 2 H) 4.92 (s, 2 H) 6.84 (d, J = 8.52 Hz, 2 H) 6.95-7.11 (m, 3 H) 7.14-7.34 (m, 1 H) 7.37-7.51 (m, 1 H) 7.66 (br dd, J = 11.82, 7.70 Hz, 1 H) |
| 4 | $^1$H NMR (CDCl$_3$) δ ppm 3.71-3.76 (m, 8 H) 4.47 (s, 2 H) 6.16-6.23 (m, 2 H) 6.36 (s, 1 H) 6.99 (t, J = 8.05 Hz, 2 H) 7.05-7.17 (m, 2 H) |
| 5 | $^1$H NMR (CDCl$_3$) δ ppm 3.82 (s, 2 H) 4.68 (s, 2 H) 6.53 (dd, J = 8.84, 2.43 Hz, 1 H) 6.83-7.00 (m, 3 H) 7.10 (dd, J = 7.97, 5.41 Hz, 2 H) 7.49 (dd, J = 8.71, 5.13 Hz, 1 H) |
| 6 | $^1$H NMR (CDCl$_3$) δ ppm 3.89 (s, 2 H) 4.79 (s, 2 H) 6.95 (s, 1 H) 7.14 (br t, J = 6.69 Hz, 3 H) 7.19-7.34 (m, 4 H) |
| 7 | $^1$H NMR (CDCl$_3$) δ ppm 3.77 (s, 3 H) 3.87 (s, 2 H) 4.79 (s, 2 H) 6.65 (br s, 1 H) 6.71 (br d, J = 7.43 Hz, 2 H) 6.94 (s, 1 H) 7.09-7.30 (m, 3 H) |

-continued

| Example | ¹H-NMR 400 |
|---|---|
| 8 | ¹H NMR (CDCl₃) δ ppm 2.41 (s, 3 H) 3.88 (s, 2 H) 4.71 (s, 2 H) 7.05 (t, J = 8.48 Hz, 2 H) 7.18 (br dd, J = 8.16, 5.32 Hz, 2 H) 8.65 (s, 1 H) |
| 9 | ¹H NMR (CDCl₃) δ ppm 3.80 (s, 2 H) 4.69 (s, 2 H) 6.91 (d, J = 8.34 Hz, 1 H) 6.96 (t, J = 8.48 Hz, 2 H) 7.07-7.13 (m, 2 H) 7.17 (dd, J = 8.34, 1.83 Hz, 1 H) 7.37 (d, J = 1.83 Hz, 1 H) |
| 10 | ¹H NMR (CDCl₃) δ ppm 1.66 (d, J = 7.24 Hz, 3 H) 3.63-3.78 (m, 2 H) 5.07 (d, J = 7.24 Hz, 1 H) 7.01 (t, J = 8.10 Hz, 2 H) 7.10 (dd, J = 8.43, 5.32 Hz, 2 H) 7.17-7.27 (m, 2 H) 7.27-7.40 (m, 3 H) |
| 11 | ¹H NMR (CDCl₃) δ ppm 1.65 (d, J = 7.24 Hz, 3 H) 3.78 (d, J = 5.96 Hz, 2 H) 5.00 (br d, J = 7.24 Hz, 1 H) 6.94-7.07 (m, 4 H) 7.08-7.27 (m, 4 H) |
| 12 | ¹H NMR (CDCl₃) δ ppm 0.77-0.94 (m, 2 H) 1.10 (br s, 3 H) 1.39-1.51 (m, 1 H) 1.51-1.75 (m, 5 H) 3.20 (d, J = 7.42 Hz, 2 H) 3.89 (s, 2 H) 7.05 (t, J = 8.48 Hz, 2 H) 7.15-7.28 (m, 2 H) |
| 13 | ¹H NMR (CDCl₃) δ ppm 3.96 (s, 2 H) 4.92 (s, 2 H) 6.92-7.01 (m, 2 H) 7.08-7.16 (m, 2 H) 7.18-7.25 (m, 1 H) 7.35 (d, J = 7.15 Hz, 1 H) |
| 14 | ¹H NMR (CDCl₃) δ ppm 3.89 (s, 2 H) 4.92 (s, 2 H) 6.89 (td, J = 8.23, 2.52 Hz, 1 H) 6.97 (t, J = 8.94 Hz, 1 H) 7.04-7.10 (m, 2 H) 7.13-7.18 (m, 1 H) 7.20-7.26 (m, 1 H) |
| 15 | ¹H NMR (CDCl₃) δ ppm 3.83 (s, 2 H) 4.91 (s, 2 H) 6.71-6.86 (m, 2 H) 6.98 (t, J = 8.89 Hz, 1 H) 7.05-7.29 (m, 3 H) |
| 16 | ¹H NMR (CDCl₃) δ ppm 3.99 (s, 2 H) 4.95 (s, 2 H) 6.93 (t, J = 8.94 Hz, 1 H) 7.08-7.13 (m, 1 H) 7.14-7.22 (m, 1 H) 7.24-7.31 (m, 2 H) 7.56-7.61 (m, 1 H) |
| 17 | ¹H NMR (CDCl₃) δ ppm 3.90 (s, 2 H) 4.92 (s, 2 H) 6.96 (t, J = 8.98 Hz, 1 H) 7.01 (d, J = 8.25 Hz, 1 H) 7.11-7.18 (m, 2 H) 7.21-7.28 (m, 1 H) 7.33 (d, J = 1.83 Hz, 1 H) |
| 18 | ¹H NMR (CDCl₃) δ ppm 3.91 (d, J = 1.01 Hz, 2 H) 5.02-5.14 (m, 2 H) 6.97-7.04 (m, 1 H) 7.05-7.12 (m, 1 H) 7.20 (t, J = 7.24 Hz, 1 H) 7.23-7.30 (m, 2 H) 7.31-7.39 (m, 1 H) |
| 19 | ¹H NMR (CDCl₃) δ ppm 3.89 (s, 2 H) 4.88 (s, 2 H) 6.92-7.18 (m, 5 H) 7.19-7.29 (m, 2 H) |
| 20 | ¹H NMR (CDCl₃) δ ppm 3.95 (s, 2 H) 4.90 (s, 2 H) 6.96 (t, J = 8.89 Hz, 1 H) 7.06-7.11 (m, 1 H) 7.12-7.24 (m, 4 H) 7.33 (dd, J = 7.47, 1.60 Hz, 1 H) |
| 21 | ¹H NMR (CD3OD) δ ppm 4.06 (s, 2 H) 4.94 (s, 2 H) 7.07 (t, J = 9.00 Hz, 1 H) 7.20-7.25 (m, 1 H) 7.30 (br d, J = 7.04 Hz, 3 H) 7.33-7.42 (m, 3 H) |
| 22 | ¹H NMR (CDCl₃) δ ppm 3.94 (s, 2 H) 4.96 (s, 2 H) 6.91-6.98 (m, 1 H) 7.08-7.21 (m, 3 H) 7.23-7.31 (m, 2 H) 7.37-7.42 (m, 1 H) |
| 23 | ¹H NMR (CDCl₃) δ ppm 3.89 (m, 2 H) 5.10 (s, 2 H) 6.91-6.99 (m, 1 H) 7.11-7.24 (m, 3 H) 7.43-7.50 (m, 1 H) 7.54-7.60 (m, 1 H) 7.73 (d, J = 7.70 Hz, 1 H) |
| 24 | ¹H NMR (CDCl₃) δ ppm 2.54 (s, 3 H) 3.93 (s, 2 H) 4.83 (s, 2 H) 6.87-6.94 (m, 1 H) 7.05-7.20 (m, 4 H) 8.42 (br d, J = 3.85 Hz, 1 H) |
| 25 | ¹H NMR (CDCl₃) δ ppm 2.31 (s, 3 H) 3.85 (s, 2 H) 4.81 (s, 2 H) 6.83-6.89 (m, 1 H) 6.90-6.99 (m, 3 H) 7.14-7.25 (m, 2 H) |
| 26 | ¹H NMR (CDCl₃) δ ppm 3.93 (s, 2 H) 4.83 (s, 2 H) 6.89-7.06 (m, 4 H) 7.16-7.27 (m, 2 H) 7.30-7.37 (m, 1 H) |
| 27 | ¹H NMR (CDCl₃) δ ppm 2.32 (s, 3 H) 3.80-3.84 (m, 2 H) 4.86 (s, 2 H) 6.97 (t, J = 8.06 Hz, 2 H) 7.12-7.27 (m, 5 H) |
| 28 | ¹H NMR (CDCl₃) δ ppm 3.88 (s, 3 H) 4.00 (s, 2 H) 4.86 (s, 2 H) 6.91 (d, J = 8.25 Hz, 1 H) 6.98 (dt, J = 11.55, 8.02 Hz, 2 H) 7.17-7.30 (m, 3 H) 7.33 (t, J = 7.88 Hz, 1 H) |
| 29 | ¹H NMR (CDCl₃) δ ppm 3.83 (s, 2 H) 5.34 (s, 2 H) 6.84 (br t, J = 8.61 Hz, 1 H) 7.02-7.15 (m, 2 H) 7.21 (br d, J = 7.06 Hz, 1 H) 7.42 (t, J = 7.65 Hz, 1 H) 7.54-7.64 (m, 2 H) 7.82-7.88 (m, 1 H) 7.91 (br d, J = 7.79 Hz, 1 H) 7.96 (br d, J = 7.97 Hz, 1 H) |
| 30 | ¹H NMR (CDCl₃) δ ppm 3.88 (s, 2 H) 5.31 (s, 2 H) 6.80 (t, J = 8.66 Hz, 1 H) 6.99-7.13 (m, 2 H) 7.28 (d, J = 7.06 Hz, 1 H) 7.52 (dd, J = 8.57, 4.17 Hz, 1 H) 7.64 (t, J = 7.84 Hz, 1 H) 8.10 (d, J = 8.52 Hz, 1 H) 8.38 (d, J = 8.52 Hz, 1 H) 8.99 (br d, J = 3.94 Hz, 1 H) |
| 31 | ¹H NMR (CDCl₃) δ ppm 2.54 (s, 3 H) 4.01 (s, 2 H) 4.99 (s, 2 H) 6.99-7.06 (m, 1 H) 7.20-7.32 (m, 2 H) 8.71 (s, 1 H) |
| 32 | ¹H NMR (CDCl₃) δ ppm 4.09-4.14 (m, 2 H) 4.94 (s, 2 H) 7.00 (t, J = 8.39 Hz, 1 H) 7.08 (s, 1 H) 7.16-7.28 (m, 2 H) 7.65 (s, 1 H) |
| 33 | ¹H NMR (CDCl₃) δ ppm 4.07 (s, 2 H) 5.04 (s, 2 H) 7.05 (t, J = 8.34 Hz, 1 H) 7.20-7.33 (m, 2 H) 7.80 (s, 1 H) 8.81 (s, 1 H) |
| 34 | ¹H NMR (CDCl₃) δ ppm 4.21 (s, 2 H) 5.13 (s, 2 H) 7.02 (t, J = 8.20 Hz, 1 H) 7.16-7.28 (m, 2 H) 7.38 (d, J = 3.21 Hz, 1 H) 7.77 (d, J = 3.21 Hz, 1 H) |
| 35 | ¹H NMR (CDCl₃) δ ppm 4.41-4.46 (m, 2 H) 5.92 (s, 2 H) 6.61 (d, J = 2.20 Hz, 1 H) 7.07 (t, J = 8.34 Hz, 1 H) 7.17-7.37 (m, 2 H) 7.74-7.83 (m, 1 H) |
| 36 | ¹H NMR (CDCl₃) δ ppm 2.22 (s, 3 H) 2.38 (s, 3 H) 3.91 (s, 2 H) 4.62 (s, 2 H) 7.00 (t, J = 8.43 Hz, 1 H) 7.14-7.30 (m, 2 H) |
| 37 | ¹H NMR (CDCl₃) δ ppm 4.04 (s, 2 H) 4.90 (s, 2 H) 6.93 (t, J = 8.44 Hz, 1 H) 7.09-7.27 (m, 2 H) 7.60-7.74 (m, 2 H) 8.53 (s, 1 H) |
| 38 | ¹H NMR (CDCl₃) δ ppm 4.06 (s, 2 H) 4.80 (s, 2 H) 6.87-7.09 (m, 1 H) 7.13-7.29 (m, 2 H) 8.59 (m, 2 H) 9.17 (s, 1 H) |

-continued

| Example | ¹H-NMR 400 |
|---|---|
| 39 | ¹H NMR (CDCl₃) δ ppm 4.07 (s, 2 H) 5.02 (s, 2 H) 6.85-7.05 (m, 1 H) 7.12-7.26 (m, 3 H) 8.66 (d, J = 4.86 Hz, 2 H) |
| 40 | ¹H NMR (CDCl₃) δ ppm 4.15 (s, 2 H) 4.89 (s, 2 H) 6.99-7.08 (m, 1 H) 7.12 (s, 1 H) 7.20-7.32 (m, 2 H) 7.87 (s, 1 H) |
| 41 | ¹H NMR (CDCl₃) δ ppm 2.54 (s, 3 H) 4.15 (s, 2 H) 5.02 (s, 2 H) 7.00-7.07 (m, 1 H) 7.21-7.33 (m, 2 H) |
| 42 | ¹H NMR (CDCl₃) δ ppm 3.98 (s, 2 H) 4.84 (s, 2 H) 6.97 (t, J = 8.52 Hz, 1 H) 7.14-7.27 (m, 2 H) 7.30 (dd, J = 7.74, 4.90 Hz, 1 H) 7.59 (br d, J = 7.88 Hz, 1 H) 8.49 (s, 1 H) 8.58 (br d, J = 3.94 Hz, 1 H) |
| 43 | ¹H NMR (CDCl₃) δ ppm 3.96 (s, 2 H) 4.83 (s, 2 H) 6.93 (t, J = 8.66 Hz, 1 H) 7.06 (br d, J = 5.13 Hz, 2 H) 7.12-7.27 (m, 2 H) 8.56 (br d, J = 5.13 Hz, 2 H) |
| 44 | ¹H NMR (CDCl₃) δ ppm 4.01 (s, 2 H) 4.68 (s, 2 H) 6.37 (s, 1 H) 6.98-7.07 (m, 1 H) 7.20-7.31 (m, 2 H) 7.42 (d, J = 1.19 Hz, 2 H) |
| 45 | ¹H NMR (CDCl₃) δ ppm 4.06 (s, 2 H) 5.02 (s, 2 H) 6.96 (br t, J = 8.57 Hz, 1 H) 7.13-7.26 (m, 2 H) 8.52 (s, 2 H) |
| 46 | ¹H NMR (CDCl₃) δ ppm 2.18 (s, 3 H) 3.79 (s, 3 H) 3.99 (s, 2 H) 4.81 (s, 2 H) 5.92 (s, 1 H) 7.00 (t, J = 8.52 Hz, 1 H) 7.17-7.27 (m, 2 H) |
| 47 | ¹H NMR (CDCl₃) δ ppm 3.71 (s, 3 H) 4.28 (d, J = 1.01 Hz, 2 H) 4.92 (s, 2 H) 6.87 (s, 1 H) 6.93-7.01 (m, 2 H) 7.13-7.25 (m, 2 H) |
| 48 | ¹H NMR (CDCl₃) δ ppm 1.91 (d, J = 7.24 Hz, 3 H) 3.63 (d, J = 16.77 Hz, 1 H) 3.88 (d, J = 16.77 Hz, 1 H) 5.32 (q, J = 7.15 Hz, 1 H) 6.94-7.02 (m, 1 H) 7.09 (t, J = 8.57 Hz, 2 H) 7.15-7.28 (m, 2 H) 7.36 (dd, J = 8.48, 5.27 Hz, 2 H) |
| 49 | ¹H NMR (CDCl₃) δ ppm 1.93 (d, J = 7.24 Hz, 3 H) 3.56 (d, J = 16.86 Hz, 1 H) 3.84 (d, J = 16.86 Hz, 1 H) 5.39 (q, J = 7.15 Hz, 1 H) 6.93-7.01 (m, 1 H) 7.14-7.26 (m, 2 H) 7.34-7.46 (m, 5 H) |
| 50 | ¹H NMR (CDCl₃) δ ppm 3.72-3.89 (m, 2 H) 4.69-4.81 (m, 2 H) 6.80 (d, J = 7.79 Hz, 1 H) 6.92 (t, J = 8.52 Hz, 2 H) 7.04-7.14 (br s, 3 H) 7.40 (d, J = 7.97 Hz, 1 H) |
| 51 | ¹H NMR (CDCl₃) δ ppm 3.81 (s, 2 H) 4.70 (s, 2 H) 6.88-7.03 (m, 4 H) 7.08-7.15 (m, 3H) |
| 52 | ¹H NMR (CDCl₃) δ ppm 3.83 (s, 2 H) 4.80 (s, 2 H) 6.87 (t, J = 8.48 Hz, 2 H) 7.01-7.10 (m, 3 H) 7.22-7.29 (m, 1 H) 7.63 (d, J = 7.79 Hz, 1 H) |
| 53 | ¹H NMR (CDCl₃) δ ppm 3.87 (s, 2 H) 4.58 (s, 2 H) 6.77-6.89 (m, 2 H) 7.01 (t, J = 8.48 Hz, 2 H) 7.18 (dd, J = 8.20, 5.27 Hz, 2 H) 7.22-7.30 (m, 1 H) |
| 54 | ¹H NMR (CDCl₃) δ ppm 3.77 (s, 2 H) 4.54 (s, 2 H) 6.98-7.06 (m, 4 H) 7.06-7.17 (m, 4 H) |
| 55 | ¹H NMR (CDCl₃) δ ppm 3.91 (s, 2 H) 4.80 (s, 2 H) 6.96 (br t, J = 8.48 Hz, 1 H) 7.03 (br t, J = 8.52 Hz, 2 H) 7.17 (br t, J = 8.43 Hz, 1 H) 7.20-7.27 (m, 3 H) |
| 56 | ¹H NMR (CDCl₃) δ ppm 4.00 (s, 2 H) 4.90 (s, 2 H) 6.95-7.02 (m, 1 H) 7.10 (t, J = 9.26 Hz, 1 H) 7.13-7.27 (m, 3 H) 7.28-7.39 (m, 2 H) |
| 57 | ¹H NMR (CDCl₃) δ ppm 3.78 (s, 3 H) 3.90 (s, 2 H) 4.81 (s, 2 H) 6.77 (s, 1 H) 6.81 (d, J = 7.61 Hz, 1 H) 6.86 (dd, J = 8.25, 2.20 Hz, 1 H) 6.93-7.00 (m, 1 H) 7.13-7.18 (m, 1 H) 7.21 (dd, J = 8.02, 5.82 Hz, 1 H) 7.27 (t, J = 7.93 Hz, 1 H) |
| 58 | ¹H NMR (CDCl₃) δ ppm 4.02 (s, 2 H) 4.97 (s, 2 H) 6.89 (br t, J = 8.57 Hz, 1 H) 7.06-7.22 (m, 3 H) 7.35 (t, J = 7.88 Hz, 1 H) 7.66 (br d, J = 7.70 Hz, 1 H) |
| 59 | ¹H NMR (CDCl₃) δ ppm 3.97 (s, 2 H) 4.94 (s, 2 H) 6.89-6.96 (m, 1 H) 7.10-7.15 (m, 1 H) 7.15-7.22 (m, 2 H) 7.42 (d, J = 8.06 Hz, 1 H) |
| 60 | ¹H NMR (CDCl₃) δ ppm 3.96 (s, 2 H) 4.90 (m, 2 H) 6.91-7.02 (m, 2 H) 7.09-7.23 (m, 4 H) |
| 61 | ¹H NMR (CDCl₃) δ ppm 4.02 (s, 2 H) 4.85 (s, 2 H) 6.82-6.94 (m, 2 H) 6.96-7.04 (m, 1 H) 7.17-7.27 (m, 2 H) 7.31-7.39 (m, 1 H) |
| 62 | ¹H NMR (CDCl₃) δ ppm 4.19 (s, 2 H) 4.92 (s, 2 H) 6.95-7.01 (m, 1 H) 7.15-7.27 (m, 3 H) 7.29 (d, J = 7.79 Hz, 1 H) 7.64-7.72 (m, 1 H) 8.54 (br d, J = 4.49 Hz, 1 H) |
| 63 | ¹H NMR (CDCl₃) δ ppm 3.95 (s, 2 H) 4.90 (s, 2 H) 6.93 (t, J = 8.52 Hz, 1 H) 7.11-7.23 (m, 2 H) 7.32 (br d, J = 7.97 Hz, 2 H) 7.59 (d, J = 8.06 Hz, 2 H) |
| 64 | ¹H NMR (CDCl₃) δ ppm 2.57 (s, 3 H) 4.00 (s, 2 H) 4.84 (s, 2 H) 6.83 (t, J = 8.85 Hz, 1 H) 7.02-7.14 (m, 2 H) 7.19 (d, J = 7.97 Hz, 1 H) 7.38 (d, J = 7.97 Hz, 1 H) |
| 65 | ¹H NMR (CDCl₃) δ ppm 3.91 (s, 2 H) 4.79 (s, 2 H) 6.95 (m, 1 H) 7.10-7.26 (m, 4 H) 7.30-7.40 (m, 2 H) |
| 66 | ¹H NMR (CDCl₃) δ ppm 4.16 (s, 2 H) 4.84 (s, 2 H) 6.49 (d, J = 3.30 Hz, 1 H) 6.65-6.87 (m, 1 H) 6.92-7.12 (t, J = 8.54 Hz, 1 H) 7.14-7.34 (m, 2 H) |
| 67 | ¹H NMR (CDCl₃) δ ppm 2.22-2.44 (m, 3 H) 3.86-4.06 (m, 2 H) 4.73-4.91 (m, 2 H) 6.93-7.03 (m, 1 H) 7.12-7.28 (m, 6 H) |
| 68 | ¹H NMR (CDCl₃) δ ppm 3.78 (s, 3 H) 3.90 (s, 2 H) 4.77 (s, 2 H) 6.87 (d, J = 8.52 Hz, 2 H) 6.96 (t, J = 8.66 Hz, 1 H) 7.13-7.25 (m, 4 H) |
| 69 | ¹H NMR (CDCl₃) δ ppm 1.77-1.88 (m, 2 H) 1.88-2.01 (m, 2 H) 2.10 (br d, J = 5.13 Hz, 2 H) 2.63-2.74 (m, 1 H) 3.65 (br d, J = 7.37 Hz, 2 H) 4.03 (s, 2 H) 7.03-7.11 (m, 1 H) 7.23-7.36 (m, 2H) |

| Example | ¹H-NMR 400 |
|---|---|
| 70 | ¹H NMR (CDCl₃) δ ppm 1.38 (br t, J = 12.07 Hz, 2 H) 1.48 (br t, J = 12.07 Hz, 2 H) 1.68-1.88 (br s, 5 H) 3.48 (br d, J = 7.26 Hz, 2 H) 3.89-4.00 (m, 4 H) 4.03 (s, 2 H) 7.03-7.13 (m, 1 H) 7.21-7.38 (m, 2 H) |
| 71 | ¹H NMR (CDCl₃) δ ppm 3.99 (s, 2 H) 4.65 (s, 2 H) 6.96-7.02 (m, 2 H) 7.04 (d, J = 6.97 Hz, 1 H) 7.09-7.17 (m, 3 H) 7.41 (dd, J = 8.02, 1.15 Hz, 1 H) |
| 72 | ¹H NMR (CDCl₃) δ ppm 4.03 (s, 2 H) 4.68 (s, 2 H) 6.96 (t, J = 8.52 Hz, 2 H) 7.12 (dd, J = 8.34, 5.22 Hz, 2 H) 7.27-7.36 (m, 2 H) 7.65 (dd, J = 7.01, 1.97 Hz, 1 H) |
| 73 | ¹H NMR (CDCl₃) δ ppm 3.91 (s, 2 H) 4.65 (s, 2 H) 6.94 (td, J = 8.20, 2.57 Hz, 1 H) 6.98-7.04 (m, 2 H) 7.10-7.18 (m, 4 H) |
| 74 | ¹H NMR (CDCl₃) δ ppm 3.91 (s, 2 H) 4.64 (s, 2 H) 7.00 (br t, J = 8.48 Hz, 2 H) 7.07 (d, J = 8.34 Hz, 1 H) 7.10-7.16 (m, 2 H) 7.19 (dd, J = 8.25, 1.56 Hz, 1 H) 7.40 (s, 1 H) |
| 75 | ¹H NMR (CDCl₃) δ ppm 3.84 (s, 2 H) 4.61 (s, 2 H) 6.94-7.00 (m, 2 H) 7.02-7.18 (m, 5 H) 7.24-7.33 (m, 1 H) |
| 76 | ¹H NMR (CDCl₃) δ ppm 3.94 (s, 2 H) 4.61 (s, 2 H) 6.96 (t, J = 8.57 Hz, 2 H) 7.08-7.26 (m, 5 H) 7.37 (d, J = 7.79 Hz, 1 H) |
| 77 | ¹H NMR (CDCl₃) δ ppm 1.73 (s, 3 H) 1.74 (s, 3 H) 4.36 (s, 2 H) 6.79 (m, 4 H) 6.86 (d, J = 7.97 Hz, 1 H) 6.91-7.00 (m, 1 H) 7.08 (td, J = 8.06, 5.59 Hz, 1 H) |
| 78 | ¹H NMR (CDCl₃) δ ppm 1.63 (d, J = 6.96 Hz, 3 H) 4.30 (d, J = 16.13 Hz, 1 H) 4.33-4.41 (m, 1 H) 4.54 (d, J = 16.13 Hz, 1 H) 6.78-6.94 (m, 5 H) 7.12-7.17 (m, 2 H) |
| 79 | ¹H NMR (CDCl₃) δ ppm 3.78 (s, 2 H) 4.56 (s, 2 H) 7.00-7.06 (m, 2 H) 7.07-7.17 (m, 4 H) 8.57-8.62 (m, 2 H) |
| 80 | ¹H NMR (CDCl₃) δ ppm 3.80 (s, 2 H) 4.65 (s, 2 H) 6.76-6.88 (m, 2 H) 7.00 (br t, J = 8.39 Hz, 2 H) 7.10-7.19 (m, 3 H) |
| 81 | ¹H NMR (CDCl₃) δ ppm 3.87 (s, 2 H) 4.84 (s, 2 H) 6.80 (br d, J = 9.26 Hz, 1 H) 6.85-7.00 (m, 3 H) 7.08-7.18 (m, 1 H) 7.18-7.29 (m, 2 H) |
| 82 | ¹H NMR (CDCl₃) δ ppm 0.92-1.06 (m, 2 H) 1.12-1.30 (m, 3 H) 1.64-1.82 (m, 6 H) 3.43 (d, J = 7.15 Hz, 2 H) 4.04 (d, J = 0.82 Hz, 2 H) 7.01-7.11 (m, 1 H) 7.24-7.34 (m, 2 H) |
| 83 | ¹H NMR (CDCl₃) δ ppm 0.39-0.46 (m, 2 H) 0.60-0.68 (m, 2 H) 1.05-1.14 (m, 1 H) 3.53 (br d, J = 7.05 Hz, 2 H) 4.10 (s, 2 H) 7.05-7.11 (m, 1 H) 7.25-7.35 (m, 2 H) |
| 84 | ¹H NMR (CDCl₃) δ ppm 1.27-1.41 (m, 2 H) 1.58-1.87 (m, 5 H) 2.05-2.18 (m, 2 H) 3.49 (d, J = 7.33 Hz, 2 H) 4.03 (s, 2 H) 7.06 (t, J = 8.66 Hz, 1 H) 7.24-7.36 (m, 2 H) |
| 85 | ¹H NMR (CDCl₃) δ ppm 1.24-1.31 (m, 2 H) 1.56-1.62 (m, 2 H) 1.65-1.72 (m, 2 H) 1.74-1.81 (m, 2 H) 2.26-2.30 (m, 1 H) 3.55 (d, J = 7.80 Hz, 2 H) 4.05 (s, 2 H) 7.05 (t, J = 8.70 Hz, 1 H) 7.24-7.30 (m, 2 H) |
| 86 | ¹H NMR (CDCl₃) δ ppm 0.88 (d, J = 15.06 Hz, 6 H) 1.11-1.20 (m, 4 H) 1.41 (br d, J = 10.79 Hz, 2 H) 1.49-1.53 (m, 2 H) 1.62 (td, J = 7.34, 3.68 Hz, 1 H) 3.46 (d, J = 7.58 Hz, 2 H) 4.04 (s, 2 H) 7.05 (t, J = 8.46 Hz, 1 H) 7.26 (m, 2 H) |
| 87 | ¹H NMR (CDCl₃) δ ppm 0.93-1.08 (m, 5 H) 1.12-1.31 (m, 3 H) 1.37-1.50 (m, 1 H) 1.57-1.80 (m, 4 H) 3.32 (dd, J = 14.30, 11.09 Hz, 1 H) 3.86 (dd, J = 14.30, 4.31 Hz, 1 H) 4.03 (s, 2 H) 7.03-7.11 (m, 1 H) 7.24-7.34 (m, 2 H) |
| 88 | ¹H NMR (CDCl₃) δ ppm 0.81 (dd, J = 12.23, 5.27 Hz, 1 H) 1.09-1.25 (m, 2 H) 1.40-1.69 (m, 3 H) 1.72-1.82 (m, 1 H) 1.95-1.95 (m, 1 H) 2.16-2.33 (m, 2 H) 3.30-3.47 (m, 1 H) 3.63 (d, J = 7.70 Hz, 2 H) 4.06 (s, 2 H) 7.03-7.12 (m, 1 H) 7.23-7.36 (m, 2 H) |
| 89 | ¹H NMR (CDCl₃) δ ppm 1.42 (dtd, J = 12.80, 8.59, 8.59, 3.94 Hz, 1 H) 1.56 (quind, J = 8.64, 8.64, 8.64, 8.64, 3.94 Hz, 1 H) 1.65-1.78 (m, 1 H) 1.79-1.88 (m, 1 H) 2.04 (dtq, J = 11.31, 7.68, 7.68, 3.88, 3.88, 3.88 Hz, 1 H) 3.35 (dd, J = 11.59, 7.38 Hz, 1 H) 3.49-3.65 (m, 3 H) 3.71-3.80 (m, 1 H) 4.00-4.13 (m, 2 H) 7.03-7.10 (m, 1 H) 7.23-7.34 (m, 2 H) |
| 90 | ¹H NMR (CDCl₃) δ ppm 1.12 (t, J = 7.51 Hz, 3 H) 2.12-2.24 (m, 2 H) 4.18-4.23 (m, 2 H) 4.40 (t, J = 2.20 Hz, 2 H) 7.05 (t, J = 8.23 Hz, 1 H) 7.20-7.34 (m, 2 H) |
| 91 | ¹H NMR (CDCl₃) δ ppm 1.32-1.42 (m, 5 H) 1.49-1.62 (m, 3 H) 1.63-1.74 (m, 2 H) 2.26-2.32 (m, 1 H) 3.83 (s, 2 H) 4.03 (s, 2 H) 7.03-7.10 (m, 1 H) 7.23-7.34 (m, 2 H) |
| 92 | ¹H NMR (CDCl₃) δ ppm 1.15-1.26 (m, 2 H) 1.36-1.64 (m, 7 H) 1.65-1.74 (m, 3 H) 1.88-2.00 (m, 1 H) 3.42 (d, J = 7.79 Hz, 2 H) 4.04 (s, 2 H) 7.03-7.10 (m, 1 H) 7.24-7.35 (m, 2 H) |
| 93 | ¹H NMR (CDCl₃) δ ppm 1.35 (qd, J = 12.19, 4.31 Hz, 2 H) 1.57 (br d, J = 12.56 Hz, 2 H) 1.89-2.03 (m, 1 H) 3.32 (br t, J = 11.68 Hz, 2 H) 3.47 (d, J = 7.42 Hz, 2 H) 3.97 (br dd, J = 11.50, 3.71 Hz, 2 H) 4.04 (s, 2 H) 7.06 (t, J = 8.61 Hz, 1 H) 7.23-7.34 (m, 2 H) |
| 94 | ¹H NMR (CDCl₃) δ ppm 1.21-1.34 (m, 1 H) 1.47-1.58 (m, 3 H) 1.67 (br d, J = 12.46 Hz, 1 H) 1.84-1.93 (m, 1 H) 3.33-3.44 (m, 1 H) 3.48-3.61 (m, 2 H) 3.69-3.77 (m, 1 H) 3.98 (br d, J = 10.72 Hz, 1 H) 4.06 (d, J = 16.95 Hz, 1 H) 4.32 (d, J = 16.86 Hz, 1 H) 6.99-7.07 (m, 1 H) 7.19-7.30 (m, 2 H) |

| Example | ¹H-NMR 400 |
| --- | --- |
| 95 | ¹H NMR (CDCl₃) δ ppm 1.78 (s, 3 H) 4.18 (s, 2 H) 4.36 (br d, J = 2.02 Hz, 2 H) 7.03 (t, J = 8.52 Hz, 1 H) 7.20-7.31 (m, 2 H) |
| 96 | ¹H NMR (CDCl₃) δ ppm 1.57 (m, 3 H) 1.60-1.68 (m, 3 H) 1.91 (br s, 2 H) 2.01 (s, 2 H) 4.03 (s, 2 H) 4.14 (s, 2 H) 7.02-7.08 (m, 1 H) 7.23-7.32 (m, 2 H) |
| 97 | ¹H NMR (CDCl₃) δ ppm 1.23-1.41 (m, 2 H) 1.52-1.67 (m, 2 H) 1.76-1.90 (m, 3 H) 2.10-2.24 (m, 1 H) 2.27-2.44 (m, 1 H) 3.61 (dd, J = 14.75, 6.51 Hz, 1 H) 3.94 (dd, J = 14.85, 7.06 Hz, 1 H) 3.98-4.06 (m, 1 H) 4.10-4.18 (m, 1 H) 7.03-7.10 (m, 1 H) 7.24-7.33 (m, 2 H) |
| 98 | ¹H NMR (CDCl₃) δ ppm 3.32 (t, J = 11.23 Hz, 1 H) 3.52-3.62 (m, 2 H) 3.67-3.77 (m, 3 H) 3.78-3.91 (m, 3 H) 4.09-4.17 (m, 1 H) 4.19-4.28 (m, 1 H) 7.01-7.08 (m, 1 H) 7.22-7.31 (m, 2 H) |
| 99 | ¹H NMR (CDCl₃) δ ppm 0.90 (s, 3 H) 1.06 (s, 3 H) 1.11-1.30 (m, 3 H) 1.34-1.45 (m, 2 H) 1.47-1.55 (m, 2 H) 1.56-1.65 (m, 1 H) 1.71-1.81 (m, 1 H) 3.35 (dd, J = 14.20, 11.46 Hz, 1 H) 3.78 (dd, J = 14.20, 3.44 Hz, 1 H) 4.02 (s, 2 H) 7.03-7.11 (m, 1 H) 7.25-7.35 (m, 2 H) |
| 100 | ¹H NMR (CDCl₃) δ ppm 3.42 (s, 3 H) 4.14 (s, 2 H) 5.03 (s, 2 H) 7.02-7.10 (m, 1 H) 7.23-7.34 (m, 2 H) |
| 101 | ¹H NMR (CDCl₃) δ ppm 1.18 (t, J = 6.92 Hz, 3 H) 3.58 (q, J = 6.97 Hz, 2 H) 4.14 (s, 2 H) 5.05 (s, 2 H) 7.03 (t, J = 8.57 Hz, 1 H) 7.19-7.30 (m, 2 H) |
| 102 | ¹H NMR (CDCl₃) δ ppm 0.91 (t, J = 7.42 Hz, 3 H) 1.58 (sxt, J = 7.07 Hz, 2 H) 3.50 (t, J = 6.51 Hz, 2 H) 4.15 (d, J = 1.10 Hz, 2 H) 5.08 (s, 2 H) 7.00-7.10 (m, 1 H) 7.22-7.33 (m, 2 H) |
| 104 | ¹H NMR (CDCl₃) δ ppm 4.00 (s, 2 H) 4.76 (s, 2 H) 6.96-7.05 (m, 2 H) 7.17-7.28 (m, 4 H) 7.64-7.71 (m, 1 H) 8.51-8.57 (m, 1 H) |
| 105 | ¹H NMR (CDCl₃) δ ppm 4.03 (s, 2 H) 4.61 (s, 2 H) 6.93 (t, J = 8.08 Hz, 2 H) 7.05-7.26 (m, 3 H) 7.41 (br t, J = 5.82 Hz, 2 H) 7.67 (d, J = 6.64 Hz, 1 H) |
| 107 | ¹H NMR (CDCl₃) δ ppm 3.79 (s, 2 H) 4.54 (s, 2 H) 6.84 (br d, J = 9.26 Hz, 1 H) 6.91-7.02 (m, 4 H) 7.04-7.10 (m, 2 H) 7.28 (td, J = 7.93, 6.05 Hz, 1H) |
| 108 | ¹H NMR (CDCl₃) δ ppm 3.79 (s, 2 H) 4.49 (s, 2 H) 6.96-7.02 (m, 3 H) 7.03-7.10 (m, 2 H) 7.14-7.19 (m, 2 H) 7.31-7.37 (m, 2 H) |
| 109 | ¹H NMR (CDCl₃) δ ppm 3.76 (m, 5 H) 4.50 (s, 2 H) 6.66 (s, 1 H) 6.73 (d, J = 7.51 Hz, 1 H) 6.82 (dd, J = 8.25, 1.83 Hz, 1 H) 6.93-7.01 (m, 2 H) 7.03-7.10 (m, 2 H) 7.24 (t, J = 7.88 Hz, 1 H) |
| 110 | ¹H NMR (CDCl₃) δ ppm 0.88 (br d, J = 9.40 Hz, 2 H) 1.10 (br s, 3 H) 1.48-1.64 (m, 4 H) 1.64-1.70 (m, 2 H) 3.33 (br d, J = 7.37 Hz, 2 H) 4.10 (s, 2 H) 7.23-7.31 (m, 2 H) 7.69 (br t, J = 7.58 Hz, 1 H) 8.54 (br d, J = 4.06 Hz, 1 H) |
| 111 | ¹H NMR (CDCl₃) δ ppm 0.88 (br d, J = 11.11 Hz, 2 H) 1.12 (m, 3 H) 1.57 (br d, J = 12.60 Hz, 3 H) 1.65 (m, 1 H) 1.68-1.80 (m, 2 H) 3.21 (d, J = 7.26 Hz, 2 H) 3.92 (s, 2 H) 7.21 (d, J = 4.49 Hz, 2 H) 8.61-8.71 (d, J = 4.49 Hz, 2 H) |
| 112 | ¹H NMR (CDCl₃) δ ppm 0.78-0.91 (m, 2H) 1.01-1.15 (m, 3 H) 1.35-1.46 (m, 1 H) 1.53 (br d, J = 12.56 Hz, 2 H) 1.58-1.70 (m, 3 H) 3.16 (d, J = 7.42 Hz, 2 H) 3.74-3.80 (m, 3 H) 3.84 (s, 2 H) 6.87 (d, J = 8.61 Hz, 2 H) 7.14 (d, J = 8.61 Hz, 2 H) |
| 113 | ¹H NMR (CDCl₃) δ ppm 0.84-0.98 (m, 2 H) 1.10 (br s, 3 H) 1.48-1.75 (m, 6 H) 3.30 (d, J = 7.42 Hz, 2 H) 4.12 (s, 2 H) 7.37-7.43 (m, 1 H) 7.50 (br d, J = 7.70 Hz, 1 H) 7.71 (d, J = 7.79 Hz, 1 H) |
| 114 | ¹H NMR (CDCl₃) δ ppm 0.83-0.95 (m, 2H) 1.03-1.15 (m, 3 H) 1.52-1.71 (m, 6 H) 3.26 (d, J = 7.15 Hz, 2 H) 3.98 (s, 2 H) 6.97 (td, J = 8.23, 2.61 Hz, 1 H) 7.14 (dd, J = 8.34, 2.57 Hz, 1 H) 7.25 (dd, J = 8.57, 5.91 Hz, 1 H) |
| 115 | ¹H NMR (CDCl₃) δ ppm 0.80-0.98 (m, 2 H) 1.06-1.20 (m, 3 H) 1.44-1.81 (m, 6 H) 3.27 (d, J = 7.42 Hz, 2 H) 4.09 (s, 2 H) 7.15-7.29 (m, 2 H) 7.47 (dd, J = 7.65, 1.60 Hz, 1 H) |
| 116 | ¹H NMR (CDCl₃) δ ppm 0.80-0.92 (m, 2H) 1.01-1.13 (m, 3 H) 1.39-1.49 (m, 1 H) 1.54 (br d, J = 12.37 Hz, 2 H) 1.60-1.72 (m, 3 H) 3.21 (d, J = 7.51 Hz, 2 H) 4.10 (s, 2 H) 7.33 (d, J = 7.70 Hz, 1 H) 7.42-7.49 (m, 1 H) 7.53-7.59 (m, 1 H) 7.73 (d, J = 7.70 Hz, 1 H) |
| 117 | ¹H NMR (CDCl₃) δ ppm 0.82-0.97 (m, 2 H) 1.10 (br s, 3 H) 1.44-1.77 (m, 6 H) 3.25 (d, J = 7.42 Hz, 2 H) 4.06 (s, 2 H) 7.24-7.31 (m, 3 H) 7.41-7.46 (m, 1 H) |
| 118 | ¹H NMR (CDCl₃) δ ppm 0.84-1.00 (m, 2 H) 1.08-1.21 (m, 3 H) 1.50-1.78 (m, 6 H) 3.27 (d, J = 7.15 Hz, 2 H) 4.01 (s, 2 H) 7.15-7.32 (m, 2 H) 7.46 (d, J = 1.47 Hz, 1 H) |
| 119 | ¹H NMR (CDCl₃) δ ppm 0.81-0.96 (m, 2H) 1.04-1.18 (m, 3 H) 1.48-1.74 (m, 6 H) 3.26 (d, J = 7.24 Hz, 2 H) 3.87 (s, 2 H) 6.77-6.92 (m, 2 H) 7.18-7.28 (m, 1 H) |
| 120 | ¹H NMR (CDCl₃) δ ppm 0.78-0.93 (m, 2 H) 1.08 (br s, 3 H) 1.40-1.51 (m, 1 H) 1.52-1.70 (m, 5 H) 3.23 (d, J = 7.33 Hz, 2 H) 3.91 (s, 2 H) 7.02-7.14 (m, 2 H) 7.20-7.25 (m, 1 H) 7.25-7.33 (m, 1 H) |
| 121 | ¹H NMR (CDCl₃) δ ppm 0.61-0.76 (m, 2 H) 0.86-1.09 (m, 4 H) 1.33 (br d, J = 11.73 Hz, 2 H) 1.49-1.75 (m, 3 H) 1.90 (d, J = 4.67 Hz, 6 H) 3.03 (d, J = 7.70 Hz, 2 H) 7.06 (ddd, J = 13.01, 8.11, 1.51 Hz, 1 H) 7.16-7.32 (m, 2 H) |

| Example | ¹H-NMR 400 |
|---|---|
| 122 | ¹H NMR (CDCl₃) δ ppm 0.67-0.79 (m, 1 H) 0.85 (qd, J = 12.04, 3.39 Hz, 1 H) 0.99-1.10 (m, 3 H) 1.22-1.31 (m, 2 H) 1.39-1.49 (m, 2 H) 1.59-1.67 (m, 2 H) 1.70 (d, J = 7.06 Hz, 3 H) 2.78 (dd, J = 14.39, 7.70 Hz, 1 H) 3.22 (dd, J = 14.39, 7.51 Hz, 1 H) 4.54 (q, J = 6.90 Hz, 1 H) 7.00-7.08 (m, 1 H) 7.24-7.34 (m, 2 H) |
| 123 | ¹H NMR (CDCl₃) δ ppm 0.80-0.94 (m, 2 H) 1.01-1.18 (m, 3 H) 1.45-1.75 (m, 6 H) 3.23 (d, J = 7.24 Hz, 2 H) 3.91 (s, 2 H) 7.31 (dd, J = 7.79, 4.67 Hz, 1 H) 7.60 (br d, J = 7.88 Hz, 1 H) 8.54 (d, J = 1.56 Hz, 1 H) 8.57 (d, J = 4.67 Hz, 1 H) |
| 125 | ¹H NMR (CDCl₃) δ ppm 0.80-0.92 (m, 2 H) 1.09 (br s, 3 H) 1.45 (ddt, J = 14.95, 7.48, 3.68, 3.68 Hz, 1 H) 1.55 (br d, J = 12.37 Hz, 2 H) 1.60-1.74 (m, 3 H) 3.19 (d, J = 7.42 Hz, 2 H) 3.91 (s, 2 H) 6.92-7.08 (m, 3 H) 7.34 (td, J = 7.90, 6.00 Hz, 1 H) |
| 126 | ¹H NMR (CDCl₃) δ ppm 0.77-0.91 (m, 2 H) 1.00-1.16 (m, 3 H) 1.41 (ddtd, J = 14.98, 11.24, 7.44, 7.44, 3.44 Hz, 1 H) 1.53 (br d, J = 12.46 Hz, 2 H) 1.58-1.72 (m, 3 H) 3.17 (d, J = 7.42 Hz, 2 H) 3.91 (s, 2 H) 7.24 (br d, J = 6.78 Hz, 2 H) 7.29-7.40 (m, 3 H) |
| 127 | ¹H NMR (CDCl₃) δ ppm 0.81-0.94 (m, 2 H) 1.03-1.16 (m, 3 H) 1.43 (dtt, J = 15.04, 7.49, 7.49, 3.87, 3.87 Hz, 1 H) 1.55 (br d, J = 12.37 Hz, 2 H) 1.60-1.74 (m, 3 H) 3.19 (d, J = 7.42 Hz, 2 H) 3.80 (s, 3 H) 3.89 (s, 2 H) 6.78 (s, 1 H) 6.81-6.91 (m, 2 H) 7.23-7.33 (m, 1 H) |
| 128 | ¹H NMR (CDCl₃) δ ppm 1.55 (dq, J = 12.72, 9.05 Hz, 1 H) 1.78-1.88 (m, 1 H) 1.90-2.09 (m, 2 H) 2.12-2.30 (m, 2 H) 2.49 (dt, J = 15.95, 8.16 Hz, 1 H) 3.60 (d, J = 7.61 Hz, 2 H) 4.03 (s, 2 H) 6.96-7.12 (m, 1 H) 7.18-7.33 (m, 2 H) |
| 129 | ¹H NMR (CDCl₃) δ ppm 0.78-1.02 (m, 4H) 1.02-1.24 (m, 6H) 1.52-1.62 (m, 4H) 1.62-1.76 (m, 8 H) 2.32 (d, J = 6.78 Hz, 2H) 3.28 (d, J = 7.51 Hz, 2H) |
| 130 | ¹H NMR (CDCl₃) δ ppm 0.77-0.91 (m, 2 H) 0.97-1.16 (m, 3 H) 1.36 (ddd, J = 10.72, 7.33, 3.30 Hz, 1 H) 1.51-1.66 (m, 5 H) 2.24 (d, J = 7.24 Hz, 2 H) 4.89 (s, 2 H) 7.00 (t, J = 8.98 Hz, 1 H) 7.19 (d, J = 8.46 Hz, 1 H) 7.24-7.32 (m, 1 H) |
| 131 | ¹H NMR (CDCl₃) δ ppm 0.81-0.94 (m, 2 H) 1.01-1.14 (m, 3 H) 1.48 (ddd, J = 10.52, 7.22, 3.25 Hz, 1 H) 1.53-1.71 (m, 5 H) 2.27 (d, J = 7.15 Hz, 2 H) 4.69 (s, 2 H) 6.96-7.04 (m, 2 H) 7.21 (dd, J = 8.11, 5.36 Hz, 2 H) |
| 132 | ¹H NMR (CDCl₃) δ ppm 1.19-1.32 (m, 2 H) 1.52-1.73 (m, 3 H) 1.79 (br d, J = 13.20 Hz, 2 H) 1.97-2.10 (m, 2 H) 2.35 (d, J = 7.06 Hz, 2 H) 4.95 (s, 2 H) 7.07 (t, J = 8.89 Hz, 1 H) 7.27 (d, J = 8.16 Hz, 1 H) 7.31-7.40 (m, 1 H) |
| 133 | ¹H NMR (CDCl₃) δ ppm 0.89-1.00 (m, 2 H) 1.11-1.27 (m, 4 H) 1.32-1.45 (m, 2 H) 1.59-1.84 (m, 8 H) 1.88-2.00 (m, 2 H) 2.03-2.16 (m, 2 H) 2.44 (d, J = 6.60 Hz, 2 H) 3.33 (d, J = 7.42 Hz, 2 H) |
| 134 | ¹H NMR (CDCl₃) δ ppm 1.20-1.34 (m, 2 H) 1.53-1.73 (m, 3 H) 1.79 (br d, J = 13.29 Hz, 2 H) 1.97-2.10 (m, 2 H) 2.35 (d, J = 6.96 Hz, 2 H) 4.71 (s, 2 H) 7.06 (t, J = 8.39 Hz, 2 H) 7.20-7.27 (m, 2 H) |
| 135 | ¹H NMR (DMSO-d6) δ ppm 5.07-5.15 (m, 1 H) 5.19-5.27 (m, 1 H) 5.87 (br s, 1 H) 7.19 (br s, OH) 7.27 (t, J = 9.16 Hz, 1 H) 7.36-7.41 (m, 1 H) 7.41-7.50 (m, 1 H) 7.59-7.67 (m, 1 H) 7.85 (d, J = 7.70 Hz, 1 H) 7.95 (d, J = 7.79 Hz, 1 H) |
| 136 | ¹H NMR (DMSO-d₆) δ ppm 4.88-4.96 (m, 1 H) 5.02-5.09 (m, 1 H) 5.96 (br s, 1 H) 7.27-7.40 (m, 6 H) 7.61 (t, J = 7.78 Hz, 1 H) 7.83 (br d, J = 7.63 Hz, 1 H) 7.99 (br d, J = 7.83 Hz, 1 H) |
| 137 | ¹H NMR (DMSO-d₆) δ ppm 4.99-5.06 (m, 1 H) 5.10-5.18 (m, 1 H) 5.89 (br d, J = 5.22 Hz, 1 H) 6.98 (br d, J = 5.22 Hz, OH) 7.08 (br t, J = 8.48 Hz, 1 H) 7.14-7.24 (m, 2 H) 7.30-7.35 (m, 1 H) 7.36-7.44 (m, 1 H) 7.52-7.62 (m, 1 H) |
| 138 | ¹H NMR (DMSO-d₆) δ ppm 5.06-5.14 (m, 1 H) 5.20-5.27 (m, 1 H) 5.81 (br s, 1 H) 7.16 (br s, OH) 7.24-7.32 (m, 1 H) 7.41 (t, J = 8.61 Hz, 1 H) 7.44-7.50 (m, 2 H) 7.64 (d, J = 7.82 Hz, 2 H) |
| 139 | ¹H NMR (CDCl₃) δ ppm 3.95 (s, 2 H) 5.05 (s, 2 H) 6.98-7.03 (m, 1 H) 7.07 (t, J = 8.61 Hz, 2 H) 7.18-7.24 (m, 2 H) 7.27 (dd, J = 8.43, 5.32 Hz, 2 H) |
| 140 | ¹H NMR (CDCl₃) δ ppm 1.01-1.15 (m, 2 H) 1.16-1.32 (m, 3 H) 1.66-1.82 (m, 5 H) 1.83-1.91 (m, 1 H) 3.69 (d, J = 7.61 Hz, 2 H) 4.07 (d, J = 1.19 Hz, 2 H) 7.02-7.10 (m, 1 H) 7.23-7.32 (br s, 2 H) |
| 141 | ¹H NMR (CDCl₃) δ ppm 1.39-1.53 (m, 2 H) 1.62-1.86 (m, 4 H) 1.92-2.04 (m, 1 H) 2.10-2.22 (m, 2 H) 3.75 (d, J = 7.51 Hz, 2 H) 4.06 (s, 2 H) 7.04-7.11 (m, 1 H) 7.24-7.33 (m, 2H) |
| 142 | ¹H NMR (CDCl₃) δ ppm 0.84-0.98 (m, 2 H) 1.09-1.33 (m, 4 H) 1.44-1.54 (q, J = 15.12, J = 6.87, 2 H) 1.61-1.75 (m, 5 H) 3.57-3.66 (t, 6.87, 2 H) 4.04 (s, 2 H) 7.02-7.10 (m, 1 H) 7.22-7.34 (m, 2 H) |
| 143 | ¹H NMR (CDCl₃) δ ppm 1.44 (br d, J = 4.86 Hz, 2 H) 1.58 (quin, J = 5.50 Hz, 4 H) 2.45 (br s, 4 H) 2.58 (t, J = 5.64 Hz, 2 H) 3.71 (t, J = 5.64 Hz, 2 H) 4.19 (s, 2 H) 7.06 (br d, J = 8.06 Hz, 1 H) 7.17-7.35 (m, 2 H) |
| 144 | ¹H NMR (CDCl₃) δ ppm 2.77 (t, J = 7.65 Hz, 2 H) 3.11 (t, J = 7.65 Hz, 2 H) 4.94 (s, 2 H) 6.90-7.12 (m, 3 H) 7.13-7.35 (m, 3 H) |
| 145 | ¹H NMR (CDCl₃) δ ppm 2.70 (t, J = 7.93 Hz, 2 H) 3.11 (t, J = 7.93 Hz, 2 H) 4.71 (s, 2 H) 6.94-7.10 (m, 3 H) 7.13-7.31 (m, 4 H) |

-continued

| Example | ¹H-NMR 400 |
|---|---|
| 146 | ¹H NMR (CDCl₃) δ ppm 0.83-1.05 (m, 2 H) 1.06-1.28 (m, 3 H) 1.58-1.78 (m, 6 H) 2.70-2.84 (m, 2 H) 3.09-3.28 (m, 2 H) 3.35 (d, J = 7.42 Hz, 2 H) 7.00 (ddd, J = 9.23, 5.98, 3.39 Hz, 1 H) 7.15-7.27 (m, 2 H) |
| 147 | ¹H NMR (CDCl₃) δ ppm 1.26-1.40 (m, 2 H) 1.58-1.79 (m, 4 H) 1.82-1.95 (m, 1 H) 2.05-2.17 (m, 2 H) 2.72-2.81 (m, 2 H) 3.21 (t, J = 7.42 Hz, 2 H) 3.43 (d, J = 7.42 Hz, 2 H) 6.98-7.06 (m, 1 H) 7.18-7.24 (m, 2 H) |
| 148 | ¹H NMR (CDCl₃) δ ppm 1.55 (dq, J = 12.72, 9.05 Hz, 1 H) 1.78-1.88 (m, 1 H) 1.90-2.09 (m, 2 H) 2.12-2.30 (m, 2 H) 2.49 (dt, J = 15.95, 8.16 Hz, 1 H) 3.60 (d, J = 7.61 Hz, 2 H) 4.03 (s, 2 H) 6.96-7.12 (m, 1 H) 7.18-7.33 (m, 2 H) |
| 149 | ¹H NMR (CDCl₃) δ ppm 1.55 (dq, J = 12.72, 9.05 Hz, 1 H) 1.78-1.88 (m, 1 H) 1.90-2.09 (m, 2 H) 2.12-2.30 (m, 2 H) 2.49 (dt, J = 15.95, 8.16 Hz, 1 H) 3.60 (d, J = 7.61 Hz, 2 H) 4.03 (s, 2 H) 6.96-7.12 (m, 1 H) 7.18-7.33 (m, 2 H) |
| 150 | ¹H NMR (CDCl₃) δ 1.13-1.29 (m, 2H), 1.44-1.67 (m, 5H), 1.95-2.10 (m, 2H), 3.32 (d, J = 7.3 Hz, 2H), 3.93 (s, 2H), 7.05-7.19 (m, 2H), 7.21-7.38 (m, 2H). |
| 151 | ¹H NMR (CDCl₃) δ 1.10-1.29 (m, 2H), 1.54 (m, 5H), 2.02 (m, 2H), 3.27 (d, J = 7.4 Hz, 2H), 3.92 (s, 2H), 6.98 (dt, J = 9.3, 2.1 Hz, 1H), 7.04 (td, J = 8.4, 2.5 Hz, 2H), 7.35 (td, J = 8.0, 5.9 Hz, 1H). |
| 152 | ¹H NMR (CDCl₃) δ 1.11-1.29 (m, 2H), 1.46-1.71 (m, 5H), 2.04 (m, 2H), 3.26 (d, J = 7.0 Hz, 2H), 3.89 (s, 2H), 7.07 (t, J = 8.5 Hz, 2H), 7.19-7.27 (m, 2H). |
| 153 | ¹H NMR (CDCl₃) δ 1.17-1.37 (m, 2H), 1.49-1.77 (m, 5H), 1.98-2.14 (m, 2H), 3.34 (d, J = 7.1 Hz, 2H), 3.88 (s, 2H), 6.82-6.94 (m, 2H), 7.20-7.30 (m, 1H). |
| 154 | ¹H NMR (CDCl₃) δ 1.08-1.26 (m, 2H), 1.42-1.63 (m, 5H), 2.01 (m, 2H), 3.24 (d, J = 7.4 Hz, 2H), 3.79 (s, 3H), 3.85 (s, 2H), 6.86-6.91 (m, 2H), 7.12-7.17 (m, 2H). |
| 155 | ¹H NMR (CDCl₃) δ 1.19-1.34 (m, 2H), 1.47-1.72 (m, 5H), 2.07 (m, 2H), 3.38 (d, J = 7.1 Hz, 2H), 4.13 (s, 2H), 7.43 (t, J = 7.8 Hz, 1H), 7.53 (dd, J = 7.8, 1.8 Hz, 1H), 7.70-7.78 (m, 1H). |
| 156 | ¹H NMR (CDCl₃) δ 1.27 (m, 2H), 1.48-1.72 (m, 5H), 2.06 (m, 2H), 3.35 (d, J = 7.2 Hz, 2H), 4.08 (s, 2H), 7.13-7.28 (m, 2H), 7.47 (dd, J = 7.7, 1.9 Hz, 1H). |
| 157 | ¹H NMR (CDCl₃) δ 1.22 (m, 2H), 1.43-1.70 (m, 5H), 2.05 (m, 2H), 3.29 (d, J = 7.3 Hz, 2H), 4.10 (s, 2H), 7.35 (d, J = 7.7 Hz, 1H), 7.48 (t, J = 7.7 Hz, 1H), 7.52-7.62 (m, 1H), 7.74 (dd, J = 7.7, 1.5 Hz, 1H). |
| 158 | ¹H NMR (CDCl₃) δ 1.23 (m, 2H), 1.44-1.73 (m, 5H), 2.04 (m, 2H), 3.32 (d, J = 7.3 Hz, 2H), 4.06 (s, 2H), 7.25-7.35 (m, 3H), 7.41-7.47 (m, 1H). |
| 159 | ¹H NMR (CDCl₃) δ 1.21-1.36 (m, 2H), 1.51-1.78 (m, 5H), 2.01-2.15 (m, 2H), 3.34 (d, J = 7.2 Hz, 2H), 4.01 (s, 2H), 7.19-7.34 (m, 2H), 7.47 (s, 1H). |
| 160 | ¹H NMR (CDCl₃) δ 1.08-1.23 (m, 2H), 1.31-1.49 (m, 2H), 1.50-1.60 (m, 3H), 1.99 (m, 2H), 3.25 (d, J = 7.4 Hz, 2H), 3.77 (s, 3H), 3.88 (s, 2H), 6.74-6.89 (m, 3H), 7.27 (t, J = 7.9 Hz, 1H). |
| 161 | ¹H NMR (CDCl₃) δ 1.07-1.23 (m, 2H), 1.30-1.59 (m, 5H), 1.91-2.05 (m, 2H), 3.25 (d, J = 7.4 Hz, 2H), 3.92 (s, 2H), 7.21-7.27 (m, 2H), 7.30-7.40 (m, 3H). |
| 162 | ¹H NMR (CDCl₃) δ 1.20-1.41 (m, 2H), 1.47-1.78 (m, 5H), 2.07 (m, 2H), 3.26-3.38 (d, J = 7.4 Hz, 2H), 4.00 (s, 2H), 7.02 (td, J = 8.2, 2.6 Hz, 1H), 7.20 (dd, J = 8.2, 2.6 Hz, 1H), 7.25-7.32 (m, 1H). |
| 163 | ¹H NMR (CDCl₃) δ 0.80-0.99 (m, 2H), 1.06-1.20 (m, 3H), 1.49 (m, 1H), 1.57-1.76 (m, 5H), 1.86 (d, J = 7.2 Hz, 3H), 2.22 (dd, J = 15.6, 7.2 Hz, 1H), 2.29 (dd, J = 15.6, 7.2 Hz, 1H), 5.13 (q, J = 7.3 Hz, 1H), 7.02-7.13 (m, 2H), 7.29-7.39 (m, 2H). |
| 164 | ¹H NMR (CDCl₃) δ 1.10-1.32 (m, 3H), 1.51-1.76 (m, 4H), 1.85 (s, 3H), 2.02 (m, 2H), 2.22 (dd, J = 16.1, 7.0 Hz, 1H), 2.33 (dd, J = 16.1, 7.0 Hz, 1H), 5.17 (q, J = 7.2 Hz, 1H), 7.04-7.13 (m, 2H), 7.28-7.36 (m, 2H). |
| 165 | ¹H NMR (CDCl₃) δ 1.22-1.38 (m, 2H), 1.53-1.75 (m, 3H), 1.81 (ddq, J = 13.6, 5.1, 2.4 Hz, 2H), 2.04 (dddd, J = 13.8, 10.5, 7.0, 3.6 Hz, 2H), 2.43 (d, J = 7.0 Hz, 2H), 4.79 (s, 2H), 7.10 (ddd, J = 9.8, 8.4, 1.3 Hz, 1H), 7.16 (td, J = 7.5, 1.2 Hz, 1H), 7.30-7.40 (m, 2H). |
| 166 | ¹H NMR (CDCl₃) δ 1.15-1.37 (m, 2H), 1.52-1.87 (m, 5H), 2.03 (tdt, J = 12.8, 5.3, 2.5 Hz, 2H), 2.35 (d, J = 6.9 Hz, 2H), 4.81 (s, 2H), 7.37 (d, J = 8.0 Hz, 2H), 7.65 (d, J = 8.0 Hz, 2H). |
| 167 | ¹H NMR (CDCl₃) δ 1.23-1.37 (m, 2H), 1.62 (m, 3H), 1.81 (m, 2H), 2.04 (tdt, J = 12.0, 7.0, 2.8 Hz, 2H), 2.39 (d, J = 7.0 Hz, 2H), 4.95 (s, 2H), 7.37 (dd, J = 7.3, 1.4 Hz, 1H), 7.44 (t, J = 7.8 Hz, 1H), 7.72-7.77 (m, 1H). |
| 168 | ¹H NMR (CDCl₃) δ 1.31-1.47 (m, 2H), 1.71 (m, 2H), 1.89 (m, 3H), 2.08 (m, 2H), 2.57 (d, J = 6.6 Hz, 2H), 4.75 (s, 2H), 6.53 (d, J = 3.4 Hz, 1H), 6.79 (d, J = 3.2, 1H). |

-continued

| Example | ¹H-NMR 400 |
|---|---|
| 169 | ¹H NMR (CDCl₃) δ 1.26-1.40 (m, 2H), 1.58-1.79 (m, 2H), 1.84 (m, 3H), 1.98-2.11 (m, 2H), 2.40 (s, 3H), 2.50 (d, J = 6.6 Hz, 2H), 4.72 (s, 2H), 6.05 (s, 1H). |
| 170 | ¹H NMR (CDCl₃) δ 1.18-1.33 (m, 2H), 1.47-1.69 (m, 3H), 1.77 (dtt, J = 13.2, 5.1, 2.5 Hz, 2H), 1.93-2.06 (m, 2H), 2.36 (d, J = 7.1 Hz, 2H), 4.88 (s, 2H), 7.13-7.21 (m, 1H), 7.29 (tt, J = 7.6, 5.5 Hz, 2H), 7.37-7.45 (m, 1H). |
| 171 | ¹H NMR (CDCl₃) δ 1.18-1.31 (m, 2H), 1.51-1.71 (m, 3H), 1.76 (d, J = 13.3 Hz, 2H), 2.02 (m, 2H), 2.25-2.29 (m, 2H), 2.31 (s, 3H), 4.72 (s, 2H), 6.84-7.00 (m, 3H). |
| 172 | ¹H NMR (CDCl₃) δ 1.05-1.22 (m, 2H), 1.65 (m, 5H), 1.78 (d, J = 6.9 Hz, 2H), 2.00 (m, 2H), 2.99 (t, J = 6.5 Hz, 2H), 3.74 (t, J = 6.5 Hz, 2H), 7.05-7.16 (m, 2H), 7.24-7.37 (m, 3H). |
| 173 | ¹H NMR (CDCl₃) δ 1.80 (m, 2H), 1.93-2.00 (m, 2H), 2.04-2.13 (m, 2H), 2.21 (tdt, J = 9.8, 6.8, 3.7 Hz, 1H), 3.56 (d, J = 7.5 Hz, 2H), 4.04 (s, 2H), 7.05 (dd, J = 9.6, 8.1 Hz, 1H), 7.21-7.34 (m, 2H). |
| 174 | ¹H NMR (CDCl₃) δ 3.21 (s, 3H), 4.04 (s, 2H), 7.04 (ddd, J = 9.5, 7.9, 1.6 Hz, 1H), 7.20-7.33 (m, 2H). |
| 175 | ¹H NMR (CDCl₃) δ 1.25 (t, J = 7.3 Hz, 3H), 3.67 (q, J = 7.3 Hz, 2H), 4.05 (s, 2H), 7.05 (ddd, J = 9.3, 7.9, 1.6 Hz, 1H), 7.21-7.34 (m, 2H). |
| 176 | ¹H NMR (CDCl₃) δ 0.94 (t, J = 7.5 Hz, 3H), 1.67 (dt, J = 14.9, 7.5 Hz, 2H), 3.51-3.60 (t, J = 7.5 Hz 2H), 4.03 (d, J = 1.5 Hz, 2H), 7.04 (m, 1H), 7.20-7.33 (m, 2H). |
| 177 | ¹H NMR (CDCl₃) δ 0.91 (t, J = 7.4 Hz, 3H), 1.34 (h, J = 7.4 Hz, 2H), 1.52-1.65 (m, 2H), 3.58 (t, J = 7.6 Hz, 2H), 4.03 (s, 2H), 7.03 (m, 1H), 7.19-7.33 (m, 2H). |
| 178 | ¹H NMR (CDCl₃) δ 0.98 (d, J = 6.7 Hz, 7H), 2.10 (dt, J = 13.5, 6.8 Hz, 1H), 3.42 (d, J = 7.7 Hz, 2H), 4.03 (s, 2H), 7.06 (m, 1H), 7.22-7.35 (m, 2H). |
| 179 | ¹H NMR (CDCl₃) δ 0.78-0.92 (m, 2H), 1.07-1.27 (m, 6H), 1.64 (ddt, J = 15.5, 12.0, 5.4 Hz, 7H), 3.55 (t, J = 7.6 Hz, 2H), 4.04 (s, 2H), 7.01-7.08 (m, 1H).7.21-7.32 (m, 2H). |
| 180 | ¹H NMR (CDCl₃) δ 1.40 (m, 2H), 1.55 (m, 4H), 1.90 (m, 2H), 2.38 (m, 6H), 3.68 (t, J = 6.8 Hz, 2H), 4.09 (s, 2H), 7.01 (ddd, J = 9.4, 7.9, 1.7 Hz, 1H), 7.17-7.31 (m, 2H). |
| 181 | ¹H NMR (CDCl₃) δ 1.99 (tt, J = 13.8, 5.7 Hz, 4H), 2.62 (t, J = 5.7 Hz, 4H), 2.67 (t, J = 5.8 Hz, 2H), 3.70 (t, J = 5.8 Hz, 2H), 4.12 (d, J = 1.6 Hz, 2H), 7.07 (m, 1H), 7.23-7.35 (m, 2H). |
| 182 | ¹H NMR (CDCl₃) δ 1.85 (p, J = 6.6 Hz, 2H), 1.95 (tt, J = 13.8, 5.7 Hz, 4H), 2.45 (t, J = 6.8 Hz, 2H), 2.50 (t, J = 5.8 Hz, 4H), 3.71 (t, J = 6.8 Hz, 2H), 4.07 (d, J = 1.6 Hz, 2H), 7.06 (m, 1H), 7.23-7.34 (m, 2H). |
| 183 | ¹H NMR (CDCl₃) δ 2.05-2.16 (m, 2H), 2.42-2.55 (m, 2H), 2.67-2.82 (m, 1H), 3.56 (d, J = 8.0, 2H), 4.03 (s, 2H), 5.68 (m, 2H), 7.00-7.10 (m, 1H), 7.20-7.34 (m, 2H). |
| 184 | ¹H NMR (CDCl₃) δ 0.97-1.13 (m, 1H), 1.20-1.36 (m, 1H), 1.48-1.88 (m, 6H), 1.99 (dt, J = 14.3, 4.8 Hz, 2H), 3.45 (d, J = 7.5 Hz, 1H), 3.57 (d, J = 7.5 Hz, 1H), 4.03 (s, 2H), 7.01-7.12 (m, 1H), 7.29 (m, 2H). |
| 185 | ¹H NMR (CDCl₃) δ 1.03-1.17 (m, 1H), 1.35-1.48 (m, 2H), 1.50-1.60 (m, 2H), 1.77-1.90 (m, 2H), 1.98-2.22 (m, 2H), 3.46 (m, 2H), 4.03 (s, 1H), 4.78-4.89 (q, 1H), 7.03-7.10 (m, 1H), 7.21-7.35 (m, 2H). |
| 186 | ¹H NMR (CDCl₃) δ 1.16 (t, J = 7.0 Hz, 6H), 3.53 (dq, J = 9.5, 7.0 Hz, 2H), 3.73 (dq, J = 9.5, 7.0 Hz, 2H), 4.87 (s, 2H), 5.19 (s, 1H), 6.92-7.06 (m, 2H), 7.33-7.43 (m, 2H). |
| 187 | ¹H NMR (Chloroform-d) δ 1.10 (t, J = 7.1 Hz, 6H), 3.48 (dq, J = 9.4, 7.1 Hz, 2H), 3.65 (dq, J = 9.5, 7.1 Hz, 2H), 5.11 (s, 2H), 5.17 (s, 2H), 6.97 (dt, J = 9.8, 1.4 Hz, 1H), 7.14-7.28 (m, 2H). |
| 188 | ¹H NMR (CDCl₃) δ 1.05-1.28 (m, 4H), 1.44-1.69 (m, 4H), 1.77 (ddt, J = 13.4, 5.2, 2.7 Hz, 1H), 1.86 (d, J = 7.3 Hz, 3H), 2.19 (dd, J = 16.0, 7.1 Hz, 1H), 2.30 (dd, J = 16.0, 7.1 Hz, 1H), 5.25 (q, J = 7.3 Hz, 1H), 7.29-7.34 (m, 2H), 7.35-7.44 (m, 3H). |
| 189 | ¹H NMR (CDCl₃) δ 1.22-1.41 (m, 2H), 1.65 (dtt, J = 33.2, 13.6, 4.0 Hz, 2H), 1.82 (ddt, J = 18.8, 12.1, 3.1 Hz, 3H), 2.03 (tdt, J = 13.3, 6.2, 2.6 Hz, 2H), 2.40 (d, J = 6.6 Hz, 2H), 4.82 (s, 2H), 7.71 (d, J = 8.1 Hz, 1H), 7.83 (dd, J = 8.3, 2.2 Hz, 1H), 8.61-8.69 (m, 1H). |
| 190 | ¹H NMR (CDCl₃) δ 1.22-1.40 (m, 2H), 1.66 (dtt, J = 33.4, 13.7, 4.0 Hz, 2H), 1.86 (m, 3H), 2.03 (m, 2H), 4.94 (d, J = 1.3 Hz, 2H), 8.55 (s, 2H). |
| 191 | ¹H NMR (CDCl₃) δ 1.24-1.42 (m, 2H), 1.56-1.77 (m, 2H), 1.79-1.92 (m, 3H), 1.96-2.12 (m, 2H), 2.59 (d, J = 6.6 Hz, 2H), 5.02 (s, 2H), 7.39 (d, J = 3.2 Hz, 1H), 7.73 (d, J = 3.2 Hz, 1H). |
| 192 | ¹H NMR (CDCl₃) δ 1.19-1.36 (m, 2H), 1.52-1.70 (m, 2H), 1.80 (ddt, J = 16.7, 13.6, 3.3 Hz, 3H), 2.02 (m, 2H), 2.31 (d, J = 6.7 Hz, 2H), 2.62 (s, 3H), 4.79 (s, 2H), 7.40 (d, J = 7.9 Hz, 1H), 7.53 (d, J = 7.9 Hz, 1H). |
| 193 | ¹H NMR (Methanol-d₄) δ 1.25-1.42 (m, 2H), 1.59-1.90 (m, 5H), 1.90-2.09 (m, 2H), 2.63 (d, J = 6.9 Hz, 2H), 5.14 (s, 2H), 7.98 (s, 1H), 9.03 (s, 1H). |
| 194 | ¹H NMR (CDCl₃) δ 1.24-1.40 (m, 2H), 1.55-1.90 (m, 5H), 2.04 (m, 2H), 2.50 (d, J = 6.9 Hz, 2H), 4.85 (s, 2H), 7.08 (s, 1H), 7.66 (s, 1H). |

| Example | ¹H-NMR 400 |
|---|---|
| 195 | ¹H NMR (CDCl₃) δ 1.23-1.37 (m, 2H), 1.57-1.76 (m, 3H), 1.82 (m, 2H), 2.05 (m, 2H), 2.18 (s, 3H), 2.41 (d, J = 6.9 Hz, 2H), 3.77 (s, 3H), 4.71 (s, 2H), 5.91 (s, 1H). |
| 196 | ¹H NMR (CDCl₃) δ 1.29-1.44 (m, 2H), 1.73 (ddt, J = 33.1, 17.5, 4.0 Hz, 2H), 1.84-1.97 (m, 3H), 2.07 (m, 2H), 2.53 (d, J = 6.6 Hz, 2H), 2.58 (s, 3H), 4.82 (s, 2H). |
| 197 | ¹H NMR (CDCl₃) δ 1.31-1.45 (m, 2H), 1.62-1.81 (m, 2H), 1.87-1.96 (m, 3H), 2.10 (m, 2H), 2.39 (s, 3H), 2.51 (d, J = 6.6 Hz, 2H), 4.94 (s, 2H). |
| 198 | ¹H NMR (CDCl₃) δ 1.33-1.50 (m, 2H), 1.63-1.82 (m, 2H), 1.86-2.01 (m, 3H), 2.10 (m, 2H), 2.77 (d, J = 6.8 Hz, 2H), 5.80 (s, 2H), 6.60 (d, J = 2.5 Hz, 1H), 7.78 (d, J = 2.5 Hz, 1H). |
| 199 | ¹H NMR (CDCl₃) δ 1.31-1.47 (m, 2H), 1.61-1.82 (m, 2H), 1.85-1.97 (m, 3H), 2.08 (ddt, J = 13.7, 10.2, 5.9 Hz, 2H), 2.57 (d, J = 6.4 Hz, 2H), 4.86 (s, 2H), 6.37 (s, 1H), 8.25 (s, 1H). |
| 200 | ¹H NMR (CDCl₃) δ 1.27-1.41 (m, 2H), 1.58-1.91 (m, 5H), 2.00-2.12 (m, 2H), 2.43 (d, J = 6.6 Hz, 2H), 2.51 (s, 3H), 4.88 (s, 2H), 8.71 (s, 1H). |
| 201 | ¹H NMR (CDCl₃) δ 1.26-1.45 (m, 2H), 1.57-1.69 (m, 1H), 1.71-1.81 (m, 2H), 1.87 (m, 2H), 2.01-2.13 (m, 2H), 2.72 (d, J = 7.0 Hz, 2H), 3.74 (s, 3H), 4.82 (s, 2H), 6.88 (d, J = 1.3 Hz, 1H), 6.95 (d, J = 1.3 Hz, 1H) |
| 202 | ¹H NMR (CDCl₃) δ 1.17-1.32 (m, 2H), 1.58-1.76 (m, 2H), 1.81 (ddq, J = 13.3, 5.2, 2.5 Hz, 2H), 1.87-1.98 (m, 1H), 1.98-2.09 (m, 2H), 2.40 (d, J = 6.8 Hz, 2H), 4.91 (s, 2H), 7.02-7.09 (m, 2H), 7.15-7.22 (m, 2H). |
| 203 | ¹H NMR (CDCl₃) δ 1.16-1.29 (m, 2H), 1.55-1.91 (m, 5H), 1.97-2.10 (m, 2H), 2.40 (d, J = 6.7 Hz, 2H), 5.12 (s, 2H), 7.04 (m, 1H) 7.21-7.36 (m, 2H). |
| 204 | ¹H NMR (CDCl₃) δ 1.43 (m, 1H), 1.64-1.79 (m, 1H), 1.93-2.21 (m, 4H), 2.25-2.40 (m, 1H), 2.47 (d, J = 2.8 Hz, 2H), 4.70 (s, 2H), 6.99-7.12 (m, 2H), 7.23 (dd, J = 8.6, 5.3 Hz, 2H). |
| 205 | ¹H NMR (CDCl₃) δ 1.43 (m, 1H), 1.62-1.78 (m, 1H), 1.91-2.18 (m, 3H), 2.22-2.44 (m, 2H), 2.48 (d, J = 6.9 Hz, 2H), 4.93 (s, 2H), 7.06 (ddd, J = 9.7, 8.3, 1.4 Hz, 1H), 7.26 (d, J = 8.1 Hz, 1H), 7.31-7.38 (m, 1H). |
| 206 | ¹H NMR (CDCl₃) δ 0.96 (qd, J = 11.8, 3.5 Hz, 2H), 1.13-1.29 (m, 4H), 1.48-1.90 (m, 8H), 2.04-2.28 (m, 3H), 2.57 (d, J = 7.2 Hz, 2H), 2.60-2.69 (m, 1H), 3.34 (d, J = 7.4 Hz, 2H). |
| 207 | ¹H NMR (CDCl₃) δ 1.17-1.42 (m, 2H), 1.48-1.95 (m, 7H), 2.05-2.25 (m, 5H), 2.45 (qd, J = 13.7, 8.0 Hz, 1H), 2.57 (d, J = 7.2 Hz, 2H), 2.64 (ddt, J = 10.6, 8.5, 4.4 Hz, 1H), 3.40 (d, J = 7.4 Hz, 2H). |
| 208 | ¹H NMR (CDCl₃) δ 2.04 (s, 3H), 2.15 (s, 3H), 3.45 (s, 2H), 4.70 (s, 2H), 6.99-7.10 (m, 2H), 7.11-7.20 (m, 2H). |
| 209 | ¹H NMR (CDCl₃) δ 2.07 (s, 3H), 2.20 (s, 3H), 3.52 (s, 2H), 4.92 (s, 2H), 7.03 (dd, J = 9.8, 8.1 Hz, 1H), 7.20-7.37 (m, 2H). |
| 210 | ¹H NMR (CDCl₃) δ 0.93 (m, 2H), 1.08-1.30 (m, 3H), 1.70 (m, 6H), 2.20 (s, 3H), 2.34 (s, 3H), 3.30 (d, J = 7.0 Hz, 2H), 3.58 (s, 2H). |
| 211 | ¹H NMR (CDCl₃) δ 1.24-1.39 (m, 2H), 1.58-1.88 (m, 5H), 2.13 (m, 2H), 2.21 (s, 3H), 2.35 (s, 3H), 3.38 (d, J = 7.4 Hz, 2H), 3.58 (s, 2H). |
| 212 | ¹H NMR (CDCl3) δ 1.95 (s, 3H), 2.04 (s, 3H), 3.53 (s, 2H), 3.58 (s, 3H), 4.59 (s, 2H), 6.94-7.08 (m, 4H). |
| 213 | ¹H NMR (CDCl₃) δ 2.07 (brs, 6H), 3.60 (s, 2H), 3.65 (s, 3H), 4.85 (s, 2H), 7.03 (m, 1H), 7.20-7.35 (m, 2H). |
| 214 | ¹H NMR (CDCl₃) δ 0.88 (m, 2H), 1.16 (m, 3H), 1.51-1.77 (m, 6H), 2.15 (d, J = 1.6 Hz, 6H), 3.22 (d, J = 7.2 Hz, 2H), 3.61 (s, 2H), 3.69 (s, 3H). |
| 215 | ¹H NMR (CDCl₃) δ 1.12-1.29 (m, 2H), 1.51-1.75 (m, 5H), 2.06 (m, 2H), 2.14 (brs, 6H), 3.28 (d, J = 7.4 Hz, 2H), 3.60 (s, 2H), 3.68 (s, 3H). |
| 216 | ¹H NMR (CDCl₃) δ 2.39 (s, 3H), 3.73 (s, 2H), 4.60 (s, 2H), 6.94-7.12 (m, 5H), 7.21-7.28 (m, 1H), 8.40 (dd, J = 5.0, 1.9 Hz, 1H). |
| 217 | ¹H NMR (CDCl₃) δ 2.36 (s, 3H), 3.75 (s, 2H), 4.86 (d, J = 1.6 Hz, 2H), 6.83-6.98 (m, 2H), 7.03-7.21 (m, 3H), 8.27 (dt, J = 4.7, 2.3 Hz, 1H). |
| 218 | ¹H NMR (CDCl₃) δ 0.86 (m, 2H), 1.05-1.21 (m, 2H), 1.44-1.78 (m, 7H), 2.54 (s, 3H), 3.22 (d, J = 7.1 Hz, 2H), 3.86 (s, 2H), 7.11 (dd, J = 7.7, 4.9 Hz, 1H), 7.40 (dd, J = 7.7, 1.7 Hz, 1H), 8.43 (dd, J = 5.0, 1.9 Hz, 1H). |
| 219 | ¹H NMR (CDCl₃) δ 1.16-1.31 (m, 2H), 1.60 (m, 5H), 1.99-2.12 (m, 2H), 2.56 (s, 3H), 3.32 (d, J = 7.0 Hz, 2H), 3.88 (s, 2H), 7.16 (dd, J = 7.8, 4.9 Hz, 1H), 7.45 (dd, J = 7.8, 1.7 Hz, 1H), 8.47 (dd, J = 4.9, 1.7 Hz, 1H). |
| 220 | ¹H NMR (CDCl₃) δ 1.89 (tt, J = 13.7, 5.7 Hz, 4H), 2.51 (t, J = 5.6 Hz, 4H), 3.35 (s, 2H), 5.11 (s, 2H), 7.05 (ddd, J = 9.8, 8.2, 1.3 Hz, 1H), 7.25 (d, J = 8.2 Hz, 1H), 7.32 (td, J = 8.1, 5.7 Hz, 1H). |
| 221 | ¹H NMR (CDCl₃) δ 1.96 (tt, J = 12.4, 5.6 Hz, 4H), 2.57 (t, J = 5.7 Hz, 4H), 3.32 (s, 2H), 4.90 (s, 2H), 7.06 (t, J = 8.5 Hz, 2H), 7.26 (dd, J = 8.5, 5.0 Hz, 2H). |

-continued

| Example | ¹H-NMR 400 |
|---|---|
| 222 | ¹H NMR (CDCl₃) δ 0.98 (qd, J = 11.9, 3.3 Hz, 2H), 1.15-1.28 (m, 4H), 1.60-1.80 (m, 5H), 2.00 (tt, J = 13.7, 5.7 Hz, 4H), 2.64 (t, J = 5.7 Hz, 4H), 3.49 (d, J = 2.0 Hz, 2H), 3.53 (dd, J = 7.4, 2.0 Hz, 2H). |
| 223 | ¹H NMR (CDCl₃) δ 1.30-1.45 (m, 2H), 1.59-1.81 (m, 4H), 2.00 m, 5H), 2.08-2.20 (m, 2H), 2.65 (t, J = 5.7 Hz, 4H), 3.49 (s, 2H), 3.61 (d, J = 7.4 Hz, 2H). |
| 224 | ¹H NMR (CDCl₃) δ 1.74 (td, J = 6.6, 4.6 Hz, 2H), 1.88 (tt, J = 13.4, 6.3 Hz, 2H), 2.45 (t, J = 5.4 Hz, 2H), 2.66 (t, J = 11.1 Hz, 2H), 3.46 (s, 2H), 5.12 (s, 2H), 7.03 (ddd, J = 9.8, 8.2, 1.4 Hz, 1H), 7.19-7.34 (m, 2H) |
| 225 | ¹H NMR (CDCl₃) δ 1.77 (dd, J = 6.3, 4.6 Hz, 2H), 1.91 (tt, J = 13.5, 6.5 Hz, 2H), 2.42 (t, J = 5.4 Hz, 2H), 2.64 (t, J = 11.0 Hz, 2H), 3.28 (s, 2H), 4.92 (s, 2H), 7.04 (d, J = 8.6 Hz, 1H), 7.25-7.34 (m, 2H). |
| 226 | ¹H NMR (CDCl₃) δ 1.09 (d, J = 6.3 Hz, 3H), 1.56-1.87 (m, 2H), 1.91-2.07 (m, 2H), 2.40 (ddd, J = 12.2, 10.8, 3.2 Hz, 1H), 2.60-2.70 (m, 1H), 2.73-2.83 (m, 1H), 3.30 (d, J = 14.5 Hz, 1H), 3.89 (d, J = 14.5 Hz, 1H), 5.08 (d, J = 15.8 Hz, 1H), 5.15 (dd, J = 15.8, 1.1 Hz, 1H), 7.04 (ddd, J = 9.9, 8.1, 1.4 Hz, 1H), 7.22-7.35 (m, 2H). |
| 227 | ¹H NMR (CDCl₃) δ 1.13 (d, J = 6.4 Hz, 3H), 2.03 (m, 3H), 2.63-2.91 (m, 2H), 3.16-3.45 (m, 1H), 3.71-3.93 (m, 1H), 4.90 (d, J = 15.5 Hz, 1H), 4.96 (d, J = 15.5 Hz, 1H), 7.07 (t, J = 8.5 Hz, 2H), 7.22-7.33 (m, 2H). |
| 228 | ¹H NMR (CDCl₃) δ 3.10-3.17 (m, 2H), 4.08-4.12 (m, 2H), 4.17 (s, 2H), 4.82 (s, 2H), 6.58 (dd, J = 7.9, 1.9 Hz, 1H), 6.74-6.88 (m, 3H), 6.97-7.09 (m, 2H), 7.13-7.23 (m, 2H). |
| 229 | ¹H NMR (CDCl₃) δ 3.22-3.27 (m, 2H), 4.17-4.24 (m, 2H), 4.27 (s, 2H), 5.03 (s, 2H), 6.57 (dd, J = 7.7, 1.8 Hz, 1H), 6.71-6.84 (m, 3H), 7.00 (ddd, J = 9.6, 8.1, 1.4 Hz, 1H), 7.21-7.34 (m, 2H). |
| 230 | ¹H NMR (CDCl₃) δ 0.97 (qd, J = 11.7, 3.3 Hz, 2H), 1.13-1.30 (m, 3H), 1.58-1.84 (m, 6H), 3.26-3.33 (m, 2H), 3.47 (d, J = 7.6 Hz, 2H), 4.23-4.29 (m, 2H), 4.31 (s, 2H), 6.75-6.82 (m, 2H), 6.87 (ddt, J = 13.4, 6.5, 1.6 Hz, 2H). |
| 231 | ¹H NMR (CDCl₃) δ 1.22-1.41 (m, 2H), 1.53-1.78 (m, 4H), 1.83-1.96(m, 1H), 2.05-2.16 (m, 2H), 3.24-3.33 (m, 2H), 3.53 (d, J = 7.5 Hz, 2H), 4.21-4.27 (m, 2H), 4.32 (s, 2H), 6.76-6.84 (m, 2H), 6.84-6.93 (m, 2H). |
| 232 | ¹H NMR (CDCl₃) δ 2.88-2.96 (m, 4H), 3.58-3.65 (m, 4H), 4.94 (s, 2H), 6.71 (d, J = 5.1 Hz, 1H), 6.93-7.02 (m, 2H), 7.13 (d, J = 5.1 Hz, 1H), 7.24-7.32 (m, 2H). |
| 233 | ¹H NMR (CDCl₃) δ 2.72-2.82 (m, 4H), 3.58-3.66 (m, 4H), 5.13 (s, 2H), 6.68 (d, J = 5.1 Hz, 1H), 6.94 (ddd, J = 9.7, 7.6, 2.0 Hz, 1H), 7.08 (d, J = 5.1 Hz, 1H), 7.13-7.22 (m, 2H). |
| 234 | ¹H NMR (CDCl₃) δ 0.89-1.02 (m, 2H), 1.08-1.19 (m, 3H), 1.60-1.74 (m, 5H), 1.74-1.87 (m, 1H), 2.85-2.92 (m, 4H), 3.56 (d, J = 7.4 Hz, 2H), 3.60-3.68 (m, 4H), 6.72 (d, J = 5.1 Hz, 1H),7.11 (d, J = 5.1 Hz, 1H). |
| 235 | ¹H NMR (CDCl₃) δ 1.17-1.42 (m, 2H), 1.46-1.65 (m, 2H), 1.66-1.75 (m, 2H), 1.90-2.13 (m, 3H), 2.86-2.93 (m, 4H), 3.60-3.64 (m, 4H), 3.66 (s, 2H), 6.72 (d, J = 5.1 Hz, 1H), 7.12 (d, J = 5.1 Hz, 1H). |
| 236 | ¹H NMR (CDCl₃) δ 2.66 (dd, J = 6.7, 3.4 Hz, 4H), 3.20 (t, J = 5.0 Hz, 4H), 3.34 (s, 2H), 4.94 (s, 2H), 6.86-7.01 (m, 3H), 7.06 (t, J = 8.5 Hz, 2H), 7.27-7.36 (m, 4H). |
| 237 | ¹H NMR (CDCl₃) δ 2.53-2.60 (m, 4H), 3.09 (dd, J = 6.2, 3.9 Hz, 4H), 3.37 (s, 2H), 5.15 (s, 2H), 6.83-6.93 (m, 3H), 7.03 (ddd, J = 9.8, 8.0, 1.5 Hz, 1H), 7.20-7.34 (m, 4H). |
| 238 | ¹H NMR (CDCl₃) δ 1.00 (qd, J = 11.9, 3.3 Hz, 2H), 1.20 (ddt, J = 20.0, 16.7, 7.7 Hz, 3H), 1.63-1.80 (m, 5H), 1.82-1.86 (m, 1H), 2.64-2.72 (m, 4H), 3.16-3.23 (m, 4H), 3.50 (s, 2H), 3.57 (d, J = 7.4 Hz, 2H), 6.83-6.95 (m, 3H), 7.22-7.31 (m, 2H). |
| 239 | ¹H NMR (CDCl₃) δ 1.33-1.45 (m, 2H), 1.66 (ddt, J = 17.6, 13.4, 4.1 Hz, 1H), 1.72-1.81 (m, 3H), 1.97-2.06 (m, 1H), 2.07-2.19 (m, 2H), 2.65-2.76 (m, 4H), 3.19 (dd, J = 6.4, 3.6 Hz, 4H), 3.50 (s, 2H), 3.65 (d, J = 7.4 Hz, 2H), 6.90 (dd, J = 15.3, 7.8 Hz, 3H), 7.27 (dd, J = 8.7, 7.2 Hz, 2H). |
| 240 | ¹H NMR (CDCl₃) δ 1.42-1.52 (m, 2H), 1.53-1.64 (m, 4H), 2.31-2.46 (m, 4H), 3.20 (s, 2H), 4.95 (s, 2H), 7.04 (t, J = 8.6 Hz, 2H), 7.28-7.34 (m, 2H). |
| 241 | ¹H NMR (CDCl₃) δ 1.34-1.44 (m, 2H), 1.44-1.55 (m, 4H), 2.25-2.39 (m, 4H), 3.27 (s, 2H), 5.14 (s, 2H), 7.00-7.08 (m, 1H), 7.18-7.34 (m, 2H). |
| 242 | ¹H NMR (CDCl₃) δ 1.40 (qd, J = 12.5, 3.6 Hz, 1H), 1.51 (ddd, J = 16.1, 8.0, 3.7 Hz, 1H), 1.75 (dt, J = 13.3, 3.2 Hz, 1H), 1.82-1.91 (m, 1H), 1.99-2.11 (m, 1H), 2.32 (s, 3H), 2.60 (tt, J = 11.5, 3.6 Hz, 1H), 2.78 (dd, J = 10.6, 4.1 Hz, 2H), 3.30 (d, J = 14.2 Hz, 1H), 3.35 (d, J = 14.2 Hz, 1H), 5.13 (d, J = 15.6 Hz, 1H), 5.19 (d, J = 15.6 Hz, 1H), 7.00-7.14 (m, 5H), 7.22-7.33 (m, 2H). |

-continued

| Example | $^1$H-NMR 400 |
|---|---|
| 243 | $^1$H NMR (CDCl$_3$) δ 1.45 (qd, J = 12.6, 3.9 Hz, 1H), 1.67 (td, J = 10.6, 8.8, 4.4 Hz, 1H), 1.83 (dt, J = 13.5, 3.3 Hz, 1H), 1.89-1.99 (m, 1H), 2.06-2.18 (m, 2H), 2.33 (s, 3H), 2.69 (td, J = 11.4, 3.7 Hz, 1H), 2.77-2.88 (m, 2H), 3.25 (d, J = 14.2 Hz, 1H), 3.30 (d, J = 14.2 Hz, 1H), 4.97 (s, 2H), 7.02-7.11 (m, 4H), 7.13 (d, J = 7.9 Hz, 2H), 7.29-7.35 (m, 2H). |
| 244 | $^1$H NMR (CDCl$_3$) δ 2.73 (t, J = 5.9 Hz, 2H), 2.82 (t, J = 5.9 Hz, 2H), 3.53 (s, 2H), 3.58 (s, 2H), 5.13 (s, 2H), 6.90-7.00 (m, 2H), 7.04-7.09 (m, 2H), 7.10-7.19 (m, 3H). |
| 245 | $^1$H NMR (CDCl$_3$) δ 1.22-1.38 (m, 2H), 1.42-1.62 (m, 2H), 1.65-1.75 (m, 2H), 1.89-2.10 (m, 3H), 2.84 (t, J = 6.0 Hz, 2H), 2.91 (t, J = 6.0 Hz, 2H), 3.60-3.65 (m, 4H), 3.68 (s, 2H), 7.00-7.06 (m, 1H), 7.10-7.21 (m, 3H). |
| 246 | $^1$H NMR (CDCl$_3$) δ 1.64-1.81 (m, 4H), 2.40-2.52 (m, 4H), 3.44 (s, 2H), 5.13 (s, 2H), 7.02 (ddd, J = 9.7, 8.0, 1.5 Hz, 1H), 7.15-7.34 (m, 2H). |
| 247 | $^1$H NMR (CDCl$_3$) δ 2.22 (s, 3H), 3.79 (s, 2H), 4.96 (s, 2H), 6.96 (m, 2H,), 7.21 (m, 2H), 8.86 (s, 1H). |
| 248 | $^1$H NMR (CDCl$_3$) 2.24 (s, 3H), 3.76 (s, 2H), 5.07 (s, 2H), 6.91 (m, 1H), 7.13 (t, J = 8.3, 1.3 Hz, 1H), 7.37 (m, 1H), 8.86 (s, 1H). |
| 249 | $^1$H NMR (CDCl$_3$) 1.21-1.52 (m, 10H), 1.75 (m, 1H), 2.21 (s, 3H), 3.69 (d, J = 3.8 Hz, 2H), 3.91 (s, 2H) 8.78 (s, 1H). |
| 250 | $^1$H NMR (CDCl$_3$) 1.50-1.81 (m, 8H), 1.99 (m, 1H), 2.21 (s, 3H), 3.69 (d, J = 3.9 Hz, 2H), 3.85 (s, 2H), 8.69 (s, 1H). |
| 251 | $^1$H NMR (CDCl$_3$) 1.70-2.01 (m, 6H), 2.21 (s, 3H), 2.33 (m, 1H), 3.72 (d, J = 4.2 Hz, 2H), 3.75 (s, 2H) 8.81 (s, 1H). |

Pharmacological Examples

Examples of the Invention were Found to be P2X7 Inhibitors Using a Screen Quest™ Fluo-8 No Wash Calcium Assay Kit.

Extracellular binding of Bz-ATP to P2X7 receptor opens the channel and allows Ca2+ influx into the cells. This Ca2+ entry was measured in HEK-293 cells stably transfected with P2X7 receptor using Screen Quest™ Fluo-8 No Wash Calcium Assay Kit (AAt Bioquest®, cat. 36316). Once inside the cell, the lipophilic blocking groups of Fluo-8 are cleaved by non-specific cell esterases, resulting in a negatively-charged fluorescent dye that stays inside cells. Its fluorescence increases upon binding to calcium. When HEK-293/P2X7 cell are stimulated with Bz-ATP, Ca$^{2+}$ enters the cells and the fluorescence of Fluo-8 NW increases. The dye has an absorption spectrum compatible with excitation at 488 nm by argon laser sources and its emission wavelength is in the range of 515-575 nm.

HEK-293 cells stably transfected with P2X7 receptor were seeded overnight in growth medium at 10,000 to 20,000 cell/well in 384-well plate. 24 hours later, the medium was removed and the cells were pre-loaded at RT for 1 hour with 20 μL/w of Fluo-8 NW. Then 10 μL/w of tests compounds and reference antagonist A438079 at 3×-concentration were injected with the FLIPR$_{TETRA}$ and the kinetic response over a period of five minutes was monitored. A second injection of 15 μL/w of 3× reference activator (Bz-ATP at EC$_{80}$) was performed with the FLIPR$_{TETRA}$ and the signal of the emitted fluorescence was recorded for additional three minutes. All the experiment was carried out in a Low Divalent Cation Assay Buffer (0.3 mM Ca$^{2+}$ and 0 mM Mg$^{2+}$). The effect of the test compounds was measured as percent inhibition vs the reference antagonist and IC50 values were calculated accordingly. Here are reported the potency ranges as A, B, C and D, where A is <200 nM; B is 200 nM-104, C is 1-10 μM, D is >10 μM.

| Example | hP2X7 (IC$_{50}$; nM) | rP2X7 (IC$_{50}$; nM) | mP2X7 (IC$_{50}$; nM) |
|---|---|---|---|
| 1 | B | B | C |
| 2 | C | D | D |
| 3 | D | D | D |
| 4 | D | D | D |
| 5 | C | D | D |
| 6 | C | C | C |
| 7 | C | D | C |
| 8 | C | D | D |
| 9 | B | C | D |
| 10 | B | C | D |
| 11 | C | C | C |
| 12 | C | B | B |
| 13 | C | C | C |
| 14 | B | C | C |
| 15 | C | C | C |
| 16 | C | C | D |
| 17 | C | C | C |
| 18 | C | C | C |
| 19 | C | C | D |
| 20 | C | C | C |
| 21 | B | C | C |
| 22 | C | C | C |
| 23 | C | C | D |
| 24 | D | D | C |
| 25 | A | B | B |
| 26 | B | A | B |
| 27 | C | C | C |
| 28 | C | D | C |
| 29 | C | D | C |
| 30 | C | C | C |
| 31 | C | D | D |
| 32 | D | D | D |
| 33 | D | D | D |
| 34 | D | D | D |
| 35 | C | C | C |
| 36 | C | D | D |
| 37 | C | D | C |
| 38 | D | D | D |
| 39 | D | D | D |
| 40 | D | D | D |
| 41 | D | D | D |
| 42 | D | D | D |
| 43 | D | D | D |
| 44 | C | C | D |
| 45 | D | D | D |

| Example | hP2X7 (IC$_{50}$; nM) | rP2X7 (IC$_{50}$; nM) | mP2X7 (IC$_{50}$; nM) | Example | hP2X7 (IC$_{50}$; nM) | rP2X7 (IC$_{50}$; nM) | mP2X7 (IC$_{50}$; nM) |
|---|---|---|---|---|---|---|---|
| 46 | D | D | D | 125 | C | B | C |
| 47 | D | D | D | 126 | C | B | C |
| 48 | B | B | B | 127 | D | D | D |
| 49 | C | B | C | 128 | A | A | B |
| 50 | D | D | D | 129 | D | C | C |
| 51 | C | C | C | 130 | B | A | B |
| 52 | D | D | D | 131 | C | C | C |
| 53 | D | B | D | 132 | A | A | A |
| 54 | C | D | D | 133 | C | C | D |
| 55 | B | B | B | 134 | C | C | C |
| 56 | C | C | C | 135 | B | D | D |
| 57 | C | C | C | 136 | C | D | D |
| 58 | C | C | C | 137 | C | C | C |
| 59 | B | B | B | 138 | C | C | C |
| 60 | B | B | C | 139 | B | B | C |
| 61 | B | B | C | 140 | B | B | C |
| 62 | D | D | D | 141 | A | A | A |
| 63 | C | C | C | 142 | B | B | B |
| 64 | C | D | D | 143 | B | B | C |
| 65 | B | B | C | 144 | B | B | C |
| 66 | B | B | C | 145 | B | B | B |
| 67 | C | C | C | 146 | C | C | D |
| 68 | C | D | D | 147 | B | B | B |
| 69 | C | B | C | 148 | A | A | B |
| 70 | B | C | C | 149 | A | A | B |
| 71 | B | C | C | 150 | B | A | B |
| 72 | D | D | D | 151 | B | B | C |
| 73 | B | B | C | 152 | B | B | C |
| 74 | C | C | C | 153 | A | A | B |
| 75 | C | C | C | 154 | C | C | C |
| 76 | B | B | C | 155 | A | B | B |
| 77 | D | D | D | 156 | A | A | B |
| 78 | D | D | D | 157 | A | A | B |
| 79 | D | D | D | 158 | A | A | B |
| 80 | C | C | D | 159 | A | A | B |
| 81 | B | B | C | 160 | B | B | C |
| 82 | A | A | A | 161 | B | B | C |
| 83 | D | D | D | 162 | D | D | D |
| 84 | A | A | A | 163 | C | C | C |
| 85 | A | A | B | 164 | C | C | C |
| 86 | B | B | B | 165 | B | A | B |
| 87 | A | A | B | 166 | C | C | C |
| 88 | A | A | B | 167 | D | C | C |
| 89 | C | C | D | 168 | C | B | B |
| 90 | C | C | D | 169 | D | C | D |
| 91 | A | A | B | 170 | A | A | B |
| 92 | A | A | B | 171 | C | B | C |
| 93 | C | B | C | 172 | D | C | D |
| 94 | B | B | C | 173 | A | A | B |
| 95 | D | D | D | 174 | D | D | D |
| 96 | B | B | B | 175 | D | D | D |
| 97 | A | A | B | 176 | D | D | D |
| 98 | D | C | D | 177 | C | C | D |
| 99 | B | B | B | 178 | C | D | D |
| 100 | D | D | D | 179 | C | D | C |
| 101 | D | D | D | 180 | D | D | D |
| 102 | C | C | D | 181 | B | C | C |
| 104 | D | D | D | 182 | C | D | D |
| 105 | C | C | C | 183 | B | B | C |
| 107 | C | C | C | 184 | A | A | A |
| 108 | C | C | C | 185 | A | A | A |
| 109 | C | C | D | 188 | C | C | C |
| 110 | D | C | D | 189 | D | D | D |
| 111 | D | C | B | 190 | D | D | D |
| 112 | C | B | C | 191 | C | B | D |
| 113 | C | C | C | 192 | D | D | D |
| 114 | B | A | B | 193 | C | B | C |
| 115 | B | B | C | 194 | C | C | D |
| 116 | B | B | C | 195 | B | B | B |
| 117 | B | A | B | 196 | D | D | D |
| 118 | B | B | C | 197 | D | D | D |
| 119 | B | A | B | 198 | D | C | C |
| 120 | B | A | B | 199 | D | C | C |
| 121 | D | D | D | 200 | B | B | B |
| 122 | D | C | D | 201 | D | C | D |
| 123 | C | C | C | 202 | C | C | C |

| Example | hP2X7 (IC$_{50}$; nM) | rP2X7 (IC$_{50}$; nM) | mP2X7 (IC$_{50}$; nM) |
|---|---|---|---|
| 203 | A | A | A |
| 204 | D | D | D |
| 205 | A | A | B |
| 208 | C | C | D |
| 209 | C | D | D |
| 210 | B | B | C |
| 211 | A | B | C |
| 212 | C | D | D |
| 213 | C | D | D |
| 214 | A | B | C |
| 215 | A | B | C |
| 216 | C | C | D |
| 217 | D | D | D |
| 218 | B | B | C |
| 219 | B | C | C |
| 220 | A | A | B |
| 221 | D | C | C |
| 222 | D | C | C |
| 223 | D | D | D |
| 224 | B | B | B |
| 225 | D | C | D |
| 226 | A | A | A |
| 227 | C | B | C |
| 228 | A | B | B |
| 229 | C | C | C |
| 230 | A | A | A |
| 231 | A | A | A |
| 240 | D | C | D |
| 241 | B | A | B |
| 244 | C | B | B |

Examples of the Invention were Found to be P2X7 Inhibitors Using YO-PRO®-1 Uptake Assay.

YO-PRO®-1 is a fluorescent DNA-binding dye with a MW of 374 Da (Molecular Probes®, cat. Y3603). This method is based upon the presumed ability of YO-PRO®-1 to enter through the dilated or "large pore form" of P2X7 receptor and to bind to intracellular DNA whereupon it increases many fold its fluorescence intensity. The dye ha an absorption spectrum compatible with excitation at 488 nm by argon laser sources and its emission wavelength is in the range of 515-575 nm. The aim of this assay was to validate the interaction of antagonists with P2X7 receptor using an alternative readout to Ca2+-sensitive fluorescent dyes.

HEK-293 cells stably transfected with P2X7 receptor were seeded overnight un growth medium at 20,000 cell/well in 384-well plate. 24 hours later, the medium was removed, the cells were washed with Low Divalent Cation Assay Buffer (0.3 mM Ca$^{2+}$ and 0 mM Mg$^{2+}$) and then pre-loaded with 20 µL/w of 5 µM YO-PRO®-1 dye.

FLIPR$_{TETRA}$ fluorescence measurement immediately started. Then 10 µL/w of test compounds and reference antagonist A438079 at 3×-concentration were injected with the FLIPR$_{TETRA}$ and the kinetic response over a period of five minutes was monitored. A second injection of 10 µL/w of 3× Bz-ATP EC$_{80}$ (30 µM) was performed with the FLIPR$_{TETRA}$ and the signal of the emitted fluorescence was recorded for additional 60 minutes. All the experiment was carried out with a Low Divalent Cation Assay Buffer (0.3 mM Ca$^{2+}$ and 0 mM Mg$^{2+}$).

The effect of the test compounds was measured as percent inhibition vs the reference antagonist and IC$_{50}$ values were calculated accordingly.

| Example | Yo-Pro (IC$_{50}$; nM) |
|---|---|
| 1 | 581 |
| 25 | 115 |
| 26 | 329 |
| 48 | 340 |
| 55 | 50 |
| 60 | 366 |
| 61 | 293 |
| 65 | 318 |
| 66 | 456 |
| 71 | 461 |
| 73 | 670 |
| 76 | 168 |
| 81 | 619 |
| 82 | 30 |
| 84 | 3.4 |
| 85 | 131 |
| 86 | 111 |
| 87 | 82 |
| 88 | 63 |
| 91 | 45 |
| 92 | 42 |
| 94 | 435 |
| 96 | 523 |
| 97 | 193 |
| 99 | 142 |
| 114 | 129 |
| 115 | 399 |
| 116 | 284 |
| 117 | 143 |
| 118 | 618 |
| 119 | 547 |
| 120 | 590 |
| 128 | 115 |
| 130 | 233 |
| 132 | 32.00 |
| 140 | 181 |
| 141 | 31 |
| 142 | 467 |
| 149 | 66 |
| 210 | 184 |
| 211 | 171 |

Examples of the Invention were Found to be Active on Human P2X7 Channel Assay by Automated Patch-Clamp.

In order to directly monitor the block of P2X7 channel, an electrophysiological assay was developed and implemented on the QPatch16X automated electrophysiology instrument.

HEK-293 cells expressing the P2X7 channels were cultured in modified EMEM.

72 hours before experiment, 5 million cells were seeded onto T225 flasks. Just before the experiment cells were washed twice, detached from the flask with trypsin-EDTA, re-suspended in the suspension solution and placed on the QPatch 16x.

The compounds (20 mM in a 100% DMSO) stored at −20° C. were prepared the day of the experiment (a first dilution 1:20 in 100% DMSO to prepare a 1 mM stock solution, then a 1 microM solution in external solution+a serial dilution 1:10).

The standard whole-cell voltage clamp experiments were performed at room temperature. From these experiments the multihole technology was used and the data were sampled at 2 KHz.

The intracellular solution contained (mM) 135 CsF, 10 NaCl, 1 EGTA, 10 HEPES, (pH 7.2 with CsOH) whereas the extracellular contained (mM) 145 NaCl, 4 KCl, 0.5 MgCl$_2$, 1 CaCl$_2$, 10 HEPES, 10 Glc (pH 7.4 with NaOH).

After establishment of the seal and the passage in the whole cell configuration, the cells were held at −80 mV. The P2XR7 current was evoked by applying 100 microM of BzATP alone (4 times) and then in the presence increasing concentrations of the compound under investigation (1, 10, 100 and 1000 nM).

The pre-incubation periods 5 to 8 contain increasing concentrations of the compound of interest (1, 10, 100 and 1000 nM), as illustrated in FIGURE (application protocol).

FIGURE: APPLICATION PROTOCOL

The maximal inward current evoked by BzATP in absence or presence of increasing concentrations of the compounds under investigation was measured and normalized. The potential agonist effect was measured as % of control and as IC50 determined fitting the dose-response curves data with the following equation:

$$Y=100/(1+10^{((Log\ IC50-X)*HillSlope)})$$

Where:

X=log of concentration

Y=normalized response, 100% down to 0%, decreasing as X increases.

Log $IC_{50}$: same log units as X

HillSlope: slope factor or HS, untiless.

| Example | Q-Patch | Q-Patch ± SEM |
|---|---|---|
| 1 | 247.08 | 25.28 |
| 25 | 51.07 | 3.58 |
| 26 | 181.86 | 57.42 |
| 48 | 386.37 | 105.26 |
| 49 | 391.17 | 133.69 |
| 55 | 33.82 | 8.21 |
| 59 | 354.98 | 90.08 |
| 60 | 623.20 | 173.15 |
| 61 | 149.08 | 77.56 |
| 65 | 348.47 | 97.58 |
| 66 | 1496.83 | 760.16 |
| 71 | 1161.77 | 274.77 |
| 73 | 423.30 | 31.73 |
| 76 | 401.24 | 112.32 |
| 81 | 292.00 | 106.70 |
| 82 | 21.37 | 14.66 |
| 84 | 8.43 | 2.38 |
| 85 | 167.03 | 56.24 |
| 86 | 153.65 | 73.85 |
| 87 | 44.08 | 6.29 |
| 88 | 34.5 | 9.87 |
| 91 | 22.02 | 9.94 |
| 92 | 18.09 | 4.27 |
| 94 | 332.33 | 61.57 |
| 96 | 245.27 | 90.23 |
| 97 | 100.38 | 32.03 |
| 99 | 124.08 | 25.92 |
| 114 | 164.7 | 46.93 |
| 115 | 72.68 | 25.01 |
| 116 | 466.43 | 140.28 |
| 117 | 94.94 | 39.42 |
| 118 | 1086.63 | 394.53 |
| 119 | 267.77 | 31.16 |
| 120 | 161.70 | 14.05 |
| 128 | 45.22 | 13.20 |
| 130 | 94.83 | 29.34 |
| 132 | 3.36 | 0.32 |
| 140 | 39.19 | 7.25 |
| 141 | 3.04 | 0.16 |
| 142 | 153.09 | 123.83 |
| 149 | 68.55 | 23.70 |
| 210 | 149.13 | 24.66 |
| 211 | 118.98 | 50.23 |

The invention claimed is:

1. A compound of the following formula (I) or a pharmaceutically acceptable salt thereof:

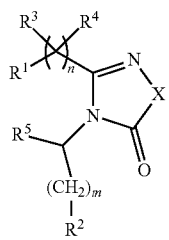

(I)

including any stereochemically isomeric form thereof, wherein:

$R^1$ is independently selected from aliphatic, aromatic, heteroaliphatic or heteroaromatic ring selected from cyclopentyl, cyclohexyl, piperidine, morpholine, pyrrolidine, piperazine, phenyl, pyridine, oxazole, pyrazole or thiazole, wherein each of said moieties is unsubstituted or substituted by one or more substituents selected from $C_1$-$C_4$ alkyl, unsubstituted or substituted by one or more halogen atom(s), halogen, $C_1$-$C_4$ alkoxy or phenyl group unsubstituted or substituted by $C_1$-$C_4$ alkyl, or the above reported aliphatic, aromatic, heteroaliphatic or heteroaromatic rings may be condensed with another aromatic, heteroaromatic or heteroaliphatic ring;

$R^2$ is independently selected from monocyclic or bicylic aliphatic, heteroaliphatic, aromatic or heteroaromatic ring, $C_1$-$C_4$ alkyloxy, alkenyl or alkynyl chain, unsubstituted or substituted by one or more substituents selected from $C_1$-$C_4$ alkyl unsubstituted or substituted by one or more halogen atom(s), halogen, $C_1$-$C_4$ alkoxy, cyano, $C_1$-$C_4$ alkylthio, SO-$C_1$-$C_4$ alkyl, or $SO_2$-$C_1$-$C_4$ alkyl;

n is 1;

m is 0;

$R^3$ and $R^4$ are —H;

X is 0;

$R^5$ is —H.

2. A compound of Formula (I) or a pharmaceutically acceptable salt thereof according to claim 1 wherein:

$R^2$ is independently selected from phenyl, pyridine, pyrimidine, pyrazole, imidazole, naphthalene, quinoline, thiazole, furan, oxazole, oxadiazole, $C_3$-$C_7$ cycloalkyl, pyran, tetrahydropyran, dioxane, $C_1$-$C_4$ alkyloxy, aliphatic, aromatic or heteroaromatic bicyclic rings, or $C_3$-$C_5$ alkynyl chain, wherein $R^2$ is unsubstituted or substituted with one or more $C_1$-$C_4$ alkyl unsubstituted or substituted by one or more halogen atom(s), halogen or $C_1$-$C_4$ alkoxy.

3. A compound of Formula (I) or a pharmaceutically acceptable salt thereof according to claim 1 wherein:

$R^1$ is independently selected from the group consisting of cyclopentyl, cyclohexyl, piperidine, morpholine, pyrrolidine, piperazine, phenyl, pyridine, oxazole, pyrazole or thiazole;

wherein $R^1$ is unsubstituted or substituted with methyl, methoxy, halogen, trifluoromethyl or phenyl group unsubstituted or substituted by methyl; and each of the above reported aliphatic, aromatic or heteroaliphatic or heteroaromatic ring may be condensed with another aromatic or heteroaromatic ring;

$R^2$ is independently selected from phenyl, pyridine, pyrimidine, pyrazole, imidazole, naphthalene, quinoline, thiazole, furan, oxazole, oxadiazole, C3-C7 cycloalkyl, pyran, tetrahydropyran, dioxane, aliphatic bicyclic rings, $C_1$-$C_3$ alkyloxy, $C_1$-$C_4$ alkyl chain or $C_3$-$C_5$ alkynyl chain; wherein each one of the above aliphatic, aromatic and heteroaliphatic ring is unsubstituted or substituted with methyl, methoxy, halogen and/or trifluoromethyl group;

n is 1;
m is 0;
'$R^3$ and $R^4$ are —H;
X is 0;
$R^5$ is H.

4. A compound of Formula (I) or a pharmaceutically acceptable salt thereof according to claim 1 wherein $R^1$ is independently selected from 3,3-difluorocyclopenthyl, cyclohexyl, 4,4-difluorocyclohexyl, piperidinyl, 3,3-difluoropiperidinyl, 4,4-difluoropiperidinyl, 4,4-difluoro-2-methylpiperidinyl, 3-(4-methylphenyl)piperidinyl, 4H,5H,6H,7H-thieno[3,2-c]pyridine-5-yl, 1,2,3,4-tetrahydroisoquinolin-2-yl, 3,4-dihydro-2H-1,4-benzoxazin-4-yl, pyrrolidinyl, 4-phenylpiperazinyl, phenyl, 2- fluorophenyl, 3-fluorophenyl, 4-fluorophenyl, 2-chlorophenyl, 2-trifluoromethylphenyl, 3-methoxyphenyl, 4-methoxyphenyl, 2,3-dichlorophenyl, 2,4-dichlorophenyl, 2-chloro-3-trifluoromethylphenyl, 2,4-difluorophenyl, 2-chloro-4-fluorophenyl, 2-chloro-6-fluorophenyl, 2-, 3- or 4-pyridine, 2-methylpyridin-3-yl, dimethyl-1,2-oxazol-4-yl, trimethyl-1H-pyrazol-4-yl and 4-methyl-1,3-thiazol-5-yl;

$R^2$ is independently selected from 2-phenylmethyl, 1-phenylethyl, 2-phenylethyl, phenyl, 2-, 3-, 4-fluorophenyl, 2-, 4-chlorophenyl, 2-methoxyphenyl, 3-methoxyphenyl, 4-methoxyphenyl, 2-, 4-trifluoromethylphenyl, 2-, 4-methylphenyl, 2,3-dichlorophenyl, 2,4-dichlorophenyl, 2,4-difluorophenyl, 2-chloro-4-fluorophenyl, 2-chloro-6-fluorophenyl, 2-chloro-3-trifluoromethylphenyl, 2,4-dimethoxyphenyl, 3,5-dimethoxyphenyl, 2-bromo-5-fluorophenyl, 4-fluoro-2-methylphenyl, 2-pyridinyl, 3-pyridinyl, 4-pyridine, 2-methylpyridin-3-yl, 6-trifluoromethylpyridin-3-yl, 2-methyl-6-(trifluoromethyl)pyridin-3-yl, naphthalen-1-yl, quinolin-5-yl, 1,3-thiazol-2-y, 1,3-thiazol-5-yl, 4-methyl-1,3-thiazol-5-yl, 5-methyl-1,2-oxazol-3-yl, 1,2-oxazol-3-yl 1,2-oxazol-5-yl, 1,3-oxazol-2-yl, 1,3-oxazol-5-yl, dimethyl-1,2-oxazol-4-yl, 3-(trifluoromethyl)-1H-pyrazol-1-yl, 1,3-dimethyl-1H-pyrazol-5-yl, 1-methyl-1H-imidazol-2-yl, furan-3-yl, 5-(trifluoromethyl)furan-2-yl, 5-methyl-1,3,4-oxadiazol-2-yl, 5-methyl-1,2,4-oxadiazol-3-yl, 3-methyl-1,2,4-oxadiazol-5-yl, pyrimidin-2-yl, pyrimidin-5-yl, 5-fluoropyrimidin-2-yl, cyclopropyl, cyclobutyl, cyclopentyl, cyclopent-3-en-1-yl, cyclohexyl, 1-fluorocyclohexyl, 2-methylcyclohexyl, 2,2-dimethylcyclohexyl, 4,4-dimethylcyclohexyl, 2,2-difluorocyclohexyl, 4,4-diflurocyclohexyl, 4-(trifluoromethyl)cyclohexyl, 4-fluorocyclohexyl, 3,3-difluorocyclopentyl, 6,6-difluorobicyclo[3.1.0] hexan-3-yl, bicyclo[2.2.1]heptan-1-yl, bicyclo[2.2.1]heptan-2-yl, 1,4-dioxaspiro[4.5]decan-8-yl, oxan-2-yl, oxan-3-yl, oxan-4-yl, 1,4-dioxane-2-yl, methoxy, ethoxy, propoxy, but-1-ynyl, prop-1-ynyl, piperidin-1-yl, and 4,4-difluoropiperidin-1-yl ;

n is 1;
m is 0;
'$R^3$ and $R^4$ are —H;
X is 0;
$R^5$ is —H.

5. A compound of formula (I) according to claim 1 which is:
4-[(2-chloro-6-fluorophenyl)methyl]-3-[(4-fluorophenyl) methyl]-4,5-dihydro-1,2,4-oxadiazol-5-one
4-[(2,4-dimethoxyphenyl)methyl]-3-[(4-fluorophenyl) methyl]-4,5-dihydro-1,2,4-oxadiazol-5-one
3-[(4-fluorophenyl)methyl]-4-[(4-methoxyphenyl) methyl]-4,5-dihydro-1,2,4-oxadiazol-5-one
4-[(3,5-dimethoxyphenyl)methyl]-3-[(4-fluorophenyl) methyl]-4,5-dihydro-1,2,4-oxadiazol-5-one
4-[(2-bromo-5-fluorophenyl)methyl]-3-[(4-fluorophenyl) methyl]-4,5-dihydro-1,2,4-oxadiazol-5-one
3-benzyl-4-[(2-chloro-6-fluorophenyl)methyl]-4,5-dihydro-1,2,4-oxadiazol-5-one
4-[(2-chloro-6-fluorophenyl)methyl]-3-[(3-methoxyphenyl)methyl]-4,5-dihydro-1,2,4-oxadiazol-5-one
3-[(4-fluorophenyl)methyl]-4-[(4-methyl-1,3-thiazol-5-yl)methyl]-4,5-dihydro-1,2,4-oxadiazol-5-one
4-[(2,4-dichlorophenyl)methyl]-3-[(4-fluorophenyl) methyl]-4,5-dihydro-1,2,4-oxadiazol-5-one
4-(cyclohexylmethyl)-3-[(4-fluorophenyl)methyl]-4,5-dihydro-1,2,4-oxadiazol-5-one
4-[(2-chloro-6-fluorophenyl)methyl]-3-[(2,3-dichlorophenyl)methyl]-4,5-dihydro-1,2,4-oxadiazol-5-one
3-[(2-chloro-4-fluorophenyl)methyl]-4-[(2-chloro-6-fluorophenyl)methyl]-4,5-dihydro-1,2,4-oxadiazol-5-one
4-[(2-chloro-6-fluorophenyl)methyl]-3-[(2,4-difluorophenyl)methyl]-4,5-dihydro-1,2,4-oxadiazol-5-one
3-{[2-chloro-3-(trifluoromethyl)phenyl]methyl}-4-[(2-chloro-6-fluorophenyl)methyl]-4,5-dihydro-1,2,4-oxadiazol-5-one
4-[(2-chloro-6-fluorophenyl)methyl]-3-[(2,4-dichlorophenyl)methyl]-4,5-dihydro-1,2,4-oxadiazol-5-one
bis[(2-chloro-6-fluorophenyl)methyl]-4,5-dihydro-1,2,4-oxadiazol-5-one
4-[(2-chloro-6-fluorophenyl)methyl]-3-[(2-fluorophenyl) methyl]-4,5-dihydro-1,2,4-oxadiazol-5-one
4-[(2-chloro-6-fluorophenyl)methyl]-3-[(2-chlorophenyl) methyl]-4,5-dihydro-1,2,4-oxadiazol-5-one
4-benzyl-3-[(2-chloro-6-fluorophenyl)methyl]-4,5-dihydro-1,2,4-oxadiazol-5-one
3-[(2-chloro-6-fluorophenyl)methyl]-4-[(2-chlorophenyl) methyl]-4,5-dihydro-1,2,4-oxadiazol-5-one
3-[(2-chloro-6-fluorophenyl)methyl]-4-{[2-(trifluoromethyl)phenyl]methyl}-4,5-dihydro-1,2,4-oxadiazol-5-one
3-[(2-chloro-6-fluorophenyl)methyl]-4-[(2-methylpyridin-3-yl)methyl]-4,5-dihydro-1,2,4-oxadiazol-5-one
3-[(2-chloro-6-fluorophenyl)methyl]-4-[(4-fluoro-2-methylphenyl)methyl]-4,5-dihydro-1,2,4-oxadiazol-5-one
3-[(2-chloro-6-fluorophenyl)methyl]-4-[(3-fluorophenyl) methyl]-4,5-dihydro-1,2,4-oxadiazol-5-one
3-[(2-chloro-6-fluorophenyl)methyl]-4-[(2-methylphenyl)methyl]-4,5-dihydro-1,2,4-oxadiazol-5-one
3-[(2-chloro-6-fluorophenyl)methyl]-4-[(2-methoxyphenyl)methyl]-4,5-dihydro-1,2,4-oxadiazol-5-one
3-[(2-chloro-6-fluorophenyl)methyl]-4-(naphthalen-1-ylmethyl)-4,5-dihydro-1,2,4-oxadiazol-5-one
3-[(2-chloro-6-fluorophenyl)methyl]-4-(quinolin-5-ylmethyl)-4,5-dihydro-1,2,4-oxadiazol-5-one
3-[(2-chloro-6-fluorophenyl)methyl]-4-[(4-methyl-1,3-thiazol-5-yl)methyl]-4,5-dihydro-1,2,4-oxadiazol-5-one
3-[(2-chloro-6-fluorophenyl)methyl]-4-(1,3-oxazol-2-yl-methyl)-4,5-dihydro-1,2,4-oxadiazol-5-one 3-[(2-chloro-6-fluorophenyl)methyl]-4-(1,3-thiazol-5-yl-methyl)-4,5-dihydro-1,2,4-oxadiazol-5-one
3-[(2-chloro-6-fluorophenyl)methyl]-4-(1,3-thiazol-2-yl-methyl)-4,5-dihydro-1,2,4-oxadiazol-5-one
3-[(2-chloro-6-fluorophenyl)methyl]-4-{[3-(trifluoromethyl)-1H-pyrazol-1-yl]methyl}-4,5-dihydro-1,2,4-oxadiazol-5-one
3-[(2-chloro-6-fluorophenyl)methyl]-4-[(dimethyl-1,2-oxazol-4-yl)methyl]-4,5-dihydro-1,2,4-oxadiazol-5-one
3-[(2-chloro-6-fluorophenyl)methyl]-4-{[6-(trifluoromethyl)pyridin-3-yl]methyl}-4,5-dihydro-1,2,4-oxadiazol-5-one
3-[(2-chloro-6-fluorophenyl)methyl]-4-(pyrimidin-5-yl-methyl)-4,5-dihydro-1,2,4-oxadiazol-5-one
3-[(2-chloro-6-fluorophenyl)methyl]-4-(pyrimidin-2-yl-methyl)-4,5-dihydro-1,2,4-oxadiazol-5-one
3-[(2-chloro-6-fluorophenyl)methyl]-4-(1,3-oxazol-5-yl-methyl)-4,5-dihydro-1,2,4-oxadiazol-5-one
3-[(2-chloro-6-fluorophenyl)methyl]-4-[(5-methyl-1,3,4-oxadiazol-2-yl)methyl]-4,5-dihydro-1,2,4-oxadiazol-5-one
3-[(2-chloro-6-fluorophenyl)methyl]-4-(pyridin-3-ylmethyl)-4,5-dihydro-1,2,4-oxadiazol-5-one
3-[(2-chloro-6-fluorophenyl)methyl]-4-(pyridin-4-ylmethyl)-4,5-dihydro-1,2,4-oxadiazol-5-one
3-[(2-chloro-6-fluorophenyl)methyl]-4-(furan-3-ylmethyl)-4,5-dihydro-1,2,4-oxadiazol-5-one
3-[(2-chloro-6-fluorophenyl)methyl]-4-[(5-fluoropyrimidin-2-yl)methyl]-4,5-dihydro-1,2,4-oxadiazol-5-one
3-[(2-chloro-6-fluorophenyl)methyl]-4-[(1,3-dimethyl-1H-pyrazol-5-yl)methyl]-4,5-dihydro-1,2,4-oxadiazol-5-one
3-[(2-chloro-6-fluorophenyl)methyl]-4-[(1-methyl-1H-imidazol-2-yl)methyl]-4,5-dihydro-1,2,4-oxadiazol-5-one
4-[(2,3-dichlorophenyl)methyl]-3-[(4-fluorophenyl)methyl]-4,5-dihydro-1,2,4-oxadiazol-5-one
4-[(2-chloro-4-fluorophenyl)methyl]-3-[(4-fluorophenyl)methyl]-4,5-dihydro-1,2,4-oxadiazol-5-one
4-{[2-chloro-3-(trifluoromethyl)phenyl]methyl}-3-[(4-fluorophenyl)methyl]-4,5-dihydro-1,2,4-oxadiazol-5-one
4-[(2,4-difluorophenyl)methyl]-3-[(4-fluorophenyl)methyl]-4,5-dihydro-1,2,4-oxadiazol-5-one
bis[(4-fluorophenyl)methyl]-4,5-dihydro-1,2,4-oxadiazol-5-one
3-[(2-chloro-6-fluorophenyl)methyl]-4-[(4-fluorophenyl)methyl]-4,5-dihydro-1,2,4-oxadiazol-5-one
3-[(2-chloro-6-fluorophenyl)methyl]-4-[(2-fluorophenyl)methyl]-4,5-dihydro-1,2,4-oxadiazol-5-one
3-[(2-chloro-6-fluorophenyl)methyl]-4-[(3-methoxyphenyl)methyl]-4,5-dihydro-1,2,4-oxadiazol-5-one
4-{[2-chloro-3-(trifluoromethyl)phenyl]methyl}-3-[(2-chloro-6-fluorophenyl)methyl]-4,5-dihydro-1,2,4-oxadiazol-5-one
3-[(2-chloro-6-fluorophenyl)methyl]-4-[(2,3-dichlorophenyl)methyl]-4,5-dihydro-1,2,4-oxadiazol-5-one
4-[(2-chloro-4-fluorophenyl)methyl]-3-[(2-chloro-6-fluorophenyl)methyl]-4,5-dihydro-1,2,4-oxadiazol-5-one
3-[(2-chloro-6-fluorophenyl)methyl]-4-[(2,4-difluorophenyl)methyl]-4,5-dihydro-1,2,4-oxadiazol-5-one
3-[(2-chloro-6-fluorophenyl)methyl]-4-(pyridin-2-ylmethyl)-4,5-dihydro-1,2,4-oxadiazol-5-one
3-[(2-chloro-6-fluorophenyl)methyl]-4-{[4-(trifluoromethyl)phenyl]methyl}-4,5-dihydro-1,2,4-oxadiazol-5-one
3-[(2-chloro-6-fluorophenyl)methyl]-4-{[2-methyl-6-(trifluoromethyl)pyridin-3-yl]methyl}-4,5-dihydro-1,2,4-oxadiazol-5-one
3-[(2-chloro-6-fluorophenyl)methyl]-4-[(4-chlorophenyl)methyl]-4,5-dihydro-1,2,4-oxadiazol-5-one
3-[(2-chloro-6-fluorophenyl)methyl]-4-{[5-(trifluoromethyl)furan-2-yl]methyl}-4,5-dihydro-1,2,4-oxadiazol-5-one
3-[(2-chloro-6-fluorophenyl)methyl]-4-[(4-methylphenyl)methyl]-4,5-dihydro-1,2,4-oxadiazol-5-one
3-[(2-chloro-6-fluorophenyl)methyl]-4-[(4-methoxyphenyl)methyl]-4,5-dihydro-1,2,4-oxadiazol-5-one
3-[(2-chloro-6-fluorophenyl)methyl]-4-(cyclobutylmethyl)-4,5-dihydro-1,2,4-oxadiazol-5-one
3-[(2-chloro-6-fluorophenyl)methyl]-4-{1,4-dioxaspiro[4.5]decan-8-ylmethyl}-4,5-dihydro-1,2,4-oxadiazol-5-one
3-[(2,3-dichlorophenyl)methyl]-4-[(4-fluorophenyl)methyl]-4,5-dihydro-1,2,4-oxadiazol-5-one
3-{[2-chloro-3-(trifluoromethyl)phenyl]methyl}-4-[(4-fluorophenyl)methyl]-4,5-dihydro-1,2,4-oxadiazol-5-one
3-[(2-chloro-4-fluorophenyl)methyl]-4-[(4-fluorophenyl)methyl]-4,5-dihydro-1,2,4-oxadiazol-5-one
3-[(2,4-dichlorophenyl)methyl]-4-[(4-fluorophenyl)methyl]-4,5-dihydro-1,2,4-oxadiazol-5-one
3-[(2-fluorophenyl)methyl]-4-[(4-fluorophenyl)methyl]-4,5-dihydro-1,2,4-oxadiazol-5-one
3-[(2-chlorophenyl)methyl]-4-[(4-fluorophenyl)methyl]-4,5-dihydro-1,2,4-oxadiazol-5-one
4-[(4-fluorophenyl)methyl]-3-(pyridin-4-ylmethyl)-4,5-dihydro-1,2,4-oxadiazol-5-one
3-[(2,4-difluorophenyl)methyl]-4-[(4-fluorophenyl)methyl]-4,5-dihydro-1,2,4-oxadiazol-5-one
4-[(2-chloro-6-fluorophenyl)methyl]-3-[(3-fluorophenyl)methyl]-4,5-dihydro-1,2,4-oxadiazol-5-one
3-[(2-chloro-6-fluorophenyl)methyl]-4-(cyclohexylmethyl)-4,5-dihydro-1,2,4-oxadiazol-5-one
3-[(2-chloro-6-fluorophenyl)methyl]-4-(cyclopropylmethyl)-4,5-dihydro-1,2,4-oxadiazol-5-one
3-[(2-chloro-6-fluorophenyl)methyl]-4-[(4,4-difluorocyclohexyl)methyl]-4,5-dihydro-1,2,4-oxadiazol-5-one
3-[(2-chloro-6-fluorophenyl)methyl]-4-(cyclopentylmethyl)-4,5-dihydro-1,2,4-oxadiazol-5-one
3-[(2-chloro-6-fluorophenyl)methyl]-4-[(4,4-dimethylcyclohexyl)methyl]-4,5-dihydro-1,2,4-oxadiazol-5-one
3-[(2-chloro-6-fluorophenyl)methyl]-4-[(2-methylcyclohexyl)methyl]-4,5-dihydro-1,2,4-oxadiazol-5-one
4-{bicyclo[2.2.1]heptan-2-ylmethyl}-3-[(2-chloro-6-fluorophenyl)methyl]-4,5-dihydro-1,2,4-oxadiazol-5-one
3-[(2-chloro-6-fluorophenyl)methyl]-4-(oxan-3-ylmethyl)-4,5-dihydro-1,2,4-oxadiazol-5-one
3-[(2-chloro-6-fluorophenyl)methyl]-4-(pent-2-yn-1-yl)-4,5-dihydro-1,2,4-oxadiazol-5-one
4-{bicyclo[2.2.1]heptan-1-ylmethyl}-3-[(2-chloro-6-fluorophenyl)methyl]-4,5-dihydro-1,2,4-oxadiazol-5-one
3-[(2-chloro-6-fluorophenyl)methyl]-4-(cycloheptylmethyl)-4,5-dihydro-1,2,4-oxadiazol-5-one
3-[(2-chloro-6-fluorophenyl)methyl]-4-(oxan-4-ylmethyl)-4,5-dihydro-1,2,4-oxadiazol-5-one
3-[(2-chloro-6-fluorophenyl)methyl]-4-(oxan-2-ylmethyl)-4,5-dihydro-1,2,4-oxadiazol-5-one 4-(but-2-yn-1-yl)-3-[(2-chloro-6-fluorophenyl)methyl]-4,5-dihydro-1,2,4-oxadiazol-5-one 3-[(2-chloro-6-fluorophenyl)methyl]-4-[(1-fluorocyclohexyl)methyl]-4,5-dihydro-1,2,4-oxadiazol-5-one
3-[(2-chloro-6-fluorophenyl)methyl]-4-[(2,2-difluorocyclohexyl)methyl]-4,5-dihydro-1,2,4-oxadiazol-5-one
3-[(2-chloro-6-fluorophenyl)methyl]-4-(1,4-dioxan-2-ylmethyl)-4,5-dihydro-1,2,4-oxadiazol-5-one
3-[(2-chloro-6-fluorophenyl)methyl]-4-[(2,2-dimethylcyclohexyl)methyl]-4,5-dihydro-1,2,4-oxadiazol-5-one
3-[(2-chloro-6-fluorophenyl)methyl]-4-(methoxymethyl)-4,5-dihydro-1,2,4-oxadiazol-5-one
3-[(2-chloro-6-fluorophenyl)methyl]-4-(ethoxymethyl)-4,5-dihydro-1,2,4-oxadiazol-5-one
3-[(2-chloro-6-fluorophenyl)methyl]-4-(propoxymethyl)-4,5-dihydro-1,2,4-oxadiazol-5-one
4-[(4-fluorophenyl)methyl]-3-(pyridin-2-ylmethyl)-4,5-dihydro-1,2,4-oxadiazol-5-one
4-[(4-fluorophenyl)methyl]-3-{[2-(trifluoromethyl)phenyl]methyl}-4,5-dihydro-1,2,4-oxadiazol-5-one
3-[(3-fluorophenyl)methyl]-4-[(4-fluorophenyl)methyl]-4,5-dihydro-1,2,4-oxadiazol-5-one
3-benzyl-4-[(4-fluorophenyl)methyl]-4,5-dihydro-1,2,4-oxadiazol-5-one
4-[(4-fluorophenyl)methyl]-3-[(3-methoxyphenyl)methyl]-4,5-dihydro-1,2,4-oxadiazol-5-one
4-(cyclohexylmethyl)-3-(pyridin-2-ylmethyl)-4,5-dihydro-1,2,4-oxadiazol-5-one
4-(cyclohexylmethyl)-3-(pyridin-4-ylmethyl)-4,5-dihydro-1,2,4-oxadiazol-5-one
4-(cyclohexylmethyl)-3-[(4-methoxyphenyl)methyl]-4,5-dihydro-1,2,4-oxadiazol-5-one
3-{[2-chloro-3-(trifluoromethyl)phenyl]methyl}-4-(cyclohexylmethyl)-4,5-dihydro-1,2,4-oxadiazol-5-one
3-[(2-chloro-4-fluorophenyl)methyl]-4-(cyclohexylmethyl)-4,5-dihydro-1,2,4-oxadiazol-5-one
4-(cyclohexylmethyl)-3-[(2,3-dichlorophenyl)methyl]-4,5-dihydro-1,2,4-oxadiazol-5-one
4-(cyclohexylmethyl)-3-{[2-(trifluoromethyl)phenyl]methyl}-4,5-dihydro-1,2,4-oxadiazol-5-one
3-[(2-chlorophenyl)methyl]-4-(cyclohexylmethyl)-4,5-dihydro-1,2,4-oxadiazol-5-one
4-(cyclohexylmethyl)-3-[(2,4-dichlorophenyl)methyl]-4,5-dihydro-1,2,4-oxadiazol-5-one7
4-(cyclohexylmethyl)-3-[(2,4-difluorophenyl)methyl]-4,5-dihydro-1,2,4-oxadiazol-5-one
4-(cyclohexylmethyl)-3-[(2-fluorophenyl)methyl]-4,5-dihydro-1,2,4-oxadiazol-5-one
3-[1-(2-chloro-6-fluorophenyfethyl]-4-(cyclohexylmethyl)-4,5-dihydro-1,2,4-oxadiazol-5-one
4-(cyclohexylmethyl)-3-(pyridin-3-ylmethyl)-4,5-dihydro-1,2,4-oxadiazol-5-one
4-(cyclohexylmethyl)-3-[(3-fluorophenyl)methyl]-4,5-dihydro-1,2,4-oxadiazol-5-one
3-benzyl-4-(cyclohexylmethyl)-4,5-dihydro-1,2,4-oxadiazol-5-one
4-(cyclohexylmethyl)-3-[(3-methoxyphenyl)methyl]-4,5-dihydro-1,2,4-oxadiazol-5-one
3-[(2-chloro-6-fluorophenyl)methyl]-4-[(3,3-difluorocyclopentyl)methyl]-4,5-dihydro-1,2,4-oxadiazol-5-one
bis(cyclohexylmethyl)-4,5-dihydro-1,2,4-oxadiazol-5-one
4-[(2-chloro-6-fluorophenyl)methyl]-3-(cyclohexylmethyl)-4,5-dihydro-1,2,4-oxadiazol-5-one
3-(cyclohexylmethyl)-4-[(4-fluorophenyl)methyl]-4,5-dihydro-1,2,4-oxadiazol-5-one
4-[(2-chloro-6-fluorophenyl)methyl]-3-[(4,4-difluorocyclohexyl)methyl]-4,5-dihydro-1,2,4-oxadiazol-5-one
4-(cyclohexylmethyl)-3-[(4,4-difluorocyclohexyl)methyl]-4,5-dihydro-1,2,4-oxadiazol-5-one 4-(cyclohexylmethyl)-3-[(4,4-difluorocyclohexyl)methyl]-4,5-dihydro-1,2,4-oxadiazol-5-one
3-(2-chloro-6-fluorobenzyl)-4-[(3,3-difluorocyclopentyl)methyl]-1,2,4-oxadiazol-5(4H)-one
3-(2-chloro-6-fluorobenzyl)-4-[(3,3-difluorocyclopentyl)methyl]-1,2,4-oxadiazol-5(4H)-one
4-[(4,4-difluorocyclohexyl)methyl]-3-[(2-fluorophenyl)methyl]-4,5-dihydro-1,2,4-oxadiazol-5-one
4-[(4,4-difluorocyclohexyl)methyl]-3-[(3-fluorophenyl)methyl]-4,5-dihydro-1,2,4-oxadiazol-5-one
4-[(4,4-difluorocyclohexyl)methyl]-3-[(4-fluorophenyl)methyl]-4,5-dihydro-1,2,4-oxadiazol-5-one
4-[(4,4-difluorocyclohexyl)methyl]-3-[(2,4-difluorophenyl)methyl]-4,5-dihydro-1,2,4-oxadiazol-5-one
4-[(4,4-difluorocyclohexyl)methyl]-3-[(4-methoxyphenyl)methyl]-4,5-dihydro-1,2,4-oxadiazol-5-one
3-{[2-chloro-3-(trifluoromethyl)phenyl]methyl}-4-[(4,4-difluorocyclohexyl)methyl]-4,5-dihydro-1,2,4-oxadiazol-5-one
3-[(2,3-dichlorophenyl)methyl]-4-[(4,4-difluorocyclohexyl)methyl]-4,5-dihydro-1,2,4-oxadiazol-5-one
4-[(4,4-difluorocyclohexyl)methyl]-3-{[2-(trifluoromethyl)phenyl]methyl}-4,5-dihydro-1,2,4-oxadiazol-5-one
3-[(2-chlorophenyl)methyl]-4-[(4,4-difluorocyclohexyl)methyl]-4,5-dihydro-1,2,4-oxadiazol-5-one
3-[(2,4-dichlorophenyl)methyl]-4-[(4,4-difluorocyclohexyl)methyl]-4,5-dihydro-1,2,4-oxadiazol-5-one
4-[(4,4-difluorocyclohexyl)methyl]-3-[(3-methoxyphenyl)methyl]-4,5-dihydro-1,2,4-oxadiazol-5-one
3-benzyl-4-[(4,4-difluorocyclohexyl)methyl]-4,5-dihydro-1,2,4-oxadiazol-5-one
3-[(2-chloro-4-fluorophenyl)methyl]-4-[(4,4-difluorocyclohexyl)methyl]-4,5-dihydro-1,2,4-oxadiazol-5-one
3-[(4,4-difluorocyclohexyl)methyl]-4-[(2-fluorophenyl)methyl]-4,5-dihydro-1,2,4-oxadiazol-5-one
3-[(4,4-difluorocyclohexyl)methyl]-4-{[4-(trifluoromethyl)phenyl]methyl}-4,5-dihydro-1,2,4-oxadiazol-5-one
4-{[2-chloro-3-(trifluoromethyl)phenyl]methyl}-3-[(4,4-difluorocyclohexyl)methyl]-4,5-dihydro-1,2,4-oxadiazol-5-one
3-[(4,4-difluorocyclohexyl)methyl]-4-{[5-(trifluoromethyl)furan-2-yl]methyl}-4,5-dihydro-1,2,4-oxadiazol-5-one
3-[(4,4-difluorocyclohexyl)methyl]-4-[(5-methyl-1,2-oxazol-3-yl)methyl]-4,5-dihydro-1,2,4-oxadiazol-5-one
4-[(2-chlorophenyl)methyl]-3-[(4,4-difluorocyclohexyl)methyl]-4,5-dihydro-1,2,4-oxadiazol-5-one
3-[(4,4-difluorocyclohexyl)methyl]-4-[(4-fluoro-2-methylphenyl)methyl]-4,5-dihydro-1,2,4-oxadiazol-5-one
3-[(2-chloro-6-fluorophenyl)methyl]-4-({6,6-difluorobicyclo[3.1.0]hexan-3-yl}methyl)-4,5-dihydro-1,2,4-oxadiazol-5-one
3-[(2-chloro-6-fluorophenyl)methyl]-4-ethyl-4,5-dihydro-1,2,4-oxadiazol-5-one
3-[(2-chloro-6-fluorophenyl)methyl]-4-propyl-4,5-dihydro-1,2,4-oxadiazol-5-one
4-butyl-3-[(2-chloro-6-fluorophenyl)methyl]-4,5-dihydro-1,2,4-oxadiazol-5-one
3-[(2-chloro-6-fluorophenyl)methyl]-4-(2-methylpropyl)-4,5-dihydro-1,2,4-oxadiazol-5-one 3-[(2-chloro-6-fluorophenyl)methyl]-4-(cyclopent-3-en-1-ylmethyl)-4,5-dihydro-1,2,4-oxadiazol-5-one
3-[(2-chloro-6-fluorophenyl)methyl]-4-{[4-(trifluoromethyl)cyclohexyl]methyl}-1,2,4-oxadiazol-5(4H)-one
3-[(2-chloro-6-fluorophenyl)methyl]-4-[(4-fluorocyclohexyl)methyl]-4,5-dihydro-1,2,4-oxadiazol-5-one
3-[(4,4-difluorocyclohexyl)methyl]-4-{[6-(trifluoromethyl)pyridin-3-yl]methyl}-4,5-dihydro-1,2,4-oxadiazol-5-one
3-[(4,4-difluorocyclohexyl)methyl]-4-[(5-fluoropyrimidin-2-yl)methyl]-4,5-dihydro-1,2,4-oxadiazol-5-one
3-[(4,4-difluorocyclohexyl)methyl]-4-(1,3-thiazol-2-ylmethyl)-4,5-dihydro-1,2,4-oxadiazol-5-one
3-[(4,4-difluorocyclohexyl)methyl]-4-{[2-methyl-6-(trifluoromethyl)pyridin-3-yl]methyl}-4,5-dihydro-1,2,4-oxadiazol-5-one
3-[(4,4-difluorocyclohexyl)methyl]-4-[(1,3-thiazol-5-yl)methyl]-1,2,4-oxadiazol-5(4H)-one
3-[(4,4-difluorocyclohexyl)methyl]-4-[(1,3-oxazol-2-yl)methyl]-1,2,4-oxadiazol-5(4H)-one
3-[(4,4-difluorocyclohexyl)methyl]-4-[(1,3-dimethyl-1H-pyrazol-5-yl)methyl]-1,2,4-oxadiazol-5(4H)-one
3-[(4,4-difluorocyclohexyl)methyl]-4-[(5-methyl-1,2,4-oxadiazol-3-yl)methyl]-1,2,4-oxadiazol-5(4H)-one
3-[(4,4-difluorocyclohexyl)methyl]-4-[(3-methyl-1,2,4-oxadiazol-5-yl)methyl]-1,2,4-oxadiazol-5(4H)-one
3-[(4,4-difluorocyclohexyl)methyl]-4-{[3-(trifluoromethyl)-1H-pyrazol-1-yl]methyl}-1,2,4-oxadiazol-5(4H)-one
3-[(4,4-difluorocyclohexyl)methyl]-4-[(1,2-oxazol-5-yl)methyl]-1,2,4-oxadiazol-5(4H)-one
3-[(4,4-difluorocyclohexyl)methyl]-4-[(4-methyl-1,3-thiazol-5-yl)methyl]-1,2,4-oxadiazol-5(4H)-one
3-[(4,4-difluorocyclohexyl)methyl]-4-[(1-methyl-1H-imidazol-2-yl)methyl]-4,5-dihydro-1,2,4-oxadiazol-5-one
3-[(3,3-difluorocyclopentyl)methyl]-4-[(4-fluorophenyl)methyl]-4,5-dihydro-1,2,4-oxadiazol-5-one
4-[(2-chloro-6-fluorophenyl)methyl]-3-[(3,3-difluorocyclopentyl)methyl]-4,5-dihydro-1,2,4-oxadiazol-5-one
4-(cyclohexylmethyl)-3-[(3,3-difluorocyclopentyl)methyl]-4,5-dihydro-1,2,4-oxadiazol-5-one
4-[(4,4-difluorocyclohexyl)methyl]-3-[(3,3-difluorocyclopentyl)methyl]-4,5-dihydro-1,2,4-oxadiazol-5-one
3-[(dimethyl-1,2-oxazol-4-yl)methyl]-4-[(4-fluorophenyl)methyl]-4,5-dihydro-1,2,4-oxadiazol-5-one
4-[(2-chloro-6-fluorophenyl)methyl]-3-[(dimethyl-1,2-oxazol-4-yl)methyl]-4,5-dihydro-1,2,4-oxadiazol-5-one
4-(cyclohexylmethyl)-3-[(dimethyl-1,2-oxazol-4-yl)methyl]-4,5-dihydro-1,2,4-oxadiazol-5-one
4-[(4,4-difluorocyclohexyl)methyl]-3-[(dimethyl-1,2-oxazol-4-yl)methyl]-4,5-dihydro-1,2,4-oxadiazol-5-one
4-[(4-fluorophenyl)methyl]-3-[(trimethyl-1H-pyrazol-4-yl)methyl]-4,5-dihydro-1,2,4-oxadiazol-5-one
4-[(2-chloro-6-fluorophenyl)methyl]-3-[(trimethyl-1H-pyrazol-4-yl)methyl]-4,5-dihydro-1,2,4-oxadiazol-5-one
4-(cyclohexylmethyl)-3-[(trimethyl-1H-pyrazol-4-yl)methyl]-4,5-dihydro-1,2,4-oxadiazol-5-one
4-[(4,4-difluorocyclohexyl)methyl]-3-[(trimethyl-1H-pyrazol-4-yl)methyl]-4,5-dihydro-1,2,4-oxadiazol-5-one
4-[(4-fluorophenyl)methyl]-3-[(2-methylpyridin-3-yl)methyl]-4,5-dihydro-1,2,4-oxadiazol-5-one
4-[(2-chloro-6-fluorophenyl)methyl]-3-[(2-methylpyridin-3-yl)methyl]-4,5-dihydro-1,2,4-oxadiazol-5-one
4-(cyclohexylmethyl)-3-[(2-methylpyridin-3-yl)methyl]-4,5-dihydro-1,2,4-oxadiazol-5-one
4-[(4,4-difluorocyclohexyl)methyl]-3-[(2-methylpyridin-3-yl)methyl]-4,5-dihydro-1,2,4-oxadiazol-5-one
4-[(2-chloro-6-fluorophenyl)methyl]-3-[(4,4-difluoropiperidin-1-yl)methyl]-4,5-dihydro-1,2,4-oxadiazol-5-one
3-[(4,4-difluoropiperidin-1-yl)methyl]-4-[(4-fluorophenyl)methyl]-4,5-dihydro-1,2,4-oxadiazol-5-one
4-(cyclohexylmethyl)-3-[(4,4-difluoropiperidin-1-yl)methyl]-4,5-dihydro-1,2,4-oxadiazol-5-one
4-[(4,4-difluorocyclohexyl)methyl]-3-[(4,4-difluoropiperidin-1-yl)methyl]-4,5-dihydro-1,2,4-oxadiazol-5-one
4-[(2-chloro-6-fluorophenyl)methyl]-3-[(3,3-difluoropiperidin-1-yl)methyl]-4,5-dihydro-1,2,4-oxadiazol-5-one
3-[(3,3-difluoropiperidin-1-yl)methyl]-4-[(4-fluorophenyl)methyl]-4,5-dihydro-1,2,4-oxadiazol-5-one
4-[(2-chloro-6-fluorophenyl)methyl]-3-[(4,4-difluoro-2-methylpiperidin-1-yl)methyl]-4,5-dihydro-1,2,4-oxadiazol-5-one
3-[(4,4-difluoro-2-methylpiperidin-1-yl)methyl]-4-[(4-fluorophenyl)methyl]-4,5-dihydro-1,2,4-oxadiazol-5-one
3-(3,4-dihydro-2H-1,4-benzoxazin-4-ylmethyl)-4-[(4-fluorophenyl)methyl]-4,5-dihydro-1,2,4-oxadiazol-5-one
4-[(2-chloro-6-fluorophenyl)methyl]-3-(3,4-dihydro-2H-1,4-benzoxazin-4-ylmethyl)-4,5-dihydro-1,2,4-oxadiazol-5-one
4-(cyclohexylmethyl)-3-(3,4-dihydro-2H-1,4-benzoxazin-4-ylmethyl)-4,5-dihydro-1,2,4-oxadiazol-5-one
4-[(4,4-difluorocyclohexyl)methyl]-3-(3,4-dihydro-2H-1,4-benzoxazin-4-ylmethyl)-4,5-dihydro-1,2,4-oxadiazol-5-one
4-[(4-fluorophenyl)methyl]-3-{4H,5H,6H,7H-thieno[3,2-c]pyridin-5-ylmethyl}-4,5-dihydro-1,2,4-oxadiazol-5-one
4-[(2-chloro-6-fluorophenyl)methyl]-3-{4H,5H,6H,7H-thieno[3,2-c]pyridin-5-ylmethyl}-4,5-dihydro-1,2,4-oxadiazol-5-one
4-(cyclohexylmethyl)-3-{4H,5H,6H,7H-thieno[3,2-c]pyridin-5-ylmethyl}-4,5-dihydro-1,2,4-oxadiazol-5-one
4-[(4,4-difluorocyclohexyl)methyl]-3-{4H,5H,6H,7H-thieno[3,2-c]pyridin-5-ylmethyl}-4,5-dihydro-1,2,4-oxadiazol-5-one
4-[(4-fluorophenyl)methyl]-3-[(4-phenylpiperazin-1-yl)methyl]-4,5-dihydro-1,2,4-oxadiazol-5-one
4-[(2-chloro-6-fluorophenyl)methyl]-3-[(4-phenylpiperazin-1-yl)methyl]-4,5-dihydro-1,2,4-oxadiazol-5-one
4-(cyclohexylmethyl)-3-[(4-phenylpiperazin-1-yl)methyl]-4,5-dihydro-1,2,4-oxadiazol-5-one
4-[(4,4-difluorocyclohexyl)methyl]-3-[(4-phenylpiperazin-1-yl)methyl]-4,5-dihydro-1,2,4-oxadiazol-5-one
4-[(4-fluorophenyl)methyl]-3-(piperidin-1-ylmethyl)-4,5-dihydro-1,2,4-oxadiazol-5-one
4-[(2-chloro-6-fluorophenyl)methyl]-3-[(piperidin-1-yl)methyl]-1,2,4-oxadiazol-5(4H)-one
4-[(2-chloro-6-fluorophenyl)methyl]-3-{[3-(4-methylphenyl)piperidin-1-yl]methyl}-4,5-dihydro-1,2,4-oxadiazol-5-one
4-[(4-fluorophenyl)methyl]-3-{[3-(4-methylphenyl)piperidin-1-yl]methyl}-4,5-dihydro-1,2,4-oxadiazol-5-one 4-[(2-chloro-6-fluorophenyl)methyl]-3-(1,2,3,4-tetrahydroisoquinolin-2-ylmethyl)-4,5-dihydro-1,2,4-oxadiazol-5-one 4-[(4,4-difluorocyclohexyl)methyl]-3-(1,2,3,4-tetrahydroisoquinolin-2-ylmethyl)-4,5-dihydro-1,2,4-oxadiazol-5-one 4-[(2-chloro-6-fluorophenyl)methyl]-3-(pyrrolidin-1-ylmethyl)-4,5-dihydro-1,2,4-oxadiazol-5-one 4-(4-fluorobenzyl)-3-[(4-methyl-1,3-thiazol-5-yl)methyl]-1,2,4-oxadiazol-5(4H)-one 4-(2-chloro-6-fluorobenzyl)-3-[(4-methyl-1,3-thiazol-5-yl)methyl]-1,2,4-oxadiazol-5(4H)-one 4-(cyclohexylmethyl)-3-[(4-methyl-1,3-thiazol-5-yl)methyl]-1,2,4-oxadiazol-5(4H)-one 4-[(4,4-difluorocyclohexyl)methyl]-3-[(4-methyl-1,3-thiazol-5-yl)methyl]-1,2,4-oxadiazol-5(4H)-one 4-[(3,3-difluorocyclopentyl)methyl]-3-[(4-methyl-1,3-thiazol-5-yl)methyl]-1,2,4-oxadiazol-5(4H)-one.

6. A pharmaceutical composition comprising a compound of Formula (I) according to claim 1 and a pharmaceutically acceptable diluent and/or carrier.

7. A method for treatment of conditions or diseases selected from P2X7 receptor mediated conditions or diseases, comprising administering to a patient in need thereof a therapeutically effective amount of a compound of Formula (I) according to claim 1.

8. The method according to claim 7, wherein the conditions or diseases selected from P2X7 receptor mediated conditions or diseases are neurodegenerative, cognitive or psychiatric disorders, neuropathic pain, chronic pain, inflammatory processes of the muscular-skeletal system, liver fibrosis, gastrointestinal tract disorders, genito-urinary tract disorders, ophthalmic diseases, Chronic Obstructive Pulmonary Disease (COPD), cancer and proliferative diseases.

* * * * *